United States Patent
Rabinowitz et al.

(10) Patent No.: US 8,796,263 B2
(45) Date of Patent: Aug. 5, 2014

(54) 4-AMINOQUINAZOLIN-2-YL-1-PYRRAZOLE-4-CARBOXYLIC ACID COMPOUNDS AS PROLYL HYDROXYLASE INHIBITORS

(75) Inventors: Michael H. Rabinowitz, San Diego, CA (US); Mark D. Rosen, San Diego, CA (US); Kyle T. Tarantino, San Diego, CA (US); Hariharan Venkatesan, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/816,747

(22) PCT Filed: Aug. 12, 2011

(86) PCT No.: PCT/US2011/047626
§ 371 (c)(1),
(2), (4) Date: Feb. 13, 2013

(87) PCT Pub. No.: WO2012/021830
PCT Pub. Date: Feb. 16, 2012

(65) Prior Publication Data
US 2013/0143871 A1 Jun. 6, 2013

Related U.S. Application Data

(60) Provisional application No. 61/373,664, filed on Aug. 13, 2010.

(51) Int. Cl.
*A61K 31/55* (2006.01)
*A61K 31/517* (2006.01)
*A61K 31/54* (2006.01)
*C07D 401/00* (2006.01)
*C07D 413/00* (2006.01)
*C07D 243/08* (2006.01)
*C07D 403/00* (2006.01)

(52) U.S. Cl.
USPC ............ 514/217.06; 514/266.23; 514/266.22; 514/218; 514/228.2; 544/284; 544/116; 540/575; 540/600

(58) Field of Classification Search
None
See application file for complete search history.

(56) References Cited

U.S. PATENT DOCUMENTS

| | | |
|---|---|---|
| 2006/0276477 A1 | 12/2006 | Klaus et al. |
| 2007/0299086 A1 | 12/2007 | Kawamoto et al. |
| 2009/0239876 A1 | 9/2009 | Clements et al. |
| 2010/0204226 A1 | 8/2010 | Bembenek et al. |

FOREIGN PATENT DOCUMENTS

| | | |
|---|---|---|
| JP | 39023409 | 10/1964 |
| WO | WO 2004 052284 A2 | 6/2004 |
| WO | WO 2004 052285 A2 | 6/2004 |
| WO | WO 2007 070359 A2 | 6/2007 |
| WO | WO 2007 103905 A2 | 9/2007 |
| WO | WO 2007 150011 A2 | 12/2007 |
| WO | WO 2009 117269 A1 | 9/2009 |
| WO | WO 2010093727 A1 | 8/2010 |

OTHER PUBLICATIONS

International Search Report for Corresponding International Application PCT/US2011/047626 Mailed on Sep. 28, 2011 3 Pgs.
International Search Report for Corresponding International Application PCT/US2010/023794 Mailed on May 7, 2010, 3 Pgs.
Abbott et al., "Stromal Cell-Derived Factor-1[Alpha] Plays a Critical Role in Stem Cell Recruitment to the Heart After Myocardial Infarction But Is Not Sufficient to Induce Homing in the Absence of Injury" Circulation, 2004 vol. 110(21), pp. 3300-3305.
Al-Sheikh et al., "Disturbance in the HIF-1 Alpha Pathway Associated With Erythrocytosis: Further Evidences Brought by Frameshift and Nonsense Mutations in the Prolyl Hydroxylase Domain Protein 2 (PHD2) Gene" Blood Cells Mol Dis., 2008 vol. 40, pp. 160-165.
Aragones et al., "Deficiency or Inhibition of Oxygen Sensor PHD1 Induces Hypdxia Tolerance by Reprogramming Basal Metabolism" Nature Genetics 2008, vol. 40(2), pp. 170-180.
Arcasoy, "The Non-Haematopoietic Biological Effects of Erythropoietin", British Journal of Haematology, 2008 vol. 141 (1), pp. 14-31.
Armellini et al. "The Effects of High Altitude Trekking on Body Composition and Resting Metabolic Rate", Hormone & Metabolic Research, 1997 vol. 29(9), pp. 458-461.
Bagshawe et al. "Antibody-Directed Enzyme Prodrug Therapy: A Review" Drug Dev Res, 1995, vol. 34, pp. 220-230.

(Continued)

*Primary Examiner* — Jeffrey H Murray
*Assistant Examiner* — Oluwafemi Masha

(57) ABSTRACT

Aminoquinazolinyl compounds of formula (I) are described, which are useful as prolyl hydroxylase inhibitors. Such compounds may be used in pharmaceutical compositions and methods for the treatment of disease states, disorders, and conditions mediated by prolyl hydroxylase activity. Thus, the compounds may be administered to treat, e.g., anemia, vascular disorders, metabolic disorders, and wound healing.

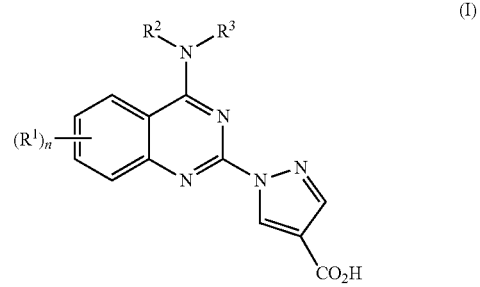

22 Claims, No Drawings

(56) References Cited

OTHER PUBLICATIONS

Berge, et al., "Pharmaceutical Salts", J Pharm Sci., 1977 vol. 66, pp. 1-19.
Bernaudin et al., "Normobaric Hypoxia Induces Tolerance to Focal Permanent Cerebral Ischemia in Association With an Increased Expression of Hypoxia-Inducible Factor-1 and Its Target Genes, Erythropoietin and VEGF, In the Adult Mouse Brain" J Cereb Blood Flow Metab., 2002 vol. 22(4), pp. 393-403.
Bernhardt et al., "Organ Protection by Hypoxia and Hypoxia-Inducible Factors" Methods Enzymol., 2007 vol. 435, pp. 221-245.
Berra et al., "HIF Prolyl-Hydroxylase 2 Is the Key Oxygen Sensor Setting Low Steady-State Levels of HIF-1Alpha in Normoxia", EMBO (European Molecular Biology Organization) Journal, 2003 vol. 22(16), pp. 4082-4090.
Bertolini et al. "A New Rational Hypothesis for the Pharmacophore of the Active Metabolite of Leflunomide, A Potent Immunosuppressive Drug" J. Med. Chem., 1997, vol. 40, pp. 2011-2016.
Bodor et al.,"Novel Approaches to the Design of Safer Drugs: Soft Drugs and Site-Specific Chemical Delivery Systems" Adv Drug Res. 1984, vol. 13 pp. 255-329.
Braliou et al., "2-Oxoglutarate-Dependent Oxygenases Control Hepcidin Gene Expression ", Journal of Hepatology, 2008 vol. 48 (5) pp. 801-810.
Breen, "VEGF in Biological Control" J Cell Biochem., 2007 vol. 102(6), pp. 1358-1367.
Notari R.E. "Pharmacokinetic Aspects of Prodrug Design and Evaluation" Chapter 3 pp. 135-156 Design of Prodrugs Ed. H. Bundgaard Elsevier Press 1985.
Cai et al., "Complete Loss of Ischaemic Preconditioning-Induced Cardioprotection in Mice With Partial Deficiency of HIF-1 Alpha " Cardiovasc Res., 2008 vol. 77(3), pp. 463-470.
Carmeliet,"Manipulating Angiogenesis in Medicine " J Intern Med., 2004 vol. 255(5), pp. 538-561.
Carrière et al. "Mitochondrial Reactive Oxygen Species Control the Transcription Factor Chop-10/GADD153 and Adipocyte Differentiation: A Mechanism for Hypdxia-Dependent Effect" J Biol Chem., 2004 vol. 279(39), pp. 40462-40469.
Chang et al "Age Decreases Endothelial Progenitor Cell Recruitment Through Decreases in Hypdxia-Inducible Factor 1A Stabilization During Ischemia" Circulation 2007 vol. 116 pp. 2818-2829.
Ceradini et al., "Homing to Hypoxia: HIF-1 As a Mediator of Progenitor Cell Recruitment to Injured Tissue" Trends Cardiovasc Med., 2005 vol. 15(2), pp. 57-63.
Ceradini et al., "Progenitor Cell Trafficking Is Regulated by Hypoxic Gradients Through HIF-1 Induction of SDF-1", Nat Med., 2004 vol. 10(8), pp. 858-864.
Chin et al. "Hypoxia-Inducible Factor 1Alpha Stabilization by Carbon Monoxide Results in Cytoprotective Preconditioning", Proc Natl Acad Sci. U.S.A., 2007 vol. 104(12), pp. 5109-5114.
Darling et al., "'Postconditioning' The Human Heart: Multiple Balloon Inflations During Primary Angioplasty May Confer Cardioprotection." Basic Res Cardiol., 2007, vol. 102(3), pp. 274-278.
Das et al., "Molecular Mechanism of Preconditioning", IUBMB Life, 2008,vol. 60(4), pp. 199-203.
Ebert et al. "Hypoxia and Mitochondrial Inhibitors Regulate Expression of Glucose Transporter-1 Via Distinct CIS-Acting Sequences", J Biol Chem., 1995 vol. 270(49), pp. 29083-29089.
Elson et al., "Induction of Hypervascularity Without Leakage or Inflammation in Transgenic Mice Overexpressing Hypoxia-Inducible Factor-1Alpha", Genes Dev., 2001 vol. 15(19), pp. 2520-2532.
Epstein et al., "C. Elegans EGL-9 and Mammalian Homologs Define a Family of Dioxygenases That Regulate HIF by Prolyl Hydroxylation", Cell, 2001 vol. 107(1), pp. 43-54.
Feldser et al., "Reciprocal Positive Regulation of Hypoxia-Inducible Factor 1Alpha and Insulin-Like Growth Factor 2", Cancer Res. 1999 vol. 59 (16), pp. 3915-3918.
Firth et al. "Oxygen-Regulated Control Elements in the Phosphoglycerate Kinase 1 and Lactate Dehydrogenase A Genes: Similarities With the Erythropoietin 3' Enhancer", Proc Natl Acad Sci. USA, 1994 vol. 91(14), pp. 6496-6500.
Fleisher et al. "Improved Oral Delivery: Solubility Limitations Overcome by the Use of Prodrugs" Advanced Drug Delivery Review, 1996, vol. 19, pp. 115-130.
Floyd et al., "Effects of Prolyl Hydroxylase Inhibitors on Adipogenesis and Hypoxia Inducible Factor 1 Alpha Levels Under Normoxic Conditions", J Cell Biochem., 2007 vol. 101(6), pp. 1545-1557.
Fukuda et al., "HIF-1 Regulates Cytochrome Oxidase Subunits to Optimize Efficiency of Respiration in Hypoxic Cells", Cell, 2007 vol. 129(1), pp. 111-122.
Grosfeld et al. "Hypoxia-Inducible Factor 1 Transactivates the Human Leptin Gene Promoter", J Biol Chem., 2002 vol. 277(45), pp. 42953-42957.
Gustafsson et al., "Exercise-Induced Angiogenesis-Related Growth and Transcription Factors in Skeletal Muscle, and Their Modification in Muscle Pathology." Frontiers in Bioscience, 2001, vol. 6, pp. 75-89.
Hu et al., "Transplantation of Hyodxia-Preconditioned Mesenchymal Stem Cells Improves Infarcted Heart Function Via Enhanced Survival of Implanted Cells and Angiogenesis", Journal of Thoracic & Cardiovascular Surgery, 2008 vol. 135(4), pp. 799-808.
Ivan et al. "Biochemical Purification and Pharmacological Inhibition of a Mammalian Prolyl Hydroxylase Acting on Hypoxia-Inducible Factor" Proc Natl Acad Sci. USA, 2002, vol. 99(21), pp. 13459-13464.
Ivan et al., "HIF[Alpha] Targeted for VHL-Mediated Destruction by Proline Hydroxylation: Implications for O2 Sensing", Science, 2001 vol. 292(5516), pp. 464-468.
Jaakkola et al., "Targeting of HIF-[Alpha] to the Von Hippel-Lindau Ubiquitylation Compex by O2-Regulated Prolyl Hydroxylation" Science, 2001, vol. 292(5516), pp. 468-472.
Kaelin, "Proline Hydroxylation and Gene Expression " Annu Rev Biochem., 2005, vol. 74, pp. 115-128.
Ke et al., "Hypdxia-Inducible Factor-1 (HIF-1)", Mol Pharmacol. 2006, vol. 70(5), pp. 1469-1480.
Kelly et al., "Cell Type-Specific Regulation of Angiogenic Growth Factor Gene Expression and Induction of Angiogenesis in Nonischemic Tissue by a Constitutively Active Form of Hypoxia-Inducible Factor 1", Circ Res., 2003 vol. 93(11), pp. 1074-1081.
Kim et al., "HIF-1-Mediated Expression of Pyruvate Dehydrogenase Kinase: A Metabolic Switch Required for Cellular Adaptation to Hypoxia, Cell Metab" 2006 vol. 3(3), pp. 177-185.
Kojima I et al.,"Protective Role of Hypdxia-Inducible Factor-2 Alpha Against Ischemic Damage and Oxidative Stress in the Kidney " J Am Soc Nephrol., 2007, vol. 18 (4), pp. 1218-1226.
Lee et al. "Hypoxia Inducible Factor-1 Mediates Transcriptional Activation of the Heme Oxygenase-1 Gene in Response to Hypoxia", J Biol Chem., 1997, vol. 272(9), pp. 5375-5381.
Lin et al. "Differentiation Arrest by Hypoxia", J Biol Chem., 2006, vol. 281(31), pp. 30678-30683.
Liu et al., "Hypdxia Regulates Vascular Endothelial Growth Factor Gene Expression in Endothelial Cells: Identification of a 5 Prime Enhancer", Circ Res., 1995, vol. 77(3), pp. 638-643.
Lok et al. "Identification of a Hypoxia Response Element in the Transferrin Receptor Gene", J Biol Chem., 1999, vol. 274(34), pp. 24147-24152.
Luttun et al., "Placental Growth Factor (PlGF) and Its Receptor FLT-1 (VEGFR-1): Novel Therapeutic Targets for Angiogenic Disorders" Series Information: Annals of the New York Academy of Sciences, 2002, vol. 979, pp. 80-93.
Mace et al., "Sustained Expression of HIF-1 Alpha in the Diabetic Environment Promotes Angiogenesis and Cutaneous Wound Repair ", Wound Repair Regen., 2007, vol. 15(5), pp. 636-645.
Mallick et al., "Ischemia-Reperfusion Injury of the Intestine and Protective Strategies Against Injury", Digestive Diseases & Sciences, 2004, vol. 49(9), pp. 1359-1377.
Metzen E. et al., "Intracellular Localisation of Human HIF-1Alpha Hydroxylases: Implications for Oxygen Sensing" J Cell Sci., 2003,vol. 116, pp. 1319-1326.

(56) References Cited

OTHER PUBLICATIONS

Mukhopadhyay et al. "Role of Hypoxia-Inducible Factor-1 in Transcriptional Activation of Ceruloplasmin by Iron Deficiency", J Biol Chem., 2000, vol. 275(28), pp. 21048-21054.
Murry et al. "Preconditioning With Ischemia: A Delay of Lethal Cell Injury in Ischemic Myocardium", Circulation, 1986 vol. 74(5), pp. 1124-1136.
Nagai et al "Becaplermin: Recombinant Platelet Derived Growth Factor, A New Treatment for Healing Diabetic Foot Ulcers" Exp Opin Biol Ther 2002 vol. 2(2) pp. 211-218.
Natarajan et al., "Hypdxia Inducible Factor-1 Upregulates Adiponectin in Diabetic Mouse Hearts and Attenuates Post-Ischemic Injury" 2008, J Cardiovasc Pharmacol., vol. 51(2), pp. 178-187.
Natarajan et al., "Hypoxia Inducible Factor-1 Activation by Prolyl 4-Hydroxylase-2 Gene Silencing Attenuates Myocardial Ischemia Reperfusion Injury", Circulation Res.,2006, vol. 98(1), pp. 133-140.
Pajusola et al., "Stabilized HIF-1Alpha Is Superior to VEGF for Angiogenesis in Skeletal Muscle Via Adeno-Associated Virus Gene Transfer" FASEB Journal, 2005, vol. 19(10), pp. 1365-1367.
Papandreou et al., "HIF-1 Mediates Adaptation to Hypoxia by Actively Downregulating Mitochondrial Oxygen Consumption" Cell Metab., 2006, vol. 3(3), pp. 187-197.
Pasupathy et al., "Ischaemic Preconditioning Protects Against Ischaemia/Reperfusion Injury: Emerging Concepts" European Journal of Vascular and Endovascular Surgery, 2005, vol. 29, pp. 106-115.
Paulekuhn, et al., "Trends in Active Pharmaceutical Ingredient Salt Selection Based on Analysis of the Organce Book Database", J. Med. Chem., 2007, vol. 50 pp. 6665-6672.
Percy et al. "A Family With Erythrocytosis Establishes a Role for Prolyl Hydroxylase Domain Protein 2 in Oxygen Homeostasis" PNAS, 2006, vol. 103(3), pp. 654-659.
Peyssonnaux et al., "Critical Role of Hif-1 Alpha in Keratinocyte Defense Against Bacterial Infection" J Invest Dermatol., 2008 vol. 128(8), pp. 1964-1968.
Peyssonnaux et al., "HIF-1 Alpha Expression Regulates the Bactericidal Capacity of Phagocytes" J Invest Dermatol, 2005, vol. 115(7), pp. 1806-1815.
Peyssonnaux et al., "Regulation of Iron Homeostasis by the Hypoxia-Inducible Transcription Factors (HIFS)." J Clin Invest., 2007, vol. 117(7), pp. 1926-1932.
Robinson et al., "Mucosal Protection by Hypdxia-Inducible Factor Prolyl Hydroxylase Inhibition" Gastroenterology, 2008, vol. 134(1), pp. 145-155.
Rolfs et al. "Oxygen-Regulated Transferrin Expression Is Mediated by Hypoxia-Inducible Factor-1" J Biol Chem., 1997, vol. 272(32), pp. 20055-20062.
Scheuermann et al., "Hypdxia-Inducible Factors PER/ARNT/SIM Domains: Structure and Function" Methods Enzymol., 2007, vol. 435, pp. 3-24.
Schmid et al., "HIF-1 and P53: Communication of Transcription Factors Undr Hypoxia" Journal of Cellular & Molecular Medicine, 2004, vol. 8(4), pp. 423-431.
Schultz et al., "Hypoxia and Hypoxia-Inducible Factor-1 Alpha Promote Growth Factor-Induced Proliferation of Human Vascular Smooth Muscle Cells" Am J Physiol Heart Circ Physiol., 2006, 290(6), pp. H2528-H2534.
Semenza et al. "A Nuclear Factor Induced by Hypoxia Via De Novo Protein Synthesis Binds to the Human Erythropoietin Gene Enhancer at a Site Required for Transcriptional Activation", , Mol Cell Biol., 1992, vol. 12(12), pp. 5447-5454.
Semenza et al., "Vasculogenesis, Angiogenesis, and Arteriogenesis: Mechanisms of Blood Vessel Formation and Remodeling", J Cell Biochem.,2007 vol. 102(4), pp. 840-847.
Semenza, "Hypoxia-Inducible Factor 1: Oxygen Homeostasis and Disease Pathophysiology" Trends in Molecular Medicine, 2001, vol. 7(8), pp. 345-350.
Semenza, "Oxygen-Dependent Regulation of Mitochondrial Respiration by Hypoxia-Inducible Factor 1", Biochem J., 2007 vol. 405 (1), pp. 1-9.
Semenza, "Regulation of Tissue Perfusion in Mammals by Hypoxia-Inducible Factor 1." Exp Physiol., 2007, vol. 92(6), pp. 988-991.
Semenza, "Hypoxia-Inducible Factor 1 (HIF-1) Pathway" Science's STKE (Signal Transduction Knowledge Environment) 2007, vol. 407(CM8), pp. 1-3.
Shan et al. "Prodrug Strategies Based on Intramolecular Cyclization Reaction", Journal of Pharmaceutical Sicences 1997, vol. 86(7), pp. 765-767.
Shaw, "Glucose Metabolism and Cancer" Curr Opin Cell Biol., 2006, vol. 18(6), pp. 598-608.
Siddiq et al. "Hypoxia-Inducible Factor Prolyl 4-Hydroxylase Inhibition: A Target for Neuroprotection in the Central Nervous System", J Biol Chem., 2005, vol. 280(50), pp. 41732-41743.
Simon et al., "The Role of Oxygen Availability in Embryonic Development and Stem Cell Function" Nature Reviews Molecular Cell Biology, 2008, vol. 9(4), pp. 285-296.
Steed, "Clinical Evaluation of Recombinant Human Platelet-Derived Growth Factor for the Treatment of Lower Extemity Ulcers" Plast Reconstr Surg., 2006 vol. 117(7 Suppl), pp. 143S-149S.
Tacchini et al. "Transferrin Receptor Induction by Hypoxia. HIF-1-Mediated Transcriptional Activation and Cell-Specific Post-Transcriptional Regulation", J Biol Chem., 1999, vol. 274(34), pp. 24142-24146.
Thurston et al., "Angiopoietin-1 Protects the Adult Vasculature Against Plasma Leakage" Nature Medicine, 2000, vol. 6(4), pp. 460-463.
Thurston et al., "Leakage-Resistant Blood Vessels in Mice Transgenically Overexpressing Angiopoietin-1", Science,1999, vol. 286, pp. 2511-2514.
Vincent et al., "Angiogenesis Is Induced in a Rabbit Model of Hindlimb Ischemia by Naked DNA Encoding an HIF-1[Alpha]/VP16 Hybrid Transcription Factor", Circulation, 2000, vol. 102 (18), pp. 2255-2261.
Wang et al. "Characterization of Hypoxia-Inducible Factor 1 and Regulation of DNA Binding Activity by Hypoxia" J Biol Chem., 1993, vol. 268(29), pp. 21513-21518.
Wang et al. "General Involvement of Hypoxia-Inducible Factor 1 in Transcriptional Response to Hypoxia " Proceedings of the National Academy of Sciences of the United States of America, 1993, vol. 90, pp. 4304-4308.
Wang et al. "Purification and Characterization of Hypoxia-Inducible Factor 1", J Biol Chem.,1995, vol. 270(3), pp. 1230-1237.
Warshakoon et al., "A Novel Series of Imidazol[1,2-A]Pyridine Derivatives As HIF-1A Prolyl Hydroxylase Inhibitors" Bioorg Med Chem Lett., 2006, vol. 16(21) pp. 5598-5601.
Warshakoon et al., "Design and Synthesis of Substituted Pyridine Derivatives As HIF-1A Prolyl Hydroxylase Inhibitors", Bioorg Med Chem Lett., 2006, vol. 16(21) pp. 5616-5620.
Wang et al "The Hypoxia Inducible Factor a Pathway Couples Angiogenesis to Osteogenesis During Skeletal Development" Clin Invest 2007 vol. 17(6) pp. 1616-1626.
Warshakoon et al., "Design and Synthesis of a Series of Novel Pyrazolopyridines as HIF 1-A Prolyl Hydroxylase Inhibitors" Bioorg Med Chem Lett., 2006, vol. 16(21) pp. 5687-5690.
Yun et al., "Inhibition of PPAR Gamma 2 Gene Expression by the HIF-1-regulated Gene DEC1/STRA13: A Mechanism for Regulation of Adipogenesis by Hypoxia." Develomental Cell, 2002, vol. 2, pp. 331-341.
Zhang H et al. "Mitochondrial Autophagy Is an HIF-1-Dependent Adaptive Metabolic Response to Hypoxia" J Biol Chem. 2008, vol. 283 pp. 10892-10903.
Bundgaard H. "Design and Application of Prodrugs" Chapter 5 pp. 113-191 A Textbook of Drug Desing and Development 1991 Krogsgaard-Larsen et Eds Hardwood Academic Publishers.
Pfander et al "HIF-1A Controls Extracellular Matrix Synthesis by Epiphyseal Chondrocytes" J Cell Sci 2003 116(9) pp. 1819-1826.
Hirota et al "Targeting Hypdxia-Inducible Factor-1 (HIF-1) Signaling in Therapeutics: Implications for the Treatment of Inflammatory Bowel Disease" Recent Patents on Inflammation and Allergy Drug Discovery 2009 vol. 3 pp. 1-16.

(56) References Cited

OTHER PUBLICATIONS

Bowker Michael J. "A Procedure for Salt Selection and Optimization" Chapter 7 pp. 161-189 Handbook of Pharmaceutical Salts, Properties, Selection and Use Stahl and Wermuth Eds 2002 Wiley-VCH and VHCA Zurich.

Zeghida et al "Concise Synthesis of 2-Amino-4(3H)-Quinazolinones From Simple (Hetero)Aromatic Amines" Journal of Organic Chemistry 2008 vol. 73(6) pp. 2473-2475.

Shyu et al "Intramyocardial Injection of Naked DNA Encoding HIF-1A/VP16 Hybrid to Enhance Angiogenesis in an Acute Myocardial Infarction Model in the Rat" Cardiovasc Res 2002 vol. 54 pp. 576-583.

Yoshida et al "Hypoxia Inducible Factor 1-A Regulates of Platelet Derived Growth Factor-B in Human Glioblastoma Cells" J of Neuro-Oncology 2006 vol. 76 pp. 13-21.

Robinson et al " Discovery of the Hemifumarate and ($\alpha$-$_L$-Alanyloxy)Methyl Ether as Prodrugs of an Antirheumatic Oxindole: Prodrugs for the Enolic OH Group" J Med Chem 1996 vol. 39(1) pp. 10-18.

Feng et al "Discovery of Alogliptin: A Potent, Selective, Bioavailable, and Efficacious Inhibitor of Dipeptidyl Peptidase IV" Journal of Medicinal Chemistry 2007 vol. 50 pp. 2297-2300.

Zhichkin et al "The Use of Formamidine Protection for the Derivatization of Aminobenzoic Acids" J Org Chem 2008 vol. 73 pp. 8954-5959.

Goto et al "The Process Development of a Novel Aldose Reductase Inhibiot, FK366, Part 1. Improvement of Discovery Process and New Syntheses of 1-Substituted Quinazolinediones" Organic Process Research and Development 2003 vol. 7 pp. 700-706.

Zinkernagel et al "Pharmacologic Augmentation of Hypoxia-Inducible Factor 1-A With Mimosine Boosts the Bacterial Capacity of Phagocytes" The Journal of Infectious Diseases 2008 vol. 197 pp. 214-217.

Ram et al "Synthesis and Antihyperglycemic Activity of Suitably Functionalized 3H-Quinazolin-4-Ones" Bioorganic & Medicinal Chemistry 2003 vol. 11 pp. 2439-2444.

Smith et al "Infection With a Helminth Parasite Prevents Experimental Colitis Via a Macrophage-Mediated Mechanism" J Immunol 2007 vol. 178 pp. 4557-4566.

4-AMINOQUINAZOLIN-2-YL-1-PYRRAZOLE-4-CARBOXYLIC ACID COMPOUNDS AS PROLYL HYDROXYLASE INHIBITORS

CROSS-REFERENCE TO RELATED APPLICATIONS

This application is a national phase of International Application No. PCT/US2011/047626 filed Aug. 12, 2011, and claims benefit of priority of U.S. Provisional Application No. 61/373,664 filed on Aug. 13, 2010.

FIELD OF THE INVENTION

The present invention relates to certain aminoquinazolinyl compounds, pharmaceutical compositions containing them, and methods of using them for the treatment of disease states, disorders, and conditions mediated by prolyl hydroxylase activity.

BACKGROUND OF THE INVENTION

Cells respond to hypoxia by activating the transcription of genes involved in cell survival, oxygen delivery and utilization, angiogenesis, cellular metabolism, regulation of blood pressure, hematopoiesis, and tissue preservation. Hypoxia-inducible factors (HIFs) are key transcriptional regulators of these genes (Semenza et al., 1992, *Mol Cell Biol.*, 12(12): 5447-54; Wang et al., 1993, *J Biol Chem.*, 268(29):21513-18; Wang et al., 1993, *Proc Natl Acad. Sci.*, 90:4304-08; Wang et al., 1995, *J Biol Chem.*, 270(3):1230-37). Three forms of HIF-α have been described: HIF-1α, HIF-2α and HIF-3α (Scheuermann et al., 2007, *Methods Enzymol.*, 435:3-24). Pairing of a HIFα sub-unit with HIF-1β forms a functional heterodimeric protein that subsequently recruits other transcriptional factors such as p300 and CBP (Semenza, 2001, *Trends Mol Med.*, 7(8):345-50).

A family of highly conserved oxygen, iron, and 2-oxoglutarate-dependent prolyl hydroxylase (PHD) enzymes mediate the cells response to hypoxia via post-translational modification of HIF (Ivan et al., 2001, *Science*, 292:464-68; Jaakkola et al., 2001, *Science*, 292:468-72). Under normoxic conditions, PHD catalyzes the hydroxylation of two conserved proline residues within HIF. Von Hippel Lindau (VHL) protein binds selectively to hydroxylated HIF. The binding of VHL renders HIF a target for polyubiquitination by the E3 ubiquitin ligase complex and its subsequent degradation by the 26S proteasome (Ke et al., 2006, *Mol Pharmacol.* 70(5):1469-80; Semenza, *Sci STKE.*, 2007, 407(cm8):1-3). As the affinity of PHD for oxygen is within the physiological range of oxygen and oxygen is a necessary co-factor for the reaction, PHD is inactivated when oxygen tension is reduced. In this way, HIF is rapidly degraded under normoxic conditions but accumulates in cells under hypoxic conditions or when PHD is inhibited.

Four isotypes of PHD have been described: PHD1, PHD2, PHD3, and PHD4 (Epstein et al., 2001, *Cell*, 107:43-54; Kaelin, 2005, *Annu Rev Biochem.*, 74:115-28; Schmid et al., 2004, *J Cell Mol Med.*, 8:423-31). The different isotypes are ubiquitously expressed but are differentially regulated and have distinct physiological roles in the cellular response to hypoxia. There is evidence that the various isotypes have different selectivity for the three different HIFα sub-types (Epstein et al., supra). In terms of cellular localization, PHD1 is primarily nuclear, PHD2 is primarily cytoplasmic, and PHD3 appears to be both cytoplasmic and nuclear (Metzen E, et al. 2003, *J Cell Sci.*, 116(7):1319-26). PHD2 appears to be the predominant HIFα prolyl hydroxylase under normoxic conditions (Ivan et al., 2002. *Proc Natl Acad. Sci. USA*, 99(21):13459-64; Berra et al., 2003, *EMBO J.*, 22:4082-90). The three isotypes have a high degree of amino-acid homology and the active site of the enzyme is highly conserved.

The HIF target gene products are involved in a number of physiological and pathophysiological processes including but not limited to: erythropoiesis, angiogenesis, regulation of energy metabolism, vasomotor function, and cell apoptosis/proliferation. The first gene described as a HIF target was that encoding erythropoietin (EPO) (Wang et al., 1993, supra). It was recognized that a reduction in the oxygen carrying capacity of the blood is sensed in the kidney and that the kidney and liver respond by releasing more EPO, the hormone that stimulates red blood cell proliferation and maturation. EPO has a number of other important effects on non-hematopoietic cell types and has emerged as a key tissue-protective cytokine (Arcasoy, 2008, *Br J Haematol.*, 141:14-31). Thus EPO is now implicated in wound healing and angiogenesis as well as the response of tissues to ischemic insult. Most of the enzymes involved in anaerobic glycolysis are encoded by HIF target genes and as a result glycolysis is increased in hypoxic tissues (Shaw, 2006, *Curr Opin Cell Biol.*, 18(6): 598-608). The known HIF target gene products in this pathway include but are not limited to: glucose transporters such as GLUT-1 (Ebert et al., 1995, *J Biol Chem.*, 270(49):29083-89), enzymes involved in the breakdown of glucose to pyruvate such as hexokinase and phosphoglycerate kinase 1 (Firth et al., 1994, *Proc Natl Acad Sci. USA*, 91:6496-6500) as well as lactate dehydrogenase (Firth et al., supra). HIF target gene products are also involved in the regulation of cellular metabolism. For example, pyruvate dehydrogenase kinase-1 is a target HIF gene product and regulates the entry of pyruvate into the Kreb's cycle by reducing the activity of pyruvate dehydrogenase by phosphorylation (Kim et al., 2006, *Cell Metab.*, 3:177-85; Papandreou et al., 2006, *Cell Metab.*, 3:187-197). HIF target gene products are also involved in angiogenesis. For example, vascular endothelial growth factor (VEGF) (Liu et al., 1995, *Circ Res.*, 77(3):638-43) is a known regulator of angiogenesis and vasculogenesis. HIF target gene products also function in the regulation of vascular tone and include heme oxygenase-1 (Lee et al., 1997, *J Biol Chem.*, 272(9):5375-81). A number of HIF regulated gene products such as platelet-derived growth factor (PDGF) (Yoshida et al., 2006, *J Neurooncol.*, 76(1):13-21), vascular endothelial growth factor (Breen, 2007, *J Cell Biochem.*, 102(6):1358-67) and EPO (Arcasoy, supra) also function in the coordinated response to wound healing.

Targeted disruption of the prolyl hydroxylase (PHD) enzyme activity by small molecules has potential utility in the treatment of disorders of oxygen sensing and distribution. Examples include but are not limited to: anemia; sickle cell anemia; peripheral vascular disease; coronary artery disease; heart failure; protection of tissue from ischemia in conditions such as myocardial ischemia, myocardial infarction and stroke; preservation of organs for transplant; treatment of tissue ischemia by regulating and/or restoring blood flow, oxygen delivery and/or energy utilization; acceleration of wound healing particularly in diabetic and aged patients; treatment of burns; treatment of infection; bone healing, and bone growth. In addition, targeted disruption of PHD is expected to have utility in treating metabolic disorders such as diabetes, obesity, ulcerative colitis, inflammatory bowel disease and related disorders such as Crohn's disease. (*Recent Patents on Inflammation & Allergy Drug Discovery*, 2009, 3, 1-16).

HIF has been shown to be the primary transcriptional factor that leads to increased erythropoietin production under conditions of hypoxia (Wang et al., 1993, supra). While treatment with recombinant human erythropoietin has been demonstrated to be an effective method of treating anemia, small molecule mediated PHD inhibition can be expected to offer advantages over treatment with erythropoietin. Specifically, the function of other HIF gene products are necessary for hematopoesis and regulation of these factors increases the efficiency of hematopoesis. Examples of HIF target gene products that are critical for hematopoesis include: transferrin (Rolfs et al., 1997, *J Biol Chem.*, 272(32):20055-62), transferrin receptor (Lok et al., 1999, *J Biol Chem.*, 274(34): 24147-52; Tacchini et al., 1999, *J Biol Chem.*, 274(34):24142-46) and ceruloplasmin (Mukhopadhyay et al., 2000, *J Biol Chem.*, 275(28):21048-54). Hepcidin expression is also suppressed by HIF (Peyssonnaux et al., 2007, *J Clin Invest.*, 117(7):1926-32) and small molecule inhibitors of PHD have been shown to reduce hepcidin production (Braliou et al., 2008, *J Hepatol.*, 48:801-10). Hepcidin is a negative regulator of the availability of the iron that is necessary for hematopoesis, so a reduction in hepcidin production is expected to be beneficial to the treatment of anemia. PHD inhibition may also be useful when used in conjunction with other treatments for anemia including iron supplementation and/or exogenous erythropoietin. Studies of mutations in the PHD2 gene occurring naturally in the human population provide further evidence for the use of PHD inhibitors to treat anemia. Two recent reports have shown that patients with dysfunctional mutations in the PHD2 gene display increased erythrocytosis and elevated blood hemoglobin (Percy et al., 2007, *PNAS*, 103(3):654-59; Al-Sheikh et al., 2008, *Blood Cells Mol Dis.*, 40:160-65). In addition, a small molecule PHD inhibitor has been evaluated in healthy volunteers and patients with chronic kidney disease (U.S. pat. appl. US2006/0276477, Dec. 7, 2006). Plasma erythropoietin was increased in a dose-dependent fashion and blood hemoglobin concentrations were increased in the chronic kidney disease patients.

Metabolic adaptation and preservation of tissues are jeopardized by ischemia. PHD inhibitors increase the expression of genes that lead to changes in metabolism that are beneficial under ischemic conditions (Semenza, 2007, *Biochem J.*, 405:1-9). Many of the genes encoding enzymes involved in anaerobic glycolysis are regulated by HIF and glycolysis is increased by inhibiting PHD (Shaw, supra). Known HIF target genes in this pathway include but are not limited to: GLUT-1 (Ebert et al., supra), hexokinase, phosphoglycerate kinase 1, lactate dehydrogenase (Firth et al., supra), pyruvate dehydrogenase kinase-1 (Kim et al., supra; Papandreou et al., supra). Pyruvate dehydrogenase kinase-1 suppresses the entry of pyruvate into the Kreb's cycle. HIF mediates a switch in the expression of the cytochromes involved in electron transport in the mitochondria (Fukuda et al., 2007, *Cell*, 129(1):111-22). This change in the cytochrome composition optimizes the efficiency in ATP production under hypoxic conditions and reduces the production of injurious oxidative phosphorylation by-products such as hydrogen peroxide and superoxide. With prolonged exposure to hypoxia, HIF drives autophagy of the mitochondria resulting in a reduction in their number (Zhang H et al., 2008, *J Biol Chem.* 283: 10892-10903). This adaptation to chronic hypoxia reduces the production of hydrogen peroxide and superoxide while the cell relies on glycolysis to produce energy. A further adaptive response produced by HIF elevation is up-regulation of cell survival factors. These factors include: Insulin-like growth factor (IGF) 2, IGF-binding protein 2 and 3 (Feldser et al., 1999, *Cancer Res.* 59:3915-18). Overall accumulation of HIF under hypoxic conditions governs an adaptive up-regulation of glycolysis, a reduction in oxidative phosphorylation resulting in a reduction in the production of hydrogen peroxide and superoxide, optimization of oxidative phosphorylation protecting cells against ischemic damage. Thus, PHD inhibitors are expected to be useful in organ and tissue transplant preservation (Bernhardt et al., 2007, *Methods Enzymol.*, 435:221-45). While benefit may be achieved by administering PHD inhibitors before harvesting organs for transplant, administration of an inhibitor to the organ/tissue after harvest, either in storage (e.g., cardioplegia solution) or post-transplant, may also be of therapeutic benefit.

PHD inhibitors are expected to be effective in preserving tissue from regional ischemia and/or hypoxia. This includes ischemia/hypoxia associated with inter alia: angina, myocardial ischemia, stroke, ischemia of skeletal muscle. There are a number of lines of experimental evidence that support the concept that PHD inhibition and subsequent elevation of HIF as a useful method for preserving ischemic tissue. Recently, ischemic pre-conditioning has been demonstrated to be a HIF-dependent phenomenon (Cai et al., 2008, *Cardiovasc Res.*, 77(3):463-70). Ischemic pre-conditioning is a well known phenomenon whereby short periods of hypoxia and/or ischemia protect tissue from subsequent longer periods of ischemia (Murry et al., 1986, *Circulation*, 74(5):1124-36; Das et al., 2008, *IUBMB Life*, 60(4):199-203). Ischemic pre-conditioning is known to occur in humans as well as experimental animals (Darling et al., 2007, *Basic Res Cardiol.*, 102(3):274-8; Kojima I et al., 2007, *J Am Soc Nephrol.*, 18:1218-26). While the concept of pre-conditioning is best known for its protective effects in the heart, it also applies to other tissues including but not limited to: liver, skeletal muscle, liver, lung, kidney, intestine and brain (Pasupathy et al., 2005, *Eur J Vasc Endovasc Surg.*, 29:106-15; Mallick et al., 2004, *Dig Dis Sci.*, 49(9):1359-77). Experimental evidence for the tissue protective effects of PHD inhibition and elevation of HIF have been obtained in a number of animal models including: germ-line knock out of PHD1 which conferred protection of the skeletal muscle from ischemic insult (Aragonés et al., 2008, *Nat Genet.*, 40(2):170-80), silencing of PHD2 through the use of siRNA which protected the heart from ischemic insult (Natarajan et al., 2006, *Circ Res.*, 98(1):133-40), inhibition of PHD by administering carbon monoxide which protected the myocardium from ischemic injury (Chin et al., 2007, *Proc Natl Acad Sci. U.S.A.*, 104(12):5109-14), hypoxia in the brain which increased the tolerance to ischemia (Bernaudin et al., 2002, *J Cereb Blood Flow Metab.*, 22(4):393-403). In addition, small molecule inhibitors of PHD protect the brain in experimental stroke models (Siddiq et al., 2005, *J Biol Chem.*, 280(50):41732-43). Moreover, HIF up-regulation has also been shown to protect the heart of diabetic mice, where outcomes are generally worse (Natarajan et al., 2008, *J Cardiovasc Pharmacol.*, 51(2):178-187). The tissue protective effects may also be observed in Buerger's disease, Raynaud's disease, and acrocyanosis.

The reduced reliance on aerobic metabolism via the Kreb's cycle in the mitochondria and an increased reliance on anaerobic glycolysis produced by PHD inhibition may have beneficial effects in normoxic tissues. It is important to note that PHD inhibition has also been shown to elevate HIF under normoxic conditions. Thus, PHD inhibition produces a pseudohypoxia associated with the hypoxic response being initiated through HIF but with tissue oxygenation remaining normal. The alteration of metabolism produced by PHD inhibition can also be expected to provide a treatment paradigm for diabetes, obesity and related disorders, including co-morbidities.

Globally, the collection of gene expression changes produced by PHD inhibition reduce the amount of energy generated per unit of glucose and will stimulate the body to burn more fat to maintain energy balance. The mechanisms for the increase in glycolysis are discussed above. Other observations link the hypoxic response to effects that are expected to be beneficial for the treatment of diabetes and obesity. Thus, high altitude training is well known to reduce body fat (Armellini et al., 1997, *Horm Metab Res.*, 29(9):458-61). Hypoxia and hypoxia mimetics such as desferrioxamine have been shown to prevent adipocyte differentiation (Lin et al., 2006, *J Biol Chem.*, 281(41):30678-83; Carrière et al., 2004, *J Biol Chem.*, 279(39):40462-69). The effect is reversible upon returning to normoxic conditions. Inhibition of PHD activity during the initial stages of adipogenesis inhibits the formation of new adipocytes (Floyd et al., 2007, *J Cell Biochem.*, 101:1545-57). Hypoxia, cobalt chloride and desferrioxamine elevated HIF and inhibited PPAR gamma 2 nuclear hormone receptor transcription (Yun et al., 2002, *Dev Cell.*, 2:331-41). As PPAR gamma 2 is an important signal for adipocyte differentiation, PHD inhibition can be expected to inhibit adipocyte differentiation. These effects were shown to be mediated by the HIF-regulated gene DEC1/Stra13 (Yun et al., supra).

Small molecular inhibitors of PHD have been demonstrated to have beneficial effects in animal models of diabetes and obesity (Intl. Pat. Appl. Publ. WO2004/052284, Jun. 24, 2004; WO2004/052285, Jun. 24, 2004). Among the effects demonstrated for PHD inhibitors in mouse diet-induced obesity, db/db mouse and Zucker fa/fa rat models were lowering of: blood glucose concentration, fat mass in both abdominal and visceral fat pads, hemoglobin A1c, plasma triglycerides, body weight as well as changes in established disease biomarkers such as increases in the levels of adrenomedullin and leptin. Leptin is a known HIF target gene product (Grosfeld et al., 2002, *J Biol Chem.*, 277(45):42953-57). Gene products involved in the metabolism in fat cells were demonstrated to be regulated by PHD inhibition in a HIF-dependent fashion (Intl. Pat. Appl. Publ. WO2004/052285, supra). These include apolipoprotein A-IV, acyl CoA thioesterase, carnitine acetyl transferase, and insulin-like growth factor binding protein (IGFBP)-1.

PHD inhibitors are expected to be therapeutically useful as stimulants of vasculogenesis, angiogenesis, and arteriogenesis. These processes establish or restore blood flow and oxygenation to the tissues under ischemia and/or hypoxia conditions (Semenza et al., 2007, *J Cell Biochem.*, 102:840-47; Semenza, 2007, *Exp Physiol.*, 92(6):988-91). It has been shown that physical exercise increases HIF-1 and vascular endothelial growth factor in experimental animal models and in humans (Gustafsson et al. 2001, *Front Biosci.*, 6:D75-89) and consequently the number of blood vessels in skeletal muscle. VEGF is a well-known HIF target gene product that is a key driver of angiogenesis (Liu et al., supra). While administration of various forms of VEGF receptor activators are potent stimuli for angiogenesis, the blood vessel resulting from this potential form of therapy are leaky. This is considered to limit the potentially utility of VEGF for the treatment of disorders of oxygen delivery. The increased expression of a single angiogenic factor may not be sufficient for functional vascularization (Semenza, 2007, supra). PHD inhibition offers a potential advantage over other such angiogenic therapies in that it stimulates a controlled expression of multiple angiogenic growth factors in a HIF-dependent fashion including but not limited to: placental growth factor (PLGF), angiopoietin-1 (ANGPT1), angiopoietin-2 (ANGPT2), platelet-derived growth factor beta (PDGFB) (Carmeliet, 2004, *J Intern Med.*, 255:538-61; Kelly et al., 2003, *Circ Res.*, 93:1074-81) and stromal cell derived factor 1 (SDF-1) (Ceradini et al., 2004, *Nat Med.*, 10(8):858-64). Expression of angiopoietin-1 during angiogenesis produces leakage-resistant blood vessels, in contrast to the vessels produced by administration of VEGF alone (Thurston et al., 1999, *Science*, 286:2511-14; Thurston et al., 2000, *Nat Med.*, 6(4):460-3; Elson et al., 2001, *Genes Dev.*, 15(19):2520-32). Stromal cell derived factor 1 (SDF-1) has been shown to be critical to the process of recruiting endothelial progenitor cells to the sites of tissue injury. SDF-1 expression increased the adhesion, migration and homing of circulating CXCR4-positive progenitor cells to ischemic tissue. Furthermore inhibition of SDF-1 in ischemic tissue or blockade of CXCR4 on circulating cells prevents progenitor cell recruitment to sites of injury (Ceradini et al., 2004, supra; Ceradini et al., 2005, *Trends Cardiovasc Med.*, 15(2):57-63). Importantly, the recruitment of endothelial progenitor cells to sites of injury is reduced in aged mice and this is corrected by interventions that increase HIF at the wound site (Chang et al., 2007, *Circulation*, 116(24):2818-29). PHD inhibition offers the advantage not only of increasing the expression of a number of angiogenic factions but also a co-ordination in their expression throughout the angiogenesis process and recruitment of endothelial progenitor cells to ischemic tissue.

Evidence for the utility of PHD inhibitors as pro-angiogenic therapies is provided by the following observations. Adenovirus-mediated over-expression of HIF has been demonstrated to induce angiogenesis in non-ischemic tissue of an adult animal (Kelly et al., 2003, *Circ Res.*, 93(11):1074-81) providing evidence that therapies that elevate HIF, such as PHD inhibition, will induce angiogenesis. Placental growth factor (PLGF), also a HIF target gene, has been show to play a critical role in angiogenesis in ischemic tissue (Carmeliet, 2004, *J Intern Med.*, 255(5):538-61; Luttun et al., 2002, *Ann N Y Acad Sci.*, 979:80-93). The potent pro-angiogenic effects of therapies that elevate HIF have been demonstrated, via HIF over-expression, in skeletal muscle (Pajusola et al., 2005, *FASEB J.*, 19(10):1365-7; Vincent et al., 2000, *Circulation*, 102:2255-61) and in the myocardium (Shyu et al., 2002, *Cardiovasc Res.*, 54:576-83). The recruitment of endothelial progenitor cells to the ischemic myocardium by the HIF target gene SDF-1 has also been demonstrated (Abbott et al., 2004, *Circulation*, 110(21):3300-05). These findings support the general concept that PHD inhibitors will be effective in stimulating angiogenesis in the setting of tissue ischemia, particularly muscle ischemia. It is expected that therapeutic angiogenesis produced by PHD inhibitors will be useful in restoring blood flow to tissues and therefore the treatment of disease including but not restricted to angina pectoris, myocardial ischemia and infarction, peripheral ischemic disease, claudication, gastric and duodenal ulcers, ulcerative colitis, and inflammatory bowel disease.

PHD and HIF play a central role in tissue repair and regeneration including healing of wounds and ulcers. Recent studies have demonstrated that an increased expression of all three PHDs at wound sites in aged mice with a resulting reduction in HIF accumulation (Chang et al., supra). Thus, elevation of HIF in aged mice by administering desferrioxamine increased the degree of wound healing back to levels observed in young mice. Similarly, in a diabetic mouse model, HIF elevation was suppressed compared to non-diabetic litter mates (Mace et al., 2007, *Wound Repair Regen.*, 15(5):636-45). Topical administration of cobalt chloride, a hypoxia mimetic, or over-expression of a murine HIF that lacks the oxygen-dependent degradation domain and thus provides for a constitutively active form of HIF, resulted in increased HIF at the wound site, increased expression of HIF target genes such as VEGF, Nos2, and Hmox1 and accelerated wound healing. The beneficial effect of PHD inhibition is not restricted to the skin and small molecule inhibitors of PHD have recently been demonstrated to provide benefit in a mouse model of colitis (Robinson et al., 2008, *Gastroenterology*, 134(1):145-55).

PHD inhibition resulting in accumulation of HIF is expected to act by at least four mechanisms to contribute to accelerated and more complete healing of wounds: 1) protection of tissue jeopardized by hypoxia and/or ischemia, 2) stimulation of angiogenesis to establish or restore appropriate blood flow to the site, 3) recruitment of endothelial progenitor cells to wound sites, 4) stimulation of the release of growth factors that specifically stimulate healing and regeneration.

Recombinant human platelet-derived growth factor (PDGF) is marketed as becaplermin (Regranex™) and has been approved by the Food and Drug Administration of the United States of America for "Treatment of lower extremity diabetic neuropathic ulcers that extend into the subcutaneous tissue or beyond, and have adequate blood supply". Becaplermin has been shown to be effective in accelerating wound healing in diabetic patients (Steed, 2006, *Plast Reconstr Surg.*, 117(7 Suppl):143S-149S; Nagai et al., 2002, *Expert Opin Biol Ther.*, 2(2):211-8). As PDGF is a HIF gene target (Schultz et al., 2006, *Am J Physiol Heart Circ Physiol.*, 290 (6):H2528-34; Yoshida et al., 2006, *J Neurooncol.*, 76(1):13-21), PHD inhibition is expected to increase the expression of endogenous PDGF and produce a similar or more beneficial effect to those produced with becaplermin alone. Studies in animals have shown that topical application of PDGF results in increased wound DNA, protein, and hydroxyproline amounts; formation of thicker granulation and epidermal tissue; and increased cellular repopulation of wound sites. PDGF exerts a local effect on enhancing the formation of new connective tissue. The effectiveness of PHD inhibition is expected to be greater than that produced by becaplermin due to the additional tissue protective and pro-angiogenic effects mediated by HIF.

The beneficial effects of inhibition of PHD are expected to extend not only to accelerated wound healing in the skin and colon but also to the healing of other tissue damage including but not limited to gastrointestinal ulcers, skin graft replacements, burns, chronic wounds and frost bite.

Stem cells and progenitor cells are found in hypoxic niches within the body and hypoxia regulates their differentiation and cell fate (Simon et al., 2008, *Nat Rev Mol Cell Biol.*, 9:285-96). Thus PHD inhibitors may be useful to maintain stem cells and progenitor cells in a pluripotent state and to drive differentiation to desired cell types. Stem cells may be useful in culturing and expanding stem cell populations and may hold cells in a pluripotent state while hormones and other factors are administered to the cells to influence the differentiation and cell fate.

A further use of PHD inhibitors in the area of stem cell and progenitor cell therapeutics relates to the use of PHD inhibitors to condition these cells to withstand the process of implantation into the body and to generate an appropriate response to the body to make the stem cell and progenitor cell implantation viable (Hu et al., 2008, *J Thorac Cardiovasc Surg.*, 135(4):799-808). More specifically PHD inhibitors may facilitate the integration of stem cells and draw in an appropriate blood supply to sustain the stem cells once they are integrated. This blood vessel formation will also function to carry hormones and other factors released from these cells to the rest of the body.

PHD inhibitors may also be useful in the treatment of infection (Peyssonnaux et al., 2005, *J Invest Dermatol.*, 115 (7):1806-15; Peyssonnaux et al., 2008 *J Invest Dermatol.*, 2008 August; 128(8):1964-8). HIF elevation has been demonstrated to increase the innate immune response to infection in phagocytes and in keratinocytes. Phagocytes in which HIF is elevated show increased bacteriacidal activity, increased nitric oxide production and increased expressed of the antibacterial peptide cathelicidin. These effects may also be useful in treating infection from burns.

HIF has also been shown to be involved in bone growth and healing (Pfander D et al., 2003 *J Cell Sci.*, 116(Pt 9):1819-26., Wang et al., 2007 *J Clin Invest.*, 17(6):1616-26.) and may therefore be used to heal or prevent fractures. HIF stimulates of glycolysis to provide energy to allow the synthesis of extracellular matrix of the epiphyseal chondrocytes under a hypoxic environment. HIF also plays a role in driving the release of VEGF and angiogenesis in bone healing process. The growth of blood vessels into growing or healing bone can be the rate limiting step in the process.

Certain small molecules with prolyl hydroxylase inhibitory activities have been described in the literature. These include, but are not limited to, certain imidazo[1,2-a]pyridine derivatives (Warshakoon et al., 2006, *Bioorg Med Chem Lett.*, 16(21):5598-601), substituted pyridine derivatives (Warshakoon et al., 2006, *Bioorg Med Chem Lett.*, 16(21):5616-20), certain pyrazolopyridines (Warshakoon et al., 2006, *Bioorg Med Chem Lett.*, 16(21):5687-90), certain bicyclic heteroaromatic N-substituted glycine derivatives (Intl. Pat. Appl. Publ. WO2007/103905, Sep. 13, 2007), quinoline based compounds (Intl. Pat. Appl. Publ. WO2007/070359, Jun. 21, 2007), certain pyrimidinetrione N-substituted glycine derivatives (Intl. Pat. Appl. Publ. WO2007/150011, Dec. 27, 2007), substituted aryl or heteroaryl amide compounds (U.S. Pat. Appl. Publ. No.: US 2007/0299086, Dec. 27, 2007) and substituted 4-hydroxypyrimidine-5-carboxamides (Intl. Pat. Appl. Publ. WO2009/117269, Sep. 24, 2009).

However, there remains a need for potent prolyl hydroxylase modulators with desirable pharmaceutical properties. Certain aminoquinazolinyl derivatives have been found in the context of this invention to have prolyl hydroxylase modulating activity.

SUMMARY OF THE INVENTION

The present invention is directed to compounds which are useful inhibitors of PHD. The compounds of the present invention are of general Formula (I),

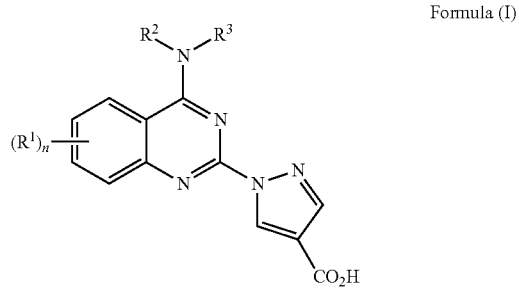

Formula (I)

wherein:
n is 0-3
$R^1$ is a member independently selected from the group consisting of halo, —O—$R^c$, —$C_{1-4}$alkyl, cyclohexyl, phenyl optionally substituted with —C$_{1-4}$alkyl, benzyl optionally substituted with —C$_{1-4}$alkyl, and —NR$^a$R$^b$;

R$^a$ is H and R$^b$ is benzyl optionally substituted with —C$_{1-4}$ alkyl, or R$^a$ and R$^b$ are taken together with the nitrogen to which they are attached to form a piperidine ring;

R$^c$ is cyclohexyl, phenyl optionally substituted with one or more R$^d$ members;

R$^d$ is a member independently selected from the group consisting of —H, halo, and —C$_{1-4}$alkyl;

R$^2$ is a member independently selected from the group consisting of —H, and —C$_{1-4}$alkyl, R$^3$ is a member independently selected from the group consisting of —H, —C$_{1-4}$alkyl optionally substituted with —OCH$_3$ or —N(C$_{1-4}$alkyl)$_2$, cyano, —SO$_2$CH$_3$, tetrahydropyran, —(CH$_2$)$_m$C$_{3-8}$cycloalkyl, —(CH$_2$)$_m$phenyl optionally substituted with one or more halo, or —C$_{1-4}$ alkyl;

m is 0-1;

R$^2$ and R$^3$ can be taken together with the nitrogen to which they are attached to form a 4 to 7 membered heterocycloalkyl ring optionally containing O, N, S optionally substituted with —OH, cyano, halo, —N—C(O)C$_{1-4}$alkyl, and —C$_{1-4}$alkyl;

and enantiomers, diastereomers, racemates, and pharmaceutically acceptable salts thereof.

Isomeric forms of the compounds of formula (I), and of their pharmaceutically acceptable salts, are encompassed within the present invention, and reference herein to one of such isomeric forms is meant to refer to at least one of such isomeric forms. One of ordinary skill in the art will recognize that compounds according to this invention may exist, for example, in a single isomeric form whereas other compounds may exist in the form of a regioisomeric mixture.

The invention also relates to pharmaceutically acceptable salts, pharmaceutically acceptable prodrugs, and pharmaceutically active metabolites of compounds of Formula (I). In certain preferred embodiments, the compound of Formula (I) is a compound selected from those species described or exemplified in the detailed description below.

In a further general aspect, the invention relates to pharmaceutical compositions each comprising: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

In another general aspect, the invention is directed to a method of treating a subject suffering from or diagnosed with a disease, disorder, or medical condition mediated by a prolyl hydroxylase enzyme activity, comprising administering to the subject in need of such treatment an effective amount of a compound of Formula (I), or a pharmaceutically acceptable salt, pharmaceutically acceptable prodrug, or pharmaceutically active metabolite thereof.

In certain preferred embodiments of the inventive method, the disease, disorder, or medical condition is selected from: anemia, vascular disorders, metabolic disorders, and wound healing.

Additional embodiments, features, and advantages of the invention will be apparent from the following detailed description and through practice of the invention.

DETAILED DESCRIPTION

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkenyl" refers to a straight- or branched-chain alkenyl group having from 2 to 12 carbon atoms in the chain. (The double bond of the alkenyl group is formed by two sp$^2$ hybridized carbon atoms.) Illustrative alkenyl groups include prop-2-enyl, but-2-enyl, but-3-enyl, 2-methylprop-2-enyl, hex-2-enyl, and the like.

The term "alkynyl" refers to a straight- or branched-chain alkynyl group having from 2 to 12 carbon atoms in the chain. (The triple bond of the alkynyl group is formed by two sp hybridized carbon atoms.) Illustrative alkynyl groups include prop-2-ynyl, but-2-ynyl, but-3-ynyl, 2-methylbut-2-ynyl, hex-2-ynyl, and the like.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

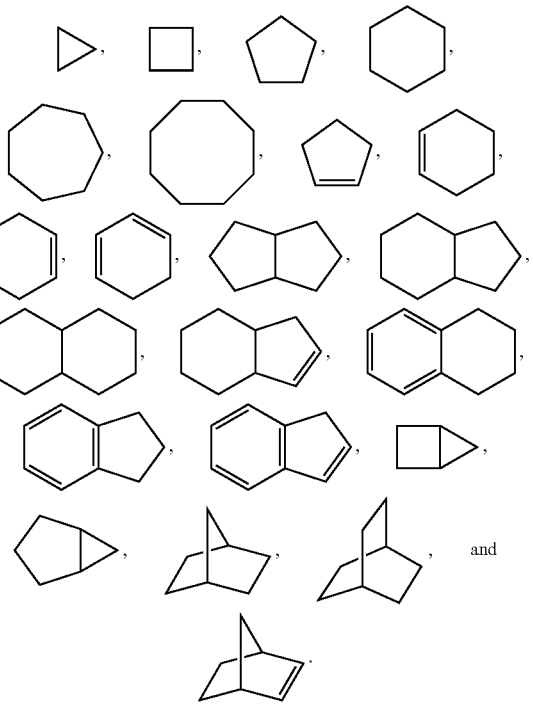

A "heterocycloalkyl" refers to a monocyclic ring structure that is saturated or partially saturated, monocyclic, fused polycyclic, and has from 3 to 8 ring atoms per ring structure selected from carbon atoms and up to two heteroatoms selected from nitrogen, oxygen, and sulfur. The ring structure may optionally contain up to two oxo groups on sulfur ring members. Illustrative entities, in the form of properly bonded moieties, include:

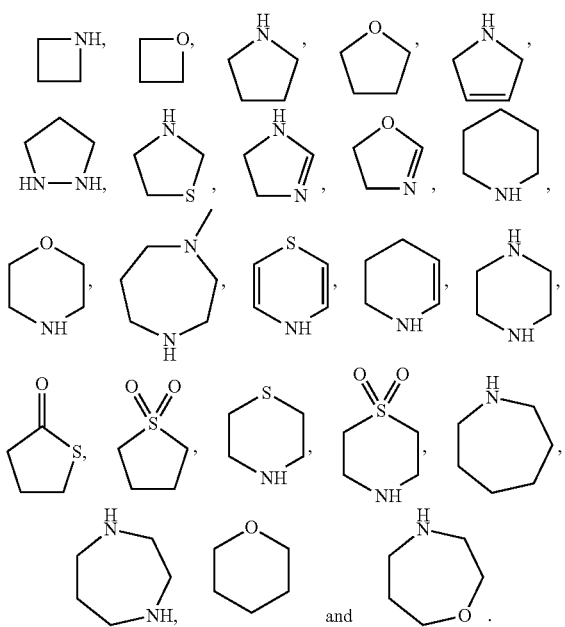

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

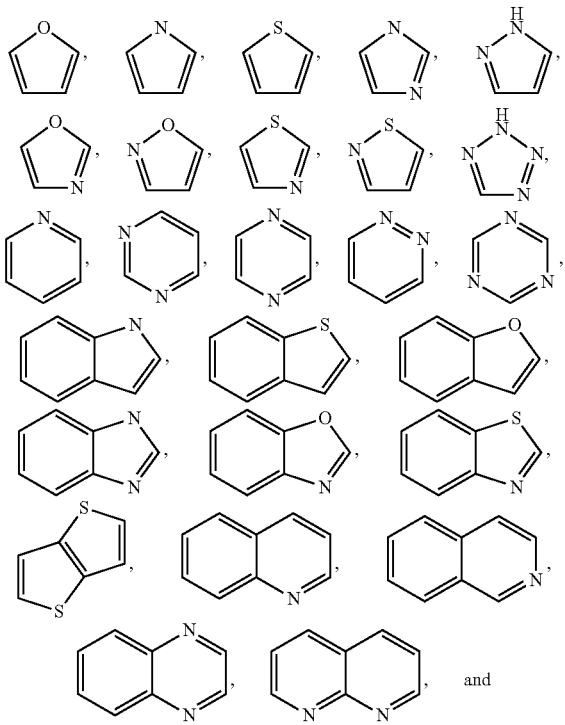

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

Additionally, any formula given herein is intended to refer also to hydrates, solvates, and polymorphs of such compounds, and mixtures thereof, even if such forms are not listed explicitly. Certain compounds of Formula (I) or pharmaceutically acceptable salts of compounds of Formula (I) may be obtained as solvates. Solvates include those formed from the interaction or complexation of compounds of the invention with one or more solvents, either in solution or as a solid or crystalline form. In some embodiments, the solvent is water and then the solvates are hydrates. In addition, certain crystalline forms of compounds of Formula (I) or pharmaceutically acceptable salts of compounds of Formula (I) may be obtained as co-crystals. In certain embodiments of the invention, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Inerest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion $^+$H$_3$NCH$_2$COO$^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^3$, A, $X^4$, $X^5$, $X^6$, $X^7$, $R^a$, $R^b$, $R^c$, and $R^d$ and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^3$, A, $X^4$, $X^5$, $X^6$, $X^7$, $R^a$, $R^b$, $R^c$ and $R^d$ and any other generic substituent symbol used herein.

The nomenclature "$C_{i-j}$" with J>i, when applied herein to a class of substituents, is meant to refer to embodiments of this invention for which each and every one of the number of carbon members, from i to J including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n.

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

Chemical depictions are intended to portray the compound portions containing the orientations as written.

The present invention includes the use of compounds of Formula (I),

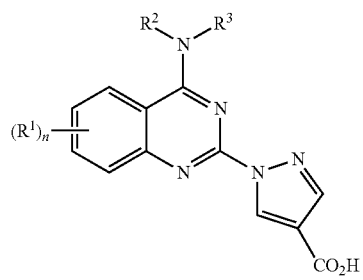

Formula (I)

the use of compounds of Formula (I) and pharmaceutical compositions containing such compounds thereof to treat patients (humans or other mammals) with disorders related to the modulation of the prolyl hydroxylase enzyme. The instant invention also includes methods of making such a compound, pharmaceutical composition, pharmaceutically acceptable salt, pharmaceutically acceptable prodrug, and pharmaceutically active metabolites thereof.

In the present invention described by of Formula (I), where n is 0-3, and $R^1$ is independently bromo, chloro, fluoro, methyl, isopropyl, cyclopropyl, cyclohexyl, cyclohexyloxy, phenyl, 2-methylphenyl, benzyl, phenoxy, 4-chlorophenoxy, 2,6-dimethyl-phenoxy, piperidinyl, and (2,6-dimethylbenzyl)amino.

In further preferred embodiments, n is 1.
In further preferred embodiments, n is 2.
In further preferred embodiments, n is 3.
In further preferred embodiments, $R^a$ is —H and $R^b$ is 2,6-dimethylbenzyl.
In further preferred embodiments, $R^a$ and $R^b$ can be taken together with the nitrogen to which they are attached to form a piperidine ring.
In further preferred embodiments, $R^c$ can be phenyl, cyclohexyl, 4-chlorophenyl, or 2,6-dimethyl-phenyl.
In further preferred embodiments, $R^d$ can independently be —H, chloro, and —$CH_3$.
In further preferred embodiments, $R^2$ is —H and $R^3$ can independently be —H, cyano, methyl, ethyl, propyl, tertbutyl, cyclopropyl, cyclopropylmethyl, tetrahydropyranyl, cyclohexylmethyl, phenyl, 2-chlorophenyl, 2,6-dimethylbenzyl, and —$SO_2CH_3$.
In further preferred embodiments, $R^2$ can be methyl, ethyl, propyl, or butyl.
In further preferred embodiments, $R^3$ can be methyl, ethyl, propyl, butyl, tertbutyl, 2-methoxyethyl, 2-methoxy-1-methyl-ethyl or diethylamino-ethyl.
In further preferred embodiments, $R^2$ and $R^3$ can be taken together with the nitrogen to which they are attached to form pyrrolidine, piperidine, 4-methyl-1,4-diazepane, thiomorpholine, 4-hydroxypiperidine, morpholine, 4-acetamidopiperidine, 4-cyanopiperidine, 4-fluoropiperidine, azepane, or 4-isopropylpiperidine.

In certain preferred embodiments, the compound of Formula (I) is selected from the group consisting of:

| Ex. | Chemical Name |
|---|---|
| 1 | 1-[4-Amino-6-(2,6-dimethyl-phenoxy)-7-fluoro-quinazolin-2-yl]-1H-pyrazole-4-carboxylic acid; |
| 2 | 1-[6-(2,6-Dimethyl-phenoxy)-7-fluoro-4-methylamino-quinazolin-2-yl]-1H-pyrazole-4-carboxylic acid; |
| 3 | 1-[4-Dimethylamino-6-(2,6-dimethyl-phenoxy)-7-fluoro-quinazolin-2-yl]-1H-pyrazole-4-carboxylic acid; |
| 4 | 1-[6-(2,6-Dimethyl-phenoxy)-7-fluoro-4-piperidin-1-yl-quinazolin-2-yl]-1H-pyrazole-4-carboxylic acid; |

-continued

| Ex. | Chemical Name |
|---|---|
| 5 | 1-[6-(2,6-Dimethyl-phenoxy)-7-fluoro-4-pyrrolidin-1-yl-quinazolin-2-yl]-1H-pyrazole-4-carboxylic acid; |
| 6 | 1-[6-(2,6-Dimethyl-phenoxy)-7-fluoro-4-phenylamino-quinazolin-2-yl]-1H-pyrazole-4-carboxylic acid; |
| 7 | 1-[4-(2-Chloro-phenylamino)-6-(2,6-dimethyl-phenoxy)-7-fluoro-quinazolin-2-yl]-1H-pyrazole-4-carboxylic acid; |
| 8 | 1-[6-(2,6-Dimethyl-phenoxy)-7-fluoro-4-propylamino-quinazolin-2-yl]-1H-pyrazole-4-carboxylic acid; |
| 9 | (rac)-1-[6-(2,6-Dimethyl-phenoxy)-7-fluoro-4-(2-methoxy-1-methyl-ethylamino)-quinazolin-2-yl]-1H-pyrazole-4-carboxylic acid; |
| 10 | 1-[4-(2-Diethylamino-ethylamino)-6-(2,6-dimethyl-phenoxy)-7-fluoro-quinazolin-2-yl]-1H-pyrazole-4-carboxylic acid; |
| 11 | 1-[6-(2,6-Dimethyl-phenoxy)-4-dibutylamino-7-fluoro-quinazolin-2-yl]-1H-pyrazole-4-carboxylic acid; |
| 12 | 1-[6-(2,6-Dimethyl-phenoxy)-4-dipropylamino-7-fluoro-quinazolin-2-yl]-1H-pyrazole-4-carboxylic acid; |
| 13 | 1-(4-((Cyclohexylmethyl)amino)-6-(2,6-dimethylphenoxy)-7-fluoroquinazolin-2-yl)-1H-pyrazole-4-carboxylic acid; |
| 14 | 1-((4-Cyclopropylamino)-6-(2,6-dimethylphenoxy)-7-fluoroquinazolin-2-yl)-1H-pyrazole-4-carboxylic acid; |
| 15 | 1-((4-Cyclopropanemethylamino)-6-(2,6-dimethylphenoxy)-7-fluoroquinazolin-2-yl)-1H-pyrazole-4-carboxylic acid; |
| 16 | 1-(6-(2,6-Dimethylphenoxy)-7-fluoro-4-((tetrahydro-2H-pyran-4-yl)amino)quinazolin-2-yl)-1H-pyrazole-4-carboxylic acid; |
| 17 | 1-(6-(2,6-Dimethylphenoxy)-7-fluoro-4-(4-methyl-1,4-diazepan-1-yl)quinazolin-2-yl)-1H-pyrazole-4-carboxylic acid; |
| 18 | 1-(6-(2,6-Dimethylphenoxy)-7-fluoro-4-thiomorpholinoquinazolin-2-yl)-1H-pyrazole-4-carboxylic acid; |
| 19 | 1-(6-(2,6-dimethylphenoxy)-7-fluoro-4-(4-hydroxypiperidin-1-yl)quinazolin-2-yl)-1H-pyrazole-4-carboxylic acid; |
| 20 | 1-(6-(2,6-Dimethylphenoxy)-7-fluoro-4-morpholinoquinazolin-2-yl)-1H-pyrazole-4-carboxylic acid; |
| 21 | 1-(4-(4-Acetamidopiperidin-1-yl)-6-(2,6-dimethylphenoxy)-7-fluoroquinazolin-2-yl)-1H-pyrazole-4-carboxylic acid; |
| 22 | 1-(6-Cyclohexyl-4-methylamino-quinazolin-2-yl)-1H-pyrazole-4-carboxylic acid; |
| 23 | 1-[6-Cyclohexyl-4-(2,6-dimethyl-benzylamino)-quinazolin-2-yl]-1H-pyrazole-4-carboxylic acid; |
| 24 | 1-(4-Amino-6-cyclohexylquinazolin-2-yl)-1H-pyrazole-4-carboxylic acid; |
| 25 | 1-(6-Cyclohexyl-4-(pyrrolidin-1-yl)quinazolin-2-yl)-1H-pyrazole-4-carboxylic acid; |
| 26 | 1-(6-Cyclohexyl-4-(piperidin-1-yl)quinazolin-2-yl)-1H-pyrazole-4-carboxylic acid; |
| 27 | 1-(6-Cyclohexyl-4-(diethylamino)quinazolin-2-yl)-1H-pyrazole-4-carboxylic acid; |
| 28 | 1-(6-Cyclohexyl-4-(phenylamino)quinazolin-2-yl)-1H-pyrazole-4-carboxylic acid; |
| 29 | 1-(4-((2-Chlorophenyl)amino)-6-cyclohexylquinazolin-2-yl)-1H-pyrazole-4-carboxylic acid; |
| 30 | 1-(4-(4-Cyanopiperidin-1-yl)-6-cyclohexylquinazolin-2-yl)-1H-pyrazole-4-carboxylic acid; |
| 31 | 1-(6-Cyclohexyl-4-(4-fluoropiperidin-1-yl)quinazolin-2-yl)-1H-pyrazole-4-carboxylic acid; |
| 32 | 1-(6-Cyclohexyl-4-(cyclopropylamino)quinazolin-2-yl)-1H-pyrazole-4-carboxylic acid; |
| 33 | 1-(6-Cyclohexyl-4-morpholinoquinazolin-2-yl)-1H-pyrazole-4-carboxylic acid; |
| 34 | 1-(6-Cyclohexyl-4-thiomorpholinoquinazolin-2-yl)-1H-pyrazole-4-carboxylic acid; |
| 35 | 1-(4-Cyanamido-6-cyclohexylquinazolin-2-yl)-1H-pyrazole-4-carboxylic acid; |
| 36 | 1-(4-(tert-Butylamino)-6-cyclohexylquinazolin-2-yl)-1H-pyrazole-4-carboxylic acid; |
| 37 | 1-(4-(Azepan-1-yl)-6-cyclohexylquinazolin-2-yl)-1H-pyrazole-4-carboxylic acid; |
| 38 | 1-(6-Cyclohexyl-4-(dimethylamino)quinazolin-2-yl)-1H-pyrazole-4-carboxylic acid; |
| 39 | 1-(6-Cyclohexyl-4-((cyclohexylmethyl)amino)quinazolin-2-yl)-1H-pyrazole-4-carboxylic acid; |
| 40 | 1-(6-Cyclohexyl-4-(methylsulfonamido)quinazolin-2-yl)-1H-pyrazole-4-carboxylic acid; |
| 41 | 1-(4-(Dimethylamino)-6-phenylquinazolin-2-yl)-1H-pyrazole-4-carboxylic acid; |
| 42 | 1-(4-(Ethyl(methyl)amino)-6-phenylquinazolin-2-yl)-1H-pyrazole-4-carboxylic acid; |
| 43 | 1-(6-Phenyl-4-(pyrrolidin-1-yl)quinazolin-2-yl)-1H-pyrazole-4-carboxylic acid; |

-continued

| Ex. | Chemical Name |
|---|---|
| 44 | 1-(6-Phenyl-4-(phenylamino)quinazolin-2-yl)-1H-pyrazole-4-carboxylic acid |
| 45 | 1-(6-Phenyl-4-(piperidin-1-yl)quinazolin-2-yl)-1H-pyrazole-4-carboxylic acid; |
| 46 | 1-(4-(Diethylamino)-6-phenylquinazolin-2-yl)-1H-pyrazole-4-carboxylic acid; |
| 47 | 1-(4-((2-Chlorophenyl)amino)-6-phenylquinazolin-2-yl)-1H-pyrazole-4-carboxylic acid; |
| 48 | 1-(4-(Azepan-1-yl)-6-phenylquinazolin-2-yl)-1H-pyrazole-4-carboxylic acid; |
| 49 | 1-(4-((Cyclohexylmethyl)amino)-6-phenylquinazolin-2-yl)-1H-pyrazole-4-carboxylic acid; |
| 50 | 1-(4-Cyanamido-6-phenylquinazolin-2-yl)-1H-pyrazole-4-carboxylic acid; |
| 51 | 1-(4-(Cyclopropylamino)-6-phenylquinazolin-2-yl)-1H-pyrazole-4-carboxylic acid; |
| 52 | 1-(4-(tert-Butylamino)-6-phenylquinazolin-2-yl)-1H-pyrazole-4-carboxylic acid; |
| 53 | 1-(4-Amino-6-phenylquinazolin-2-yl)-1H-pyrazole-4-carboxylic acid; |
| 54 | 1-(6-Phenyl-4-thiomorpholinoquinazolin-2-yl)-1H-pyrazole-4-carboxylic acid; |
| 55 | 1-(4-(4-Acetamidopiperidin-1-yl)-6-phenylquinazolin-2-yl)-1H-pyrazole-4-carboxylic acid; |
| 56 | 1-(6-Phenyl-4-((tetrahydro-2H-pyran-4-yl)amino)quinazolin-2-yl)-1H-pyrazole-4-carboxylic acid; |
| 57 | 1-(4-(4-Methyl-1,4-diazepan-1-yl)-6-phenylquinazolin-2-yl)-1H-pyrazole-4-carboxylic acid; |
| 58 | 1-(4-Morpholino-6-phenylquinazolin-2-yl)-1H-pyrazole-4-carboxylic acid; |
| 59 | 1-(4-(4-Cyanopiperidin-1-yl)-6-phenylquinazolin-2-yl)-1H-pyrazole-4-carboxylic acid; |
| 60 | 1-(6-(4-Chlorophenoxy)-4-(diethylamino)quinazolin-2-yl)-1H-pyrazole-4-carboxylic acid; |
| 61 | 1-(6-(4-Chlorophenoxy)-4-(pyrrolidin-1-yl)quinazolin-2-yl)-1H-pyrazole-4-carboxylic acid; |
| 62 | 1-(6-(4-Chlorophenoxy)-4-(cyclopropylamino)quinazolin-2-yl)-1H-pyrazole-4-carboxylic acid; |
| 63 | 1-(6-(4-Chlorophenoxy)-4-(piperidin-1-yl)quinazolin-2-yl)-1H-pyrazole-4-carboxylic acid; |
| 64 | 1-(6-(4-Chlorophenoxy)-4-((cyclohexylmethyl)amino)quinazolin-2-yl)-1H-pyrazole-4-carboxylic acid; |
| 65 | 1-(6-(4-chlorophenoxy)-4-(4-cyanopiperidin-1-yl)quinazolin-2-yl)-1H-pyrazole-4-carboxylic acid; |
| 66 | 1-(4-(Azepan-1-yl)-6-(4-chlorophenoxy)quinazolin-2-yl)-1H-pyrazole-4-carboxylic acid; |
| 67 | 1-(6-(4-Chlorophenoxy)-4-thiomorpholinoquinazolin-2-yl)-1H-pyrazole-4-carboxylic acid; |
| 68 | 1-(6-(4-Chlorophenoxy)-4-((tetrahydro-2H-pyran-4-yl)amino)quinazolin-2-yl)-1H-pyrazole-4-carboxylic acid; |
| 69 | 1-(6-(4-Chlorophenoxy)-4-(phenylamino)quinazolin-2-yl)-1H-pyrazole-4-carboxylic acid; |
| 70 | 1-(4-(4-Acetamidopiperidin-1-yl)-6-(4-chlorophenoxy)quinazolin-2-yl)-1H-pyrazole-4-carboxylic acid; |
| 71 | 1-(6-(4-Chlorophenoxy)-4-(4-methyl-1,4-diazepan-1-yl)quinazolin-2-yl)-1H-pyrazole-4-carboxylic acid; |
| 72 | 1-(4-(tert-Butylamino)-6-phenoxyquinazolin-2-yl)-1H-pyrazole-4-carboxylic acid; |
| 73 | 1-(6-Phenoxy-4-(pyrrolidin-1-yl)quinazolin-2-yl)-1H-pyrazole-4-carboxylic acid; |
| 74 | 1-(4-(Diethylamino)-6-phenoxyquinazolin-2-yl)-1H-pyrazole-4-carboxylic acid; |
| 75 | 1-(4-(Cyclopropylamino)-6-phenoxyquinazolin-2-yl)-1H-pyrazole-4-carboxylic acid; |
| 76 | 1-(6-Phenoxy-4-((tetrahydro-2H-pyran-4-yl)amino)quinazolin-2-yl)-1H-pyrazole-4-carboxylic acid; |
| 77 | 1-(4-(Dimethylamino)-7-phenoxyquinazolin-2-yl)-1H-pyrazole-4-carboxylic acid; |
| 78 | 1-(7-Phenoxy-4-(pyrrolidin-1-yl)quinazolin-2-yl)-1H-pyrazole-4-carboxylic acid; |
| 79 | 1-(7-Phenoxy-4-(piperidin-1-yl)quinazolin-2-yl)-1H-pyrazole-4-carboxylic acid; |
| 80 | 1-(4-(Dimethylamino)-7-phenylquinazolin-2-yl)-1H-pyrazole-4-carboxylic acid; |
| 81 | 1-(7-Phenyl-4-(pyrrolidin-1-yl)quinazolin-2-yl)-1H-pyrazole-4-carboxylic acid; |
| 82 | 1-(7-Phenyl-4-(piperidin-1-yl)quinazolin-2-yl)-1H-pyrazole-4-carboxylic acid; |
| 83 | 1-(4-(Diethylamino)-7-phenoxyquinazolin-2-yl)-1H-pyrazole-4-carboxylic acid; |
| 84 | 1-(4-((Cyclohexylmethyl)amino)-7-phenoxyquinazolin-2-yl)-1H-pyrazole-4-carboxylic acid; |
| 85 | 1-(4-(4-Isopropylpiperidin-1-yl)-7-phenoxyquinazolin-2-yl)-1H-pyrazole-4-carboxylic acid; |

| Ex. | Chemical Name |
|---|---|
| 86 | 1-(4-(Cyclopropylamino)-7-phenoxyquinazolin-2-yl)-1H-pyrazole-4-carboxylic acid; |
| 87 | 1-(4-(Azepan-1-yl)-7-phenoxyquinazolin-2-yl)-1H-pyrazole-4-carboxylic acid; |
| 88 | 1-(4-(Diethylamino)-6-(piperidin-1-yl)quinazolin-2-yl)-1H-pyrazole-4-carboxylic acid; |
| 89 | 1-(4-Morpholino-7-phenoxyquinazolin-2-yl)-1H-pyrazole-4-carboxylic acid; |
| 90 | 1-(7-Phenoxy-4-thiomorpholinoquinazolin-2-yl)-1H-pyrazole-4-carboxylic acid; |
| 91 | 1-(4-(4-Fluoropiperidin-1-yl)-7-phenoxyquinazolin-2-yl)-1H-pyrazole-4-carboxylic acid; |
| 92 | 1-(4-(Dibutylamino)-7-phenoxyquinazolin-2-yl)-1H-pyrazole-4-carboxylic acid; |
| 93 | 1-(4-(Dipropylamino)-7-phenoxyquinazolin-2-yl)-1H-pyrazole-4-carboxylic acid; |
| 94 | 1-(4-(Ethyl(methyl)amino)-7-phenoxyquinazolin-2-yl)-1H-pyrazole-4-carboxylic acid; |
| 95 | 1-(4-((2-Methoxyethyl)(methyl)amino)-7-phenoxyquinazolin-2-yl)-1H-pyrazole-4-carboxylic acid; |
| 96 | 1-(7-Bromo-4-(diethylamino)quinazolin-2-yl)-1H-pyrazole-4-carboxylic acid; |
| 97 | 1-(4-(Cyclohexylamino)-7-phenoxyquinazolin-2-yl)-1H-pyrazole-4-carboxylic acid; |
| 98 | 1-(4-((Cyclopropylmethyl)amino)-7-phenoxyquinazolin-2-yl)-1H-pyrazole-4-carboxylic acid; |
| 99 | 1-(4-(tert-Butylamino)-7-phenoxyquinazolin-2-yl)-1H-pyrazole-4-carboxylic acid. |
| 100 | 1-(6-(Cyclohexyloxy)-7-fluoro-4-morpholinoquinazolin-2-yl)-1H-pyrazole-4-carboxylic acid; |
| 101 | 1-(6-(Cyclohexyloxy)-4-(dimethylamino)-7-fluoroquinazolin-2-yl)-1H-pyrazole-4-carboxylic acid; |
| 102 | 1-(6-(Cyclohexyloxy)-4-(diethylamino)-7-fluoroquinazolin-2-yl)-1H-pyrazole-4-carboxylic acid; |
| 103 | 1-(6-(Cyclohexyloxy)-7-fluoro-4-(pyrrolidin-1-yl)quinazolin-2-yl)-1H-pyrazole-4-carboxylic acid; |
| 104 | 1-(6-(Cyclohexyloxy)-4-(ethyl(methyl)amino)-7-fluoroquinazolin-2-yl)-1H-pyrazole-4-carboxylic acid; |
| 105 | 1-(6-(Cyclohexyloxy)-4-(cyclopropylamino)-7-fluoroquinazolin-2-yl)-1H-pyrazole-4-carboxylic acid; |
| 106 | 1-(6-Benzyl-7-fluoro-4-morpholinoquinazolin-2-yl)-1H-pyrazole-4-carboxylic acid; |
| 107 | 1-(6-Benzyl-4-(dimethylamino)-7-fluoroquinazolin-2-yl)-1H-pyrazole-4-carboxylic acid; |
| 108 | 1-(6-Benzyl-4-(diethylamino)-7-fluoroquinazolin-2-yl)-1H-pyrazole-4-carboxylic acid; |
| 109 | 1-(6-Benzyl-7-fluoro-4-(pyrrolidin-1-yl)quinazolin-2-yl)-1H-pyrazole-4-carboxylic acid; |
| 110 | 1-(6-Benzyl-4-(ethyl(methyl)amino)-7-fluoroquinazolin-2-yl)-1H-pyrazole-4-carboxylic acid; |
| 111 | 1-(6-Benzyl-4-(cyclopropylamino)-7-fluoroquinazolin-2-yl)-1H-pyrazole-4-carboxylic acid; |
| 112 | 1-(6-((2,6-Dimethylbenzyl)amino)-7-fluoro-4-morpholinoquinazolin-2-yl)-1H-pyrazole-4-carboxylic acid; |
| 113 | 1-(4-(Dimethylamino)-6-((2,6-dimethylbenzyl)amino)-7-fluoroquinazolin-2-yl)-1H-pyrazole-4-carboxylic acid; |
| 114 | 1-(4-(Diethylamino)-6-((2,6-dimethylbenzyl)amino)-7-fluoroquinazolin-2-yl)-1H-pyrazole-4-carboxylic acid;; |
| 115 | 1 1-(6-((2,6-Dimethylbenzyl)amino)-7-fluoro-4-(pyrrolidin-1-yl)quinazolin-2-yl)-1H-pyrazole-4-carboxylic acid; |
| 116 | 1-(6-((2,6-Dimethylbenzyl)amino)-4-(ethyl(methyl)amino)-7-fluoroquinazolin-2-yl)-1H-pyrazole-4-carboxylic acid; |
| 117 | 1-(4-(Cyclopropylamino)-6-((2,6-dimethylbenzyl)amino)-7-fluoroquinazolin-2-yl)-1H-pyrazole-4-carboxylic acid; |
| 118 | 1-(7-Fluoro-4-morpholino-6-(o-tolyl)quinazolin-2-yl)-1H-pyrazole-4-carboxylic acid; |
| 119 | 1-(4-(Dimethylamino)-7-fluoro-6-(o-tolyl)quinazolin-2-yl)-1H-pyrazole-4-carboxylic acid; |
| 120 | 1-(4-(Diethylamino)-7-fluoro-6-(o-tolyl)quinazolin-2-yl)-1H-pyrazole-4-carboxylic acid |
| 121 | 1-(7-Fluoro-4-(pyrrolidin-1-yl)-6-(o-tolyl)quinazolin-2-yl)-1H-pyrazole-4-carboxylic acid; |
| 122 | 1-(4-(Ethyl(methyl)amino)-7-fluoro-6-(o-tolyl)quinazolin-2-yl)-1H-pyrazole-4-carboxylic acid; |
| 123 | 1-(4-(Cyclopropylamino)-7-fluoro-6-(o-tolyl)quinazolin-2-yl)-1H-pyrazole-4-carboxylic acid; |
| 124 | 1-(7-Fluoro-6-isopropyl-4-morpholinoquinazolin-2-yl)-1H-pyrazole-4-carboxylic acid; |

-continued

| Ex. | Chemical Name |
|---|---|
| 125 | 1-(4-(Dimethylamino)-7-fluoro-6-isopropylquinazolin-2-yl)-1H-pyrazole-4-carboxylic acid; |
| 126 | 1-(4-(Diethylamino)-7-fluoro-6-isopropylquinazolin-2-yl)-1H-pyrazole-4-carboxylic acid; |
| 127 | 1-(7-Fluoro-6-isopropyl-4-(pyrrolidin-1-yl)quinazolin-2-yl)-1H-pyrazole-4-carboxylic acid; |
| 128 | 1-(4-(Ethyl(methyl)amino)-7-fluoro-6-isopropylquinazolin-2-yl)-1H-pyrazole-4-carboxylic acid; |
| 129 | 1-(4-(Cyclopropylamino)-7-fluoro-6-isopropylquinazolin-2-yl)-1H-pyrazole-4-carboxylic acid; |
| 130 | 1-(7-Fluoro-4-morpholino-6-(piperidin-1-yl)quinazolin-2-yl)-1H-pyrazole-4-carboxylic acid; |
| 131 | 1-(4-(Dimethylamino)-7-fluoro-6-(piperidin-1-yl)quinazolin-2-yl)-1H-pyrazole-4-carboxylic acid; |
| 132 | 1-(4-(Diethylamino)-7-fluoro-6-(piperidin-1-yl)quinazolin-2-yl)-1H-pyrazole-4-carboxylic acid; |
| 133 | 1-(7-Fluoro-6-(piperidin-1-yl)-4-(pyrrolidin-1-yl)quinazolin-2-yl)-1H-pyrazole-4-carboxylic acid; |
| 134 | 1-(4-(Ethyl(methyl)amino)-7-fluoro-6-(piperidin-1-yl)quinazolin-2-yl)-1H-pyrazole-4-carboxylic acid; |
| 135 | 1-(4-(Cyclopropylamino)-7-fluoro-6-(piperidin-1-yl)quinazolin-2-yl)-1H-pyrazole-4-carboxylic acid; |
| 136 | 1-(6-(Cyclohexyloxy)-7-chloro-4-morpholinoquinazolin-2-yl)-1H-pyrazole-4-carboxylic acid; |
| 137 | 1-(6-(Cyclohexyloxy)-4-(dimethylamino)-7-chloroquinazolin-2-yl)-1H-pyrazole-4-carboxylic acid; |
| 138 | 1-(6-(Cyclohexyloxy)-4-(diethylamino)-7-chloroquinazolin-2-yl)-1H-pyrazole-4-carboxylic acid; |
| 139 | 1-(6-(Cyclohexyloxy)-7-chloro-4-(pyrrolidin-1-yl)quinazolin-2-yl)-1H-pyrazole-4-carboxylic acid; |
| 140 | 1-(6-(Cyclohexyloxy)-4-(ethyl(methyl)amino)-7-chloroquinazolin-2-yl)-1H-pyrazole-4-carboxylic acid; |
| 141 | 1-(6-(Cyclohexyloxy)-4-(cyclopropylamino)-7-chloroquinazolin-2-yl)-1H-pyrazole-4-carboxylic acid; |
| 142 | 1-(6-Benzyl-7-chloro-4-morpholinoquinazolin-2-yl)-1H-pyrazole-4-carboxylic acid; |
| 143 | 1-(6-Benzyl-4-(dimethylamino)-7-chloroquinazolin-2-yl)-1H-pyrazole-4-carboxylic acid; |
| 144 | 1-(6-Benzyl-4-(diethylamino)-7-chloroquinazolin-2-yl)-1H-pyrazole-4-carboxylic acid; |
| 145 | 1-(6-Benzyl-7-chloro-4-(pyrrolidin-1-yl)quinazolin-2-yl)-1H-pyrazole-4-carboxylic acid; |
| 146 | 1-(6-Benzyl-4-(ethyl(methyl)amino)-7-chloroquinazolin-2-yl)-1H-pyrazole-4-carboxylic acid; |
| 147 | 1-(6-Benzyl-4-(cyclopropylamino)-7-chloroquinazolin-2-yl)-1H-pyrazole-4-carboxylic acid; |
| 148 | 1-(6-((2,6-Dimethylbenzyl)amino)-7-chloro-4-morpholinoquinazolin-2-yl)-1H-pyrazole-4-carboxylic acid; |
| 149 | 1-(4-(Dimethylamino)-6-((2,6-dimethylbenzyl)amino)-7-chloroquinazolin-2-yl)-1H-pyrazole-4-carboxylic acid;; |
| 150 | 1-(4-(Diethylamino)-6-((2,6-dimethylbenzyl)amino)-7-chloroquinazolin-2-yl)-1H-pyrazole-4-carboxylic acid; |
| 151 | 1-(6-((2,6-Dimethylbenzyl)amino)-7-chloro-4-(pyrrolidin-1-yl)quinazolin-2-yl)-1H-pyrazole-4-carboxylic acid; |
| 152 | 1-(6-((2,6-Dimethylbenzyl)amino)-4-(ethyl(methyl)amino)-7-chloroquinazolin-2-yl)-1H-pyrazole-4-carboxylic acid; |
| 153 | 1-(4-(Cyclopropylamino)-6-((2,6-dimethylbenzyl)amino)-7-chloroquinazolin-2-yl)-1H-pyrazole-4-carboxylic acid; |
| 154 | 1-(7-Chloro-4-morpholino-6-(o-tolyl)quinazolin-2-yl)-1H-pyrazole-4-carboxylic acid; |
| 155 | 1-(4-(Dimethylamino)-7-chloro-6-(o-tolyl)quinazolin-2-yl)-1H-pyrazole-4-carboxylic acid; |
| 156 | 1-(4-(Diethylamino)-7-chloro-6-(o-tolyl)quinazolin-2-yl)-1H-pyrazole-4-carboxylic acid; |
| 157 | 1-(7-Chloro-4-(pyrrolidin-1-yl)-6-(o-tolyl)quinazolin-2-yl)-1H-pyrazole-4-carboxylic acid; |
| 158 | 1-(4-(Ethyl(methyl)amino)-7-chloro-6-(o-tolyl)quinazolin-2-yl)-1H-pyrazole-4-carboxylic acid; |
| 159 | 1-(4-(Cyclopropylamino)-7-chloro-6-(o-tolyl)quinazolin-2-yl)-1H-pyrazole-4-carboxylic acid; |
| 160 | 1-(7-Chloro-6-isopropyl-4-morpholinoquinazolin-2-yl)-1H-pyrazole-4-carboxylic acid; |
| 161 | 1-(4-(Dimethylamino)-7-chloro-6-isopropylquinazolin-2-yl)-1H-pyrazole-4-carboxylic acid; |
| 162 | 1-(4-(Diethylamino)-7-chloro-6-isopropylquinazolin-2-yl)-1H-pyrazole-4-carboxylic acid; |

| Ex. | Chemical Name |
|---|---|
| 163 | 1-(7-Chloro-6-isopropyl-4-(pyrrolidin-1-yl)quinazolin-2-yl)-1H-pyrazole-4-carboxylic acid; |
| 164 | 1-(4-(Ethyl(methyl)amino)-7-chloro-6-isopropylquinazolin-2-yl)-1H-pyrazole-4-carboxylic acid; |
| 165 | 1-(4-(Cyclopropylamino)-7-chloro-6-isopropylquinazolin-2-yl)-1H-pyrazole-4-carboxylic acid; |
| 166 | 1-(7-Chloro-4-morpholino-6-(piperidin-1-yl)quinazolin-2-yl)-1H-pyrazole-4-carboxylic acid; |
| 167 | 1-(4-(Dimethylamino)-7-chloro-6-(piperidin-1-yl)quinazolin-2-yl)-1H-pyrazole-4-carboxylic acid; |
| 168 | 1-(4-(Diethylamino)-7-chloro-6-(piperidin-1-yl)quinazolin-2-yl)-1H-pyrazole-4-carboxylic acid; |
| 169 | 1-(7-Chloro-6-(piperidin-1-yl)-4-(pyrrolidin-1-yl)quinazolin-2-yl)-1H-pyrazole-4-carboxylic acid; |
| 170 | 1-(4-(Ethyl(methyl)amino)-7-chloro-6-(piperidin-1-yl)quinazolin-2-yl)-1H-pyrazole-4-carboxylic acid; |
| 171 | 1-(4-(Cyclopropylamino)-7-chloro-6-(piperidin-1-yl)quinazolin-2-yl)-1H-pyrazole-4-carboxylic acid; |
| 172 | 1-(6-(Cyclohexyloxy)-4-morpholinoquinazolin-2-yl)-1H-pyrazole-4-carboxylic acid; |
| 173 | 1-(6-(Cyclohexyloxy)-4-(dimethylamino)quinazolin-2-yl)-1H-pyrazole-4-carboxylic acid; |
| 174 | 1-(6-(Cyclohexyloxy)-4-(diethylamino)quinazolin-2-yl)-1H-pyrazole-4-carboxylic acid; |
| 175 | 1-(6-(Cyclohexyloxy)-4-(pyrrolidin-1-yl)quinazolin-2-yl)-1H-pyrazole-4-carboxylic acid; |
| 176 | 1-(6-(Cyclohexyloxy)-4-(cyclopropylamino)quinazolin-2-yl)-1H-pyrazole-4-carboxylic acid; |
| 177 | 1-(6-(Cyclohexyloxy)-4-(ethyl(methyl)amino)quinazolin-2-yl)-1H-pyrazole-4-carboxylic acid; |
| 178 | 1-(6-Benzyl-4-morpholinoquinazolin-2-yl)-1H-pyrazole-4-carboxylic acid; |
| 179 | 1-(6-Benzyl-4-(dimethylamino)quinazolin-2-yl)-1H-pyrazole-4-carboxylic acid; |
| 180 | 1-(6-Benzyl-4-(diethylamino)quinazolin-2-yl)-1H-pyrazole-4-carboxylic acid; |
| 181 | 1-(6-Benzyl-4-(pyrrolidin-1-yl)quinazolin-2-yl)-1H-pyrazole-4-carboxylic acid; |
| 182 | 1-(6-Benzyl-4-(cyclopropylamino)quinazolin-2-yl)-1H-pyrazole-4-carboxylic acid; |
| 183 | 1-(6-Benzyl-4-(ethyl(methyl)amino)quinazolin-2-yl)-1H-pyrazole-4-carboxylic acid; |
| 184 | 1-(6-Isopropyl-4-morpholinoquinazolin-2-yl)-1H-pyrazole-4-carboxylic acid; |
| 185 | 1-(6-Isopropyl-4-(dimethylamino)quinazolin-2-yl)-1H-pyrazole-4-carboxylic acid; |
| 186 | 1-(6-Isopropyl-4-(diethylamino)quinazolin-2-yl)-1H-pyrazole-4-carboxylic acid; |
| 187 | 1-(6-Isopropyl-4-(pyrrolidin-1-yl)quinazolin-2-yl)-1H-pyrazole-4-carboxylic acid; |
| 188 | 1-(6-Isopropyl-4-(cyclopropylamino)quinazolin-2-yl)-1H-pyrazole-4-carboxylic acid; |
| 189 | 1-(6-Isopropyl-4-(ethyl(methyl)amino)quinazolin-2-yl)-1H-pyrazole-4-carboxylic acid; |
| 190 | 1-(6-((2,6-Dimethylbenzyl)amino)-4-morpholinoquinazolin-2-yl)-1H-pyrazole-4-carboxylic acid; |
| 191 | 1-(6-((2,6-Dimethylbenzyl)amino)-4-(dimethylamino)quinazolin-2-yl)-1H-pyrazole-4-carboxylic acid; |
| 192 | 1-(6-((2,6-Dimethylbenzyl)amino)-4-(diethylamino)quinazolin-2-yl)-1H-pyrazole-4-carboxylic acid; |
| 193 | 1-(6-((2,6-Dimethylbenzyl)amino)-4-(pyrrolidin-1-yl)quinazolin-2-yl)-1H-pyrazole-4-carboxylic acid; |
| 194 | 1-(6-((2,6-Dimethylbenzyl)amino)-4-(cyclopropylamino)quinazolin-2-yl)-1H-pyrazole-4-carboxylic acid; |
| 195 | 1-(6-((2,6-Dimethylbenzyl)amino)-4-(ethyl(methyl)amino)quinazolin-2-yl)-1H-pyrazole-4-carboxylic acid; |
| 196 | 1-(4-Morpholino-6-(o-tolyl)quinazolin-2-yl)-1H-pyrazole-4-carboxylic acid; |
| 197 | 1-(4-(Dimethylamino)-6-(o-tolyl)quinazolin-2-yl)-1H-pyrazole-4-carboxylic acid; |
| 198 | 1-(4-(Diethylamino)-6-(o-tolyl)quinazolin-2-yl)-1H-pyrazole-4-carboxylic acid; |
| 199 | 1-(4-(Pyrrolidin-1-yl)-6-(o-tolyl)quinazolin-2-yl)-1H-pyrazole-4-carboxylic acid; |
| 200 | 1-(4-(Cyclopropylamino)-6-(o-tolyl)quinazolin-2-yl)-1H-pyrazole-4-carboxylic acid; |
| 201 | 1-(4-(ethyl(methyl)amino)-6-(o-tolyl)quinazolin-2-yl)-1H-pyrazole-4-carboxylic acid; |
| 202 | 1-(4-Morpholino-6-(piperidin-1-yl)quinazolin-2-yl)-1H-pyrazole-4-carboxylic acid; |

| Ex. | Chemical Name |
|---|---|
| 203 | 1-(4-(Dimethylamino)-6-(piperidin-1-yl)quinazolin-2-yl)-1H-pyrazole-4-carboxylic acid; |
| 204 | 1-(4-(Diethylamino)-6-(piperidin-1-yl)quinazolin-2-yl)-1H-pyrazole-4-carboxylic acid; |
| 205 | 1-(6-(Piperidin-1-yl)-4-(pyrrolidin-1-yl)quinazolin-2-yl)-1H-pyrazole-4-carboxylic acid; |
| 206 | 1-(4-(Cyclopropylamino)-6-(piperidin-1-yl)quinazolin-2-yl)-1H-pyrazole-4-carboxylic acid; |
| 207 | 1-(4-(Ethyl(methyl)amino)-6-(piperidin-1-yl)quinazolin-2-yl)-1H-pyrazole-4-carboxylic acid; |
| 208 | 1-(6-(2,6-Dimethylphenoxy)-7-methyl-4-morpholinoquinazolin-2-yl)-1H-pyrazole-4-carboxylic acid; |
| 209 | 1-(6-(2,6-Dimethylphenoxy)-7-methyl-4-dimethylaminoquinazolin-2-yl)-1H-pyrazole-4-carboxylic acid; |
| 210 | 1-(6-(2,6-Dimethylphenoxy)-7-methyl-4-diethylaminoquinazolin-2-yl)-1H-pyrazole-4-carboxylic acid; |
| 211 | 1-(6-(2,6-Dimethylphenoxy)-7-methyl-4-(pyrrolidin-1-yl)quinazolin-2-yl)-1H-pyrazole-4-carboxylic acid; |
| 212 | 1-(6-(2,6-Dimethylphenoxy)-7-methyl-4-cyclopropylaminoquinazolin-2-yl)-1H-pyrazole-4-carboxylic acid; |
| 213 | 1-(6-(2,6-Dimethylphenoxy)-4-(ethyl(methyl)amino)-7-methylquinazolin-2-yl)-1H-pyrazole-4-carboxylic acid; | and pharmaceutically acceptable salts thereof.

The invention includes also pharmaceutically acceptable salts of the compounds of Formula (I), preferably of those described above and of the specific compounds exemplified herein, and methods of treatment using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I), which may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites of the present invention are useful as modulators of PHD in the methods of the invention. "Modulators" include both inhibitors and activators, where "inhibitors" refer to compounds that decrease, prevent, inactivate, desensitize or down-regulate PHD expression or activity, and "activators" are compounds that increase, activate, facilitate, sensitize, or up-regulate PHD expression or activity.

The term "treat" or "treating" as used herein is intended to refer to administration of an active agent or composition of the invention to a subject for the purpose of effecting a therapeutic or prophylactic benefit through modulation of prolyl hydroxylase activity. Treating includes reversing, ameliorating, alleviating, inhibiting the progress of, lessening the severity of, or preventing a disease, disorder, or condition, or one or more symptoms of such disease, disorder or condition mediated through modulation of PHD activity. The term "subject" refers to a mammalian patient in need of such treatment, such as a human.

Accordingly, the invention relates to methods of using the compounds described herein to treat subjects diagnosed with or suffering from a disease, disorder, or condition mediated by Prolyl Hydroxylase, such as: Anemia, vascular disorders, metabolic disorders, and wound healing. Symptoms or disease states are intended to be included within the scope of "medical conditions, disorders, or diseases."

As used herein the term "hypoxia" or "hypoxic disorder" refers to a condition where there is an insufficient level of oxygen provided in the blood or to tissues and organs. Hypoxic disorders can occur through a variety of mechanisms including where there is an insufficient capacity of the blood to carry oxygen (i.e. anemia), where there is an inadequate flow of blood to the tissue and/or organ caused by either heart failure or blockage of blood vessels and/or arteries (i.e. ischemia), where there is reduced barometric pressure (i.e. elevation sickness at high altitudes), or where dysfunctional cells are unable to properly make use of oxygen (i.e. hystotoxic conditions). Accordingly, one of skill in the art would readily appreciate the present invention to be useful in the treatment of a variety of hypoxic conditions including anemia, heart failure, coronary artery disease, thromboembolism, stroke, angina and the like.

In a preferred embodiment, molecules of the present invention are useful in the treatment or prevention of anemia comprising treatment of anemic conditions associated with chronic kidney disease, polycystic kidney disease, aplastic anemia, autoimmune hemolytic anemia, bone marrow transplantation anemia, Churg-Strauss syndrome, Diamond Blackfan anemia, Fanconi's anemia, Felty syndrome, graft versus host disease, hematopoietic stem cell transplantation, hemolytic uremic syndrome, myelodysplastic syndrome, nocturnal paroxysmal hemoglobinuria, osteomyelofibrosis, pancytopenia, pure red-cell aplasia, purpura Schoenlein-Henoch, refractory anemia with excess of blasts, rheumatoid arthritis, Shwachman syndrome, sickle cell disease, thalassemia major, thalassemia minor, thrombocytopenic purpura, anemic or non-anemic patients undergoing surgery, anemia associated with or secondary to trauma, sideroblastic anemia, anemic secondary to other treatment including: reverse transcriptase inhibitors to treat HIV, corticosterol hormones, cyclic cisplatin or non-cisplatin-containing chemotherapeutics, vinca alkaloids, mitotic inhibitors, topoisomerase II inhibitors, anthracyclines, alkylating agents, particularly anemia secondary to inflammatory, aging and/or chronic diseases. PHD inhibition may also be used to treat symptoms of anemia including chronic fatigue, pallor and dizziness.

In another preferred embodiment, molecules of the present invention are useful for the treatment or prevention of diseases of metabolic disorders, including but not limited to diabetes and obesity. In another preferred embodiment, molecules of the present invention are useful for the treatment or prevention of vascular disorders. These include but are not limited to hypoxic or wound healing related diseases requiring pro-angiogenic mediators for vasculogenesis, angiogenesis, and arteriogenesis In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the agents of the invention may be used in combination with additional active ingredients in the treatment of the above conditions. The additional compounds may be co-administered separately with an agent of Formula (I) or included with such an agent as an additional active ingredient in a pharmaceutical composition according to the invention. In an exemplary embodiment, additional active ingredients are those that are known or discovered to be effective in the treatment of conditions, disorders, or diseases mediated by PHD enzyme or that are active against another targets associated with the particular condition, disorder, or disease, such as an alternate PHD modulator. The combination may serve to increase efficacy (e.g., by including in the combination a compound potentiating the potency or effectiveness of a compound according to the invention), decrease one or more side effects, or decrease the required dose of the compound according to the invention.

The compounds of the invention are used, alone or in combination with one or more other active ingredients, to formulate pharmaceutical compositions of the invention. A pharmaceutical composition of the invention comprises: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a compound of the invention and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the compounds of the invention may be prepared using suitable pharmaceutical excipients and compounding techniques now or later known or available to those skilled in the art. The compositions may be administered in the inventive methods by oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration. A preferred mode of use of the invention is local administration of PHD inhibitors particularly to sites where tissue has become or has been made ischemic. This may be achieved via a specialized catheter, angioplasty balloon or stent placement balloon.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and diglycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 μg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Examples include lotions, creams, ointments and the like and can be formulated by known methods. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Abbreviations and acronyms used herein including the following:

| Term | Acronym |
|---|---|
| Diisopropylethylamine | DIEA |
| Tetrahydrofuran | THF |
| Dichloromethane | DCM |
| Dimethyl Sulfoxide | DMSO |
| Dimethylacetamide | DMA |
| N,N-Dimethylformamide | DMF |
| Ethanol | EtOH |
| Acetonitrile | ACN |
| Ethyl Acetate | EtOAc |
| N-(3-Dimethylaminopropyl)-N-ethylcarbodiimide | EDCI |
| N,N'-Diisopropylcarbodiimide | DIC |
| Dichloroethane | DCE |

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may also be conducted in sealed pressure vessels above the normal reflux temperature of the solvent.

Scheme A

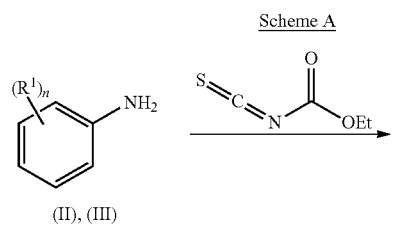

(II), (III)

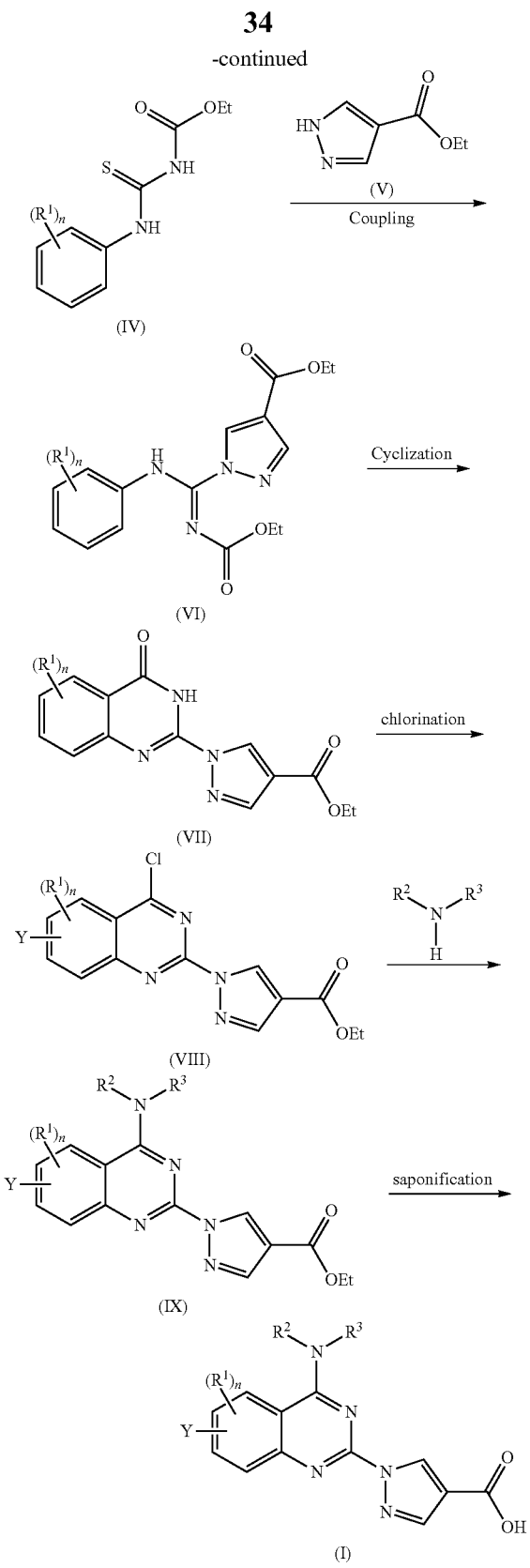

Compounds of Formula (I) are prepared according to Scheme A from appropriately substituted commercially available or synthetically accessible anilines of formula (II) or (III), prepared using known methods, methods described in Scheme B, or methods as described in the *Journal of Organic Chemistry,* 2008, 73 (6), 2473-75. Referring to Scheme A, functionalized anilines of formula (II) or (III) are condensed with isothiocyanates such as ethyl isothiocyanatoformate in a solvent such as dichloromethane (DCM) at temperatures between room temperature and the reflux temperature of the solvent, to provide compounds of formula (IV). Subsequent coupling with commercially available substituted pyrazole-4-carboxylates of formula (V), in the presence of a coupling reagent such as EDCI, DIC and the like, with or without an amine base such as triethylamine provides compounds of formula (VI). Cyclization of compounds of formula (VI) with an appropriate Lewis acid such as chlorotrimethylsilane, titanium (IV) chloride, and the like, in a solvent such as DCE or DMF, toluene and the like, at temperatures between room temperature and the reflux temperature of the solvent, provides compounds of formula (VII). Treatment of compounds of the formula (VII) with an appropriate chlorinating agent such as $POCl_3$ in the presence of a base such as DIEA in an appropriate solvent such as acetonitrile at temperatures between rt and reflux provide compounds of the formula (VIII). In certain cases it may be advantageous to add chloride ion from an appropriate source such as LiCl. Compounds of the formula (VIII) are treated with amines to afford compounds of the formula (IX). Saponification with a suitable base such as aq. NaOH, aq. LiOH or aq. KOH or a mixture thereof in a solvent such as THF at temperatures between rt and reflux provides compounds of Formula (I). There are an abundance of known and commercially available anilines that may be employed in the schemes herein. The schemes illustrated herein also provide guidance for synthesizing a variety of intermediates that are not readily available and are useful for making compounds of the present invention

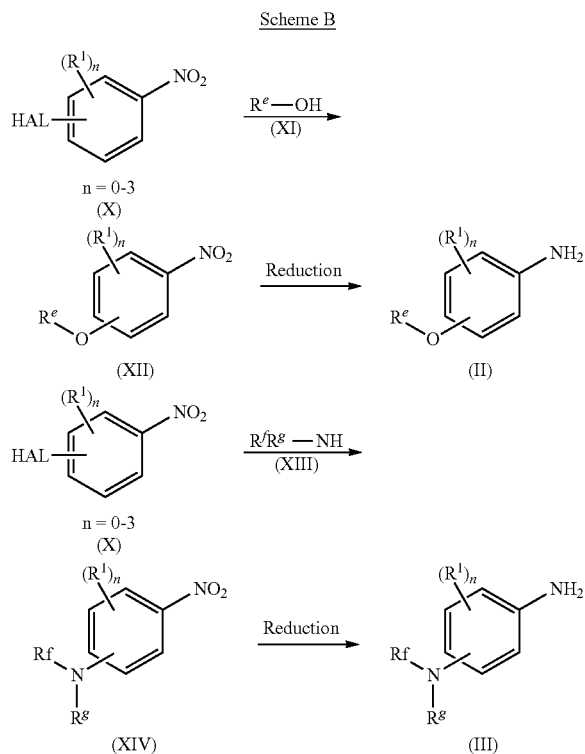

Ether intermediates of formula (II) are prepared according to Scheme B, where HAL is F, Cl. Commercially available appropriately substituted halo-nitro-benzenes of formula (X) are allowed to react with substituted phenols (XI) in the presence of a base such as potassium carbonate, in a solvent such as DMSO, DMF, DMA, and the like, at temperatures between room temperature and the reflux temperature of the solvent, providing nitro intermediates of formula (XII). Reduction of the nitro group, employing methods known to one skilled in the art, for example zinc powder in the presence of a saturated aqueous solution of $NH_4Cl$ in a solvent such as acetone, and the like, affords aniline intermediates of formula (II).

Amino intermediates of formula (III) may be prepared similarly to the methods utilized for the ether intermediates as described above, by replacing phenols with substituted alkyl amines, heterocycloalkyl amines and aryl amines of formula (XIII).

EXAMPLES

Chemistry

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure.

Thin-layer chromatography (TLC) was performed using Merck silica gel 60 $F_{254}$ 2.5 cm×7.5 cm 250 μm or 5.0 cm×10.0 cm 250 μm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone.

Normal-phase flash column chromatography (FCC) was performed on silica gel ($SiO_2$) eluting with hexanes/ethyl acetate, unless otherwise noted.

Reversed-phase HPLC was performed on a Hewlett Packard HPLC Series 1100, with a Phenomenex Luna $C_{18}$ (5 μm, 4.6×150 mm) column. Detection was done at λ=230, 254 and 280 nm. The gradient was 10 to 99% acetonitrile/water (0.05% trifluoroacetic acid) over 5.0 min with a flow rate of 1 mL/min. Alternately, preparative HPLC purification was performed on a Gilson automated HPLC system running Gilson Unipoint LC software with uv peak detection done at λ=220 nm and fitted with a reverse phase YMC-Pack ODS-A (5 μm, 30×250 mm) column; mobile gradient of 10-99% of acetonitrile/water (0.05% trifluoroacetic acid) over 15-20 min and flow rates of 10-20 mL/min.

Mass spectra (MS) were obtained on an Agilent series 1100 MSD equipped with a ESI/APCI positive and negative multimode source unless otherwise indicated.

Nuclear magnetic resonance (NMR) spectra were obtained on Bruker model DRX spectrometers. The format of the $^1H$ NMR data below is: chemical shift in ppm downfield of the tetramethylsilane reference (apparent multiplicity, coupling constant J in Hz, integration).

Chemical names were generated using ChemDraw Version 6.0.2 (CambridgeSoft, Cambridge, Mass.) or ACD/Name Version 9 (Advanced Chemistry Development, Toronto, Ontario, Canada).

Example 1

1-[4-Amino-6-(2,6-dimethyl-phenoxy)-7-fluoro-quinazolin-2-yl]-1H-pyrazole-4-carboxylic acid

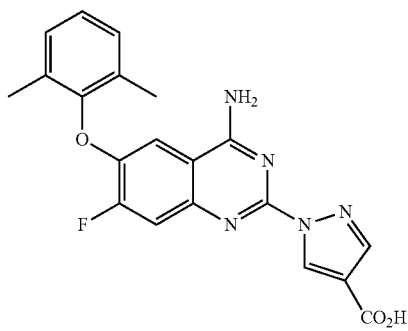 [SMILES: Cc1cccc(C)c1Oc1cc2c(N)nc(-n3cc(C(=O)O)cn3)nc2cc1F]

Step A: Preparation of 3-fluoro-4-(2,6-dimethyl-phenoxy) aniline. Solid 2,6-dimethylphenol (42.4 g, 346 mmol) was added in portions to a stirred mixture of 3,4-difluoronitrobenzene (50.0 g, 314 mmol), $K_2CO_3$ (65.0 g, 138 mmol), and DMSO (500 mL). After the addition was complete, the mixture was heated to 80° C. for 8 h and then allowed to cool to rt. The mixture was poured into ice water, and the resulting precipitate was collected and dried. This material was dissolved in acetone (1 L), then 150 mL of saturated aqueous $NH_4Cl$ was added and the mixture was immersed in an ice bath with mechanical stirring. Solid Zn powder (204 g, 65.4 mmol) was added in portions at such a rate that the internal temperature of the reaction mixture did not rise above 20° C. Following completion of the addition, the mixture was allowed to warm to rt and stirring was maintained for 6 h. EtOAc (ethyl acetate) (1.5 L) and anhydrous sodium sulfate (500 g) were added, and stirring was continued for 30 min. The mixture was then filtered though a pad of Celite®, rinsing well with EtOAc, and the filtrate was concentrated. The residue was triturated with hexanes to afford a solid (64.5 g, 90%). $^1$H NMR (400 MHz, $CDCl_3$): 7.10-6.99 (m, 3H), 6.55 (ddd, J=12.5, 2.1, 0.8 Hz, 1H), 6.25-6.19 (m, 2H), 3.50 (s, 2H), 2.15 (s, 6H).

Step B: Preparation of 1-(4-(2,6-dimethylphenoxy)-3-fluorophenyl)-3-ethoxycarbonylthiourea. A mixture of 3-fluoro-4-(2,6-dimethyl-phenoxy)aniline (15.4 g, 66.6 mmol) and DCM (250 mL) was cooled in an ice bath, then neat ethyl isocyanatoformate (9.61 g, 73.2 mmol) was added over 10 min. The resulting solution was allowed to warm to rt and was maintained for 2 h. The solution was concentrated, and the residue was triturated with 50:50 hexanes/ether, affording the titled compound as a solid (21.8 g, 90%). MS (ESI): mass calcd. for $C_{18}H_{19}FN_2O_3S$, 362.1; m/z found, 363.1 $[M+H]^+$.

Step C: Preparation of 1-(6-(2,6-dimethylphenoxy)-7-fluoro-4-oxo-3,4-dihydroquinazolin-2-yl)-1H-pyrazole-4-carboxylic acid, ethyl ester. Neat diisopropylcarbodiimide (45.4 g, 290 mmol) was added to a solution of 1-(4-(2,6-dimethylphenoxy)-3-fluorophenyl)-3-ethoxycarbonylthiourea (100 g, 276 mmol), ethyl pyrazole-4-carboxylate (45.4 g, 290 mmol), and DCM (1 L). The solution was maintained at rt for 24 h, then concentrated. The residue was stirred with ether (500 mL) for 3 h in an ice bath, then filtered. The filtrate was concentrated to a thick orange oil (180 g, ca. 70% purity, 97%). A portion of this material (20 g, ca. 30 mmol) was dissolved in DCE (150 mL), then neat $TiCl_4$ was added. The mixture was then heated to reflux for 6 h, then cooled in an ice bath. EtOH (750 mL) was added, and the mixture was stirred for 3 h. The resulting precipitate was collected by filtration, washed with cold EtOH, and dried to provide the titled compound (3.9 g, 31%). $^1$H NMR (500 MHz, DMSO): 13.03 (s, 1H), 8.95 (d, J=0.6 Hz, 1H), 8.29 (s, 1H), 7.75 (d, J=11.5 Hz, 1H), 7.31-7.24 (m, 2H), 7.22 (dd, J=8.5, 6.4 Hz, 1H), 6.96 (d, J=9.1 Hz, 1H), 4.29 (q, J=7.1 Hz, 2H), 2.11 (s, 6H), 1.32 (t, J=7.1 Hz, 3H).

Step D: Preparation of 1-[4-chloro-6-(2,6-dimethyl-phenoxy)-7-fluoro-quinazolin-2-yl]-1H-pyrazole-4-carboxylic acid, ethyl ester. A mixture of the above 1-[6-(2,6-dimethyl-phenoxy)-7-fluoro-4-oxo-3,4-dihydro-quinazolin-2-yl]-1H-pyrazole-4-carboxylic acid ethyl ester (5.0 g, 12 mmol), LiCl (2.5 g, 59 mmol), $POCl_3$ (5.5 ml, 59 mmol), DIEA (10 mL, 59 mmol), and acetonitrile (ACN) (50 mL) was heated to reflux for 6 h. The mixture was allowed to cool to rt and then concentrated. The residue was taken up in a minimal amount of DCM and passed through a pad of silica gel, eluting with 50:50 hexanes/EtOAc. The resulting solution was concentrated to provide the titled compound. (5.2 g, >99%). $^1$H NMR (500 MHz, DMSO-$d_6$): 9.13 (d, J=0.6 Hz, 1H), 8.23 (d, J=0.6 Hz, 1H), 7.92 (d, J=10.7 Hz, 1H), 7.23-7.19 (m, 3H), 7.07 (d, J=8.6 Hz, 1H), 4.36 (q, J=7.1 Hz, 2H), 2.19 (s, 6H), 1.40 (t, J=7.1 Hz, 3H).

Step E: Preparation of 1-[4-amino-6-(2,6-dimethyl-phenoxy)-7-fluoro-quinazolin-2-yl]-1H-pyrazole-4-carboxylic acid, ethyl ester. A methanol solution of ammonia (7M, 0.39 mL, 2.7 mmol) was added to a solution of the above 1-[4-chloro-6-(2,6-dimethyl-phenoxy)-7-fluoro-quinazolin-2-yl]-1H-pyrazole-4-carboxylic acid, ethyl ester (120 mg, 0.27 mmol) and THF (2 mL). The mixture was stirred for 6 h, then concentrated. The residue was triturated with $Et_2O$, providing the titled compound (72 mg, 64%). $^1$H NMR (500 MHz, DMSO-$d_6$): 8.96 (d, J=0.8 Hz, 1H), 8.44-8.02 (m, 3H), 7.71 (d, J=11.9 Hz, 1H), 7.37 (d, J=9.0 Hz, 1H), 7.24-7.20 (m, 2H), 7.17 (dd, J=8.6, 6.2 Hz, 1H), 4.27 (q, J=7.1 Hz, 2H), 2.12 (s, 6H), 1.31 (t, J=7.1 Hz, 3H).

Step F: Preparation of 1-[4-amino-6-(2,6-dimethyl-phenoxy)-7-fluoro-quinazolin-2-yl]-1H-pyrazole-4-carboxylic acid. A mixture of 1-[4-amino-6-(2,6-dimethyl-phenoxy)-7-fluoro-quinazolin-2-yl]-1H-pyrazole-4-carboxylic acid, ethyl ester (65 mg, 0.15 mmol), 1M aqueous LiOH (1.5 mL, 1.5 mmol), and THF (3 mL) was heated to 40° C. for 16 h with rapid stirring. The mixture was then cooled in an ice bath, and 1M HCl (1.5 mL, 1.5 mmol) was added. The resulting precipitate was collected by filtration, washed with water, and dried to furnish the titled compound (45 mg, 74%). MS (ESI): mass calcd. for $C_{20}H_{16}FN_5O_3$, 393.1; m/z found, 394.1 $[M+H]^+$. $^1$H NMR (500 MHz, DMSO-$d_6$): 12.72 (s, 1H), 8.91 (d, J=0.7 Hz, 1H), 8.42-7.98 (m, 3H), 7.70 (d, J=11.9 Hz, 1H), 7.37 (d, J=9.0 Hz, 1H), 7.25-7.20 (m, 2H), 7.17 (dd, J=8.6, 6.2 Hz, 1H), 2.12 (s, 6H).

Example 2

1-[6-(2,6-Dimethyl-phenoxy)-7-fluoro-4-methylamino-quinazolin-2-yl]-1H-pyrazole-4-carboxylic acid

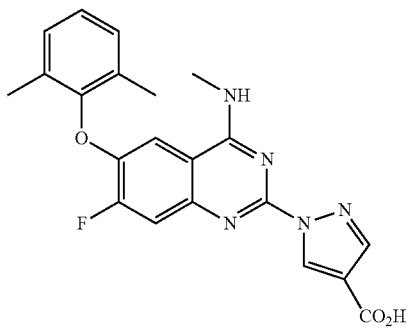 [SMILES: CNc1nc(-n2cc(C(=O)O)cn2)nc2cc(F)c(Oc3c(C)cccc3C)cc12]

The titled compound was prepared in a manner analogous to EXAMPLE 1, using methylamine in step E. MS (ESI): mass calcd. for $C_{21}H_{18}FN_5O_3$, 407.1; m/z found, 408.1 [M+H]$^+$. $^1$H NMR (500 MHz, DMSO-$d_6$): 12.76 (s, 1H), 8.99 (d, J=0.7 Hz, 1H), 8.60 (d, J=4.5 Hz, 1H), 8.08 (d, J=0.7 Hz, 1H), 7.71 (d, J=11.9 Hz, 1H), 7.34 (d, J=8.9 Hz, 1H), 7.27-7.22 (m, 2H), 7.19 (dd, J=8.6, 6.2 Hz, 1H), 3.00 (d, J=4.5 Hz, 3H), 2.12 (s, 6H).

Example 3

1-[4-Dimethylamino-6-(2,6-dimethyl-phenoxy)-7-fluoro-quinazolin-2-yl]-1H-pyrazole-4-carboxylic acid

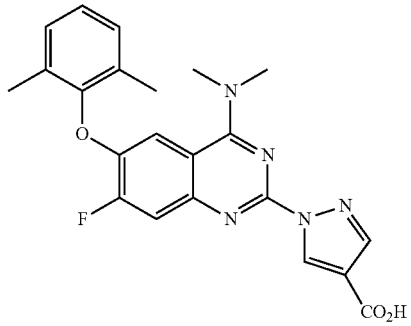 [SMILES: Cc1cccc(C)c1Oc1cc2c(N(C)C)nc(-n3cc(C(=O)O)cn3)nc2cc1F]

The titled compound was prepared in a manner analogous to EXAMPLE 1, using dimethylamine in step E. MS (ESI): mass calcd. for $C_{22}H_{20}FN_5O_3$, 421.2; m/z found, 422.1 [M+H]$^+$. $^1$H NMR (500 MHz, DMSO-$d_6$): 12.77 (s, 1H), 8.97 (d, J=0.7 Hz, 1H), 8.09 (d, J=0.7 Hz, 1H), 7.79 (d, J=11.9 Hz, 1H), 7.32-7.16 (m, 3H), 6.99 (d, J=9.1 Hz, 1H), 3.12 (s, 6H), 2.13 (s, 6H).

Example 4

1-[6-(2,6-Dimethyl-phenoxy)-7-fluoro-4-piperidin-1-yl-quinazolin-2-yl]-1H-pyrazole-4-carboxylic acid

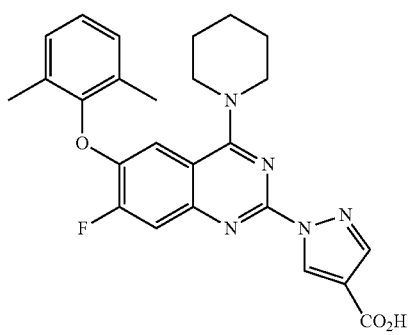 [SMILES: Cc1cccc(C)c1Oc1cc2c(N3CCCCC3)nc(-n3cc(C(=O)O)cn3)nc2cc1F]

The titled compound was prepared in a manner analogous to EXAMPLE 1, using piperidine in step E. MS (ESI): mass calcd. for $C_{25}H_{24}FN_5O_3$, 461.2; m/z found, 462.1 [M+H]$^+$. $^1$H NMR (500 MHz, DMSO-$d_6$): 12.77 (s, 1H), 8.96 (d, J=0.7 Hz, 1H), 8.09 (d, J=0.7 Hz, 1H), 7.83 (d, J=11.8 Hz, 1H), 7.31-7.19 (m, 3H), 6.70 (d, J=9.1 Hz, 1H), 3.58-3.48 (m, 4H), 2.13 (s, 6H), 1.66-1.53 (m, 2H), 1.47-1.35 (m, 4H).

Example 5

1-[6-(2,6-Dimethyl-phenoxy)-7-fluoro-4-pyrrolidin-1-yl-quinazolin-2-yl]-1H-pyrazole-4-carboxylic acid

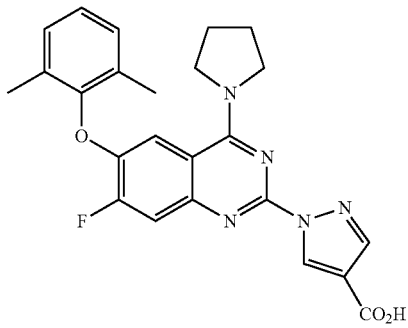 [SMILES: Cc1cccc(C)c1Oc1cc2c(N3CCCC3)nc(-n3cc(C(=O)O)cn3)nc2cc1F]

The titled compound was prepared in a manner analogous to EXAMPLE 1, using pyrrolidine in step E. MS (ESI): mass calcd. for $C_{24}H_{22}FN_5O_3$, 447.2; m/z found, 448.2 [M+H]$^+$. $^1$H NMR (500 MHz, DMSO-$d_6$): 12.74 (s, 1H), 8.95 (s, 1H), 8.08 (s, 1H), 7.75 (d, J=12.0 Hz, 1H), 7.30-7.12 (m, 4H), 3.66-3.48 (m, 4H), 2.14 (s, 6H), 1.91-1.80 (m, 4H).

Example 6

1-[6-(2,6-Dimethyl-phenoxy)-7-fluoro-4-phenylamino-quinazolin-2-yl]-1H-pyrazole-4-carboxylic acid

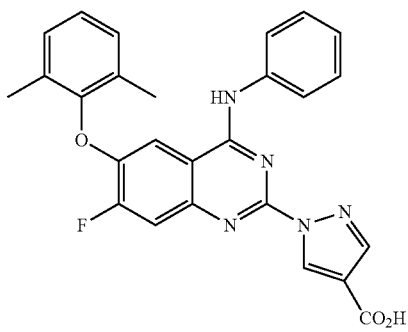 [SMILES: Cc1cccc(C)c1Oc1cc2c(Nc3ccccc3)nc(-n3cc(C(=O)O)cn3)nc2cc1F]

The titled compound was prepared in a manner analogous to EXAMPLE 1, using aniline in step E with heating to 80° C. for 16 h. MS (ESI): mass calcd. for $C_{26}H_{20}FN_5O_3$, 469.2; m/z found, 470.1 [M+H]$^+$. $^1$H NMR (500 MHz, DMSO-$d_6$): 12.76 (s, 1H), 10.14 (s, 1H), 8.69 (d, J=0.7 Hz, 1H), 8.07 (d, J=0.7 Hz, 1H), 7.82 (d, J=11.8 Hz, 1H), 7.71-7.59 (m, 3H), 7.47-7.39 (m, 2H), 7.28-7.15 (m, 4H), 2.16 (s, 6H).

Example 7

1-[4-(2-Chloro-phenylamino)-6-(2,6-dimethyl-phenoxy)-7-fluoro-quinazolin-2-yl]-1H-pyrazole-4-carboxylic acid

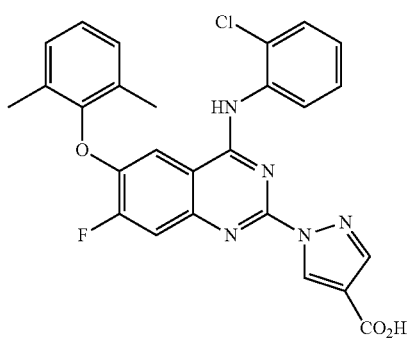 [SMILES: Cc1cccc(C)c1Oc1cc2c(Nc3ccccc3Cl)nc(-n3cc(C(=O)O)cn3)nc2cc1F]

The titled compound was prepared in a manner analogous to EXAMPLE 1, using 2-chloroaniline in step E and heating to 80° C. for 16 h. MS (ESI): mass calcd. for $C_{26}H_{19}ClFN_5O_3$, 503.1; m/z found, 504.0 [M+H]$^+$. $^1$H NMR (500 MHz, DMSO-d$_6$): 12.72 (s, 1H), 10.30 (s, 1H), 8.42 (d, J=0.7 Hz, 1H), 8.03 (d, J=0.7 Hz, 1H), 7.85 (d, J=11.8 Hz, 1H), 7.66-7.59 (m, 2H), 7.54 (dd, J=7.8, 1.7 Hz, 1H), 7.48-7.38 (m, 2H), 7.28-7.23 (m, 2H), 7.19 (dd, J=8.3, 6.6 Hz, 1H), 2.17 (s, 6H).

Example 8

1-[6-(2,6-Dimethyl-phenoxy)-7-fluoro-4-propylamino-quinazolin-2-yl]-1H-pyrazole-4-carboxylic acid

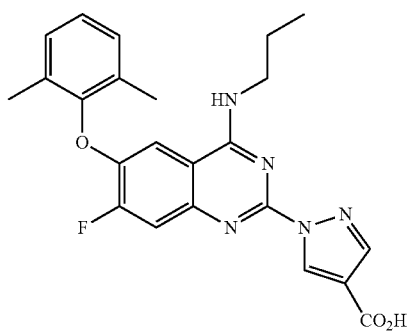 [SMILES: CCCNc1nc(-n2cc(C(=O)O)cn2)nc2cc(F)c(Oc3c(C)cccc3C)cc12]

The titled compound was prepared in a manner analogous to EXAMPLE 1, using propylamine in step E. MS (ESI): mass calcd. for $C_{23}H_{22}FN_5O_3$, 435.2; m/z found, 436.1 [M+H]$^+$. $^1$H NMR (500 MHz, DMSO-d$_6$): 12.76 (s, 1H), 8.94 (d, J=0.7 Hz, 1H), 8.67 (t, J=5.6 Hz, 1H), 8.09 (d, J=0.7 Hz, 1H), 7.70 (d, J=11.9 Hz, 1H), 7.39 (d, J=8.9 Hz, 1H), 7.27-7.14 (m, 3H), 3.49 (dd, J=14.0, 6.1 Hz, 2H), 2.12 (s, 6H), 1.71-1.57 (m, 2H), 0.90 (t, J=7.4 Hz, 3H).

Example 9

(rac)-1-[6-(2,6-Dimethyl-phenoxy)-7-fluoro-4-(2-methoxy-1-methyl-ethylamino)-quinazolin-2-yl]-1H-pyrazole-4-carboxylic acid

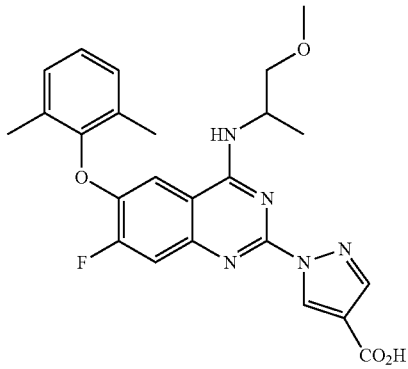 [SMILES: COCC(C)Nc1nc(-n2cc(C(=O)O)cn2)nc2cc(F)c(Oc3c(C)cccc3C)cc12]

The titled compound was prepared in a manner analogous to EXAMPLE 1, using racemic 2-methoxy-1-methylethylamine in step E. MS (ESI): mass calcd. for $C_{24}H_{24}FN_5O_4$, 465.2; m/z found, 467.1 [M+H]$^+$. $^1$H NMR (500 MHz, DMSO-d$_6$): 12.82 (s, 1H), 8.96 (d, J=0.7 Hz, 1H), 8.37 (d, J=7.9 Hz, 1H), 8.09 (d, J=0.7 Hz, 1H), 7.67 (d, J=11.8 Hz, 1H), 7.54 (d, J=8.9 Hz, 1H), 7.20-7.08 (m, 3H), 4.80-4.67 (m, 1H), 3.51 (dd, J=9.7, 6.5 Hz, 1H), 3.44-3.35 (m, 1H, partially obstructed by water), 3.24 (d, J=3.3 Hz, 3H), 2.11 (s, 6H), 1.21 (d, J=6.8 Hz, 3H).

Example 10

1-[4-(2-Diethylamino-ethylamino)-6-(2,6-dimethyl-phenoxy)-7-fluoro-quinazolin-2-yl]-1H-pyrazole-4-carboxylic acid

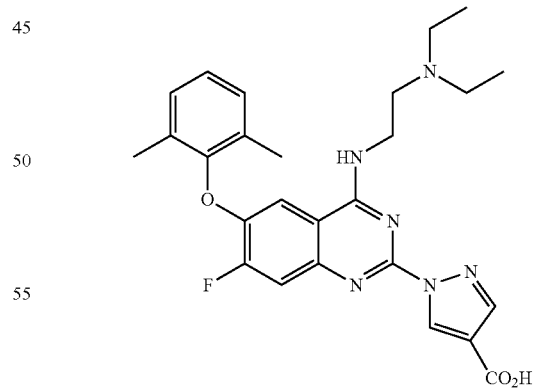

The titled compound was prepared in a manner analogous to EXAMPLE 1, using 2-dimethylaminoethylamine in step E. MS (ESI): mass calcd. for $C_{26}H_{29}FN_6O_3$, 492.2; m/z found, 493.5 [M+H]$^+$. $^1$H NMR (500 MHz, DMSO-d$_6$): 9.00 (s, 1H), 8.83 (s, 1H), 8.15 (s, 1H), 7.76 (d, J=11.8 Hz, 1H), 7.34 (d, J=8.8 Hz, 1H), 7.27-7.14 (m, 3H), 3.71 (d, J=5.3 Hz, 2H), 3.08-2.84 (m, 6H), 2.12 (s, 6H), 1.07 (t, J=7.0 Hz, 6H).

Example 11

1-[6-(2,6-Dimethyl-phenoxy)-4-dibutylamino-7-fluoro-quinazolin-2-yl]-1H-pyrazole-4-carboxylic acid

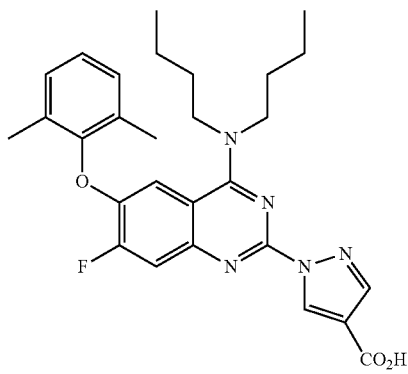 [SMILES: CCCCN(CCCC)c1nc(-n2cc(C(=O)O)cn2)nc2cc(F)c(Oc3c(C)cccc3C)cc12]

The titled compound was prepared in a manner analogous to EXAMPLE 1, using dibutylamine in step E. MS (ESI): mass calcd. for $C_{28}H_{32}FN_5O_3$, 505.2; m/z found, 506.3 [M+H]$^+$. $^1$H NMR (500 MHz, DMSO-d$_6$): 12.76 (s, 1H), 8.87 (d, J=0.7 Hz, 1H), 8.09 (d, J=0.7 Hz, 1H), 7.79 (d, J=11.8 Hz, 1H), 7.30-7.17 (m, 3H), 6.90 (d, J=9.0 Hz, 1H), 3.47-3.40 (m, 4H), 2.13 (s, 6H), 1.52-1.37 (m, 4H), 1.15-1.03 (m, 4H), 0.85 (t, J=7.3 Hz, 6H).

Example 12

1-[6-(2,6-Dimethyl-phenoxy)-4-dipropylamino-7-fluoro-quinazolin-2-yl]-1H-pyrazole-4-carboxylic acid

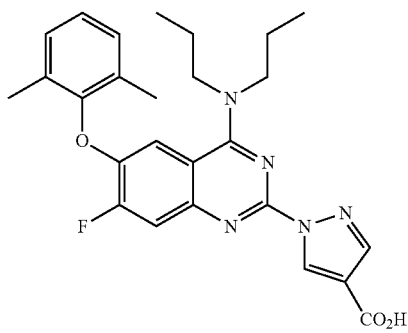 [SMILES: CCCN(CCC)c1nc(-n2cc(C(=O)O)cn2)nc2cc(F)c(Oc3c(C)cccc3C)cc12]

The titled compound was prepared in a manner analogous to EXAMPLE 1, using dipropylamine in step E. MS (ESI): mass calcd. for $C_{26}H_{28}FN_5O_3$, 477.2; m/z found, 478.4 [M+H]$^+$. $^1$H NMR (500 MHz, DMSO-d$_6$): 12.77 (s, 1H), 8.87 (d, J=0.6 Hz, 1H), 8.10 (d, J=0.6 Hz, 1H), 7.79 (d, J=11.8 Hz, 1H), 7.30-7.24 (m, 2H), 7.20 (dd, J=8.4, 6.6 Hz, 1H), 6.88 (d, J=9.0 Hz, 1H), 3.43-3.37 (m, 4H), 2.13 (s, 6H), 1.55-1.41 (m, 4H), 0.70 (t, J=7.4 Hz, 6H).

Example 13

1-(4-((Cyclohexylmethyl)amino)-6-(2,6-dimethylphenoxy)-7-fluoroquinazolin-2-yl)-1H-pyrazole-4-carboxylic acid

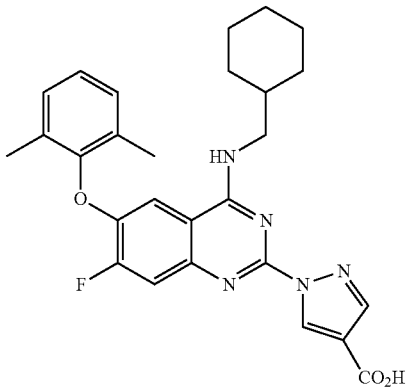 [SMILES: Cc1cccc(C)c1Oc1cc2c(NCC3CCCCC3)nc(-n3cc(C(=O)O)cn3)nc2cc1F]

The titled compound was prepared in a manner analogous to EXAMPLE 1, using cyclohexanemethylamine in step E. MS (ESI): mass calcd. for $C_{27}H_{28}FN_5O_3$, 490.1; m/z found, 489.2 [M+H]$^+$. $^1$H NMR (500 MHz, DMSO-d$_6$): 8.90 (d, J=0.6 Hz, 1H), 8.65 (t, J=5.7 Hz, 1H), 8.08 (d, J=0.6 Hz, 1H), 7.68 (d, J=11.9 Hz, 1H), 7.43 (d, J 8.9 Hz, 1H), 7.25-7.14 (m, J=8.5, 6.8 Hz, 3H), 3.39 (t, J=6.0 Hz, 2H), 2.12 (s, 6H), 1.73-1.53 (m, 6H), 1.14 (t, J=9.4 Hz, 3H), 0.97 (t, J=11.6 Hz, 2H).

Example 14

1-((4-Cyclopropylamino)-6-(2,6-dimethylphenoxy)-7-fluoroquinazolin-2-yl)-1H-pyrazole-4-carboxylic acid

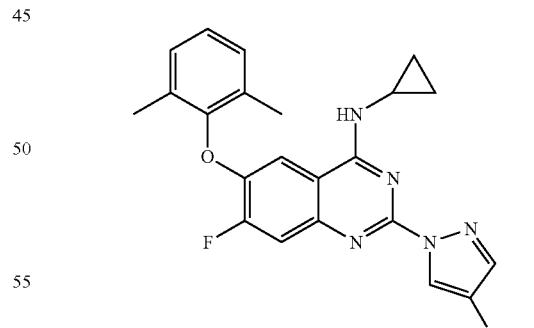

The titled compound was prepared in a manner analogous to EXAMPLE 1, using cycloproplyamine in step E. MS (ESI): mass calcd. for $C_{23}H_{20}FN_5O_3$, 433.2; m/z found, 434.0 [M+H]$^+$. $^1$H NMR (500 MHz, DMSO-d$_6$): 12.77 (s, 1H), 9.00 (d, J=0.7 Hz, 1H), 8.72 (d, J=2.7 Hz, 1H), 8.10 (d, J=0.7 Hz, 1H), 7.72 (d, J=11.8 Hz, 1H), 7.41 (d, J=8.9 Hz, 1H), 7.23-7.13 (m, 3H), 3.04-2.93 (m, 1H), 2.11 (s, 6H), 0.88-0.76 (m, 2H), 0.68-0.57 (m, 2H).

Example 15

1-((4-Cyclopropanemethylamino)-6-(2,6-dimethylphenoxy)-7-fluoroquinazolin-2-yl)-1H-pyrazole-4-carboxylic acid

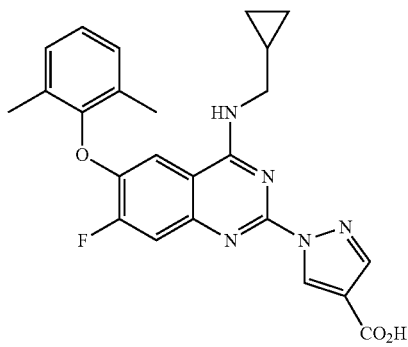 [SMILES: Cc1cccc(C)c1Oc1cc2c(NCC3CC3)nc(-n3cc(C(=O)O)cn3)nc2cc1F]

The titled compound was prepared in a manner analogous to EXAMPLE 1, using cyclopropanemethylamine in step E. MS (ESI): mass calcd. for $C_{24}H_{22}FN_5O_3$, 447.2; m/z found, 448.0 [M+H]$^+$. $^1$H NMR (500 MHz, DMSO-d$_6$): 12.75 (s, 1H), 8.95 (d, J=0.7 Hz, 1H), 8.76 (t, J=5.7 Hz, 1H), 8.09 (d, J=0.7 Hz, 1H), 7.71 (d, J=11.8 Hz, 1H), 7.39 (d, J=8.9 Hz, 1H), 7.28-7.14 (m, J=8.5, 6.9 Hz, 3H), 3.43-3.38 (m, 2H), 2.13 (s, 6H), 1.29-1.14 (m, 1H), 0.48-0.40 (m, 2H), 0.35-0.27 (m, 2H).

Example 16

1-(6-(2,6-Dimethylphenoxy)-7-fluoro-4-((tetrahydro-2H-pyran-4-yl)amino)quinazolin-2-yl)-1H-pyrazole-4-carboxylic acid

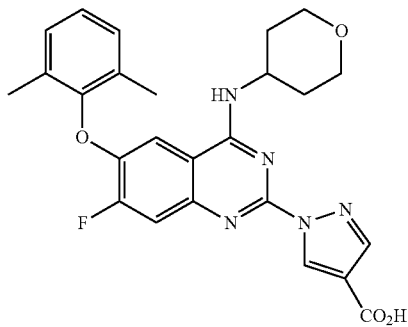 [SMILES: Cc1cccc(C)c1Oc1cc2c(NC3CCOCC3)nc(-n3cc(C(=O)O)cn3)nc2cc1F]

The titled compound was prepared in a manner analogous to EXAMPLE 1, using 4-aminotetrahydro-2H-pyran in step E. MS (ESI): mass calcd. for $C_{25}H_{24}FN_5O_4$, 477.2; m/z found, 478.0 [M+H]$^+$. $^1$H NMR (500 MHz, DMSO-d$_6$): 12.77 (s, 1H), 8.95 (d, J=0.5 Hz, 1H), 8.29 (d, J=7.5 Hz, 1H), 8.10 (d, J=0.5 Hz, 1H), 7.70 (d, J=11.8 Hz, 1H), 7.49 (d, J=8.9 Hz, 1H), 7.24-7.12 (m, 3H), 4.55-4.39 (m, 1H), 3.91 (dd, J=11.0, 4.0 Hz, 2H), 3.65-3.56 (m, 2H), 3.45 (t, J=11.1 Hz, 2H), 2.12 (s, 6H), 1.87 (dd, J=12.4, 2.6 Hz, 2H), 1.78-1.73 (m, 2H), 1.72-1.59 (m, 2H).

Example 17

1-(6-(2,6-Dimethylphenoxy)-7-fluoro-4-(4-methyl-1,4-diazepan-1-yl)quinazolin-2-yl)-1H-pyrazole-4-carboxylic acid

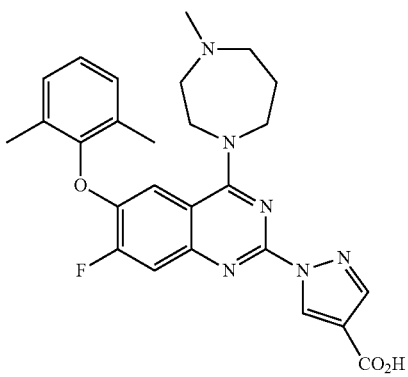 [SMILES: Cc1cccc(C)c1Oc1cc2c(N3CCCN(C)CC3)nc(-n3cc(C(=O)O)cn3)nc2cc1F]

The titled compound was prepared in a manner analogous to EXAMPLE 1, using 4-methyl-1,4-diazepane) in step E. MS (ESI): mass calcd. for $C_{26}H_{27}FN_6O_3$, 490.2; m/z found, 491.3 [M+H]$^+$. $^1$H NMR (400 MHz, DMSO-d$_6$): 8.94 (s, 1H), 8.09 (d, J=0.4 Hz, 1H), 7.81 (d, J=11.9 Hz, 1H), 7.32-7.18 (m, 3H), 6.89 (d, J=9.1 Hz, 1H), 3.84-3.73 (m, 2H), 3.66 (t, J=5.9 Hz, 2H), 2.73-2.54 (m, 4H), 2.31 (s, 3H), 2.13 (s, 6H), 1.87-1.75 (m, 2H).

Example 18

1-(6-(2,6-Dimethylphenoxy)-7-fluoro-4-thiomorpholinoquinazolin-2-yl)-1H-pyrazole-4-carboxylic acid

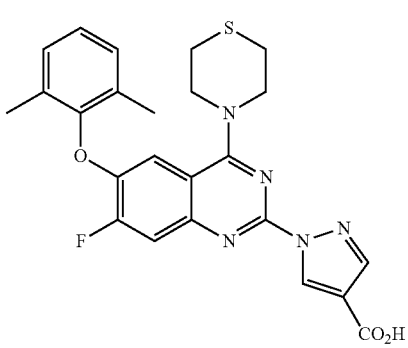

The titled compound was prepared in a manner analogous to EXAMPLE 1, using thiomorpholine in step E. MS (ESI): mass calcd. for $C_{24}H_{22}FN_5O_3S$, 479.1; m/z found, 480.0 [M+H]$^+$. $^1$H NMR (500 MHz, DMSO-d$_6$): 12.79 (s, 1H), 8.98 (d, J=0.7 Hz, 1H), 8.11 (d, J=0.7 Hz, 1H), 7.88 (d, J=11.8 Hz, 1H), 7.33-7.21 (m, 3H), 6.65 (d, J=9.1 Hz, 1H), 3.86-3.75 (m, 4H), 2.56-2.51 (m, 4H), 2.14 (s, 6H).

Example 19

1-(6-(2,6-Dimethylphenoxy)-7-fluoro-4-(4-hydroxypiperidin-1-yl)quinazolin-2-yl)-1H-pyrazole-4-carboxylic acid

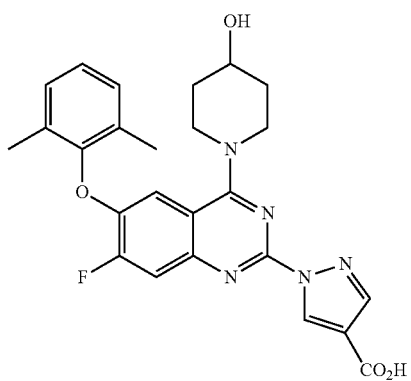 [SMILES: Cc1cccc(C)c1Oc1cc2c(N3CCC(O)CC3)nc(-n3cc(C(=O)O)cn3)nc2cc1F]

The titled compound was prepared in a manner analogous to EXAMPLE 1, using 4-hydroxypiperidine in step E. MS (ESI): mass calcd. for $C_{25}H_{24}FN_5O_3$, 477.2; m/z found, 478.1 [M+H]$^+$. $^1$H NMR (500 MHz, DMSO-d$_6$): 12.78 (s, 1H), 8.96 (d, J=0.7 Hz, 1H), 8.10 (d, J=0.7 Hz, 1H), 7.84 (d, J=11.8 Hz, 1H), 7.32-7.19 (m, 3H), 6.71 (d, J=9.1 Hz, 1H), 4.81 (d, J=4.0 Hz, 1H), 3.87-3.66 (m, 3H), 3.32-3.24 (m, 2H), 1.73-1.61 (m, 2H), 1.35-1.13 (m, 2H).

Example 20

1-(6-(2,6-Dimethylphenoxy)-7-fluoro-4-morpholinoquinazolin-2-yl)-1H-pyrazole-4-carboxylic acid

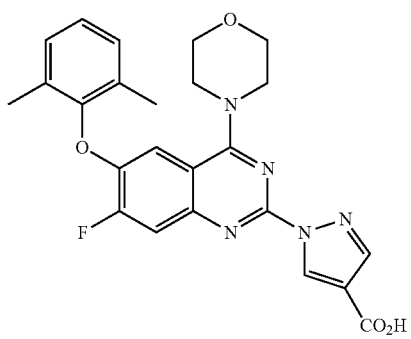 [SMILES: Cc1cccc(C)c1Oc1cc2c(N3CCOCC3)nc(-n3cc(C(=O)O)cn3)nc2cc1F]

The titled compound was prepared in a manner analogous to EXAMPLE 1, using morpholine in step E. MS (ESI): mass calcd. for $C_{24}H_{22}FN_5O_4$, 436.2; m/z found, 464.2 [M+H]$^+$. $^1$H NMR (500 MHz, DMSO-d$_6$): 12.79 (s, 1H), 9.00 (d, J=0.7 Hz, 1H), 8.11 (d, J=0.7 Hz, 1H), 7.89 (d, J=11.8 Hz, 1H), 7.31-7.21 (m, 3H), 6.68 (d, J=9.1 Hz, 1H), 3.56 (s, 8H), 2.12 (s, 6H).

Example 21

1-(4-(4-Acetamidopiperidin-1-yl)-6-(2,6-dimethylphenoxy)-7-fluoroquinazolin-2-yl)-1H-pyrazole-4-carboxylic acid

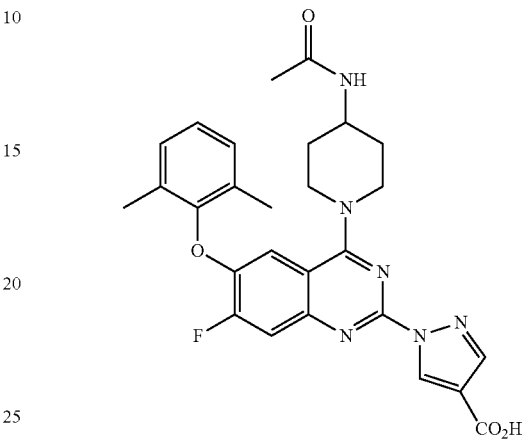

The titled compound was prepared in a manner analogous to EXAMPLE 1, using 4-acetamidopiperidine in step E. MS (ESI): mass calcd. for $C_{27}H_{27}FN_6O_4$, 518.2; m/z found, 519.1 [M+H]$^+$. $^1$H NMR (500 MHz, DMSO-d$_6$): 12.80 (s, 1H), 8.97 (d, J=0.7 Hz, 1H), 8.11 (d, J=0.7 Hz, 1H), 7.91-7.80 (m, 2H), 7.32-7.19 (m, 3H), 6.70 (d, J=9.0 Hz, 1H), 3.96 (d, J=13.5 Hz, 2H), 3.88-3.76 (m, 1H), 3.20 (t, J=11.1 Hz, 2H), 2.14 (s, 6H), 1.80 (s, 3H), 1.75-1.66 (m, 2H), 1.34-1.20 (m, 2H).

Example 22

1-(6-Cyclohexyl-4-methylamino-quinazolin-2-yl)-1H-pyrazole-4-carboxylic acid

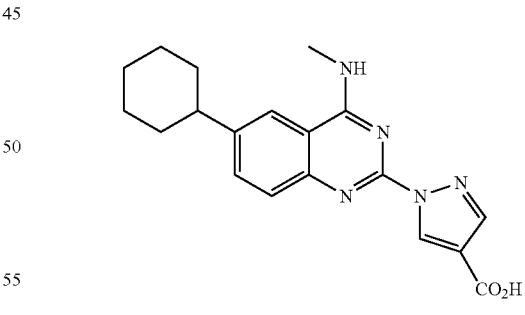

The titled compound was prepared in a manner analogous to EXAMPLE 1, Steps B-F using 4-cyclohexylaniline in step B and methylamine in step E. MS (ESI): mass calcd. for $C_{19}H_{21}N_5O_2$, 351.2; m/z found, 352.2 [M+H]$^+$. $^1$H NMR (500 MHz, DMSO-d$_6$): 12.74 (s, 1H), 9.04 (s, 1H), 8.78 (s, 1H), 8.10 (s, 2H), 7.70 (d, J=8.6 Hz, 1H), 7.66 (d, J=8.4 Hz, 1H), 3.17-3.07 (m, 3H), 2.65 (t, J=11.5 Hz, 1H), 1.95-1.80 (m, 4H), 1.75 (d, J=12.5 Hz, 1H), 1.60-1.35 (m, 4H), 1.30-1.20 (m, 1H).

Example 23

1-[6-Cyclohexyl-4-(2,6-dimethyl-benzylamino)-quinazolin-2-yl]-1H-pyrazole-4-carboxylic acid

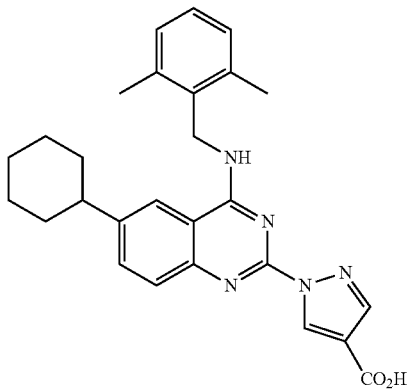 [SMILES: Cc1cccc(C)c1CNc1nc(-n2cc(C(=O)O)cn2)nc2ccc(C3CCCCC3)cc12]

The titled compound was prepared in a manner analogous to EXAMPLE 1, Steps B-F using 4-cyclohexylaniline in step B and 2,6-dimethylbenzylamine in step E. MS (ESI): mass calcd. for $C_{27}H_{29}N_5O_2$, 455.2; m/z found, 456.2 [M+H]$^+$. $^1$H NMR (500 MHz, DMSO-d$_6$): 12.72 (s, 1H), 9.09 (s, 1H), 8.56 (s, 1H), 8.26 (s, 1H), 8.11 (s, 1H), 7.75-7.63 (m, 2H), 7.20-7.13 (m, 1H), 7.13-7.06 (m, 2H), 4.87 (d, J=4.3 Hz, 2H), 2.68-2.56 (m, 1H), 2.38 (s, 6H), 1.82 (t, J=12.0 Hz, 4H), 1.71 (d, J=12.9 Hz, 1H), 1.55-1.43 (m, 2H), 1.43-1.30 (m, 2H), 1.30-1.18 (m, 1H).

Example 24

1-(4-Amino-6-cyclohexylquinazolin-2-yl)-1H-pyrazole-4-carboxylic acid

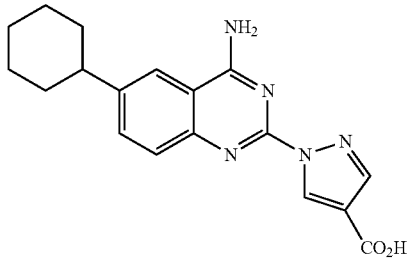 [SMILES: Nc1nc(-n2cc(C(=O)O)cn2)nc2ccc(C3CCCCC3)cc12]

The titled compound was prepared in a manner analogous to EXAMPLE 1 steps B through F using 4-cyclohexylaniline in step B and ammonia in dioxane in step E. MS (ESI): mass calcd. for $C_{18}H_{19}N_5O_2$, 337.2; m/z found, 338.2 [M+H]$^+$. $^1$H NMR (400 MHz, DMSO-d$_6$) 13.57-11.64 (m, 1H), 8.93 (s, 1H), 8.59 (s, 2H), 8.17 (d, J=9.6 Hz, 2H), 7.75 (q, J=8.7 Hz, 2H), 2.66 (t, J=11.7 Hz, 1H), 1.86 (t, J=12.7 Hz, 4H), 1.75 (d, J=12.2 Hz, 1H), 1.59-1.34 (m, 4H), 1.34-1.21 (m, 1H).

Example 25

1-(6-Cyclohexyl-4-(pyrrolidin-1-yl)quinazolin-2-yl)-1H-pyrazole-4-carboxylic acid

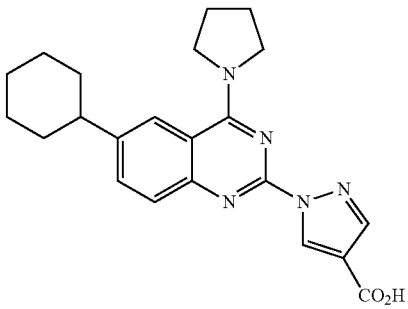 [SMILES: O=C(O)c1cnn(-c2nc(N3CCCC3)c3cc(C4CCCCC4)ccc3n2)c1]

The titled compound was prepared in a manner analogous to EXAMPLE 1 steps B through F using 4-cyclohexylaniline in step B and pyrrolidine in step E. MS (ESI): mass calcd. for $C_{22}H_{25}N_5O_2$, 391.2; m/z found, 392.1 [M+H]$^+$. $^1$H NMR (500 MHz, DMSO-d$_6$): 12.80 (s, 1H), 9.04 (s, 1H), 8.17 (s, 1H), 8.12 (s, 1H), 7.77 (s, 2H), 4.05 (s, 4H), 2.81-2.66 (m, 1H), 2.03 (s, 4H), 1.92-1.79 (m, 4H), 1.73 (d, J=12.8 Hz, 1H), 1.58-1.35 (m, 4H), 1.31-1.16 (m, 1H).

Example 26

1-(6-Cyclohexyl-4-(piperidin-1-yl)quinazolin-2-yl)-1H-pyrazole-4-carboxylic acid

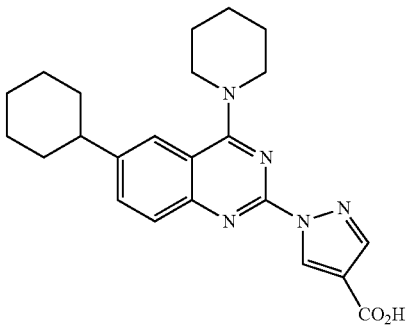 [SMILES: O=C(O)c1cnn(-c2nc(N3CCCCC3)c3cc(C4CCCCC4)ccc3n2)c1]

The titled compound was prepared in a manner analogous to EXAMPLE 1 steps B through F using 4-cyclohexylaniline in step B and piperidine in step E. MS (ESI): mass calcd. for $C_{23}H_{27}N_5O_2$, 405.2; m/z found, 406.1 [M+H]$^+$. $^1$H NMR (400 MHz, DMSO-d$_6$) 12.78-11.82 (m, 1H), 8.99 (s, 1H), 8.10 (s, 1H), 7.75 (s, 2H), 7.73 (s, 1H), 3.85 (s, 4H), 2.69 (s, 1H), 1.94-1.89 (m, 2H), 1.83-1.75 (m, 2H), 1.75 (s, 6H), 1.55-1.39 (m, 4H), 1.34-1.28 (m, 2H).

Example 27

1-(6-Cyclohexyl-4-(diethylamino)quinazolin-2-yl)-1H-pyrazole-4-carboxylic acid

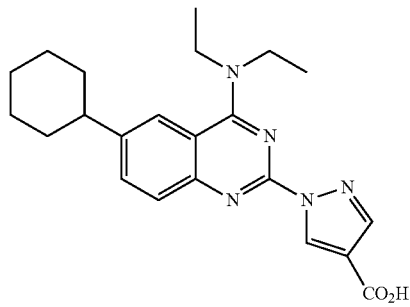 [SMILES: CCN(CC)c1nc(-n2cc(C(=O)O)cn2)nc2ccc(C3CCCCC3)cc12]

The titled compound was prepared in a manner analogous to EXAMPLE 1 steps B through F using 4-cyclohexylaniline in step B and diethylamine in step E. MS (ESI): mass calcd. for $C_{22}H_{27}N_5O_2$, 393.2; m/z found, 394.1 [M+H]$^+$. $^1$H NMR (400 MHz, DMSO-d$_6$): 12.76 (s, 1H), 8.94 (s, 1H), 8.10 (s, 1H), 7.80 (s, 1H), 7.73 (s, 1H), 7.72 (s, 1H), 3.82 (q, J=6.9 Hz, 4H), 2.67 (s, 1H), 1.91 (s, 2H), 1.84 (s, 2H), 1.74 (d, J=12.1 Hz, 1H), 1.51-1.35 (m, 11H).

Example 28

1-(6-Cyclohexyl-4-(phenylamino)quinazolin-2-yl)-1H-pyrazole-4-carboxylic acid

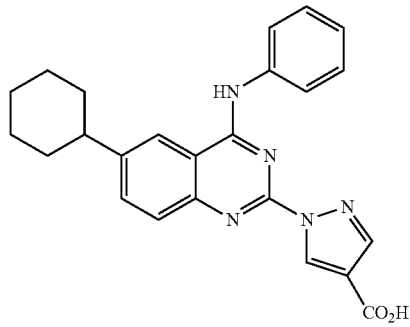 [SMILES: O=C(O)c1cnn(-c2nc(Nc3ccccc3)c3cc(C4CCCCC4)ccc3n2)c1]

The titled compound was prepared in a manner analogous to EXAMPLE 1 steps B through F using 4-cyclohexylaniline in step B and aniline in step E. MS (ESI): mass calcd. for $C_{24}H_{23}N_5O_2$, 413.2; m/z found, 414.3 [M+H]$^+$. $^1$H NMR (400 MHz, DMSO-d$_6$): 12.79 (s, 1H), 10.22 (s, 1H), 8.82 (s, 1H), 8.45 (s, 1H), 8.13 (s, 1H), 7.91 (d, J=7.6 Hz, 2H), 7.81 (d, J=8.6 Hz, 1H), 7.76 (d, J=8.5 Hz, 1H), 7.52-7.45 (m, 2H), 7.23 (t, J=7.4 Hz, 1H), 3.65-3.56 (m, 1H), 2.72 (t, J=11.8 Hz, 1H), 1.96-1.83 (m, 4H), 1.82-1.72 (m, 2H), 1.66-1.52 (m, 2H), 1.44-1.32 (m, 2H), 1.30-1.23 (m, 1H).

Example 29

1-(4-((2-Chlorophenyl)amino)-6-cyclohexylquinazolin-2-yl)-1H-pyrazole-4-carboxylic acid

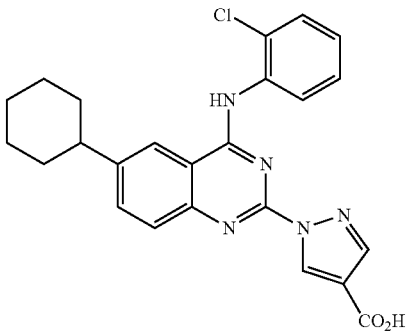 [SMILES: O=C(O)c1cnn(-c2nc(Nc3ccccc3Cl)c3cc(C4CCCCC4)ccc3n2)c1]

The titled compound was prepared in a manner analogous to EXAMPLE 1 steps B through F using 4-cyclohexylaniline in step B and 2-chloroaniline in step E. MS (ESI): mass calcd. for $C_{24}H_{22}ClN_5O_2$, 447.2; m/z found, 448.3 [M+H]$^+$. $^1$H NMR (400 MHz, DMSO-d$_6$): 10.35 (s, 1H), 8.50 (s, 1H), 8.42 (s, 1H), 8.04 (s, 1H), 7.83 (dd, J=8.7, 1.7 Hz, 1H), 7.76 (d, J=8.6 Hz, 1H), 7.69 (dd, J=4.0, 1.6 Hz, 1H), 7.67 (dd, J=3.9, 1.6 Hz, 1H), 7.51 (td, J=7.6, 1.5 Hz, 1H), 7.43 (td, J=7.7, 1.7 Hz, 1H), 2.83-2.64 (m, 1H), 1.94 (d, J=11.8 Hz, 2H), 1.87 (d, J=12.7 Hz, 2H), 1.79-1.73 (m, 1H), 1.68-1.51 (m, 2H), 1.51-1.36 (m, 2H), 1.36-1.22 (m, 1H).

Example 30

1-(4-(4-Cyanopiperidin-1-yl)-6-cyclohexylquinazolin-2-yl)-1H-pyrazole-4-carboxylic acid

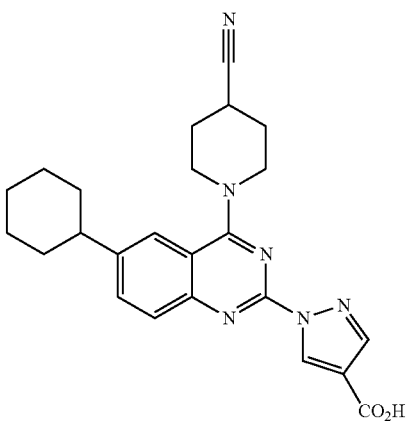 [SMILES: N#CC1CCN(c2nc(-n3cc(C(=O)O)cn3)nc3ccc(C4CCCCC4)cc23)CC1]

The titled compound was prepared in a manner analogous to EXAMPLE 1 steps B through F using 4-cyclohexylaniline in step B and 4-cyanopiperidine in step E. MS (ESI): mass calcd. for $C_{24}H_{26}N_6O_2$, 430.2; m/z found, 431.1 [M+H]$^+$. $^1$H NMR (500 MHz, DMSO-d$_6$): 12.78 (s, 1H), 9.02 (s, 1H), 8.11 (s, 1H), 7.78 (s, 2H), 7.75 (s, 1H), 4.16-4.09 (m, 2H), 3.75-3.64 (m, 2H), 3.30-3.20 (m, 1H), 2.89-2.73 (m, 1H), 2.27-2.14 (m, 2H), 2.01-1.91 (m, 2H), 1.88 (d, J=12.3 Hz, 2H), 1.84 (d, J=12.4 Hz, 2H), 1.74 (d, J=12.6 Hz, 1H), 1.57-1.36 (m, 5H), 1.35-1.23 (m, 1H).

Example 31

1-(6-Cyclohexyl-4-(4-fluoropiperidin-1-yl)quinazolin-2-yl)-1H-pyrazole-4-carboxylic acid

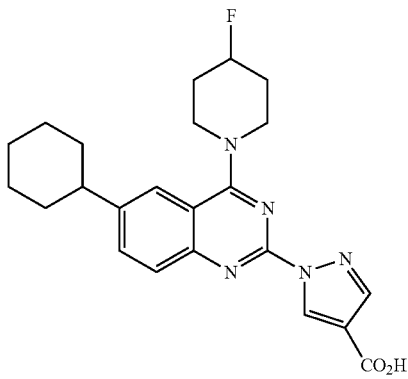 [SMILES: O=C(O)c1cnn(-c2nc(N3CCC(F)CC3)c3cc(C4CCCCC4)ccc3n2)c1]

The titled compound was prepared in a manner analogous to EXAMPLE 1 steps B through F using 4-cyclohexylaniline in step B and 4-fluoropiperidine in step E. MS (ESI): mass calcd. for $C_{23}H_{26}FN_5O_2$, 423.2; m/z found, 424.1 $[M+H]^+$. $^1$H NMR (500 MHz, DMSO-$d_6$): 12.78 (s, 1H), 9.01 (s, 1H), 8.11 (s, 1H), 7.78 (s, 3H), 5.19-4.93 (m, 1H), 3.92-3.79 (m, 4H), 2.72-2.64 (m, 1H), 2.23-2.08 (m, 2H), 2.03-1.92 (m, 2H), 1.89 (d, J=12.7 Hz, 2H), 1.83 (d, J=12.5 Hz, 2H), 1.74 (d, J=12.7 Hz, 1H), 1.52-1.39 (m, 4H), 1.33-1.22 (m, 1H).

Example 32

1-(6-Cyclohexyl-4-(cyclopropylamino)quinazolin-2-yl)-1H-pyrazole-4-carboxylic acid

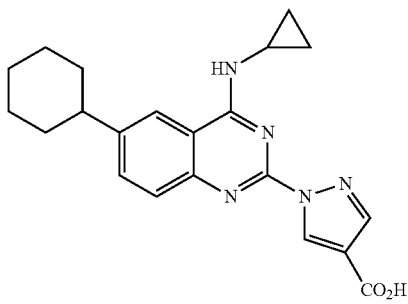 [SMILES: O=C(O)c1cnn(-c2nc(NC3CC3)c3cc(C4CCCCC4)ccc3n2)c1]

The titled compound was prepared in a manner analogous to EXAMPLE 1 steps B through F using 4-cyclohexylaniline in step B and cyclopropylamine in step E. MS (ESI): mass calcd. for $O_{21}H_{23}N_5O_2$, 377.1; m/z found, 378.1 $[M+H]^+$. $^1$H NMR (400 MHz, DMSO-$d_6$): 9.33 (5, 1H), 9.14 (5, 1H), 8.26 (5, 1H), 8.25 (5, 1H), 7.83-7.73 (m, 2H), 2.81-2.65 (m, 1H), 1.84 (d, J=8.0 Hz, 4H), 1.74-1.62 (m, 1H), 1.52-1.48 (m, 2H), 1.46-1.33 (m, 2H), 1.26-1.14 (m, 1H), 0.98-0.88 (m, 2H), 0.88-0.80 (m, 2H).

Example 33

1-(6-Cyclohexyl-4-morpholinoquinazolin-2-yl)-1H-pyrazole-4-carboxylic acid

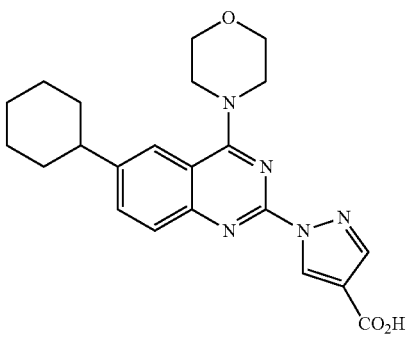

The titled compound was prepared in a manner analogous to EXAMPLE 1 steps B through F using 4-cyclohexylaniline in step B and morpholine in step E. MS (ESI): mass calcd. for $C_{22}H_{25}N_5O_3$, 407.2; m/z found, 408.1 $[M+H]^+$. $^1$H NMR (400 MHz, DMSO-$d_6$): 12.79 (s, 1H), 9.03 (s, 1H), 8.12 (s, 1H), 7.79 (5, 1H), 7.78 (5, 2H), 4.02-3.92 (m, 4H), 3.82 (d, J=4.3 Hz, 4H), 2.73-2.64 (m, 1H), 1.92-1.85 (m, 4H), 1.73-1.68 (m, 1H), 1.53-1.38 (m, 4H), 1.34-1.21 (m, 1H).

Example 34

1-(6-Cyclohexyl-4-thiomorpholinoquinazolin-2-yl)-1H-pyrazole-4-carboxylic acid

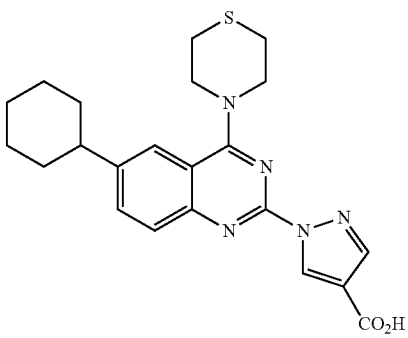 [SMILES: O=C(O)c1cnn(-c2nc(N3CCSCC3)c3cc(C4CCCCC4)ccc3n2)c1]

The titled compound was prepared in a manner analogous to EXAMPLE 1 steps B through F using 4-cyclohexylaniline in step B and thiomorpholine in step E. MS (ESI): mass calcd. for $C_{22}H_{25}N_5O_2S$, 423.1; m/z found, 424.1 $[M+H]^+$. $^1$H NMR (500 MHz, DMSO-$d_6$): 12.80 (s, 1H), 9.01 (s, 1H), 8.11 (s, 1H), 7.78 (s, 2H), 7.73 (s, 1H), 4.19-4.12 (m, 4H), 2.98-2.87 (m, 4H), 2.72-2.64 (m, 1H), 2.06-1.89 (m, 2H), 1.88-1.82 (m, 2H), 1.76-1.70 (m, 1H), 1.52-1.39 (m, 4H), 1.29-1.14 (m, 1H).

Example 35

1-(4-Cyanamido-6-cyclohexylquinazolin-2-yl)-1H-pyrazole-4-carboxylic acid

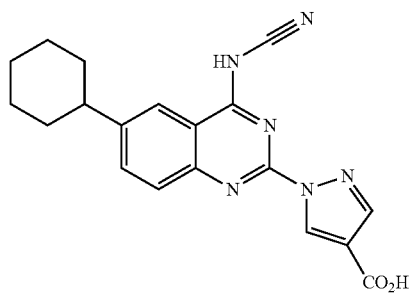 [SMILES: N#CNc1nc(-n2cc(C(=O)O)cn2)nc2ccc(C3CCCCC3)cc12]

The titled compound was prepared in a manner analogous to EXAMPLE 1 steps B through F using 4-cyclohexylaniline in step B and sodium cyanamide in step E. MS (ESI): mass calcd. for $C_{19}H_{18}N_6O_2$, 362.1; m/z found, 363.1 [M+H]$^+$. $^1$H NMR (400 MHz, DMSO-d$_6$): 13.19 (s, 1H), 8.89 (s, 1H), 8.43 (s, 1H), 7.97 (s, 1H), 7.87 (d, J=8.6 Hz, 1H), 7.79 (d, J=8.6 Hz, 1H), 2.66 (s, 1H), 1.82 (s, 4H), 1.72-1.68 (m, 1H), 1.42-1.30 (m, 4H), 1.26-1.19 (m, 1H).

Example 36

1-(4-(tert-Butylamino)-6-cyclohexylquinazolin-2-yl)-1H-pyrazole-4-carboxylic acid

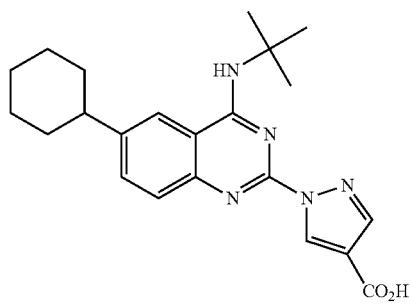 [SMILES: CC(C)(C)Nc1nc(-n2cc(C(=O)O)cn2)nc2ccc(C3CCCCC3)cc12]

The titled compound was prepared in a manner analogous to EXAMPLE 1 steps B through F using 4-cyclohexylaniline in step B and tert-butylamine in step E. MS (ESI): mass calcd. for $C_{22}H_{27}N_5O_2$, 393.2; m/z found, 394.2 [M+H]$^+$. $^1$H NMR (400 MHz, DMSO-d$_6$): 13.27-12.44 (m, 1H), 8.89 (s, 1H), 8.29 (s, 1H), 8.18 (s, 1H), 7.94 (s, 1H), 7.76-7.71 (m, 1H), 7.69 (d, J=8.6 Hz, 1H), 2.67 (t, J=11.8 Hz, 1H), 1.85 (d, J=10.5 Hz, 4H), 1.75 (d, J=12.4 Hz, 1H), 1.63 (s, 9H), 1.59-1.50 (m, 2H), 1.48-1.38 (m, 2H), 1.35-1.24 (m, 1H).

Example 37

1-(4-(Azepan-1-yl)-6-cyclohexylquinazolin-2-yl)-1H-pyrazole-4-carboxylic acid

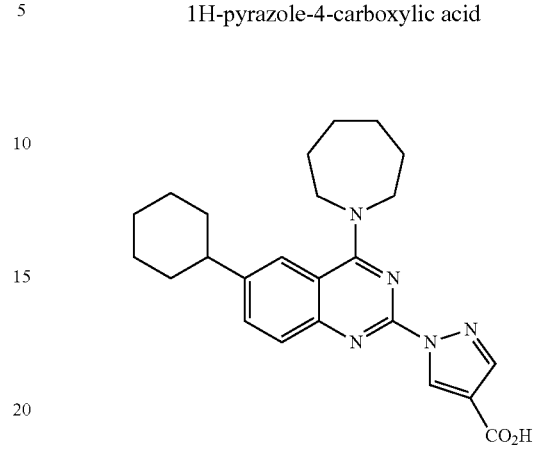

The titled compound was prepared in a manner analogous to EXAMPLE 1 steps B through F using 4-cyclohexylaniline in step B and homopiperidine in step E. MS (ESI): mass calcd. for $C_{24}H_{29}N_5O_2$, 419.2; m/z found, 420.1 [M+H]$^+$. $^1$H NMR (400 MHz, DMSO-d$_6$): 12.76 (s, 1H), 8.95 (s, 1H), 8.09 (s, 1H), 7.92 (s, 1H), 7.74-7.69 (m, 2H), 4.08-3.96 (m, 4H), 2.68 (s, 1H), 1.98 (s, 4H), 1.89 (d, J=10.5 Hz, 2H), 1.83 (d, J=12.0 Hz, 2H), 1.73 (d, J=11.9 Hz, 1H), 1.61 (s, 4H), 1.57-1.44 (m, 4H), 1.27 (d, J=12.2 Hz, 1H).

Example 38

1-(6-Cyclohexyl-4-(dimethylamino)quinazolin-2-yl)-1H-pyrazole-4-carboxylic acid

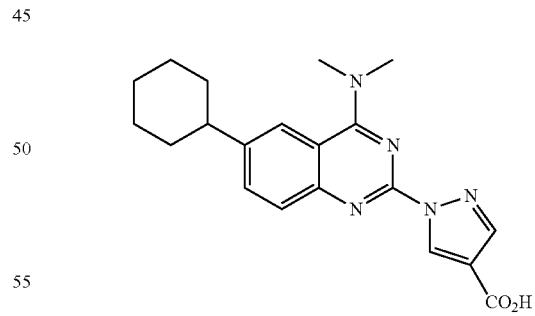

The titled compound was prepared in a manner analogous to EXAMPLE 1 steps B through F using 4-cyclohexylaniline in step B and dimethylamine in step E. MS (ESI): mass calcd. for $C_{20}H_{23}N_5O_2$, 365.2; m/z found, 366.2 [M+H]$^+$. $^1$H NMR (400 MHz, DMSO-d$_6$): 13.57-11.86 (m, 1H), 9.11 (s, 1H), 8.24 (s, 1H), 8.05 (s, 1H), 7.82 (q, J=8.8 Hz, 2H), 3.54 (s, 6H), 2.73 (t, J=11.5 Hz, 1H), 1.85 (t, J=12.7 Hz, 4H), 1.73 (d, J=11.6 Hz, 1H), 1.57-1.44 (m, 4H), 1.34-1.20 (m, 1H).

Example 39

1-(6-Cyclohexyl-4-((cyclohexylmethyl)amino)quinazolin-2-yl)-1H-pyrazole-4-carboxylic acid

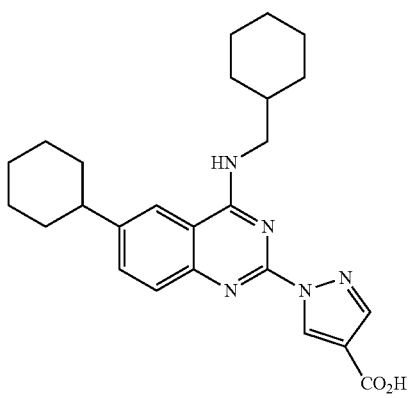 [SMILES: O=C(O)c1cnn(-c2nc(NCC3CCCCC3)c3cc(C4CCCCC4)ccc3n2)c1]

The titled compound was prepared in a manner analogous to EXAMPLE 1 steps B through F using 4-cyclohexylaniline in step B and cyclohexylmethylamine in step E. MS (ESI): mass calcd. for $C_{25}H_{31}N_5O_2$, 433.2; m/z found, 434.2 [M+H]$^+$. $^1$H NMR (400 MHz, DMSO-d$_6$): 12.76 (s, 1H), 8.95 (s, 1H), 8.09 (s, 1H), 7.92 (5, 1H), 7.74-7.69 (m, 2H), 4.08-3.96 (m, 4H), 2.68 (s, 1H), 1.98 (s, 4H), 1.89 (d, J=10.5 Hz, 2H), 1.83 (d, J=12.0 Hz, 2H), 1.73 (d, J=11.9 Hz, 1H), 1.61 (s, 4H), 1.44-1.31 (m, 4H), 1.27 (d, J=12.2 Hz, 1H).

Example 40

1-(6-Cyclohexyl-4-(methylsulfonamido)quinazolin-2-yl)-1H-pyrazole-4-carboxylic acid

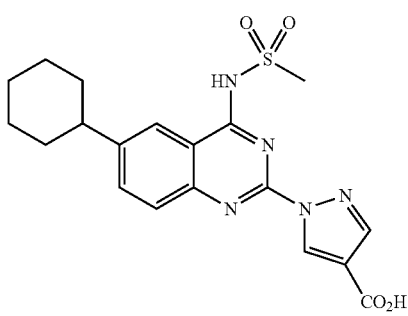 [SMILES: CS(=O)(=O)Nc1nc(-n2cc(C(=O)O)cn2)nc2ccc(C3CCCCC3)cc12]

The titled compound was prepared in a manner analogous to EXAMPLE 1 steps B through F using 4-cyclohexylaniline in step B and methanesulfonamide in step E. MS (ESI): mass calcd. for $C_{19}H_{21}N_5O_4S$, 415.1; m/z found, 416.2 [M+H]$^+$. $^1$H NMR (400 MHz, DMSO-d$_6$): 12.88 (s, 1H), 8.93 (s, 1H), 8.32 (s, 1H), 8.26 (s, 1H), 7.91-7.81 (m, 2H), 3.65 (s, 3H), 2.70 (t, J=11.6 Hz, 1H), 1.87 (t, J=14.8 Hz, 4H), 1.79-1.70 (m, 1H), 1.59-1.34 (m, 5H), 1.28-1.12 (m, 1H).

Example 41

1-(4-(Dimethylamino)-6-phenylquinazolin-2-yl)-1H-pyrazole-4-carboxylic acid

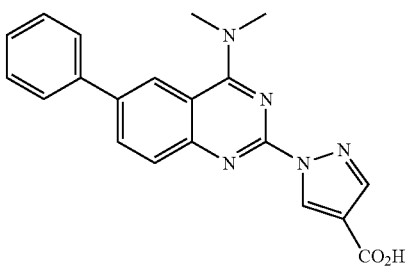 [SMILES: CN(C)c1nc(-n2cc(C(=O)O)cn2)nc2ccc(-c3ccccc3)cc12]

The titled compound was prepared in a manner analogous to EXAMPLE 1 steps B through F using 4-phenylaniline in step B and dimethylamine in step E. MS (ESI): mass calcd. for $C_{20}H_{17}N_5O_2$, 359.1; m/z found, 360.1 [M+H]$^+$. $^1$H NMR (400 MHz, DMSO-d$_6$): 9.11 (s, 1H), 8.45 (s, 1H), 8.21 (s, 1H), 8.18 (d, J=8.7, 1H), 7.94 (d, J=8.7 Hz, 1H), 7.81 (d, J=7.7 Hz, 2H), 7.53 (t, J=7.7 Hz, 2H), 7.43 (t, J=7.3 Hz, 1H), 3.59 (s, 6H).

Example 42

1-(4-(Ethyl(methyl)amino)-6-phenylquinazolin-2-yl)-1H-pyrazole-4-carboxylic acid

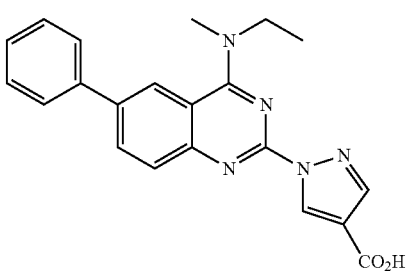 [SMILES: CCN(C)c1nc(-n2cc(C(=O)O)cn2)nc2ccc(-c3ccccc3)cc12]

The titled compound was prepared in a manner analogous to EXAMPLE 1 steps B through F using 4-phenylaniline in step B and N-methylethylamine in step E. MS (ESI): mass calcd. for $C_{21}H_{19}N_5O_2$, 373.1; m/z found, 374.1 [M+H]$^+$. $^1$H NMR (400 MHz, DMSO-d$_6$): 13.24-12.33 (m, 1H), 9.05 (s, 1H), 8.37 (s, 1H), 8.19 (s, 1H), 8.17 (dd, J=8.8, 2.0 Hz, 1H), 7.92 (d, J=8.7 Hz, 1H), 7.83-7.78 (m, 2H), 7.53 (t, J=7.6 Hz, 2H), 7.43 (t, J=7.4 Hz, 1H), 3.96 (q, J=7.0 Hz, 2H), 3.57 (s, 3H), 1.41 (t, J=7.0 Hz, 3H).

Example 43

1-(6-Phenyl-4-(pyrrolidin-1-yl)quinazolin-2-yl)-1H-pyrazole-4-carboxylic acid

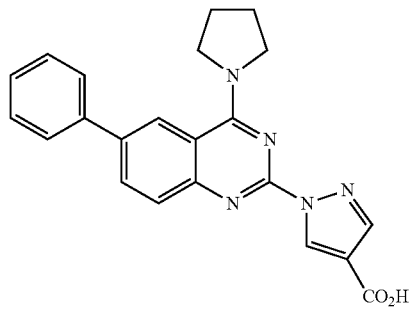 [SMILES: O=C(O)c1cnn(-c2nc(N3CCCC3)c3cc(-c4ccccc4)ccc3n2)c1]

The titled compound was prepared in a manner analogous to EXAMPLE 1 steps B through F using 4-phenylaniline in step B and pyrrolidine in step E. MS (ESI): mass calcd. for $C_{22}H_{19}N_5O_2$, 385.1; m/z found, 386.1 [M+H]$^+$. $^1$H NMR (400 MHz, DMSO-$d_6$): 9.09 (s, 1H), 8.51 (s, 1H), 8.24 (s, 1H), 8.20 (dd, J=8.7, 1.6 Hz, 1H), 7.96 (d, J=8.7 Hz, 1H), 7.85-7.79 (m, 2H), 7.53 (t, J=7.6 Hz, 2H), 7.44 (t, J=7.4 Hz, 1H), 4.16 (s, 4H), 2.05 (s, 4H).

Example 44

1-(6-Phenyl-4-(phenylamino)quinazolin-2-yl)-1H-pyrazole-4-carboxylic acid

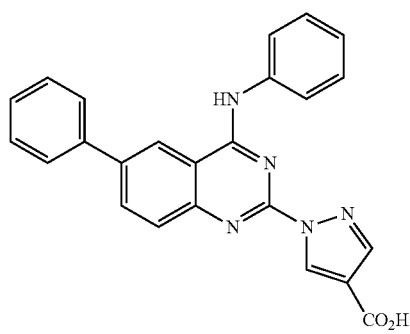 [SMILES: O=C(O)c1cnn(-c2nc(Nc3ccccc3)c3cc(-c4ccccc4)ccc3n2)c1]

The titled compound was prepared in a manner analogous to EXAMPLE 1 steps B through F using 4-phenylaniline in step B and aniline in step E. MS (ESI): mass calcd. for $C_{24}H_{17}N_5O_2$, 407.1; m/z found, 408.0 [M+H]$^+$. $^1$H NMR (400 MHz, DMSO-$d_6$): 12.81 (s, 1H), 10.39 (s, 1H), 8.94 (s, 1H), 8.86 (s, 1H), 8.25 (dd, J=8.7, 1.9 Hz, 1H), 8.14 (d, J=0.6 Hz, 1H), 7.93-7.81 (m, 5H), 7.58 (t, J=7.7 Hz, 2H), 7.49 (dd, J=15.4, 7.2 Hz, 3H), 7.25 (t, J=7.4 Hz, 1H).

Example 45

1-(6-Phenyl-4-(piperidin-1-yl)quinazolin-2-yl)-1H-pyrazole-4-carboxylic acid

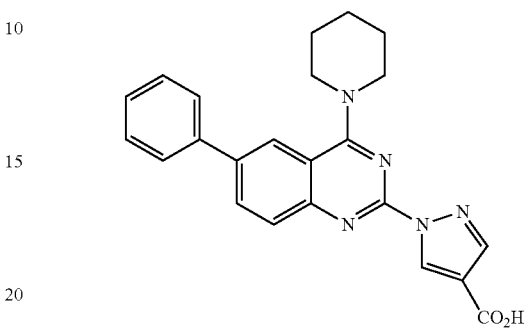

The titled compound was prepared in a manner analogous to EXAMPLE 1 steps B through F using 4-phenylaniline in step B and piperidine in step E. MS (ESI): mass calcd. for $C_{23}H_{21}N_5O_2$, 399.1; m/z found, 400.1 [M+H]$^+$. $^1$H NMR (400 MHz, DMSO-$d_6$): 12.80 (5, 1H), 9.03 (s, 1H), 8.19-8.12 (m, 3H), 7.92-7.87 (m, 1H), 7.83-7.77 (m, 2H), 7.54 (t, J=7.6 Hz, 2H), 7.43 (t, J=7.4 Hz, 1H), 3.94 (5, 4H), 1.77 (5, 6H).

Example 46

1-(4-(Diethylamino)-6-phenylquinazolin-2-yl)-1H-pyrazole-4-carboxylic acid

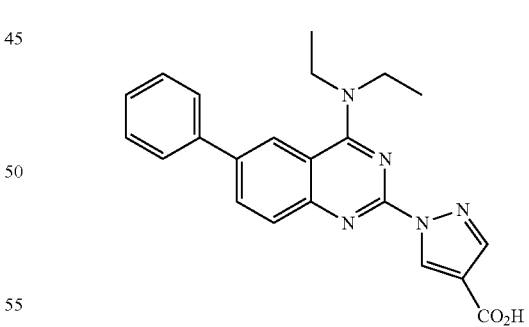

The titled compound was prepared in a manner analogous to EXAMPLE 1 steps B through F using 4-phenylaniline in step B and diethylamine in step E. MS (ESI): mass calcd. for $C_{22}H_{21}N_5O_2$, 387.1; m/z found, 388.1 [M+H]$^+$. $^1$H NMR (400 MHz, DMSO-$d_6$): 8.97 (s, 1H), 8.22 (d, J=1.8 Hz, 1H), 8.14 (dd, J=8.9, 2.1 Hz, 1H), 8.13 (s, 1H), 7.87 (d, J=8.7 Hz, 1H), 7.81-7.75 (m, 2H), 7.54 (t, J=7.7 Hz, 2H), 7.43 (t, J=7.4 Hz, 1H), 3.89 (q, J=6.9 Hz, 4H), 1.45 (t, J=7.0 Hz, 6H).

Example 47

1-(4-((2-Chlorophenyl)amino)-6-phenylquinazolin-2-yl)-1H-pyrazole-4-carboxylic acid

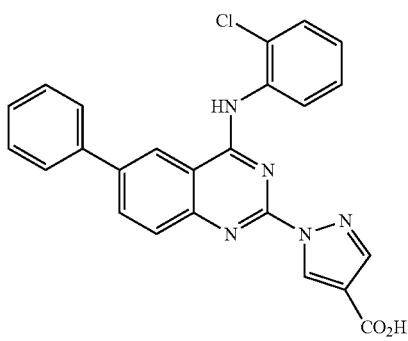 [SMILES: O=C(O)c1cnn(-c2nc(Nc3ccccc3Cl)c3cc(-c4ccccc4)ccc3n2)c1]

The titled compound was prepared in a manner analogous to EXAMPLE 1 steps B through F using 4-phenylaniline in step B and 2-chloroaniline in step E. MS (ESI): mass calcd. for $C_{24}H_{16}ClN_5O_2$, 441.1; m/z found, 442.1 [M+H]$^+$. $^1$H NMR (400 MHz, DMSO-d$_6$): 10.56 (s, 1H), 8.94 (s, 1H), 8.54 (s, 1H), 8.29 (dd, J=8.7, 1.9 Hz, 1H), 8.07 (s, 1H), 7.93 (d, J=8.7 Hz, 3H), 7.75-7.68 (m, 2H), 7.58 (t, J=7.7 Hz, 2H), 7.62-7.53 (m, 1H), 7.49-7.42 (m, 2H).

Example 48

1-(4-(Azepan-1-yl)-6-phenylquinazolin-2-yl)-1H-pyrazole-4-carboxylic acid

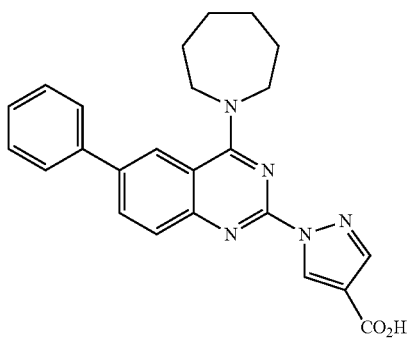 [SMILES: O=C(O)c1cnn(-c2nc(N3CCCCCC3)c3cc(-c4ccccc4)ccc3n2)c1]

The titled compound was prepared in a manner analogous to EXAMPLE 1 steps B through F using 4-phenylaniline in step B and homopiperidine in step E. MS (ESI): mass calcd. for $C_{24}H_{23}N_5O_2$, 413.1; m/z found, 414.1 [M+H]$^+$. $^1$H NMR (400 MHz, DMSO-d$_6$): 12.81 (s, 1H), 9.00 (s, 1H), 8.34 (s, 1H), 8.14 (dd, J=8.3, 1.2 Hz, 2H), 7.88 (d, J=8.7 Hz, 1H), 7.81-7.75 (m, 2H), 7.53 (t, J=7.7 Hz, 2H), 7.45-7.40 (m, 1H), 4.15-4.02 (m, 4H), 2.01 (s, 4H), 1.62 (s, 4H).

Example 49

1-(4-((Cyclohexylmethyl)amino)-6-phenylquinazolin-2-yl)-1H-pyrazole-4-carboxylic acid

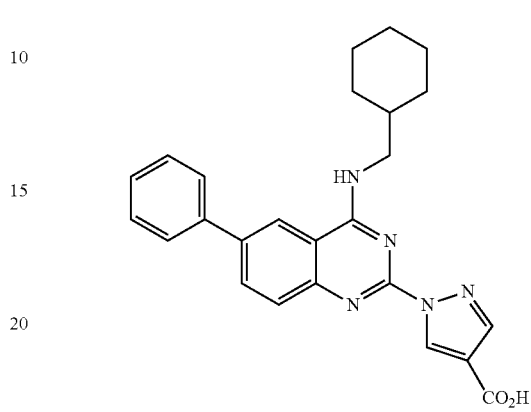

The titled compound was prepared in a manner analogous to EXAMPLE 1 steps B through F using 4-phenylaniline in step B and N-methylcyclohexylamine in step E. MS (ESI): mass calcd. for $C_{25}H_{25}N_5O_2$, 427.2; m/z found, 428.1 [M+H]$^+$. $^1$H NMR (400 MHz, DMSO-d$_6$): 12.80 (s, 1H), 9.02 (s, 1H), 8.97 (s, 1H), 8.70 (s, 1H), 8.19-8.12 (m, 2H), 7.89-7.84 (m, 2H), 7.82 (d, J=8.7 Hz, 1H), 7.55 (t, J=7.7 Hz, 2H), 7.44 (t, J=7.3 Hz, 1H), 3.56 (s, 3H), 1.92-1.83 (m, 3H), 1.81-1.72 (m, 2H), 1.64 (s, 1H), 1.31-1.13 (m, 3H), 1.13-1.08 (m, 2H).

Example 50

1-(4-Cyanamido-6-phenylquinazolin-2-yl)-1H-pyrazole-4-carboxylic acid

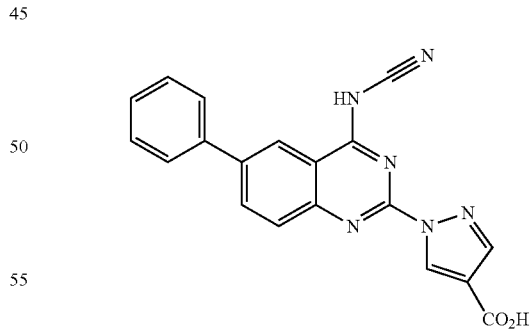

The titled compound was prepared in a manner analogous to EXAMPLE 1 steps B through F using 4-phenylaniline in step B and sodium cyanamide in step E. MS (ESI): mass calcd. for $C_{19}H_{12}N_6O_2$, 356.1; m/z found, 357.1 [M+H]$^+$. $^1$H NMR (500 MHz, DMSO-d$_6$): 13.15 (s, 1H), 8.91 (s, 1H), 8.40 (s, 1H), 8.35 (s, 1H), 8.19 (dd, J=8.7, 2.0 Hz, 1H), 7.97 (d, J=8.6 Hz, 1H), 7.76 (d, J=7.4 Hz, 2H), 7.52 (t, J=7.6 Hz, 2H), 7.43 (t, J=7.4 Hz, 1H).

Example 51

1-(4-(Cyclopropylamino)-6-phenylquinazolin-2-yl)-1H-pyrazole-4-carboxylic acid

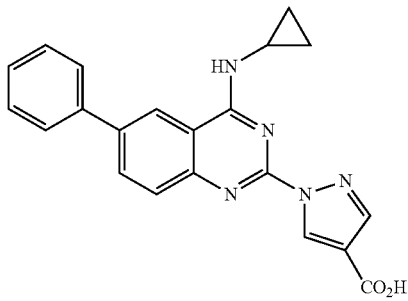 [SMILES: O=C(O)c1cnn(-c2nc(NC3CC3)c3cc(-c4ccccc4)ccc3n2)c1]

The titled compound was prepared in a manner analogous to EXAMPLE 1 steps B through F using 4-phenylaniline in step B and cyclopropylamine in step E. MS (ESI): mass calcd. for $C_{21}H_{17}N_5O_2$, 371.1; m/z found, 372.1 [M+H]$^+$. $^1$H NMR (400 MHz, DMSO-d$_6$): 9.36 (5, 1H), 9.14 (5, 1H), 8.75 (5, 1H), 8.24-8.22 (m, 1H), 8.21 (dd, J=8.7, 1.9 Hz, 1H), 7.90 (d, J=8.7 Hz, 1H), 7.88-7.85 (m, 2H), 7.55 (dd, J=10.5, 4.8 Hz, 2H), 7.48-7.40 (m, 1H), 3.44-3.38 (m, 1H), 1.00-0.90 (m, 2H), 0.89-0.80 (m, 2H).

Example 52

1-(4-(tert-Butylamino)-6-phenylquinazolin-2-yl)-1H-pyrazole-4-carboxylic acid

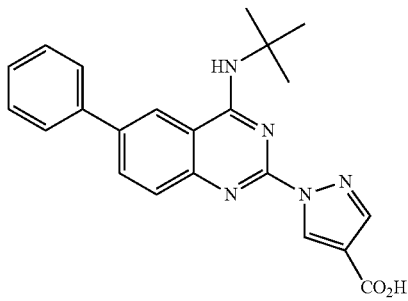 [SMILES: CC(C)(C)Nc1nc(-n2cc(C(=O)O)cn2)nc2ccc(-c3ccccc3)cc12]

The titled compound was prepared in a manner analogous to EXAMPLE 1 steps B through F using 4-phenylaniline in step B and tert-butylamine in step E. MS (ESI): mass calcd. for $C_{22}H_{21}N_5O_2$, 387.1; m/z found, 388.1 [M+H]$^+$. $^1$H NMR (400 MHz, DMSO-d$_6$): 8.93 (s, 1H), 8.77 (s, 1H), 8.23 (s, 1H), 8.21 (s, 1H), 8.16 (dd, J=8.7, 1.9 Hz, 1H), 7.87 (dd, J=12.5, 5.0 Hz, 3H), 7.55 (t, J=7.6 Hz, 2H), 7.44 (t, J=8.4 Hz, 1H), 1.66 (s, 9H).

Example 53

1-(4-Amino-6-phenylquinazolin-2-yl)-1H-pyrazole-4-carboxylic acid

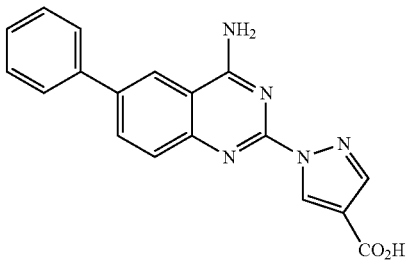 [SMILES: Nc1nc(-n2cc(C(=O)O)cn2)nc2ccc(-c3ccccc3)cc12]

The titled compound was prepared in a manner analogous to EXAMPLE 1 steps B through F using 4-phenylaniline in step B and ammonia in dioxane in step E. MS (ESI): mass calcd. for $C_{18}H_{13}N_5O_2$, 331.1; m/z found, 332.1 [M+H]$^+$. $^1$H NMR (400 MHz, DMSO-d$_6$): 13.34-12.10 (m, 1H), 8.98 (s, 1H), 8.73 (s, 1H), 8.68 (d, J=1.9 Hz, 1H), 8.55 (s, 1H), 8.21 (dd, J=8.7, 1.9 Hz, 1H), 8.15 (s, 1H), 7.89-7.83 (m, 3H), 7.55 (t, J=7.7 Hz, 2H), 7.43 (t, J=7.4 Hz, 1H).

Example 54

1-(6-Phenyl-4-thiomorpholinoquinazolin-2-yl)-1H-pyrazole-4-carboxylic acid

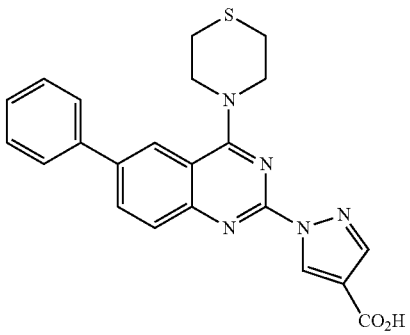 [SMILES: O=C(O)c1cnn(-c2nc(N3CCSCC3)c3cc(-c4ccccc4)ccc3n2)c1]

The titled compound was prepared in a manner analogous to EXAMPLE 1 steps B through F using 4-phenylaniline in step B and thiomorpholine in step E. MS (ESI): mass calcd. for $C_{22}H_{19}N_5O_2S$, 417.1; m/z found, 418.1 [M+H]$^+$. $^1$H NMR (500 MHz, DMSO-d$_6$): 12.79 (s, 1H), 9.04 (s, 1H), 8.18 (dd, J=8.7, 2.0 Hz, 1H), 8.15 (d, J=1.9 Hz, 1H), 8.14 (d, J=0.7 Hz, 1H), 7.92 (d, J=8.7 Hz, 1H), 7.85-7.80 (m, 2H), 7.57-7.52 (m, 2H), 7.46-7.41 (m, 1H), 4.26-4.16 (m, 4H), 2.94-2.79 (m, 4H).

Example 55

1-(4-(4-Acetamidopiperidin-1-yl)-6-phenylquinazolin-2-yl)-1H-pyrazole-4-carboxylic acid

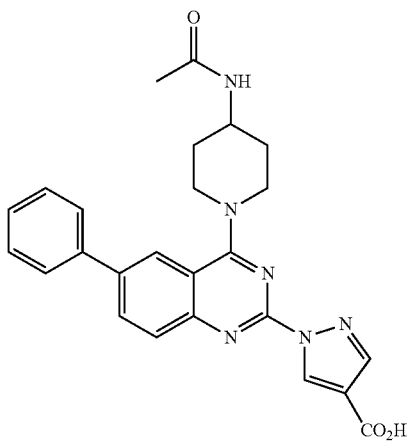 [SMILES: CC(=O)NC1CCN(c2nc(-n3cc(C(=O)O)cn3)nc3ccc(-c4ccccc4)cc23)CC1]

The titled compound was prepared in a manner analogous to EXAMPLE 1 steps B through F using 4-phenylaniline in step B and N-(piperidin-4-yl)acetamide in step E. MS (ESI): mass calcd. for $C_{25}H_{24}N_6O_3$, 456.1; m/z found, 457.1 [M+H]$^+$. $^1$H NMR (500 MHz, DMSO-d$_6$): 12.81 (s, 1H), 9.05 (s, 1H), 8.17 (d, J=8.7 Hz, 1H), 8.14 (s, 2H), 7.92 (d, J=8.7 Hz, 2H), 7.80 (dd, J=8.3, 1.1 Hz, 2H), 7.54 (dd, J=10.5, 4.9 Hz, 2H), 7.44-7.38 (m, 1H), 4.48-4.36 (m, 2H), 4.05-3.91 (m, 1H), 3.52 (t, J=11.5 Hz, 2H), 2.00 (d, J=9.5 Hz, 2H), 1.84 (s, 3H), 1.62-1.51 (m, 2H).

Example 56

1-(6-Phenyl-4-((tetrahydro-2H-pyran-4-yl)amino)quinazolin-2-yl)-1H-pyrazole-4-carboxylic acid

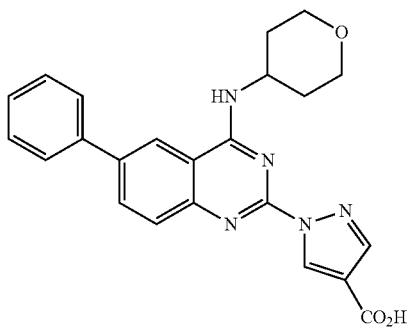 [SMILES: O=C(O)c1cnn(-c2nc(NC3CCOCC3)c3cc(-c4ccccc4)ccc3n2)c1]

The titled compound was prepared in a manner analogous to EXAMPLE 1 steps B through F using 4-phenylaniline in step B and 4-aminotetrahydropyran in step E. MS (ESI): mass calcd. for $C_{23}H_{21}N_5O_3$, 415.1; m/z found, 416.1 [M+H]$^+$. $^1$H NMR (400 MHz, DMSO-d$_6$): 9.12 (s, 1H), 9.05 (s, 1H), 8.79 (s, 1H), 8.22 (s, 1H), 8.20 (dd, J=8.8, 1.9 Hz, 1H), 7.89 (dd, J=8.2, 6.7 Hz, 3H), 7.56 (t, J=7.6 Hz, 2H), 7.45 (t, J=7.4 Hz, 1H), 4.76-4.60 (m, 1H), 3.98 (dd, J=11.2, 3.2 Hz, 2H), 3.56 (dd, J=11.8, 10.1 Hz, 2H), 1.99 (dd, J=12.5, 2.4 Hz, 2H), 1.80-1.72 (m, 2H).

Example 57

1-(4-(4-Methyl-1,4-diazepan-1-yl)-6-phenylquinazolin-2-yl)-1H-pyrazole-4-carboxylic acid

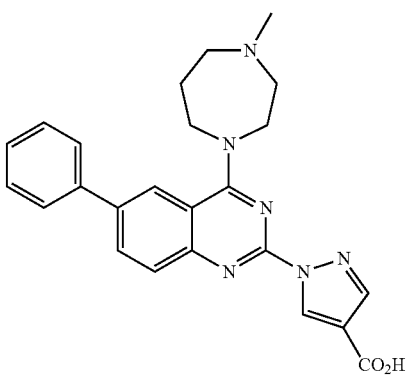 [SMILES: CN1CCCN(c2nc(-n3cc(C(=O)O)cn3)nc3ccc(-c4ccccc4)cc23)CC1]

The titled compound was prepared in a manner analogous to EXAMPLE 1 steps B through F using 4-phenylaniline in step B and N-methylhomopiperazine in step E. MS (ESI): mass calcd. for $C_{24}H_{24}N_6O_2$, 428.2; m/z found, 429.1 [M+H]$^+$. $^1$H NMR (400 MHz, DMSO-d$_6$): 12.10-11.18 (m, 1H), 9.05 (s, 1H), 8.32 (s, 1H), 8.16 (dd, J=8.7, 1.8 Hz, 1H), 8.14 (s, 1H), 7.89 (d, J=8.7 Hz, 1H), 7.83-7.79 (m, 2H), 7.53 (t, J=7.6 Hz, 2H), 7.43 (t, J=7.3 Hz, 1H), 4.28 (d, J=16.6 Hz, 2H), 4.24 (s, 2H), 3.51 (s, 2H), 3.18 (s, 2H), 2.69 (s, 3H), 2.35 (s, 2H).

Example 58

1-(4-Morpholino-6-phenylquinazolin-2-yl)-1H-pyrazole-4-carboxylic acid

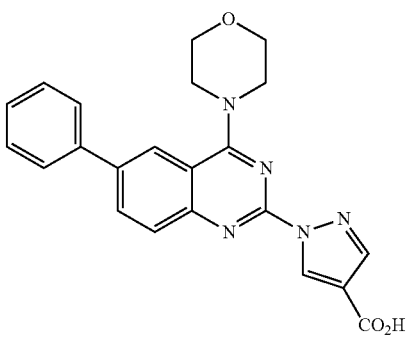 [SMILES: O=C(O)c1cnn(-c2nc(N3CCOCC3)c3cc(-c4ccccc4)ccc3n2)c1]

The titled compound was prepared in a manner analogous to EXAMPLE 1 steps B through F using 4-phenylaniline in step B and morpholine in step E. MS (ESI): mass calcd. for $C_{22}H_{19}N_5O_3$, 401.1; m/z found, 402.1 [M+H]$^+$. $^1$H NMR (500 MHz, DMSO-d$_6$): 13.09-12.49 (m, 1H), 9.09 (s, 1H), 8.21 (s, 1H), 8.18 (dd, J=8.7, 2.0 Hz, 1H), 8.16 (s, 1H), 7.94

(d, J=8.7 Hz, 1H), 7.82 (dd, J=8.3, 1.1 Hz, 2H), 7.54 (dd, J=10.5, 4.9 Hz, 2H), 7.46-7.41 (m, 1H), 4.12-4.01 (m, 4H), 3.88-3.77 (m, 4H).

Example 59

1-(4-(4-Cyanopiperidin-1-yl)-6-phenylquinazolin-2-yl)-1H-pyrazole-4-carboxylic acid

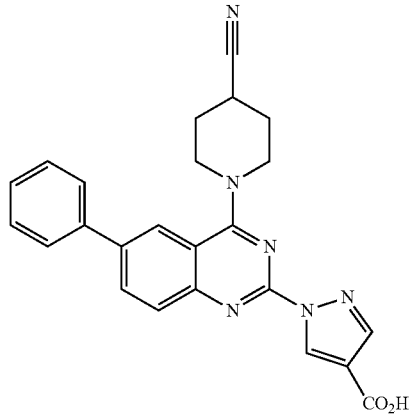 [SMILES: N#CC1CCN(c2nc(-n3cc(C(=O)O)cn3)nc3ccc(-c4ccccc4)cc23)CC1]

The titled compound was prepared in a manner analogous to EXAMPLE 1 steps B through F using 4-phenylaniline in step B and 4-cyanopiperidine in step E. MS (ESI): mass calcd. for $C_{24}H_{20}N_6O_2$, 424.1; m/z found, 425.1 [M+H]$^+$. $^1$H NMR (500 MHz, DMSO-$d_6$): 13.35-12.09 (m, 1H), 9.09 (s, 1H), 8.19 (dd, J=8.7, 1.9 Hz, 1H), 8.17 (d, J=4.6 Hz, 2H), 7.94 (d, J=8.6 Hz, 1H), 7.86-7.80 (m, 2H), 7.55 (dd, J=10.5, 4.9 Hz, 2H), 7.47-7.41 (m, 1H), 4.29-4.16 (m, 2H), 3.87-3.76 (m, 2H), 3.30-3.24 (m, 1H), 2.21-2.11 (m, 2H), 2.08-1.97 (m, 2H).

Example 60

1-(6-(4-Chlorophenoxy)-4-(diethylamino)quinazolin-2-yl)-1H-pyrazole-4-carboxylic acid

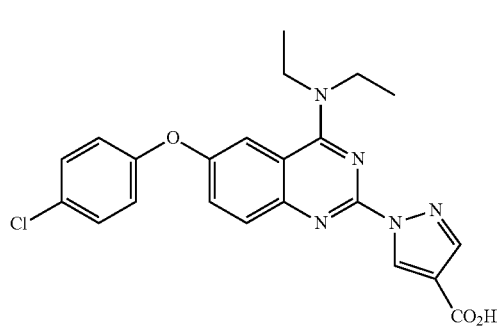 [SMILES: CCN(CC)c1nc(-n2cc(C(=O)O)cn2)nc2ccc(Oc3ccc(Cl)cc3)cc12]

The titled compound was prepared in a manner analogous to EXAMPLE 1 steps B through F using 4-(4-chloro)phenoxyaniline in step B and diethylamine in step E. MS (ESI): mass calcd. for $C_{22}H_{20}ClN_5O_3$, 437.1; m/z found, 438.1 [M+H]$^+$. $^1$H NMR (400 MHz, DMSO-$d_6$): 12.77 (s, 1H), 8.93 (s, 1H), 8.11 (s, 1H), 7.84 (d, J=9.1 Hz, 1H), 7.66 (dd, J=9.1, 2.6 Hz, 1H), 7.56-7.50 (m, 2H), 7.31 (d, J=2.6 Hz, 1H), 7.27-7.17 (m, 2H), 3.68 (q, J=6.9 Hz, 4H), 1.20 (t, J=7.0 Hz, 6H).

Example 61

1-(6-(4-Chlorophenoxy)-4-(pyrrolidin-1-yl)quinazolin-2-yl)-1H-pyrazole-4-carboxylic acid

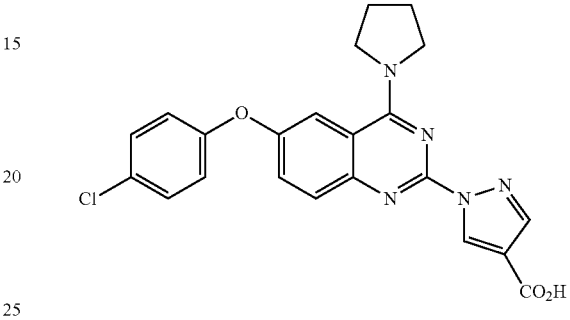

The titled compound was prepared in a manner analogous to EXAMPLE 1 steps B through F using 4-(4-chloro)phenoxyaniline in step B and pyrrolidine in step E. MS (ESI): mass calcd. for $C_{22}H_{18}ClN_5O_3$, 435.1; m/z found, 436.1 [M+H]$^+$. $^1$H NMR (500 MHz, DMSO-$d_6$): 12.74 (s, 1H), 8.98 (s, 1H), 8.09 (s, 1H), 7.87 (d, J=2.1 Hz, 1H), 7.80 (d, J=9.0 Hz, 1H), 7.57 (dd, J=9.0, 2.5 Hz, 1H), 7.49-7.44 (m, 2H), 7.15-7.08 (m, 2H), 3.89 (s, 4H), 1.97 (t, J=6.3 Hz, 4H).

Example 62

1-(6-(4-Chlorophenoxy)-4-(cyclopropylamino)quinazolin-2-yl)-1H-pyrazole-4-carboxylic acid

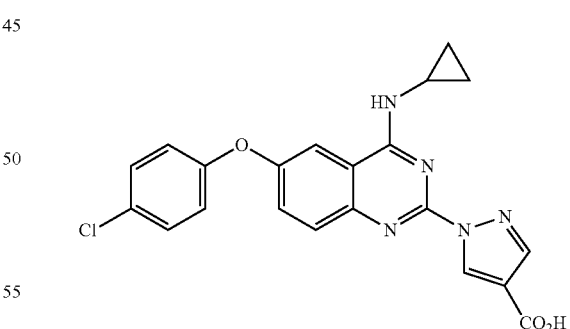

The titled compound was prepared in a manner analogous to EXAMPLE 1 steps B through F using 4-(4-chloro)phenoxyaniline in step B and cyclopropylamine in step E. MS (ESI): mass calcd. for $C_{21}H_{16}ClN_5O_3$, 421.0; m/z found, 422.0 [M+H]$^+$. $^1$H NMR (500 MHz, DMSO-$d_6$): 12.78 (s, 1H), 9.06 (s, 1H), 8.66 (d, J=3.6 Hz, 1H), 8.12 (s, 1H), 8.04 (d, J=2.1 Hz, 1H), 7.82 (d, J=9.0 Hz, 1H), 7.58 (dd, J=9.0, 2.5 Hz, 1H), 7.50-7.43 (m, 2H), 7.14-7.06 (m, 2H), 3.26-3.15 (m, 1H), 0.91-0.83 (m, 2H), 0.73-0.67 (m, 2H).

Example 63

1-(6-(4-Chlorophenoxy)-4-(piperidin-1-yl)quinazolin-2-yl)-1H-pyrazole-4-carboxylic acid

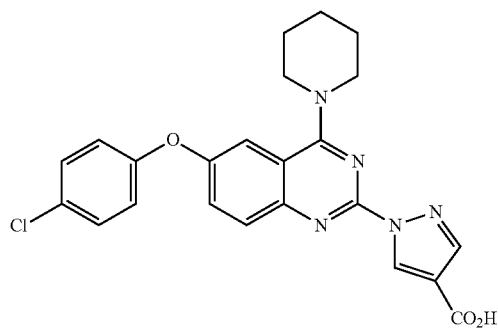 [SMILES: O=C(O)c1cnn(-c2nc(N3CCCCC3)c3cc(Oc4ccc(Cl)cc4)ccc3n2)c1]

The titled compound was prepared in a manner analogous to EXAMPLE 1 steps B through F using 4-(4-chloro)phenoxyaniline in step B and piperidine in step E. MS (ESI): mass calcd. for $C_{23}H_{20}ClN_5O_3$, 449.1; m/z found, 450.1 [M+H]$^+$. $^1$H NMR (500 MHz, DMSO-d$_6$): 12.78 (s, 1H), 8.99 (s, 1H), 8.11 (s, 1H), 7.88 (d, J=9.1 Hz, 1H), 7.64 (dd, J=9.1, 2.6 Hz, 1H), 7.54-7.48 (m, 2H), 7.34 (d, J=2.5 Hz, 1H), 7.24-7.18 (m, 2H), 3.75 (d, J=5.3 Hz, 4H), 1.68 (s, 2H), 1.63 (d, J=3.7 Hz, 4H).

Example 64

1-(6-(4-Chlorophenoxy)-4-((cyclohexylmethyl)amino)quinazolin-2-yl)-1H-pyrazole-4-carboxylic acid

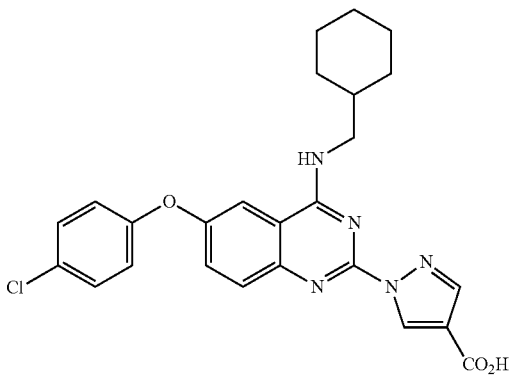 [SMILES: O=C(O)c1cnn(-c2nc(NCC3CCCCC3)c3cc(Oc4ccc(Cl)cc4)ccc3n2)c1]

The titled compound was prepared in a manner analogous to EXAMPLE 1 steps B through F using 4-(4-chloro)phenoxyaniline in step B and cyclohexylmethanamine in step E. MS (ESI): mass calcd. for $C_{25}H_{24}ClN_5O_3$, 477.2; m/z found, 478.2 [M+H]$^+$. $^1$H NMR (400 MHz, DMSO-d$_6$): 12.78 (s, 1H), 8.98 (s, 1H), 8.67 (s, 1H), 8.12 (s, 1H), 8.10 (d, J=2.6 Hz, 1H), 7.80 (d, J=9.0 Hz, 1H), 7.57 (dd, J=9.0, 2.6 Hz, 1H), 7.49-7.44 (m, 2H), 7.14-7.09 (m, 2H), 3.48 (t, J=5.9 Hz, 2H), 1.77 (d, J=11.7 Hz, 3H), 1.67 (t, J=16.5 Hz, 3H), 1.19 (t, J=11.0 Hz, 3H), 1.03 (t, J=11.3 Hz, 2H).

Example 65

1-(6-(4-Chlorophenoxy)-4-(4-cyanopiperidin-1-yl)quinazolin-2-yl)-1H-pyrazole-4-carboxylic acid

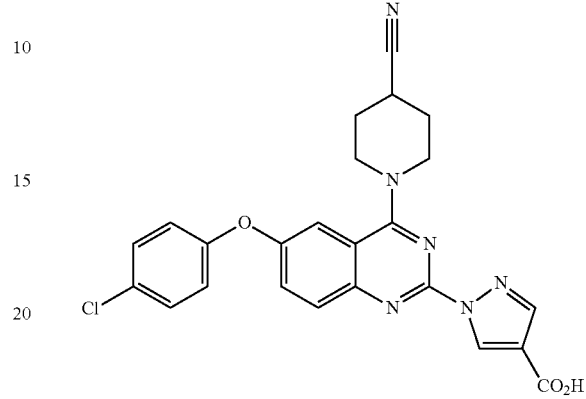

The titled compound was prepared in a manner analogous to EXAMPLE 1 steps B through F using 4-(4-chloro)phenoxyaniline in step B and 4-cyanopiperidine in step E. MS (ESI): mass calcd. for $C_{24}H_{19}ClN_6O_3$, 474.1; m/z found, 475.1 [M+H]$^+$. $^1$H NMR (400 MHz, DMSO-d$_6$): 12.80 (s, 1H), 9.03 (s, 1H), 8.12 (s, 1H), 7.91 (d, J=9.1 Hz, 1H), 7.65 (dd, J=9.1, 2.6 Hz, 1H), 7.53-7.49 (m, 2H), 7.42 (d, J=2.6 Hz, 1H), 7.22-7.17 (m, 2H), 4.08-3.92 (m, 2H), 3.70-3.55 (m, 2H), 3.27-3.18 (m, 1H), 2.03 (d, J=5.9 Hz, 2H), 1.88-1.72 (m, 2H).

Example 66

1-(4-(Azepan-1-yl)-6-(4-chlorophenoxy)quinazolin-2-yl)-1H-pyrazole-4-carboxylic acid

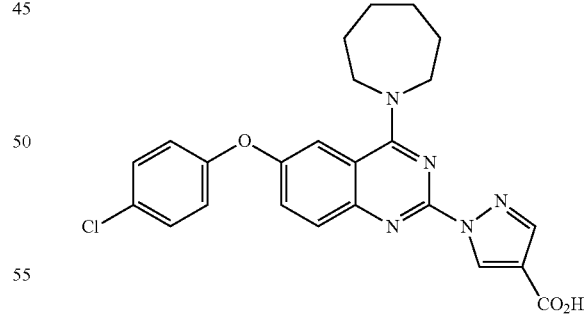

The titled compound was prepared in a manner analogous to EXAMPLE 1 steps B through F using 4-(4-chloro)phenoxyaniline in step B and homopiperidine in step E. MS (ESI): mass calcd. for $C_{24}H_{22}ClN_5O_3$, 474.1; m/z found, 475.1 [M+H]$^+$. $^1$H NMR (400 MHz, DMSO-d$_6$): 12.80 (s, 1H), 9.03 (s, 1H), 8.12 (s, 1H), 7.91 (d, J=9.1 Hz, 1H), 7.65 (dd, J=9.1, 2.6 Hz, 1H), 7.53-7.49 (m, 2H), 7.42 (s, 1H), 7.22-7.17 (m, 2H), 4.08-3.92 (m, 2H), 3.70-3.55 (m, 2H), 3.27-3.18 (m, 1H), 2.03 (d, J=5.9 Hz, 2H), 1.88-1.72 (m, 2H).

Example 67

1-(6-(4-Chlorophenoxy)-4-thiomorpholinoquinazolin-2-yl)-1H-pyrazole-4-carboxylic acid

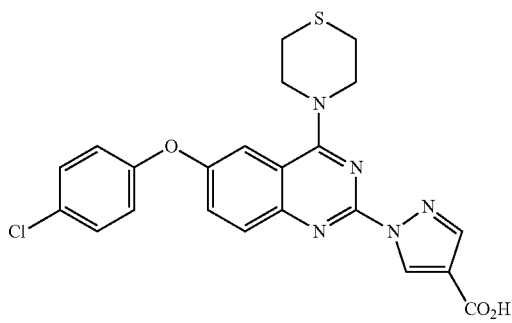 [SMILES: O=C(O)c1cnn(-c2nc(N3CCSCC3)c3cc(Oc4ccc(Cl)cc4)ccc3n2)c1]

The titled compound was prepared in a manner analogous to EXAMPLE 1 steps B through F using 4-(4-chloro)phenoxyaniline in step B and thiomorpholine in step E. MS (ESI): mass calcd. for $C_{22}H_{18}ClN_5O_3S$, 467.1; m/z found, 468.1 [M+H]$^+$. $^1$H NMR (400 MHz, DMSO-d$_6$): 8.81 (s, 1H), 7.94 (s, 1H), 7.89 (d, J=9.1 Hz, 1H), 7.64 (dd, J=9.1, 2.7 Hz, 1H), 7.55-7.47 (m, 2H), 7.34 (d, J=2.7 Hz, 1H), 7.24-7.17 (m, 2H), 4.04-3.95 (m, 4H), 2.82-2.73 (m, 4H).

Example 68

1-(6-(4-Chlorophenoxy)-4-((tetrahydro-2H-pyran-4-yl)amino)quinazolin-2-yl)-1H-pyrazole-4-carboxylic acid

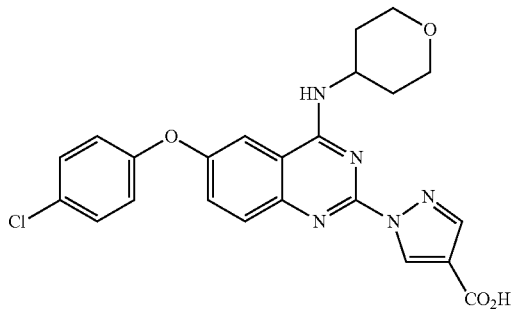 [SMILES: O=C(O)c1cnn(-c2nc(NC3CCOCC3)c3cc(Oc4ccc(Cl)cc4)ccc3n2)c1]

The titled compound was prepared in a manner analogous to EXAMPLE 1 steps B through F using 4-(4-chloro)phenoxyaniline in step B and 4-aminotetrahydropyran in step E. MS (ESI): mass calcd. for $C_{23}H_{20}ClN_5O_4$, 465.1; m/z found, 466.2 [M+H]$^+$. $^1$H NMR (400 MHz, DMSO-d$_6$): 12.81 (s, 1H), 9.02 (s, 1H), 8.41 (d, J=7.3 Hz, 1H), 8.21 (s, 1H), 8.13 (s, 1H), 7.81 (d, J=9.1 Hz, 1H), 7.59 (dd, J=8.9, 2.3 Hz, 1H), 7.50-7.43 (m, 2H), 7.15-7.04 (m, 2H), 4.62-4.43 (m, 1H), 3.94 (d, J=8.6 Hz, 2H), 3.49-3.44 (m, 2H), 1.95-1.82 (m, 2H), 1.68-1.52 (m, 2H).

Example 69

1-(6-(4-Chlorophenoxy)-4-(phenylamino)quinazolin-2-yl)-1H-pyrazole-4-carboxylic acid

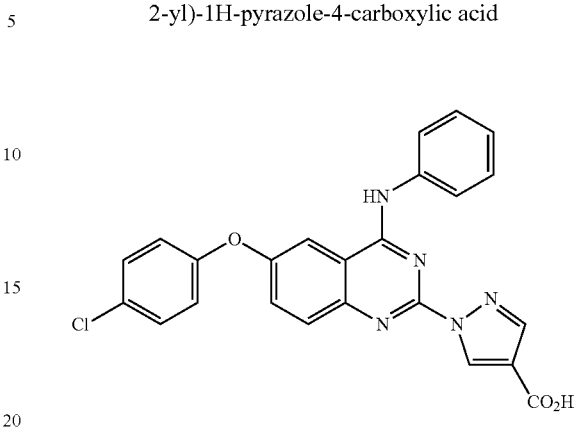

The titled compound was prepared in a manner analogous to EXAMPLE 1 steps B through F using 4-(4-chloro)phenoxyaniline in step B and aniline in step E. MS (ESI): mass calcd. for $C_{24}H_{16}ClN_5O_3$, 457.1; m/z found, 458.1 [M+H]$^+$. $^1$H NMR (400 MHz, DMSO-d$_6$): 12.78 (s, 1H), 10.16 (s, 1H), 8.83 (s, 1H), 8.39 (d, J=2.5 Hz, 1H), 8.13 (s, 1H), 7.92-7.85 (m, 3H), 7.67 (dd, J=9.0, 2.6 Hz, 1H), 7.53-7.43 (m, 4H), 7.22 (t, J=7.4 Hz, 1H), 7.19-7.12 (m, 2H).

Example 70

1-(4-(4-Acetamidopiperidin-1-yl)-6-(4-chlorophenoxy)quinazolin-2-yl)-1H-pyrazole-4-carboxylic acid

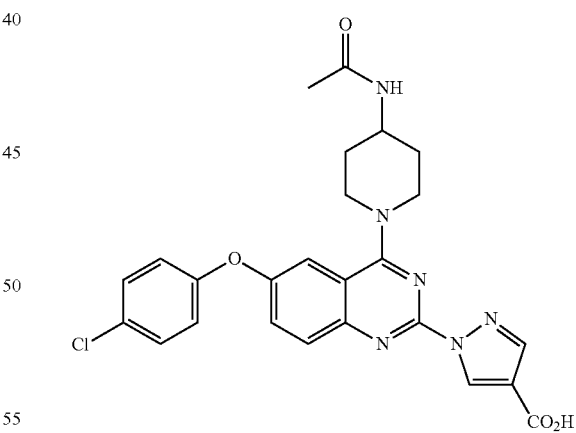

The titled compound was prepared in a manner analogous to EXAMPLE 1 steps B through F using 4-(4-chloro)phenoxyaniline in step B and N-(piperidin-4-yl)acetamide in step E. MS (ESI): mass calcd. for $C_{25}H_{23}ClN_6O_4$, 506.2; m/z found, 507.2 [M+H]$^+$. $^1$H NMR (400 MHz, DMSO-d$_6$): 12.83 (s, 1H), 9.01 (s, 1H), 8.13 (s, 1H), 7.89 (dd, J=8.4, 4.7 Hz, 2H), 7.65 (dd, J=9.1, 2.6 Hz, 1H), 7.55-7.45 (m, 2H), 7.38 (d, J=2.5 Hz, 1H), 7.26-7.15 (m, 2H), 4.26 (d, J=13.4 Hz, 2H), 3.99-3.78 (m, 1H), 3.36 (d, J=11.4 Hz, 2H), 1.88 (d, J=9.9 Hz, 2H), 1.80 (s, 3H), 1.48 (dd, J=20.8, 10.3 Hz, 2H).

Example 71

1-(6-(4-Chlorophenoxy)-4-(4-methyl-1,4-diazepan-1-yl)quinazolin-2-yl)-1H-pyrazole-4-carboxylic acid

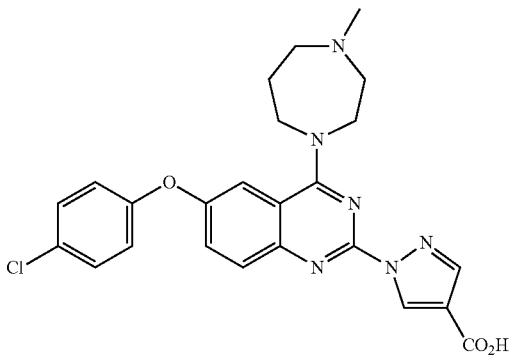 [SMILES: CN1CCCN(c2nc(-n3cc(C(=O)O)cn3)nc3ccc(Oc4ccc(Cl)cc4)cc23)CC1]

The titled compound was prepared in a manner analogous to EXAMPLE 1 steps B through F using 4-(4-chloro)phenoxyaniline in step B and N-methylhomopiperazine in step E. MS (ESI): mass calcd. for $C_{24}H_{23}ClN_6O_3$, 484.2; m/z found, 479.2 [M+H]$^+$. $^1$H NMR (400 MHz, DMSO-$d_6$): 13.04-11.93 (m, 1H), 9.03 (s, 1H), 8.13 (s, 1H), 7.88 (d, J=9.1 Hz, 1H), 7.68 (d, J=2.4 Hz, 1H), 7.63 (dd, J=9.1, 2.6 Hz, 1H), 7.54-7.43 (m, 2H), 7.18-7.10 (m, 2H), 4.05 (s, 3H), 3.47-3.32 (m, 3H), 3.29-3.14 (m, 2H), 2.74 (s, 3H), 2.28 (s, 2H).

Example 72

1-(4-(tert-Butylamino)-6-phenoxyquinazolin-2-yl)-1H-pyrazole-4-carboxylic acid

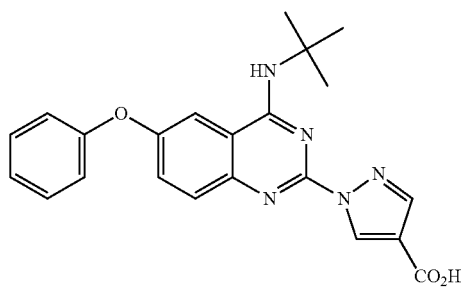 [SMILES: CC(C)(C)Nc1nc(-n2cc(C(=O)O)cn2)nc2ccc(Oc3ccccc3)cc12]

The titled compound was prepared in a manner analogous to EXAMPLE 1 steps B through F using 4-phenoxyaniline in step B and tert-butylamine in step E. MS (ESI): mass calcd. for $C_{22}H_{21}N_5O_3$, 403.2; m/z found, 404.2 [M+H]$^+$. $^1$H NMR (500 MHz, DMSO-$d_6$): 12.80 (s, 1H), 8.91 (s, 1H), 8.37 (d, J=2.6 Hz, 1H), 8.13 (s, 1H), 7.77 (d, J=9.1 Hz, 2H), 7.51 (dd, J=9.0, 2.6 Hz, 1H), 7.43-7.37 (m, 2H), 7.17-7.11 (m, 1H), 7.06-6.97 (m, 2H), 1.60 (s, 9H).

Example 73

1-(6-Phenoxy-4-(pyrrolidin-1-yl)quinazolin-2-yl)-1H-pyrazole-4-carboxylic acid

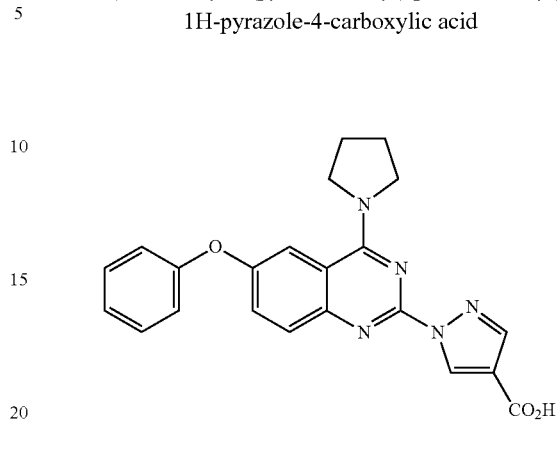

The titled compound was prepared in a manner analogous to EXAMPLE 1 steps B through F using 4-phenoxyaniline in step B and pyrrolidine in step E. MS (ESI): mass calcd. for $C_{22}H_{19}N_5O_3$, 401.2; m/z found, 402.2 [M+H]$^+$. $^1$H NMR (500 MHz, DMSO-$d_6$): 12.74 (s, 1H), 8.99 (s, 1H), 8.09 (s, 1H), 7.83 (d, J=2.6 Hz, 1H), 7.81 (d, J=9.0 Hz, 1H), 7.56 (dd, J=9.0, 2.6 Hz, 1H), 7.47-7.40 (m, 2H), 7.22-7.16 (m, 1H), 7.13-7.08 (m, 2H), 3.88 (s, 4H), 1.96 (t, J=6.4 Hz, 4H).

Example 74

1-(4-(Diethylamino)-6-phenoxyquinazolin-2-yl)-1H-pyrazole-4-carboxylic acid

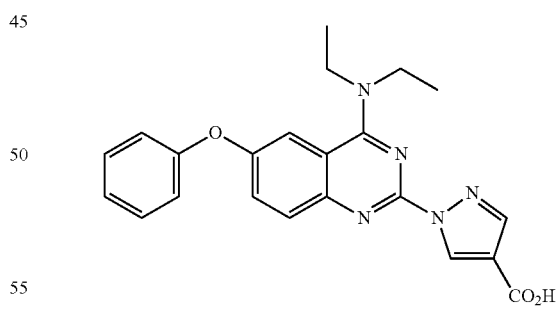

The titled compound was prepared in a manner analogous to EXAMPLE 1 steps B through F using 4-phenoxyaniline in step B and diethylamine in step E. MS (ESI): mass calcd. for $C_{22}H_{21}N_5O_3$, 403.2; m/z found, 404.2 [M+H]$^+$. $^1$H NMR (500 MHz, DMSO-$d_6$): 12.75 (s, 1H), 8.92 (s, 1H), 8.10 (s, 1H), 7.84 (d, J=9.1 Hz, 1H), 7.65 (dd, J=9.1, 2.4 Hz, 1H), 7.50 (t, J=7.9 Hz, 2H), 7.27 (dd, J=8.9, 5.0 Hz, 2H), 7.21 (d, J=7.8 Hz, 2H), 3.65 (q, J=6.9 Hz, 4H), 1.15 (t, J=6.9 Hz, 6H).

Example 75

1-(4-(Cyclopropylamino)-6-phenoxyquinazolin-2-yl)-1H-pyrazole-4-carboxylic acid

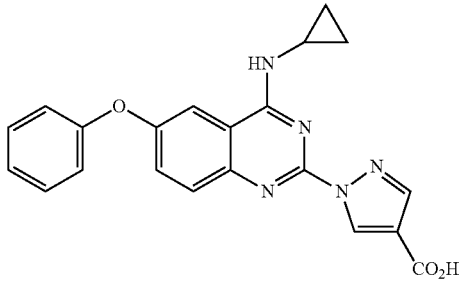 [SMILES: O=C(O)c1cnn(-c2nc(NC3CC3)c3cc(Oc4ccccc4)ccc3n2)c1]

The titled compound was prepared in a manner analogous to EXAMPLE 1 steps B through F using 4-phenoxyaniline in step B and cyclopropylamine in step E. MS (ESI): mass calcd. for $C_{21}H_{17}N_5O_3$, 387.1; m/z found, 388.2 [M+H]⁺. ¹H NMR (400 MHz, DMSO-$d_6$): 12.83 (5, 1H), 9.08 (5, 1H), 8.80 (d, J=3.4 Hz, 1H), 8.15 (5, 1H), 8.11 (d, J=2.6 Hz, 1H), 7.83 (d, J=9.0 Hz, 1H), 7.55 (dd, J=9.0, 2.6 Hz, 1H), 7.45-7.38 (m, 2H), 7.20-7.13 (m, 1H), 7.09-7.03 (m, 2H), 3.27-3.14 (m, 1H), 0.96-0.83 (m, 2H), 0.77-0.69 (m, 2H).

Example 76

1-(6-Phenoxy-4-(((tetrahydro-2H-pyran-4-yl)amino)quinazolin-2-yl)-1H-pyrazole-4-carboxylic acid

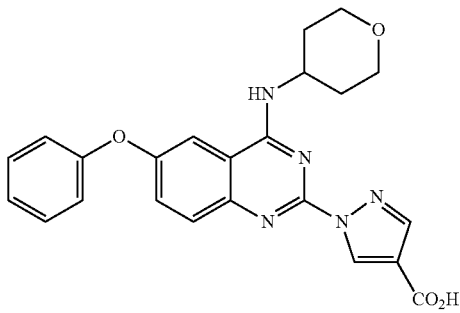 [SMILES: O=C(O)c1cnn(-c2nc(NC3CCOCC3)c3cc(Oc4ccccc4)ccc3n2)c1]

The titled compound was prepared in a manner analogous to EXAMPLE 1 steps B through F using 4-phenoxyaniline in step B and 4-aminotetrahydropyran in step E. MS (ESI): mass calcd. for $C_{23}H_{21}N_5O_4$, 431.2; m/z found, 432.2 [M+H]⁺. ¹H NMR (400 MHz, DMSO-$d_6$): 12.78 (s, 1H), 9.01 (s, 1H), 8.41 (d, J=7.4 Hz, 1H), 8.22 (d, J=2.5 Hz, 1H), 8.12 (s, 1H), 7.80 (d, J=9.0 Hz, 1H), 7.54 (dd, J=9.0, 2.6 Hz, 1H), 7.45-7.37 (m, 2H), 7.16 (t, J=7.4 Hz, 1H), 7.05 (dd, J=8.7, 1.0 Hz, 2H), 4.53 (dd, J=11.4, 4.1 Hz, 1H), 3.94 (d, J=8.8 Hz, 2H), 3.53-3.47 (m, 2H), 2.00-1.90 (m, 2H), 1.72-1.63 (m, 2H).

Example 77

1-(4-(Dimethylamino)-7-phenoxyquinazolin-2-yl)-1H-pyrazole-4-carboxylic acid

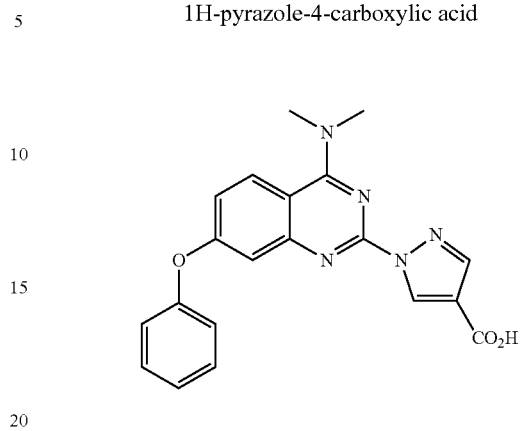

Step A: Preparation of Ethyl 1-(N-(ethoxycarbonyl)-N'-(3-phenoxyphenyl)carbamimidoyl)-1H-pyrazole-4-carboxylate. To a mixture of 3-phenoxyaniline (0.93 g, 5.0 mmol) and DCM (17 mL) neat ethyl isocyanatoformate (0.65 mL, 5.5 mmol) was added and the resulting solution was stirred for 15 min. Ethyl pyrazole-4-carboxylate (0.77 g, 5.5 mmol), and neat diisopropylcarbodiimide (0.78 mL, 5.0 mmol) were added sequentially to the reaction mixture. The solution was stirred at rt for 24 h, and then concentrated. The residue was stirred with ether (10 mL) for 3 h in an ice bath, and then filtered. The residue was purified by FCC (0 to 25% EtOAc/hexanes) to yield the title compound (1.6 g, 76%, ca 70% purity). MS (ESI/CI): mass calcd. for $C_{22}H_{22}N_4O_5$, 422.1; m/z found, 423.3 [M+H]⁺.

Step B: Preparation of ethyl 1-(4-oxo-7-phenoxy-3,4-dihydroquinazolin-2-yl)-1H-pyrazole-4-carboxylate. To a solution of ethyl 1-(N-(ethoxycarbonyl)-N'-(3-phenoxyphenyl)carbamimidoyl)-1H-pyrazole-4-carboxylate (1.51 g, ca 2.51 mmol) in dichloroethane (DCE) (18 mL), neat $TiCl_4$ (1.18 mL, 10.7 mmol) was added over 2 min. The mixture was then heated to reflux for 2 h, and then cooled in an ice bath. EtOH (50 mL) was added, and the mixture was stirred for 3 h. The resulting precipitate was collected by filtration, washed with cold EtOH, and dried to provide the titled compound (0.77 g, 57%). MS (ESI/CI): mass calcd. for $C_{20}H_{16}N_4O_4$, 376.1; m/z found, 377.3 [M+H]⁺. ¹H NMR (400 MHz, DMSO-$d_6$): 12.85 (s, 1H), 9.00 (d, J=0.5 Hz, 1H), 8.31 (s, 1H), 8.13 (d, J=8.8 Hz, 1H), 7.58-7.45 (m, 2H), 7.38-7.27 (m, 1H), 7.26-7.20 (m, 2H), 7.18 (dd, J=8.8, 2.4 Hz, 1H), 6.98 (s, 1H), 4.39-4.13 (m, 2H), 1.42-1.21 (m, 3H).

Step C: Preparation of ethyl 1-(4-chloro-7-phenoxyquinazolin-2-yl)-1H-pyrazole-4-carboxylate. A mixture of the above ethyl 1-(4-oxo-7-phenoxy-3,4-dihydroquinazolin-2-yl)-1H-pyrazole-4-carboxylate (0.31 g, 0.82 mmol), and $POCl_3$ (3.08 mL, 32.9 mmol), was heated to reflux for 3 h. The mixture was allowed to cool to rt and then concentrated. The residue was taken up in a minimal amount of DCM and purified by FCC (0 to 25% EtOAc/hexanes) to yield the title compound (250 mg, 77%). ¹H NMR (600 MHz, DMSO-$d_6$): 9.06 (d, J=0.7 Hz, 1H), 8.35 (d, J=9.2 Hz, 1H), 8.23 (dd, J=10.6, 6.6 Hz, 1H), 7.63-7.59 (m, 1H), 7.60-7.54 (m, 2H), 7.41-7.36 (m, 1H), 7.31-7.29 (m, 2H), 7.18 (d, J=2.4 Hz, 1H), 4.30 (q, J=7.1 Hz, 2H), 1.35-1.24 (t, J=7.2 Hz, 3H).

Step D: Preparation of ethyl 1-(4-(dimethylamino)-7-phenoxyquinazolin-2-yl)-1H-pyrazole-4-carboxylate. A THF solution of dimethylamine (2M, 0.44 mL, 0.88 mmol) was added to a solution of the above ethyl 1-(4-chloro-7-phenoxyquinazolin-2-yl)-1H-pyrazole-4-carboxylate (70 mg, 0.18 mmol) and THF (1.4 mL). The mixture was stirred 1 h, and then concentrated. The residue was triturated with ethanol, providing the titled compound (45 mg, 63%). MS (ESI/CI): mass calcd. for $C_{22}H_{21}N_5O_3$, 403.1; m/z found, 404.3 [M+H]$^+$. $^1$H NMR (400 MHz, DMSO-d$_6$): 9.02 (s, 1H), 8.31 (d, J=9.3 Hz, 1H), 8.12 (s, 1H), 7.53 (dd, J=11.1, 4.8 Hz, 2H), 7.32 (t, J=7.4 Hz, 1H), 7.27-7.21 (m, 2H), 7.18 (dd, J=9.3, 2.7 Hz, 1H), 6.96 (d, J=2.7 Hz, 1H), 4.27 (q, J=7.1 Hz, 2H), 3.46 (s, 6H), 1.30 (t, J=7.1 Hz, 3H).

Step E: Preparation of 1-(4-(dimethylamino)-7-phenoxyquinazolin-2-yl)-1H-pyrazole-4-carboxylic acid. A mixture of ethyl 1-(4-(dimethylamino)-7-phenoxyquinazolin-2-yl)-1H-pyrazole-4-carboxylate (35 mg, 0.09 mmol), 1M aqueous KOH (0.43 mL, 0.43 mmol), and THF (1.3 mL) was heated to 40° C. for 48 h with rapid stirring. The mixture was then concentrated, cooled in an ice bath, and 1M aqueous HCl was added until the mixture was slightly acidic (pH ca 5-6). The resulting precipitate was collected by filtration, washed with water, and dried to furnish the titled compound (22 mg, 68%). MS (ESI): mass calcd. for $C_{20}H_{17}N_5O_3$, 375.1; m/z found, 376.3 [M+H]$^+$. $^1$H NMR (500 MHz, DMSO-d$_6$): 12.73 (s, 1H), 8.98 (d, J=0.6 Hz, 1H), 8.31 (d, J=9.3 Hz, 1H), 8.07 (s, 1H), 7.52 (ddd, J=7.6, 5.9, 2.2 Hz, 2H), 7.36-7.28 (m, 1H), 7.28-7.20 (m, 2H), 7.17 (dd, J=9.3, 2.7 Hz, 1H), 6.97 (d, J=2.7 Hz, 1H), 3.46 (s, 6H).

Example 78

1-(7-Phenoxy-4-(pyrrolidin-1-yl)quinazolin-2-yl)-1H-pyrazole-4-carboxylic acid

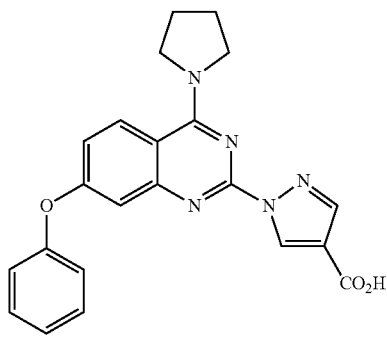 [SMILES: O=C(O)c1cnn(-c2nc(N3CCCC3)c3ccc(Oc4ccccc4)cc3n2)c1]

The titled compound was prepared in a manner analogous to EXAMPLE 77 using 3-phenoxyaniline in step A and pyrrolidine in step D. MS (ESI): mass calcd. for $C_{22}H_{19}N_5O_3$, 401.1; m/z found, 402.3 [M+H]$^+$. $^1$H NMR (500 MHz, DMSO-d$_6$): 12.72 (s, 1H), 8.97 (d, J=0.6 Hz, 1H), 8.38 (d, J=9.3 Hz, 1H), 8.06 (d, J=0.6 Hz, 1H), 7.56-7.46 (m, 2H), 7.35-7.27 (m, 1H), 7.26-7.19 (m, 2H), 7.16 (dd, J=9.3, 2.7 Hz, 1H), 6.97 (d, J=2.7 Hz, 1H), 3.97 (s, 4H), 2.01 (s, 4H).

Example 79

1-(7-Phenoxy-4-(piperidin-1-yl)quinazolin-2-yl)-1H-pyrazole-4-carboxylic acid

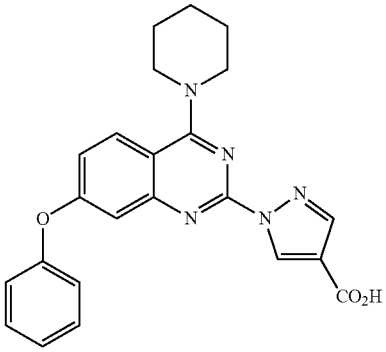 [SMILES: O=C(O)c1cnn(-c2nc(N3CCCCC3)c3ccc(Oc4ccccc4)cc3n2)c1]

The titled compound was prepared in a manner analogous to EXAMPLE 77 using 3-phenoxyaniline in step A and piperidine in step D. MS (ESI): mass calcd. for $C_{23}H_{21}N_5O_3$, 415.1; m/z found, 416.3 [M+H]$^+$. $^1$H NMR (500 MHz, DMSO-d$_6$): 12.74 (s, 1H), 8.97 (d, J=0.7 Hz, 1H), 8.08 (d, J=0.7 Hz, 1H), 8.04 (d, J=9.2 Hz, 1H), 7.56-7.49 (m, 2H), 7.32 (t, J=7.4 Hz, 1H), 7.25-7.21 (m, 3H), 6.99 (d, J=2.6 Hz, 1H), 3.86 (s, 4H), 1.74 (s, 6H).

Example 80

1-(4-(Dimethylamino)-7-phenylquinazolin-2-yl)-1H-pyrazole-4-carboxylic acid

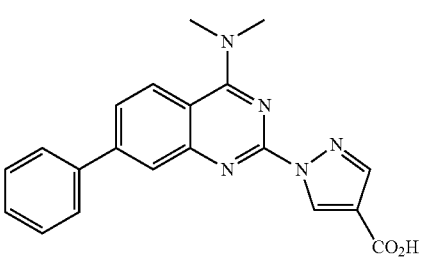

The titled compound was prepared in a manner analogous to EXAMPLE 77 using 3-phenylaniline in step A and dimethylamine in step D. MS (ESI): mass calcd. for $C_{20}H_{17}N_5O_2$, 359.1; m/z found, 360.3 [M+H]$^+$. $^1$H NMR (400 MHz, DMSO-d$_6$): 9.13 (d, J=0.5 Hz, 1H), 8.40 (d, J=8.8 Hz, 1H), 8.24 (s, 1H), 8.15 (d, J=1.9 Hz, 1H), 7.89-7.81 (m, 3H), 7.59-7.48 (m, 2H), 7.53-7.44 (m, 1H), 3.59 (s, 6H).

Example 81

1-(7-Phenyl-4-(pyrrolidin-1-yl)quinazolin-2-yl)-1H-pyrazole-4-carboxylic acid

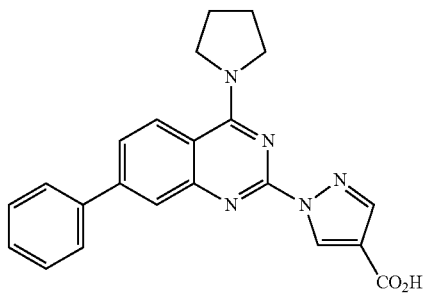 [SMILES: O=C(O)c1cnn(-c2nc(N3CCCC3)c3ccc(-c4ccccc4)cc3n2)c1]

The titled compound was prepared in a manner analogous to EXAMPLE 77 using 3-phenylaniline in step A and pyrrolidine in step D. MS (ESI): mass calcd. for $C_{22}H_{19}N_5O_2$, 385.1; m/z found, 386.3 [M+H]$^+$. $^1$H NMR (400 MHz, DMSO-$d_6$): 9.08 (d, J=0.5 Hz, 1H), 8.45 (d, J=8.9 Hz, 1H), 8.21 (s, 1H), 8.12 (d, J=1.8 Hz, 1H), 7.90-7.78 (m, 3H), 7.62-7.53 (m, 2H), 7.53-7.45 (m, 1H), 4.07 (s, 4H), 2.05 (s, 4H).

Example 82

1-(7-Phenyl-4-(piperidin-1-yl)quinazolin-2-yl)-1H-pyrazole-4-carboxylic acid

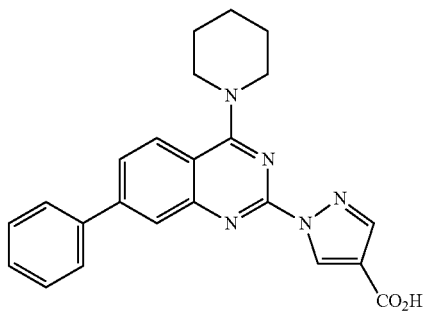 [SMILES: O=C(O)c1cnn(-c2nc(N3CCCCC3)c3ccc(-c4ccccc4)cc3n2)c1]

The titled compound was prepared in a manner analogous to EXAMPLE 77 using 3-phenylaniline in step A and piperidine in step D. MS (ESI): mass calcd. for $C_{23}H_{21}N_5O_2$, 399.1; m/z found, 400.3 [M+H]$^+$. $^1$H NMR (400 MHz, DMSO-$d_6$): 12.80 (s, 1H), 9.03 (d, J=0.5 Hz, 1H), 8.13 (d, J=0.5 Hz, 1H), 8.10 (d, J=8.7 Hz, 1H), 8.06 (d, J=1.9 Hz, 1H), 7.89-7.80 (m, 3H), 7.60-7.52 (m, 2H), 7.51-7.45 (m, 1H), 3.92 (s, 4H), 1.77 (s, 6H).

Example 83

1-(4-(Diethylamino)-7-phenoxyquinazolin-2-yl)-1H-pyrazole-4-carboxylic acid

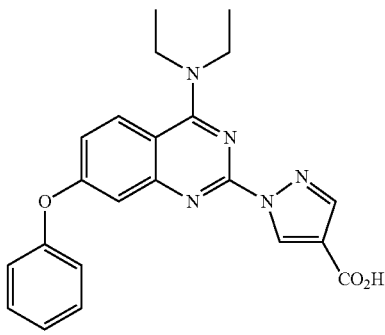 [SMILES: CCN(CC)c1nc(-n2cc(C(=O)O)cn2)nc2cc(Oc3ccccc3)ccc12]

The titled compound was prepared in a manner analogous to EXAMPLE 77 using 3-phenoxyaniline in step A and diethylamine in step D. MS (ESI): mass calcd. for $C_{22}H_{21}N_5O_3$, 403.1; m/z found, 404.3 [M+H]$^+$. $^1$H NMR (600 MHz, DMSO-$d_6$): 8.91 (d, J=0.7 Hz, 1H), 8.09-8.07 (m, 2H), 7.56-7.48 (m, 2H), 7.35-7.28 (m, 1H), 7.25-7.22 (m, 2H), 7.20 (dd, J=9.3, 2.7 Hz, 1H), 6.99 (d, J=2.7 Hz, 1H), 3.82 (q, J=7.0 Hz, 4H), 1.38 (t, J=7.0 Hz, 6H).

Example 84

1-(4-(((Cyclohexylmethyl)amino)-7-phenoxyquinazolin-2-yl)-1H-pyrazole-4-carboxylic acid

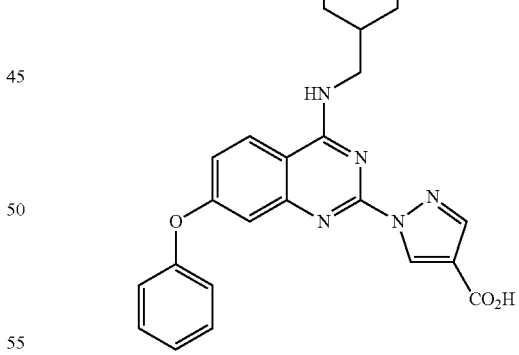

The titled compound was prepared in a manner analogous to EXAMPLE 77 using 3-phenoxyaniline in step A and cyclohexylmethanamine in step D. MS (ESI): mass calcd. for $C_{25}H_{25}N_5O_3$, 443.2; m/z found, 444.4 [M+H]$^+$. $^1$H NMR (600 MHz, DMSO-$d_6$): 12.74 (s, 1H), 8.96 (s, 1H), 8.75 (s, 1H), 8.38 (d, J=9.1 Hz, 1H), 8.09 (s, 1H), 7.56-7.46 (m, 2H), 7.30 (t, J=7.4 Hz, 1H), 7.26 (dd, J=9.0, 2.5 Hz, 1H), 7.21 (dd, J=8.6, 1.0 Hz, 2H), 6.98 (d, J=2.4 Hz, 1H), 3.51 (t, J=6.0 Hz, 2H), 1.80-1.62 (m, 7H), 1.27-1.11 (m, 2H), 1.04 (m, 2H).

Example 85

1-(4-(4-Isopropylpiperidin-1-yl)-7-phenoxyquinazolin-2-yl)-1H-pyrazole-4-carboxylic acid

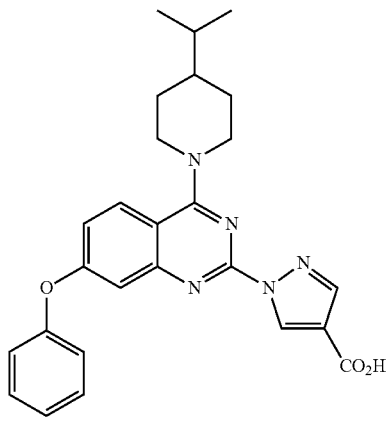 [SMILES: CC(C)C1CCN(c2nc(-n3cc(C(=O)O)cn3)nc3cc(Oc4ccccc4)ccc23)CC1]

The titled compound was prepared in a manner analogous to EXAMPLE 77 using 3-phenoxyaniline in step A and 4-isopropylpiperidine in step D. MS (ESI): mass calcd. for $C_{26}H_{27}N_5O_3$, 457.2; m/z found, 458.4 [M+H]$^+$. $^1$H NMR (500 MHz, DMSO-d$_6$): 12.75 (s, 1H), 8.97 (d, J=0.7 Hz, 1H), 8.08 (d, J=0.7 Hz, 1H), 8.06 (d, J=9.2 Hz, 1H), 7.57-7.48 (m, 2H), 7.34-7.31 (m, 1H), 7.24-7.23 (m, 3H), 6.99 (d, J=2.6 Hz, 1H), 4.54 (d, J=13.0 Hz, 2H), 3.22 (t, J=12.0 Hz, 2H), 1.84 (d, J=9.8 Hz, 2H), 1.56-1.33 (m, 4H), 0.91 (d, J=6.6 Hz, 6H)

Example 86

1-(4-(Cyclopropylamino)-7-phenoxyquinazolin-2-yl)-1H-pyrazole-4-carboxylic acid

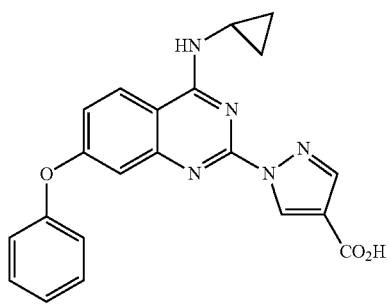 [SMILES: O=C(O)c1cnn(-c2nc(NC3CC3)c3ccc(Oc4ccccc4)cc3n2)c1]

The titled compound was prepared in a manner analogous to EXAMPLE 77 using 3-phenoxyaniline in step A and cyclopropylamine in step D. MS (ESI): mass calcd. for $C_{21}H_{17}N_5O_3$, 387.1; m/z found, 388.3 [M+H]$^+$. $^1$H NMR (600 MHz, DMSO-d$_6$): 12.74 (S, 1H), 9.01 (S, 1H), 8.64 (d, J=3.9 Hz, 1H), 8.31 (d, J=9.1 Hz, 1H), 8.06 (s, 1H), 7.55-7.45 (m, 2H), 7.31-7.29 (m, 1H), 7.24 (dd, J=9.0, 2.5 Hz, 1H), 7.22-7.19 (m, 2H), 6.95 (d, J=2.5 Hz, 1H), 3.25-3.20 (m, 1H), 0.93-0.84 (m, 2H), 0.76-0.69 (m, 2H).

Example 87

1-(4-(Azepan-1-yl)-7-phenoxyquinazolin-2-yl)-1H-pyrazole-4-carboxylic acid

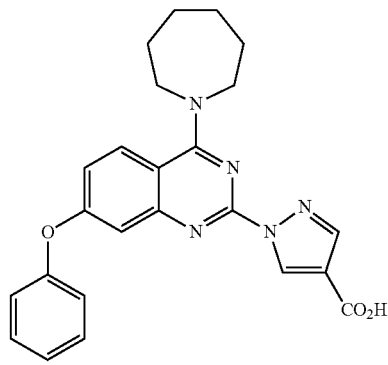 [SMILES: O=C(O)c1cnn(-c2nc(N3CCCCCC3)c3ccc(Oc4ccccc4)cc3n2)c1]

The titled compound was prepared in a manner analogous to EXAMPLE 77 using 3-phenoxyaniline in step A and homopiperidine in step D. MS (ESI): mass calcd. for $C_{24}H_{23}N_5O_3$, 429.1; m/z found, 430.3 [M+H]$^+$. $^1$H NMR (600 MHz, DMSO-d$_6$): 12.72 (s, 1H), 8.92 (s, 1H), 8.21 (d, J=9.3 Hz, 1H), 8.06 (s, 1H), 7.56-7.47 (m, 2H), 7.31 (t, J=7.4 Hz, 1H), 7.23 (dd, J=8.5, 0.9 Hz, 2H), 7.16 (dd, J=9.3, 2.7 Hz, 1H), 6.97 (d, J=2.7 Hz, 1H), 4.08-3.94 (m, 4H), 1.95 (s, 4H), 1.58 (s, 4H).

Example 88

1-(4-(Diethylamino)-6-(piperidin-1-yl)quinazolin-2-yl)-1H-pyrazole-4-carboxylic acid

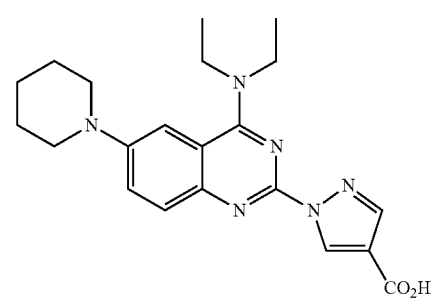 [SMILES: CCN(CC)c1nc(-n2cc(C(=O)O)cn2)nc2ccc(N3CCCCC3)cc12]

The titled compound was prepared in a manner analogous to EXAMPLE 77 using 4-piperidin-1-yl-aniline in step A and diethylamine in step D. MS (ESI): mass calcd. for $C_{21}H_{26}N_6O_2$, 394.2; m/z found, 395.3 [M+H]$^+$. $^1$H NMR (400 MHz, DMSO-d$_6$): 8.89 (S, 1H), 8.06 (s, 1H), 7.65 (br s, 2H), 7.18 (s, 1H), 3.78 (q, J=7.0 Hz, 4H), 3.28-3.23 (m, 4H), 1.72-1.64 (m, 4H), 1.62-1.54 (m, 2H), 1.40 (t, J=7.0 Hz, 6H).

Example 89

1-(4-Morpholino-7-phenoxyquinazolin-2-yl)-1H-pyrazole-4-carboxylic acid

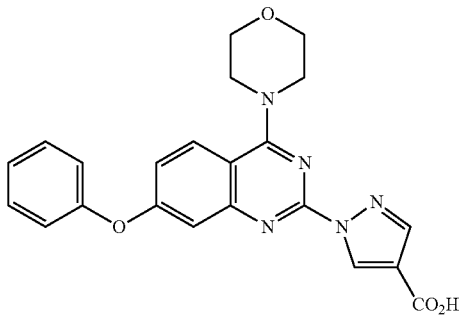 [SMILES: O=C(O)c1cnn(-c2nc(N3CCOCC3)c3ccc(Oc4ccccc4)cc3n2)c1]

The titled compound was prepared in a manner analogous to EXAMPLE 77 using 3-phenoxy aniline in step A and morpholine in step D. MS (ESI): mass calcd. for $C_{22}H_{19}N_5O_4$, 417.1; m/z found, 418.1 [M+H]$^+$. $^1$H NMR (600 MHz, DMSO-d$_6$): 9.02 (5, 1H), 8.13-8.12 (m, 1H), 8.11 (s, 1H), 7.59-7.45 (m, 2H), 7.33 (t, J=7.4 Hz, 1H), 7.28-7.18 (m, 3H), 7.04 (d, J=2.5 Hz, 1H), 3.94-3.92 (m, 4H), 3.88-3.76 (m, 4H).

Example 90

1-(7-Phenoxy-4-thiomorpholinoquinazolin-2-yl)-1H-pyrazole-4-carboxylic acid

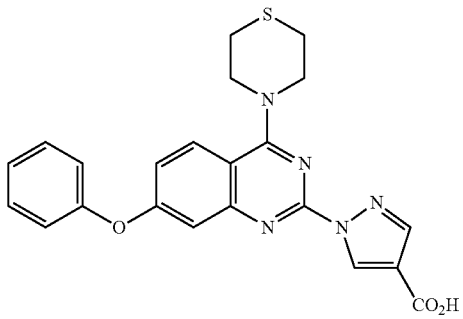 [SMILES: O=C(O)c1cnn(-c2nc(N3CCSCC3)c3ccc(Oc4ccccc4)cc3n2)c1]

The titled compound was prepared in a manner analogous to EXAMPLE 77 using 3-phenoxy aniline in step A and thiomorpholine in step D. MS (ESI): mass calcd. for $C_{22}H_{19}N_5O_3S$, 433.1; m/z found, 434.1 [M+H]$^+$. $^1$H NMR (600 MHz, DMSO-d$_6$): 9.04-8.97 (m, 1H), 8.10 (s, 1H), 8.05 (d, J=9.2 Hz, 1H), 7.58-7.48 (m, 2H), 7.36-7.29 (m, 1H), 7.28-7.20 (m, 3H), 7.05 (d, J=2.5 Hz, 1H), 4.22-4.08 (m, 4H), 2.96-2.86 (m, 4H).

Example 91

1-(4-(4-Fluoropiperidin-1-yl)-7-phenoxyquinazolin-2-yl)-1H-pyrazole-4-carboxylic acid

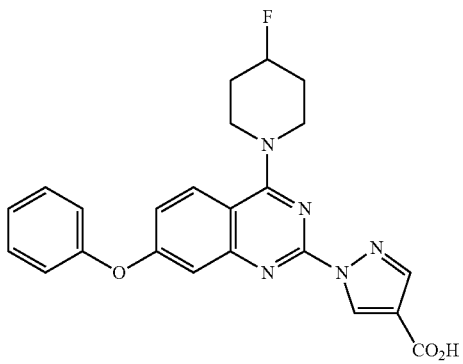 [SMILES: O=C(O)c1cnn(-c2nc(N3CCC(F)CC3)c3ccc(Oc4ccccc4)cc3n2)c1]

The titled compound was prepared in a manner analogous to EXAMPLE 77 using 3-phenoxy aniline in step A and 4-fluoropiperidine in step D. MS (ESI): mass calcd. for $C_{23}H_{20}FN_5O_3$, 433.2; m/z found, 434.1 [M+H]$^+$. $^1$H NMR (600 MHz, DMSO-d$_6$): 9.02 (s, 1H), 8.14-8.09 (m, 2H), 7.58-7.48 (m, 2H), 7.37-7.30 (m, 1H), 7.27-7.20 (m, 3H), 7.06 (d, J=2.5 Hz, 1H), 5.14-4.92 (m, 1H), 4.06-3.65 (m, 4H), 2.23-2.03 (m, 2H), 1.97-1.92 (m, 2H).

Example 92

1-(4-(Dibutylamino)-7-phenoxyquinazolin-2-yl)-1H-pyrazole-4-carboxylic acid

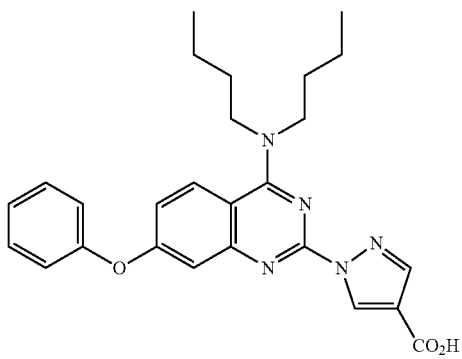 [SMILES: CCCCN(CCCC)c1nc(-n2cc(C(=O)O)cn2)nc2cc(Oc3ccccc3)ccc12]

The titled compound was prepared in a manner analogous to EXAMPLE 77 using 3-phenoxy aniline in step A and dibutylamine in step D. MS (ESI): mass calcd. for $C_{26}H_{29}N_5O_3$, 459.2; m/z found, 460.2 [M+H]$^+$. $^1$H NMR (600 MHz, DMSO-d$_6$): 8.91 (s, 1H), 8.10 (s, 1H), 8.04 (d, J=9.3 Hz, 1H), 7.57-7.48 (m, 2H), 7.37-7.28 (m, 1H), 7.24-7.22 (m, 3H), 7.04 (d, J=2.3 Hz, 1H), 3.80-3.77 (m, 4H), 1.79 (dt, J=15.3, 7.7 Hz, 4H), 1.44-1.38 (m, 4H), 0.96 (t, J=7.4 Hz, 6H).

Example 93

1-(4-(Dipropylamino)-7-phenoxyquinazolin-2-yl)-1H-pyrazole-4-carboxylic acid

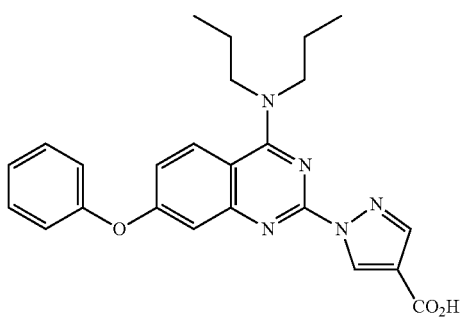 [SMILES: CCCN(CCC)c1nc(-n2cc(C(=O)O)cn2)nc2cc(Oc3ccccc3)ccc12]

The titled compound was prepared in a manner analogous to EXAMPLE 77 using 3-phenoxy aniline in step A and dipropylamine in step D. MS (ESI): mass calcd. for $C_{24}H_{25}N_5O_3$, 431.2; m/z found, 432.2 [M+H]$^+$. $^1$H NMR (600 MHz, DMSO-d$_6$): 8.91 (s, 1H), 8.10 (s, 1H), 8.03 (d, J=9.2 Hz, 1H), 7.56-7.47 (m, 2H), 7.32 (t, J=7.4 Hz, 1H), 7.23 (dd, J=8.6, 1.0 Hz, 3H), 7.04 (s, 1H), 3.77-3.74 (m, 4H), 1.93-1.70 (m, 4H), 0.98-0.96 (m, 6H).

Example 94

1-(4-(Ethyl(methyl)amino)-7-phenoxyquinazolin-2-yl)-1H-pyrazole-4-carboxylic acid

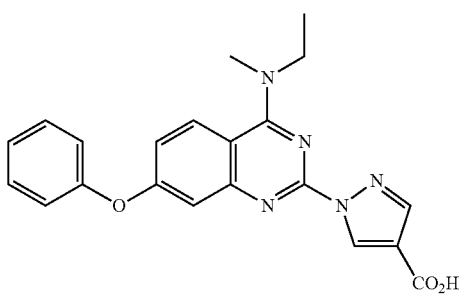 [SMILES: CCN(C)c1nc(-n2cc(C(=O)O)cn2)nc2cc(Oc3ccccc3)ccc12]

The titled compound was prepared in a manner analogous to EXAMPLE 77 using 3-phenoxy aniline in step A and N-methylethylamine in step D. MS (ESI): mass calcd. for $C_{21}H_{19}N_5O_3$, 389.2; m/z found, 390.1 [M+H]$^+$. $^1$H NMR (600 MHz, DMSO-d$_6$): 8.97 (s, 1H), 8.26 (d, J=9.1 Hz, 1H), 8.11 (s, 1H), 7.59-7.43 (m, 2H), 7.37-7.29 (m, 1H), 7.24-7.22 (m, 2H), 7.20-7.18 (m, 1H), 7.05 (s, 1H), 3.90-3.87 (m, 2H), 3.47 (s, 3H), 1.35 (t, J=7.1 Hz, 3H).

Example 95

1-(4-((2-Methoxyethyl)(methyl)amino)-7-phenoxyquinazolin-2-yl)-1H-pyrazole-4-carboxylic acid

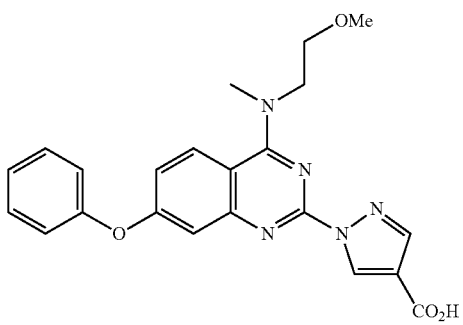 [SMILES: COCCN(C)c1nc(-n2cc(C(=O)O)cn2)nc2cc(Oc3ccccc3)ccc12]

The titled compound was prepared in a manner analogous to EXAMPLE 77 using 3-phenoxy aniline in step A and 2-methoxy-N-methyl ethylamine in step D. MS (ESI): mass calcd. for $C_{22}H_{21}N_5O_4$, 419.2; m/z found, 420.1 [M+H]$^+$. $^1$H NMR (600 MHz, DMSO-d$_6$): 8.98 (s, 1H), 8.36 (d, J=9.2 Hz, 1H), 8.10 (s, 1H), 7.57-7.47 (m, 2H), 7.37-7.29 (m, 1H), 7.27-7.21 (m, 2H), 7.18 (dd, J=9.3, 2.5 Hz, 1H), 7.04 (s, 1H), 4.07 (t, J=5.5 Hz, 2H), 3.77-3.74 (m, 2H), 3.53 (s, 3H), 3.31 (s, 3H).

Example 96

1-(7-Bromo-4-(diethylamino)quinazolin-2-yl)-1H-pyrazole-4-carboxylic acid

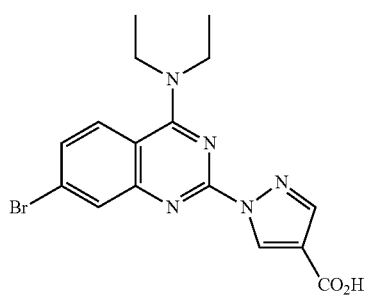 [SMILES: CCN(CC)c1nc(-n2cc(C(=O)O)cn2)nc2cc(Br)ccc12]

The titled compound was prepared in a manner analogous to EXAMPLE 77 using 3-bromoaniline in step A and diethylamine in step D. MS (ESI): mass calcd. for $C_{16}H_{16}BrN_5O_2$, 389.1; m/z found, 390.0 [M+H]$^+$. $^1$H NMR (600 MHz, DMSO-d$_6$): 12.75 (s, 1H), 8.94 (d, J=0.7 Hz, 1H), 8.11 (d, J=0.7 Hz, 1H), 7.97 (s, 1H), 7.96 (d, J=2.0 Hz, 2H), 3.83 (q, J=7.0 Hz, 4H), 1.44-1.33 (m, 6H).

Example 97

1-(4-(Cyclohexylamino)-7-phenoxyquinazolin-2-yl)-1H-pyrazole-4-carboxylic acid

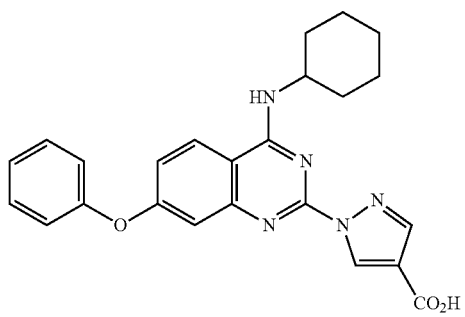 [SMILES: O=C(O)c1cnn(-c2nc(NC3CCCCC3)c3ccc(Oc4ccccc4)cc3n2)c1]

The titled compound was prepared in a manner analogous to EXAMPLE 77 using 3-phenoxyaniline in step A and cyclohexylamine in step D. MS (ESI): mass calcd. for $C_{24}H_{23}N_5O_3$, 429.2; m/z found, 430.1 [M+H]$^+$. $^1$H NMR (600 MHz, DMSO-d$_6$): 8.97 (s, 1H), 8.49-8.45 (m, 2H), 8.11 (s, 1H), 7.51 (t, J=7.9 Hz, 2H), 7.30 (t, J=7.4 Hz, 1H), 7.26 (d, J=9.1 Hz, 1H), 7.20 (d, J=7.7 Hz, 2H), 7.01 (s, 1H), 4.30 (s, 1H), 2.05-2.00 (m, 2H), 1.82-1.80 (m, 2H), 1.70-1.68 (m, 1H), 1.52-1.36 (m, 4H), 1.29-1.13 (m, 1H).

Example 98

1-(4-((Cyclopropylmethyl)amino)-7-phenoxyquinazolin-2-yl)-1H-pyrazole-4-carboxylic acid

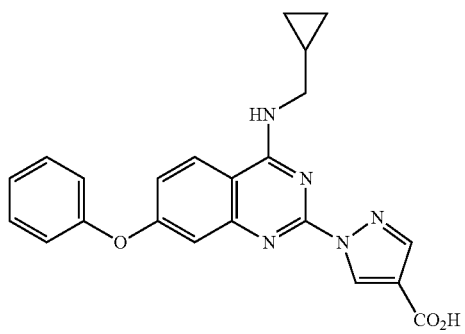 [SMILES: O=C(O)c1cnn(-c2nc(NCC3CC3)c3ccc(Oc4ccccc4)cc3n2)c1]

The titled compound was prepared in a manner analogous to EXAMPLE 77 using 3-phenoxyaniline in step A and cyclopropylmethylamine in step D. MS (ESI): mass calcd. for $C_{22}H_{19}N_5O_3$, 401.2; m/z found, 402.1 [M+H]$^+$. $^1$H NMR (600 MHz, DMSO-d$_6$): 8.99 (s, 1H), 8.92 (s, 1H), 8.38 (d, J=8.5 Hz, 1H), 8.10 (s, 1H), 7.56-7.45 (m, 2H), 7.33-7.29 (m, 1H), 7.27 (d, J=9.0 Hz, 1H), 7.21 (dd, J=8.5, 1.0 Hz, 2H), 7.00 (s, 1H), 3.72-3.28 (m, 2H), 1.33-1.14 (m, 1H), 0.58-0.46 (m, 2H), 0.43-0.32 (m, 2H).

Example 99

1-(4-(tert-Butylamino)-7-phenoxyquinazolin-2-yl)-1H-pyrazole-4-carboxylic acid

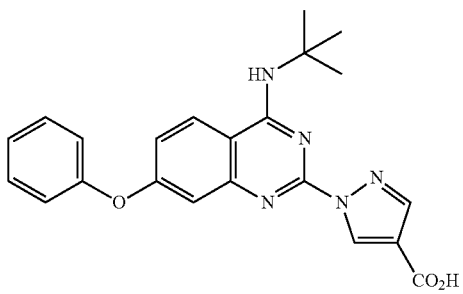 [SMILES: CC(C)(C)Nc1nc(-n2cc(C(=O)O)cn2)nc2cc(Oc3ccccc3)ccc12]

The titled compound was prepared in a manner analogous to EXAMPLE 77 using 3-phenoxyaniline in step A and 2-methylpropan-2-amine in step D. MS (ESI): mass calcd. for $C_{22}H_{21}N_5O_3$, 403.2; m/z found, 404.2 [M+H]$^+$. $^1$H NMR (600 MHz, DMSO-d$_6$): 8.87 (d, J=0.7 Hz, 1H), 8.51 (d, J=9.1 Hz, 1H), 8.11 (d, J=0.6 Hz, 1H), 7.83 (s, 1H), 7.56-7.44 (m, 2H), 7.32-7.28 (m, 1H), 7.24 (dd, J=9.1, 2.6 Hz, 1H), 7.22-7.18 (m, 2H), 6.97 (d, J=2.5 Hz, 1H), 1.61 (s, 9H).

Example 100

1-(7-Fluoro-6-(cyclohexyloxy)-4-morpholino-quinazolin-2-yl)-1H-pyrazole-4-carboxylic acid

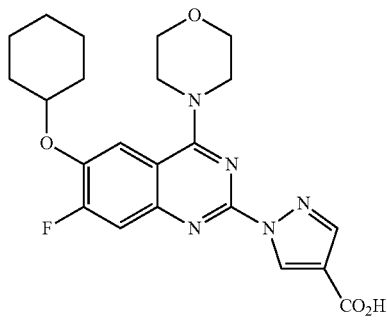 [SMILES: O=C(O)c1cnn(-c2nc(N3CCOCC3)c3cc(OC4CCCCC4)c(F)cc3n2)c1]

The titled compound was prepared in a manner analogous to EXAMPLE 1 steps B through F using 3-fluoro-4-cyclohexyloxyaniline in step B and morpholine in step E. MS (ESI): mass calcd. for $C_{22}H_{24}FN_5O_4$, 441.5; m/z found, 442.3 [M+H]+. 1H NMR (400 MHz, DMSO-d$_6$): 12.68 (s, 1H), 9.00 (s, 1H), 8.10 (s, 1H), 7.68 (d, J=12.0 Hz, 1H), 7.49 (d, J=9.1 Hz, 1H), 4.58 (s, 1H), 3.87 (s, 4H), 3.82 (s, 4H), 1.97 (s, 2H), 1.74 (s, 2H), 1.65-1.29 (m, 6H).

Example 101

1-(7-fluoro-6-(cyclohexyloxy)-4-(dimethylamino)quinazolin-2-yl)-1H-pyrazole-4-carboxylic acid

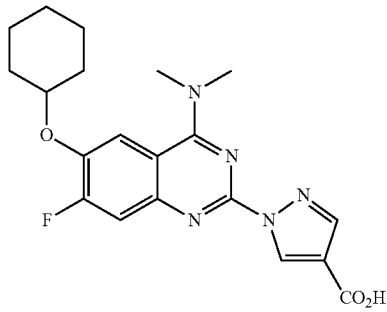 [SMILES: CN(C)c1nc(-n2cc(C(=O)O)cn2)nc2cc(F)c(OC3CCCCC3)cc12]

The titled compound was prepared in a manner analogous to EXAMPLE 1 steps B through F using 3-fluoro-4-cyclohexyloxyaniline in step B and dimethylamine in step E. MS (ESI): mass calcd. for $C_{20}H_{22}FN_5O_3$, 399.4; m/z found, 400.1 [M+H]+. 1H NMR (400 MHz, DMSO-d$_6$): 12.77 (s, 1H), 8.97 (s, 1H), 8.08 (s, 1H), 7.74 (d, J=8.7 Hz, 1H), 7.59 (d, J=11.7 Hz, 1H), 4.56 (s, 1H), 3.43 (s, 6H), 1.98 (s, 2H), 1.74 (s, 2H), 1.64-1.25 (m, 6H).

Example 102

1-(7-fluoro-6-(cyclohexyloxy)-4-(pyrrolidin-1-yl)quinazolin-2-yl)-1H-pyrazole-4-carboxylic acid

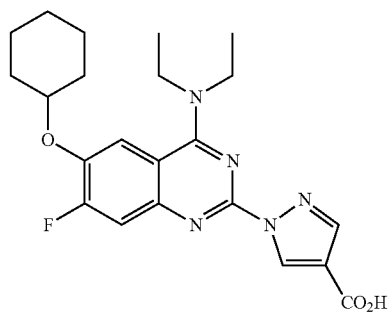 [SMILES: CCN(CC)c1nc(-n2cc(C(=O)O)cn2)nc2cc(F)c(OC3CCCCC3)cc12]

The titled compound was prepared in a manner analogous to EXAMPLE 1 steps B through F using 3-fluoro-4-cyclohexyloxyaniline in step B and diethylamine in step E. MS (ESI): mass calcd. for $C_{22}H_{26}FN_5O_3$, 427.5; m/z found, 428.2 [M+H]+. 1H NMR (400 MHz, DMSO-d$_6$): 12.78 (s, 1H), 8.92 (s, 1H), 8.10 (s, 1H), 7.62 (d, J=12.1 Hz, 1H), 7.48 (d, J=8.8 Hz, 1H), 4.49 (s, 1H), 3.79 (q, J=6.4 Hz, 4H), 2.03 (s, 2H), 1.76 (s, 2H), 1.64-1.26 (m, 12H).

Example 103

1-(7-fluoro-6-(cyclohexyloxy)-4-(pyrrolidin-1-yl)quinazolin-2-yl)-1H-pyrazole-4-carboxylic acid

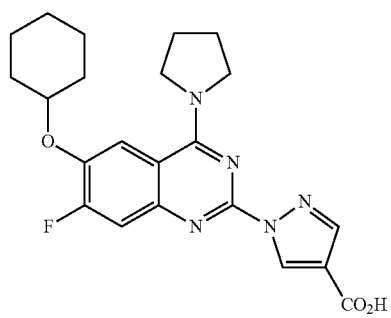 [SMILES: O=C(O)c1cnn(-c2nc(N3CCCC3)c3cc(OC4CCCCC4)c(F)cc3n2)c1]

The titled compound was prepared in a manner analogous to EXAMPLE 1 steps B through F using 3-fluoro-4-cyclohexyloxyaniline in step B and pyrrolidine in step E. MS (ESI): mass calcd. for $C_{22}H_{24}FN_5O_3$, 425.5; m/z found, 426.1 [M+H]+. 1H NMR (400 MHz, DMSO-d$_6$): 12.73 (s, 1H), 8.96 (s, 1H), 8.07 (s, 1H), 7.84 (d, J=9.1 Hz, 1H), 7.56 (d, J=12.1 Hz, 1H), 4.53 (s, 1H), 3.98 (s, 4H), 2.01 (s, 6H), 1.74 (s, 2H), 1.63-1.27 (m, 6H).

Example 104

1-(7-fluoro-6-(cyclohexyloxy)-4-(ethyl(methyl)amino)quinazolin-2-yl)-1H-pyrazole-4-carboxylic acid

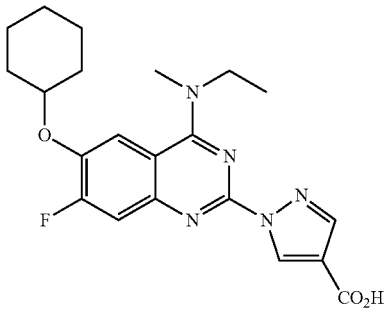 [SMILES: CCN(C)c1nc(-n2cc(C(=O)O)cn2)nc2cc(F)c(OC3CCCCC3)cc12]

The titled compound was prepared in a manner analogous to EXAMPLE 1 steps B through F using 3-fluoro-4-cyclohexyloxyaniline in step B and N-ethyl-N-methylamine in step E. MS (ESI): mass calcd. for $C_{21}H_{24}FN_5O_3$, 413.5; m/z found, 414.1 [M+H]+. 1H NMR (400 MHz, DMSO-$d_6$): 12.81 (S, 1H), 8.94 (S, 1H), 8.08 (S, 1H), 7.64-7.58 (m, 2H), 4.53 (S, 1H), 3.80 (q, J=6.5 Hz, 2H), 3.39 (S, 3H), 2.00 (S, 2H), 1.74 (S, 2H), 1.64-1.26 (m, 9H).

Example 105

1-(7-fluoro-6-(cyclohexyloxy)-4-(cyclopropylamino)quinazolin-2-yl)-1H-pyrazole-4-carboxylic acid

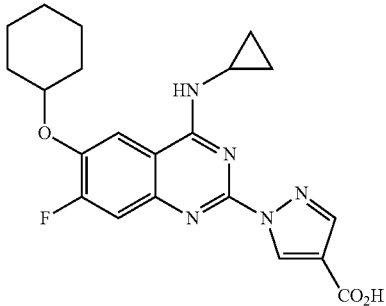 [SMILES: O=C(O)c1cnn(-c2nc(NC3CC3)c3cc(OC4CCCCC4)c(F)cc3n2)c1]

The titled compound was prepared in a manner analogous to EXAMPLE 1 steps B through F using 3-fluoro-4-cyclohexyloxyaniline in step B and cyclopropylamine in step E. MS (ESI): mass calcd. for $O_{21}H_{22}FN_5O_3$, 411.4; m/z found, 412.2 [M+H]+. 1H NMR (400 MHz, DMSO-$d_6$): 8.96 (s, 1H), 8.61 (S, 1H), 8.03 (S, 1H), 7.94 (d, J=8.9 Hz, 1H), 7.55 (d, J=12.1 Hz, 1H), 4.55 (S, 1H), 3.19-3.07 (m, 1H), 1.95 (S, 2H), 1.74 (S, 2H), 1.64-1.26 (m, 6H), 0.97-0.85 (m, 2H), 0.77-0.67 (m, 2H).

Examples 106-135 are prophetic Examples which may be synthesized using the general schemes provided above.

Example 106

1-(6-Benzyl-7-fluoro-4-morpholinoquinazolin-2-yl)-1H-pyrazole-4-carboxylic acid

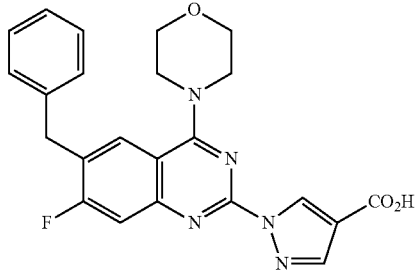 [SMILES: O=C(O)c1cnn(-c2nc(N3CCOCC3)c3cc(Cc4ccccc4)c(F)cc3n2)c1]

The above compound may be made analogous to Example 1 using ethyl 1-(6-benzyl-7-fluoro-4-oxo-3,4-dihydroquinazolin-2-yl)-1H-pyrazole-4-carboxylate in step D and morpholine in step E. MS (ESI): predicted mass calcd. for $C_{23}H_{20}FN_5O_3$, 433.2

Example 107

1-(6-Benzyl-4-(dimethylamino)-7-fluoroquinazolin-2-yl)-1H-pyrazole-4-carboxylic acid

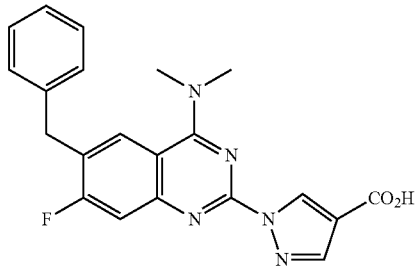 [SMILES: CN(C)c1nc(-n2cc(C(=O)O)cn2)nc2cc(F)c(Cc3ccccc3)cc12]

The above compound may be made analogous to Example 1 using ethyl 1-(6-benzyl-7-fluoro-4-oxo-3,4-dihydroquinazolin-2-yl)-1H-pyrazole-4-carboxylate in step D and dimethylamine in step E. MS (ESI): predicted mass calcd. for $C_{21}H_{18}FN_5O_2$, 391.1

Example 108

1-(6-Benzyl-4-(diethylamino)-7-fluoroquinazolin-2-yl)-1H-pyrazole-4-carboxylic acid

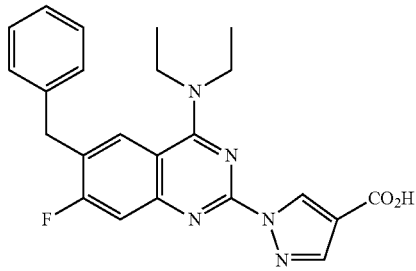 [SMILES: CCN(CC)c1nc(-n2cc(C(=O)O)cn2)nc2cc(F)c(Cc3ccccc3)cc12]

The above compound may be made analogous to Example 1 using ethyl 1-(6-benzyl-7-fluoro-4-oxo-3,4-dihydroquinazolin-2-yl)-1H-pyrazole-4-carboxylate in step D and diethylamine in step E. MS (ESI): predicted mass calcd. for $C_{23}H_{22}FN_5O_2$, 419.2

Example 109

1-(6-Benzyl-7-fluoro-4-(pyrrolidin-1-yl)quinazolin-2-yl)-1H-pyrazole-4-carboxylic acid

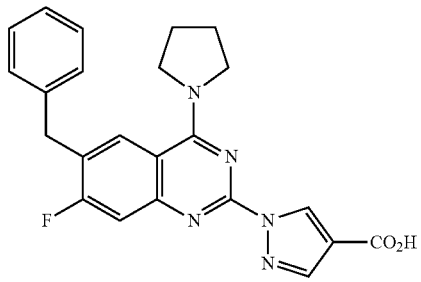 [SMILES: O=C(O)c1cnn(-c2nc(N3CCCC3)c3cc(Cc4ccccc4)c(F)cc3n2)c1]

The above compound may be made analogous to Example 1 using ethyl 1-(6-benzyl-7-fluoro-4-oxo-3,4-dihydroquinazolin-2-yl)-1H-pyrazole-4-carboxylate in step D and pyrrolidine in step E. MS (ESI): predicted mass calcd. for $C_{23}H_{20}FN_5O_2$, 417.2

Example 110

1-(6-Benzyl-4-(ethyl(methyl)amino)-7-fluoroquinazolin-2-yl)-1H-pyrazole-4-carboxylic acid

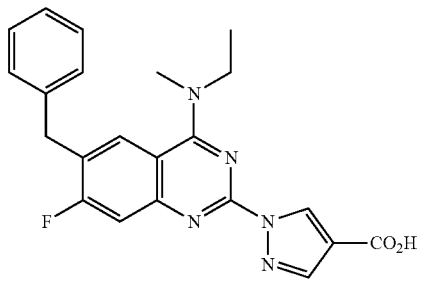 [SMILES: CCN(C)c1nc(-n2cc(C(=O)O)cn2)nc2cc(F)c(Cc3ccccc3)cc12]

The above compound may be made analogous to Example 1 using ethyl 1-(6-benzyl-7-fluoro-4-oxo-3,4-dihydroquinazolin-2-yl)-1H-pyrazole-4-carboxylate in step D and N-methylethanamine in step E. MS (ESI): predicted mass calcd. for $C_{22}H_{20}FN_5O_2$, 405.2

Example 111

1-(6-Benzyl-4-(cyclopropylamino)-7-fluoroquinazolin-2-yl)-1H-pyrazole-4-carboxylic acid

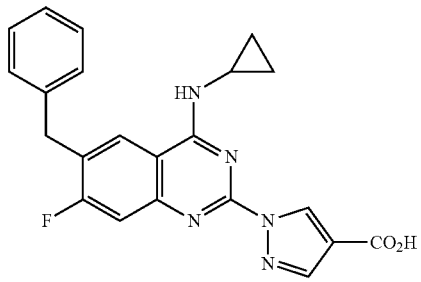 [SMILES: O=C(O)c1cnn(-c2nc(NC3CC3)c3cc(Cc4ccccc4)c(F)cc3n2)c1]

The above compound may be made analogous to Example 1 using ethyl 1-(6-benzyl-7-fluoro-4-oxo-3,4-dihydroquinazolin-2-yl)-1H-pyrazole-4-carboxylate in step D and cyclopropyl amine in step E. MS (ESI): predicted mass calcd. for $C_{22}H_{18}FN_5O_2$, 403.1

Example 112

1-(6-((2,6-Dimethylbenzyl)amino)-7-fluoro-4-morpholinoquinazolin-2-yl)-1H-pyrazole-4-carboxylic acid

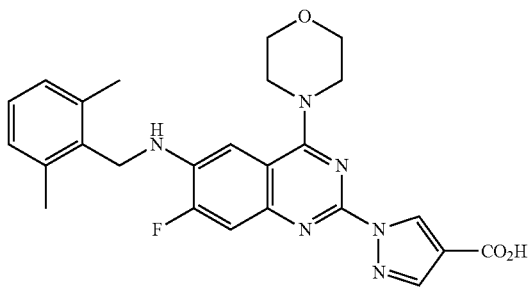 [SMILES: Cc1cccc(C)c1CNc1cc2c(N3CCOCC3)nc(-n3cc(C(=O)O)cn3)nc2cc1F]

The above compound may be made analogous to Example 1 using ethyl 1-(6-((2,6-dimethylbenzyl)amino)-7-fluoro-4-oxo-3,4-dihydroquinazolin-2-yl)-1H-pyrazole-4-carboxylate in step D and morpholine in step E. MS (ESI): predicted mass calcd. for $C_{25}H_{25}FN_6O_3$, 476.2

Example 113

1-(4-(Dimethylamino)-6-((2,6-dimethylbenzyl)amino)-7-fluoroquinazolin-2-yl)-1H-pyrazole-4-carboxylic acid

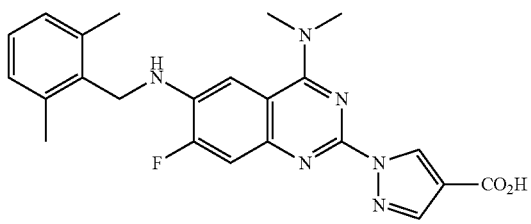 [SMILES: Cc1cccc(C)c1CNc1cc2c(N(C)C)nc(-n3cc(C(=O)O)cn3)nc2cc1F]

The above compound may be made analogous to Example 1 using ethyl 1-(6-((2,6-dimethylbenzyl)amino)-7-fluoro-4-oxo-3,4-dihydroquinazolin-2-yl)-1H-pyrazole-4-carboxylate in step D and dimethylamine in step E. MS (ESI): predicted mass calcd. for $C_{23}H_{23}FN_6O_2$, 434.2

Example 114

1-(4-(Diethylamino)-6-(2,6-dimethylbenzyl)amino)-7-fluoroquinazolin-2-yl)-1H-pyrazole-4-carboxylic acid

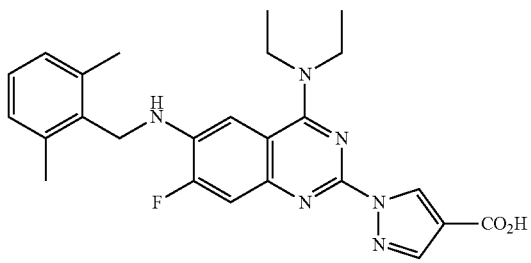

The above compound may be made analogous to Example 1 using ethyl 1-(6-((2,6-dimethylbenzyl)amino)-7-fluoro-4-oxo-3,4-dihydroquinazolin-2-yl)-1H-pyrazole-4-carboxylate in step D and diethylamine in step E. MS (ESI): predicted mass calcd. for $C_{25}H_{27}FN_6O_2$, 462.2

Example 115

1 1-(6-((2,6-Dimethylbenzyl)amino)-7-fluoro-4-(pyrrolidin-1-yl)quinazolin-2-yl)-1H-pyrazole-4-carboxylic acid

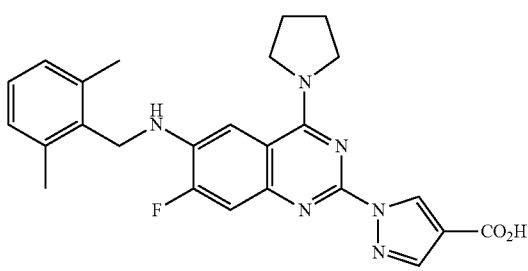 [SMILES: Cc1cccc(C)c1CNc1cc2c(N3CCCC3)nc(-n3cc(C(=O)O)cn3)nc2cc1F]

The above compound may be made analogous to Example 1 using ethyl 1-(6-((2,6-dimethylbenzyl)amino)-7-fluoro-4-oxo-3,4-dihydroquinazolin-2-yl)-1H-pyrazole-4-carboxylate in step D and pyrrolidine in step E. MS (ESI): predicted mass calcd. for $C_{25}H_{25}FN_6O_2$, 460.2

Example 116

1-(6-((2,6-Dimethylbenzyl)amino)-4-(ethyl(methyl)amino)-7-fluoroquinazolin-2-yl)-1H-pyrazole-4-carboxylic acid

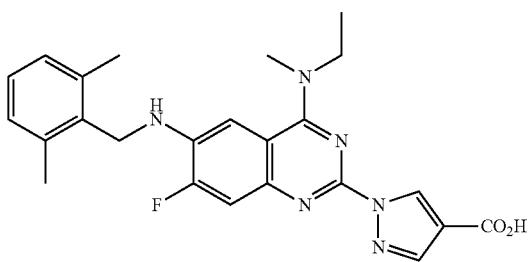 [SMILES: CCN(C)c1nc(-n2cc(C(=O)O)cn2)nc2cc(F)c(NCc3c(C)cccc3C)cc12]

The above compound may be made analogous to Example 1 using ethyl 1-(6-((2,6-dimethylbenzyl)amino)-7-fluoro-4-oxo-3,4-dihydroquinazolin-2-yl)-1H-pyrazole-4-carboxylate in step D and N-methylethanamine in step E. MS (ESI): predicted mass calcd. for $C_{24}H_{25}FN_6O_2$, 448.2

Example 117

1-(4-(Cyclopropylamino)-6-((2,6-dimethylbenzyl)amino)-7-fluoroquinazolin-2-yl)-1H-pyrazole-4-carboxylic acid

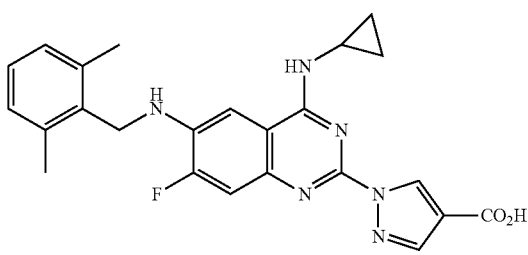 [SMILES: Cc1cccc(C)c1CNc1cc2c(NC3CC3)nc(-n3cc(C(=O)O)cn3)nc2cc1F]

The above compound may be made analogous to Example 1 using ethyl 1-(6-((2,6-dimethylbenzyl)amino)-7-fluoro-4-oxo-3,4-dihydroquinazolin-2-yl)-1H-pyrazole-4-carboxylate in step D and cyclopropyl amine in step E. MS (ESI): predicted mass calcd. for $C_{24}H_{23}FN_6O_2$, 446.2

Example 118

1-(7-Fluoro-4-morpholino-6-(o-tolyl)quinazolin-2-yl)-1H-pyrazole-4-carboxylic acid

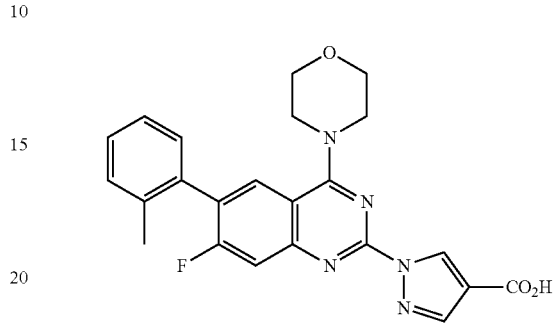

The above compound may be made analogous to Example 1 using ethyl 1-(7-fluoro-4-oxo-6-(o-tolyl)-3,4-dihydroquinazolin-2-yl)-1H-pyrazole-4-carboxylate in step D and morpholine in step E. MS (ESI): predicted mass calcd. for $C_{23}H_{20}FN_5O_3$, 433.2

Example 119

1-(4-(Dimethylamino)-7-fluoro-6-(o-tolyl)quinazolin-2-yl)-1H-pyrazole-4-carboxylic acid

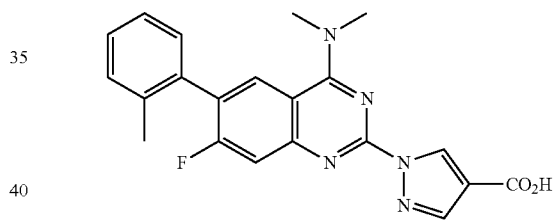

The above compound may be made analogous to Example 1 using ethyl 1-(7-fluoro-4-oxo-6-(o-tolyl)-3,4-dihydroquinazolin-2-yl)-1H-pyrazole-4-carboxylate in step D and dimethylamine in step E. MS (ESI): predicted mass calcd. for $C_{21}H_{18}FN_5O_2$, 391.1

Example 120

1-(4-(Diethylamino)-7-fluoro-6-(o-tolyl)quinazolin-2-yl)-1H-pyrazole-4-carboxylic acid

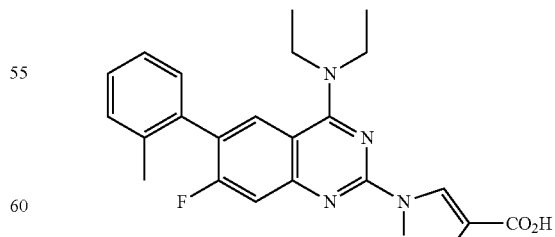

The above compound may be made analogous to Example 1 using ethyl 1-(7-fluoro-4-oxo-6-(o-tolyl)-3,4-dihydroquinazolin-2-yl)-1H-pyrazole-4-carboxylate in step D and diethylamine in step E. MS (ESI): predicted mass calcd. for $C_{23}H_{22}FN_5O_2$, 419.2

Example 121

1-(7-Fluoro-4-(pyrrolidin-1-yl)-6-(o-tolyl)quinazolin-2-yl)-1H-pyrazole-4-carboxylic acid

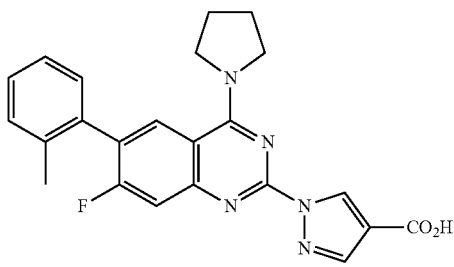 [SMILES: Cc1ccccc1-c1cc2c(N3CCCC3)nc(-n3cc(C(=O)O)cn3)nc2cc1F]

The above compound may be made analogous to Example 1 using ethyl 1-(7-fluoro-4-oxo-6-(o-tolyl)-3,4-dihydroquinazolin-2-yl)-1H-pyrazole-4-carboxylate in step D and pyrrolidine in step E. MS (ESI): predicted mass calcd. for $C_{23}H_{20}FN_5O_2$, 417.2

Example 122

1-(4-(Ethyl(methyl)amino)-7-fluoro-6-(o-tolyl)quinazolin-2-yl)-1H-pyrazole-4-carboxylic acid

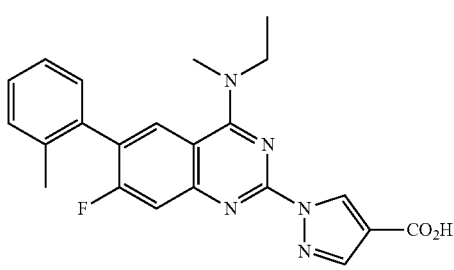

The above compound may be made analogous to Example 1 using ethyl 1-(7-fluoro-4-oxo-6-(o-tolyl)-3,4-dihydroquinazolin-2-yl)-1H-pyrazole-4-carboxylate in step D and N-methylethanamine in step E. MS (ESI): predicted mass calcd. for $C_{22}H_{20}FN_5O_2$, 405.2

Example 123

1-(4-(Cyclopropylamino)-7-fluoro-6-(o-tolyl)quinazolin-2-yl)-1H-pyrazole-4-carboxylic acid

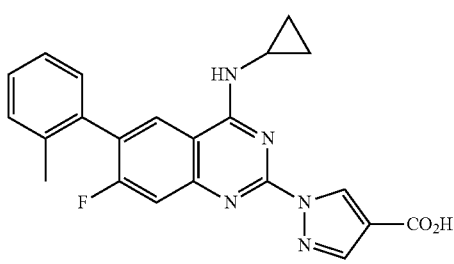 [SMILES: Cc1ccccc1-c1cc2c(NC3CC3)nc(-n3cc(C(=O)O)cn3)nc2cc1F]

The above compound may be made analogous to Example 1 using ethyl 1-(7-fluoro-4-oxo-6-(o-tolyl)-3,4-dihydroquinazolin-2-yl)-1H-pyrazole-4-carboxylate in step D and cyclopropyl amine in step E. MS (ESI): predicted mass calcd. for $C_{22}H_{18}FN_5O_2$, 403.1

Example 124

1-(7-Fluoro-6-isopropyl-4-morpholinoquinazolin-2-yl)-1H-pyrazole-4-carboxylic acid

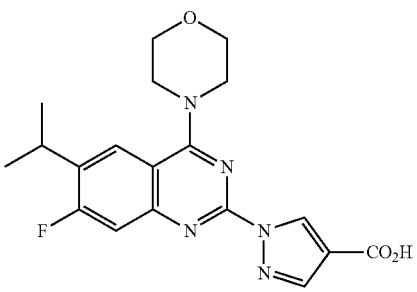 [SMILES: CC(C)c1cc2c(N3CCOCC3)nc(-n3cc(C(=O)O)cn3)nc2cc1F]

The above compound may be made analogous to Example 1 using ethyl 1-(7-fluoro-6-isopropyl-4-oxo-3,4-dihydroquinazolin-2-yl)-1H-pyrazole-4-carboxylate in step D and morpholine in step E. MS (ESI): predicted mass calcd. for $C_{19}H_{20}FN_5O_3$, 385.2

Example 125

1-(4-(Dimethylamino)-7-fluoro-6-isopropylquinazolin-2-yl)-1H-pyrazole-4-carboxylic acid

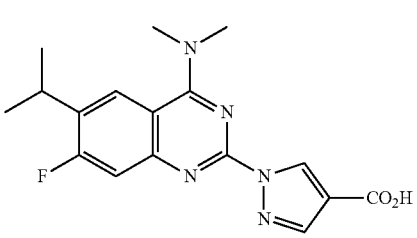 [SMILES: CC(C)c1cc2c(N(C)C)nc(-n3cc(C(=O)O)cn3)nc2cc1F]

The above compound may be made analogous to Example 1 using ethyl 1-(7-fluoro-6-isopropyl-4-oxo-3,4-dihydroquinazolin-2-yl)-1H-pyrazole-4-carboxylate in step D and dimethylamine in step E. MS (ESI): predicted mass calcd. for $C_{17}H_{18}FN_5O_2$, 343.1

Example 126

1-(4-(Diethylamino)-7-fluoro-6-isopropylquinazolin-2-yl)-1H-pyrazole-4-carboxylic acid

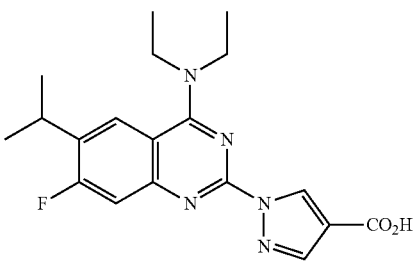 [SMILES: CCN(CC)c1nc(-n2cc(C(=O)O)cn2)nc2cc(F)c(C(C)C)cc12]

The above compound may be made analogous to Example 1 using ethyl 1-(7-fluoro-6-isopropyl-4-oxo-3,4-dihydroquinazolin-2-yl)-1H-pyrazole-4-carboxylate in step D and diethylamine in step E. MS (ESI): predicted mass calcd. for $C_{19}H_{22}FN_5O_2$, 371.2

Example 127

1-(7-Fluoro-6-isopropyl-4-(pyrrolidin-1-yl)quinazolin-2-yl)-1H-pyrazole-4-carboxylic acid

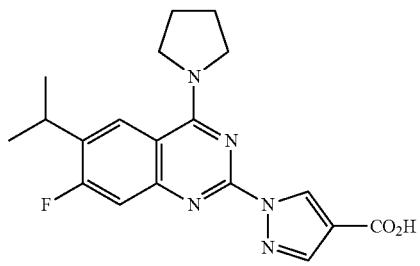 [SMILES: CC(C)c1cc2c(N3CCCC3)nc(-n3cc(C(=O)O)cn3)nc2cc1F]

The above compound may be made analogous to Example 1 using ethyl 1-(7-fluoro-6-isopropyl-4-oxo-3,4-dihydroquinazolin-2-yl)-1H-pyrazole-4-carboxylate in step D and pyrrolidine in step E. MS (ESI): predicted mass calcd. for $C_{19}H_{20}FN_5O_2$, 369.2

Example 128

1-(4-(Ethyl(methyl)amino)-7-fluoro-6-isopropylquinazolin-2-yl)-1H-pyrazole-4-carboxylic acid

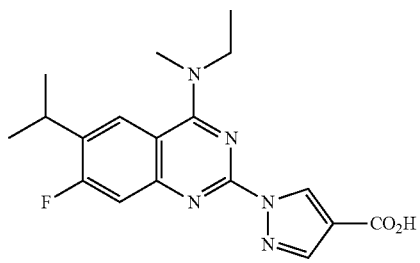 [SMILES: CCN(C)c1nc(-n2cc(C(=O)O)cn2)nc2cc(F)c(C(C)C)cc12]

The above compound may be made analogous to Example 1 using ethyl 1-(7-fluoro-6-isopropyl-4-oxo-3,4-dihydroquinazolin-2-yl)-1H-pyrazole-4-carboxylate in step D and N-methylethanamine in step E. MS (ESI): predicted mass calcd. for $C_{18}H_{20}FN_5O_2$, 357.2

Example 129

1-(4-(Cyclopropylamino)-7-fluoro-6-isopropylquinazolin-2-yl)-1H-pyrazole-4-carboxylic acid

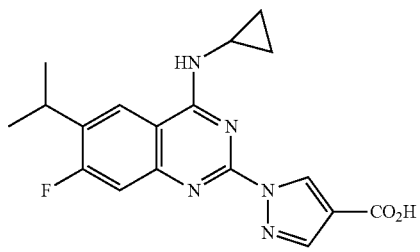 [SMILES: CC(C)c1cc2c(NC3CC3)nc(-n3cc(C(=O)O)cn3)nc2cc1F]

The above compound may be made analogous to Example 1 using ethyl 1-(7-fluoro-6-isopropyl-4-oxo-3,4-dihydroquinazolin-2-yl)-1H-pyrazole-4-carboxylate in step D and cyclopropyl amine in step E. MS (ESI): predicted mass calcd. for $C_{18}H_{18}FN_5O_2$, 355.1

Example 130

1-(7-Fluoro-4-morpholino-6-(piperidin-1-yl)quinazolin-2-yl)-1H-pyrazole-4-carboxylic acid

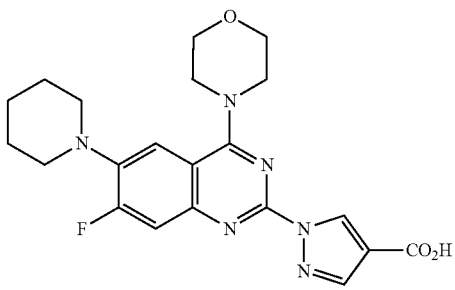 [SMILES: O=C(O)c1cnn(-c2nc(N3CCOCC3)c3cc(N4CCCCC4)c(F)cc3n2)c1]

The above compound may be made analogous to Example 1 using ethyl 1-(7-fluoro-4-oxo-6-(piperidin-1-yl)-3,4-dihydroquinazolin-2-yl)-1H-pyrazole-4-carboxylate in step D and morpholine in step E. MS (ESI): predicted mass calcd. for $C_{21}H_{23}FN_6O_3$, 426.2

Example 131

1-(4-(Dimethylamino)-7-fluoro-6-(piperidin-1-yl)quinazolin-2-yl)-1H-pyrazole-4-carboxylic acid

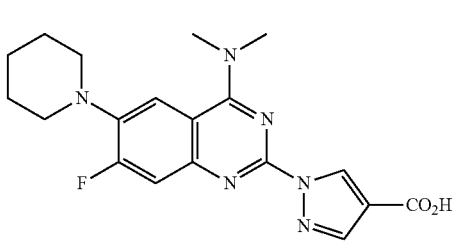 [SMILES: CN(C)c1nc(-n2cc(C(=O)O)cn2)nc2cc(F)c(N3CCCCC3)cc12]

The above compound may be made analogous to Example 1 using ethyl 1-(7-fluoro-4-oxo-6-(piperidin-1-yl)-3,4-dihydroquinazolin-2-yl)-1H-pyrazole-4-carboxylate in step D and dimethylamine in step E. MS (ESI): predicted mass calcd. for $C_{19}H_{21}FN_6O_2$, 384.2

Example 132

1-(4-(Diethylamino)-7-fluoro-6-(piperidin-1-yl)quinazolin-2-yl)-1H-pyrazole-4-carboxylic acid

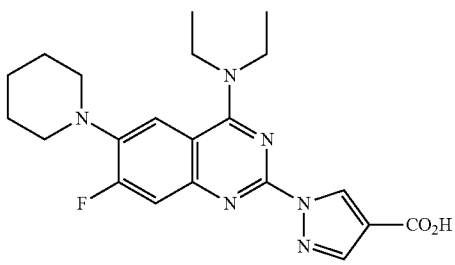 [SMILES: CCN(CC)c1nc(-n2cc(C(=O)O)cn2)nc2cc(F)c(N3CCCCC3)cc12]

The above compound may be made analogous to Example 1 using ethyl 1-(7-fluoro-4-oxo-6-(piperidin-1-yl)-3,4-dihydroquinazolin-2-yl)-1H-pyrazole-4-carboxylate in step D and diethylamine in step E. MS (ESI): predicted mass calcd. for $O_{21}H_{25}FN_6O_2$, 412.2

Example 133

1-(7-Fluoro-6-(piperidin-1-yl)-4-(pyrrolidin-1-yl)quinazolin-2-yl)-1H-pyrazole-4-carboxylic acid

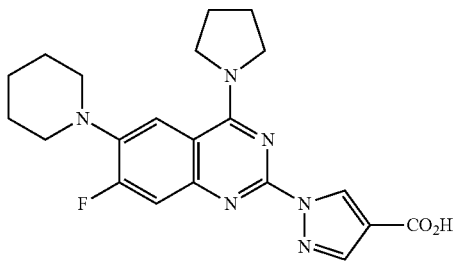 [SMILES: O=C(O)c1cnn(-c2nc(N3CCCC3)c3cc(N4CCCCC4)c(F)cc3n2)c1]

The above compound may be made analogous to Example 1 using ethyl 1-(7-fluoro-4-oxo-6-(piperidin-1-yl)-3,4-dihydroquinazolin-2-yl)-1H-pyrazole-4-carboxylate in step D and pyrrolidine in step E. MS (ESI): predicted mass calcd. for $C_{21}H_{23}FN_6O_2$, 410.2

Example 134

1-(4-(Ethyl(methyl)amino)-7-fluoro-6-(piperidin-1-yl)quinazolin-2-yl)-1H-pyrazole-4-carboxylic acid

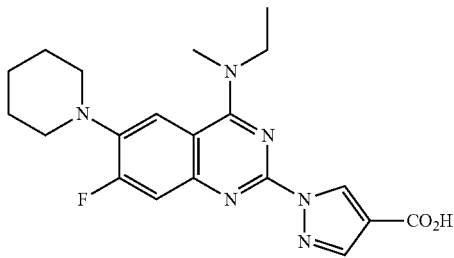 [SMILES: CCN(C)c1nc(-n2cc(C(=O)O)cn2)nc2cc(F)c(N3CCCCC3)cc12]

The above compound may be made analogous to Example 1 using ethyl 1-(7-fluoro-4-oxo-6-(piperidin-1-yl)-3,4-dihydroquinazolin-2-yl)-1H-pyrazole-4-carboxylate in step D and N-methylethanamine in step E. MS (ESI): predicted mass calcd. for $C_{20}H_{23}FN_6O_2$, 398.2

Example 135

1-(4-(Cyclopropylamino)-7-fluoro-6-(piperidin-1-yl)quinazolin-2-yl)-1H-pyrazole-4-carboxylic acid

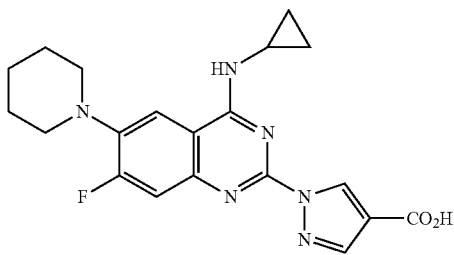 [SMILES: O=C(O)c1cnn(-c2nc(NC3CC3)c3cc(N4CCCCC4)c(F)cc3n2)c1]

The above compound may be made analogous to Example 1 using ethyl 1-(7-fluoro-4-oxo-6-(piperidin-1-yl)-3,4-dihydroquinazolin-2-yl)-1H-pyrazole-4-carboxylate in step D and cyclopropylamine in step E. MS (ESI): predicted mass calcd. for $C_{20}H_{21}FN_6O_2$, 396.2

Example 136

1-(7-chloro-6-(cyclohexyloxy)-4-morpholinoquinazolin-2-yl)-1H-pyrazole-4-carboxylic acid

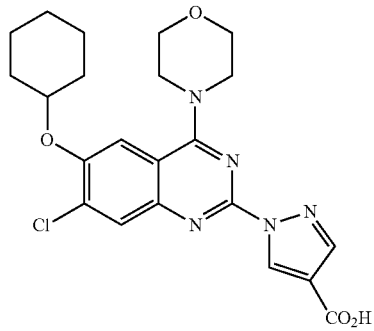 [SMILES: O=C(O)c1cnn(-c2nc(N3CCOCC3)c3cc(OC4CCCCC4)c(Cl)cc3n2)c1]

The titled compound was prepared in a manner analogous to EXAMPLE 1 steps B through F using 3-chloro-4-cyclohexyloxyaniline in step B and morpholine in step E. MS (ESI): mass calcd. for $C_{22}H_{24}ClN_5O_4$, 457.9; m/z found, 458.1 [M+H]+. 1H NMR (400 MHz, DMSO-$d_6$): 8.88 (s, 1H), 8.01 (s, 1H), 7.94 (s, 1H), 7.43 (s, 1H), 4.65 (s, 1H), 3.87 (s, 4H), 3.83 (s, 4H), 1.94 (s, 2H), 1.75 (s, 2H), 1.70-1.33 (m, 6H).

Example 137

1-(7-chloro-6-(cyclohexyloxy)-4-(dimethylamino)quinazolin-2-yl)-1H-pyrazole-4-carboxylic acid

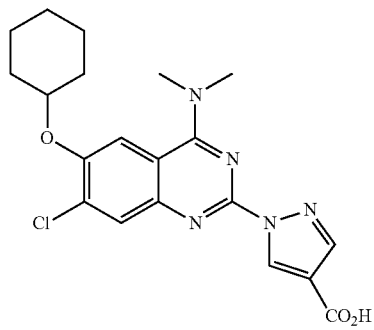 [SMILES: CN(C)c1nc(-n2cc(C(=O)O)cn2)nc2cc(Cl)c(OC3CCCCC3)cc12]

The titled compound was prepared in a manner analogous to EXAMPLE 1 steps B through F using 3-chloro-4-cyclohexyloxyaniline in step B and dimethylamine in step E. MS (ESI): mass calcd. for $C_{20}H_{22}ClN_5O_3$, 415.9; m/z found, 416.1 [M+H]+. 1H NMR (400 MHz, DMSO-$d_6$): 12.77 (s, 1H), 8.98 (s, 1H), 8.08 (s, 1H), 7.88 (s, 1H), 7.69 (s, 1H), 4.64 (s, 1H), 3.44 (s, 6H), 1.95 (s, 2H), 1.83-1.35 (m, 8H).

Example 138

1-(7-chloro-6-(cyclohexyloxy)-4-(diethylamino) quinazolin-2-yl)-1H-pyrazole-4-carboxylic acid

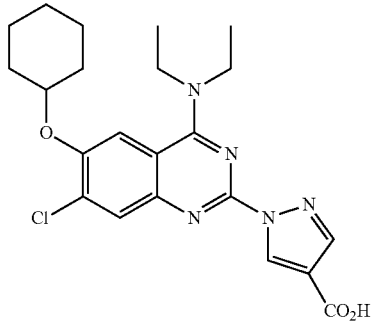 [SMILES: CCN(CC)c1nc(-n2cc(C(=O)O)cn2)nc2cc(Cl)c(OC3CCCCC3)cc12]

The titled compound was prepared in a manner analogous to EXAMPLE 1 steps B through F using 3-chloro-4-cyclohexyloxyaniline in step B and diethylamine in step E. MS (ESI): mass calcd. for $C_{22}H_{26}ClN_5O_3$, 443.9; m/z found, 444.2 [M+H]+. 1H NMR (400 MHz, DMSO-$d_6$): 12.77 (s, 1H), 8.91 (s, 1H), 8.09 (s, 1H), 7.89 (s, 1H), 7.43 (s, 1H), 4.54 (s, 1H), 3.80 (q, J=6.6 Hz, 4H), 1.99 (s, 2H), 1.77 (s, 2H), 1.68-1.50 (m, 3H), 1.48-1.33 (m, 9H).

Example 139

1-(7-chloro-6-(cyclohexyloxy)-4-(pyrrolidin-1-yl) quinazolin-2-yl)-1H-pyrazole-4-carboxylic acid

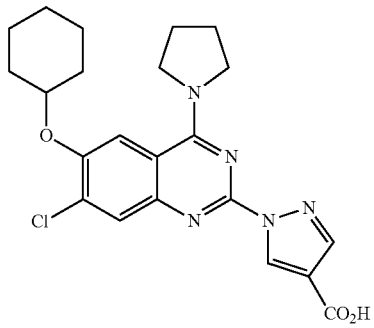 [SMILES: O=C(O)c1cnn(-c2nc(N3CCCC3)c3cc(OC4CCCCC4)c(Cl)cc3n2)c1]

The titled compound was prepared in a manner analogous to EXAMPLE 1 steps B through F using 3-chloro-4-cyclohexyloxyaniline in step B and pyrrolidine in step E. MS (ESI): mass calcd. for $C_{22}H_{24}ClN_5O_3$, 441.9; m/z found, 442.2 [M+H]+. 1H NMR (400 MHz, DMSO-$d_6$): 8.96 (s, 1H), 8.07 (s, 1H), 7.84 (s, 1H), 7.78 (s, 1H), 4.61 (s, 1H), 3.99 (s, 4H), 2.10-1.88 (m, 6H), 1.83-1.32 (m, 8H).

Example 140

1-(7-chloro-6-(cyclohexyloxy)-4-(ethyl(methyl) amino)quinazolin-2-yl)-1H-pyrazole-4-carboxylic acid

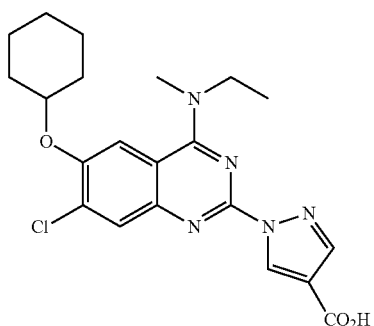

The titled compound was prepared in a manner analogous to EXAMPLE 1 steps B through F using 3-chloro-4-cyclohexyloxyaniline in step B and N-ethyl-N-methylamine in step E. MS (ESI): mass calcd. for $C_{21}H_{24}ClN_5O_3$, 429.9; m/z found, 430.1 [M+H]+. 1H NMR (400 MHz, DMSO-$d_6$): 8.94 (s, 1H), 8.08 (s, 1H), 7.86 (s, 1H), 7.56 (s, 1H), 4.65-4.54 (m, 1H), 3.81 (q, J=7.5 Hz, 2H), 3.40 (s, 3H), 1.96 (s, 2H), 1.75 (s, 2H), 1.68-1.36 (m, 9H).

Example 141

1-(7-chloro-6-(cyclohexyloxy)-4-(cyclopropylamino) quinazolin-2-yl)-1H-pyrazole-4-carboxylic acid

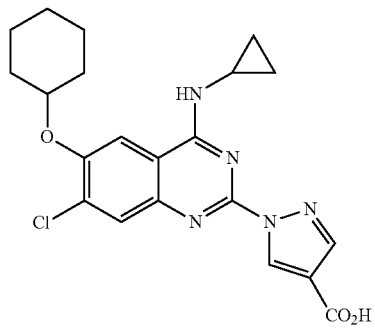 [SMILES: O=C(O)c1cnn(-c2nc(NC3CC3)c3cc(OC4CCCCC4)c(Cl)cc3n2)c1]

The titled compound was prepared in a manner analogous to EXAMPLE 1 steps B through F using 3-chloro-4-cyclohexyloxyaniline in step B and cyclopropylamine in step E. MS (ESI): mass calcd. for $O_{21}H_{22}ClN_5O_3$, 428.1; m/z found, 442.2 [M+H]+. 1H NMR (400 MHz, DMSO-$d_6$): 12.75 (s, 1H), 9.01 (s, 1H), 8.68 (s, 1H), 8.09 (s, 1H), 7.88 (5, 1H), 7.84 (5, 1H), 4.65 (5, 1H), 3.17 (5, 1H), 1.91 (5, 2H), 1.76 (5, 2H), 1.69-1.37 (m, 6H), 0.95-0.89 (m, 2H), 0.73 (s, 2H).

Examples 142-159 are prophetic Examples which may be synthesized using the general schemes provided above.

Example 142

1-(6-Benzyl-7-chloro-4-morpholinoquinazolin-2-yl)-1H-pyrazole-4-carboxylic acid

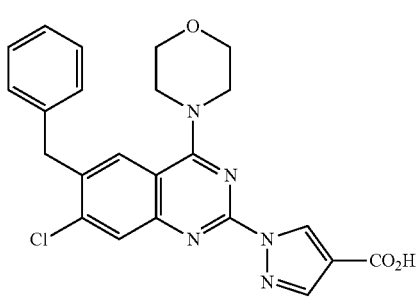 [SMILES: O=C(O)c1cnn(-c2nc(N3CCOCC3)c3cc(Cc4ccccc4)c(Cl)cc3n2)c1]

The above compound may be made analogous to Example 1 using ethyl 1-(6-benzyl-7-chloro-4-oxo-3,4-dihydroquinazolin-2-yl)-1H-pyrazole-4-carboxylate in step D and morpholine in step E. MS (ESI): predicted mass calcd. for $C_{23}H_{20}ClN_5O_3$, 449.9

Example 143

1-(6-Benzyl-4-(dimethylamino)-7-chloroquinazolin-2-yl)-1H-pyrazole-4-carboxylic acid

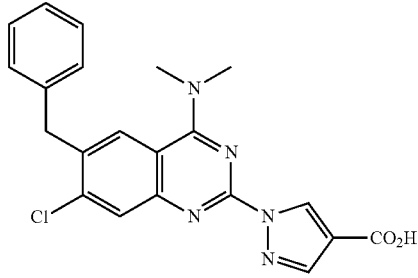 [SMILES: CN(C)c1nc(-n2cc(C(=O)O)cn2)nc2cc(Cl)c(Cc3ccccc3)cc12]

The above compound may be made analogous to Example 1 using ethyl 1-(6-benzyl-7-chloro-4-oxo-3,4-dihydroquinazolin-2-yl)-1H-pyrazole-4-carboxylate in step D and dimethylamine in step E. MS (ESI): predicted mass calcd. for $C_{21}H_{18}ClN_5O_2$, 407.9

Example 144

1-(6-Benzyl-4-(diethylamino)-7-chloroquinazolin-2-yl)-1H-pyrazole-4-carboxylic acid

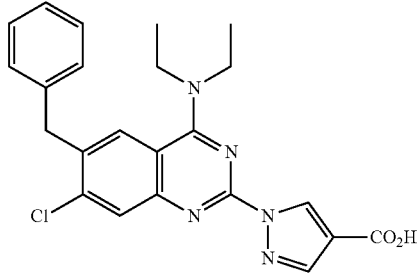 [SMILES: CCN(CC)c1nc(-n2cc(C(=O)O)cn2)nc2cc(Cl)c(Cc3ccccc3)cc12]

The above compound may be made analogous to Example 1 using ethyl 1-(6-benzyl-7-chloro-4-oxo-3,4-dihydroquinazolin-2-yl)-1H-pyrazole-4-carboxylate in step D and diethylamine in step E. MS (ESI): predicted mass calcd. for $C_{23}H_{22}ClN_5O_2$, 435.9

Example 145

1-(6-Benzyl-7-chloro-4-(pyrrolidin-1-yl)quinazolin-2-yl)-1H-pyrazole-4-carboxylic acid

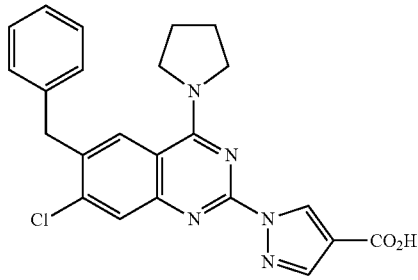

The above compound may be made analogous to Example 1 using ethyl 1-(6-benzyl-7-chloro-4-oxo-3,4-dihydroquinazolin-2-yl)-1H-pyrazole-4-carboxylate in step D and pyrrolidine in step E. MS (ESI): predicted mass calcd. for $C_{23}H_{20}ClN_5O_2$, 433.9

Example 146

1-(6-Benzyl-4-(ethyl(methyl)amino)-7-chloroquinazolin-2-yl)-1H-pyrazole-4-carboxylic acid

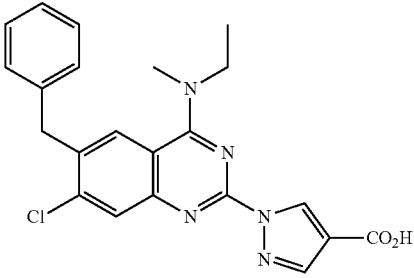 [SMILES: CCN(C)c1nc(-n2cc(C(=O)O)cn2)nc2cc(Cl)c(Cc3ccccc3)cc12]

The above compound may be made analogous to Example 1 using ethyl 1-(6-benzyl-7-chloro-4-oxo-3,4-dihydroquinazolin-2-yl)-1H-pyrazole-4-carboxylate in step D and N-methylethanamine in step E. MS (ESI): predicted mass calcd. for $C_{22}H_{20}ClN_5O_2$, 421.9

Example 147

1-(6-Benzyl-4-(cyclopropylamino)-7-chloroquinazolin-2-yl)-1H-pyrazole-4-carboxylic acid

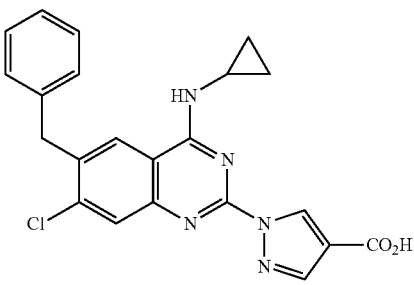 [SMILES: O=C(O)c1cnn(-c2nc(NC3CC3)c3cc(Cc4ccccc4)c(Cl)cc3n2)c1]

The above compound may be made analogous to Example 1 using ethyl 1-(6-benzyl-7-chloro-4-oxo-3,4-dihydroquinazolin-2-yl)-1H-pyrazole-4-carboxylate in step D and cyclopropyl amine in step E. MS (ESI): predicted mass calcd. for $C_{22}H_{18}ClN_5O_2$, 419.9

Example 148

1-(6-((2,6-Dimethylbenzyl)amino)-7-chloro-4-morpholinoquinazolin-2-yl)-1H-pyrazole-4-carboxylic acid

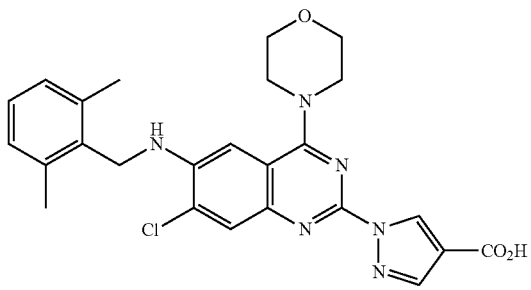 [SMILES: Cc1cccc(C)c1CNc1cc2c(N3CCOCC3)nc(-n3cc(C(=O)O)cn3)nc2cc1Cl]

The above compound may be made analogous to Example 1 using ethyl 1-(6-((2,6-dimethylbenzyl)amino)-7-chloro-4-oxo-3,4-dihydroquinazolin-2-yl)-1H-pyrazole-4-carboxylate in step D and morpholine in step E. MS (ESI): predicted mass calcd. for $C_{25}H_{25}ClN_6O_3$, 492.9

Example 149

1-(4-(Dimethylamino)-6-((2,6-dimethylbenzyl)amino)-7-chloroquinazolin-2-yl)-1H-pyrazole-4-carboxylic acid

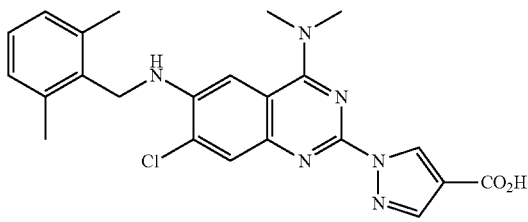 [SMILES: Cc1cccc(C)c1CNc1cc2c(N(C)C)nc(-n3cc(C(=O)O)cn3)nc2cc1Cl]

The above compound may be made analogous to Example 1 using ethyl 1-(6-((2,6-dimethylbenzyl)amino)-7-chloro-4-oxo-3,4-dihydroquinazolin-2-yl)-1H-pyrazole-4-carboxylate in step D and dimethylamine in step E. MS (ESI): predicted mass calcd. for $C_{23}H_{23}ClN_6O_2$, 450.9

Example 150

1-(4-(Diethylamino)-6-((2,6-dimethylbenzyl)amino)-7-chloroquinazolin-2-yl)-1H-pyrazole-4-carboxylic acid

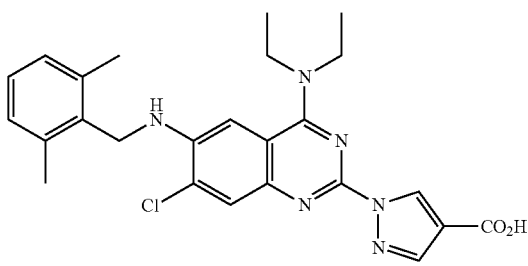 [SMILES: CCN(CC)c1nc(-n2cc(C(=O)O)cn2)nc2cc(Cl)c(NCc3c(C)cccc3C)cc12]

The above compound may be made analogous to Example 1 using ethyl 1-(6-((2,6-dimethylbenzyl)amino)-7-chloro-4-oxo-3,4-dihydroquinazolin-2-yl)-1H-pyrazole-4-carboxylate in step D and diethylamine in step E. MS (ESI): predicted mass calcd. for $C_{25}H_{27}ClN_6O_2$, 479.0

Example 151

1-(6-((2,6-Dimethylbenzyl)amino)-7-chloro-4-(pyrrolidin-1-yl)quinazolin-2-yl)-1H-pyrazole-4-carboxylic acid

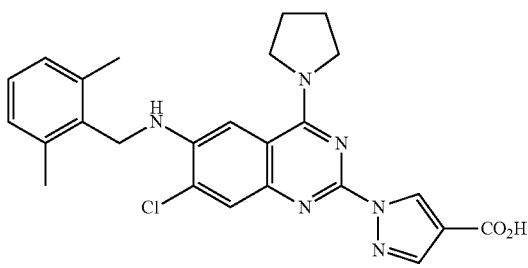 [SMILES: Cc1cccc(C)c1CNc1cc2c(N3CCCC3)nc(-n3cc(C(=O)O)cn3)nc2cc1Cl]

The above compound may be made analogous to Example 1 using ethyl 1-(6-((2,6-dimethylbenzyl)amino)-7-chloro-4-oxo-3,4-dihydroquinazolin-2-yl)-1H-pyrazole-4-carboxylate in step D and pyrrolidine in step E. MS (ESI): predicted mass calcd. for $C_{25}H_{25}ClN_6O_2$, 479.0

Example 152

1-(6-((2,6-Dimethylbenzyl)amino)-4-(ethyl(methyl)amino)-7-chloroquinazolin-2-yl)-1H-pyrazole-4-carboxylic acid

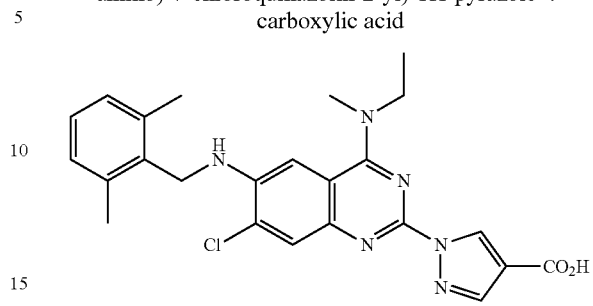

The above compound may be made analogous to Example 1 using ethyl 1-(6-((2,6-dimethylbenzyl)amino)-7-chloro-4-oxo-3,4-dihydroquinazolin-2-yl)-1H-pyrazole-4-carboxylate in step D and N-methylethanamine in step E. MS (ESI): predicted mass calcd. for $C_{24}H_{25}ClN_6O_2$, 464.9

Example 153

1-(4-(Cyclopropylamino)-6-((2,6-dimethylbenzyl)amino)-7-chloroquinazolin-2-yl)-1H-pyrazole-4-carboxylic acid

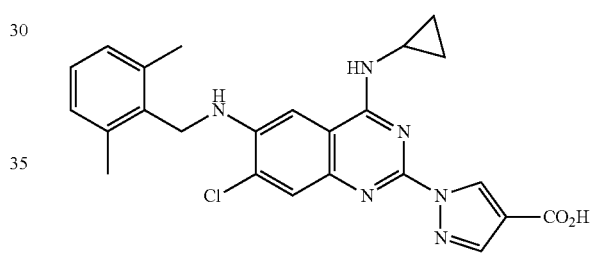

The above compound may be made analogous to Example 1 using ethyl 1-(6-((2,6-dimethylbenzyl)amino)-7-chloro-4-oxo-3,4-dihydroquinazolin-2-yl)-1H-pyrazole-4-carboxylate in step D and cyclopropyl amine in step E. MS (ESI): predicted mass calcd. for $C_{24}H_{23}ClN_6O_2$, 462.9

Example 154

1-(7-Chloro-4-morpholino-6-(o-tolyl)quinazolin-2-yl)-1H-pyrazole-4-carboxylic acid

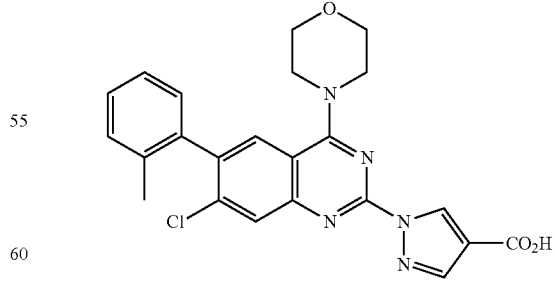

The above compound may be made analogous to Example 1 using ethyl 1-(7-chloro-4-oxo-6-(o-tolyl)-3,4-dihydroquinazolin-2-yl)-1H-pyrazole-4-carboxylate in step D and morpholine in step E. MS (ESI): predicted mass calcd. for $C_{23}H_{20}ClN_5O_3$, 449.9

Example 155

1-(4-(Dimethylamino)-7-chloro-6-(o-tolyl)quinazolin-2-yl)-1H-pyrazole-4-carboxylic acid

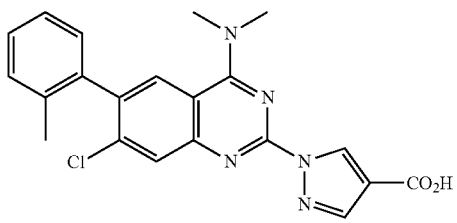

The above compound may be made analogous to Example 1 using ethyl 1-(7-chloro-4-oxo-6-(o-tolyl)-3,4-dihydroquinazolin-2-yl)-1H-pyrazole-4-carboxylate in step D and dimethylamine in step E. MS (ESI): predicted mass calcd. for $C_{21}H_{18}ClN_5O_2$, 407.9

Example 156

1-(4-(Diethylamino)-7-chloro-6-(o-tolyl)quinazolin-2-yl)-1H-pyrazole-4-carboxylic acid

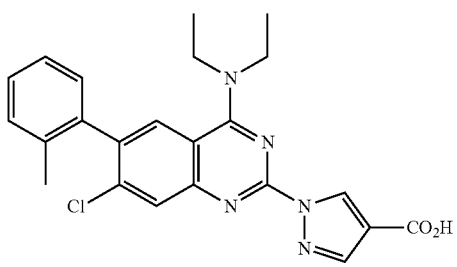

The above compound may be made analogous to Example 1 using ethyl 1-(7-chloro-4-oxo-6-(o-tolyl)-3,4-dihydroquinazolin-2-yl)-1H-pyrazole-4-carboxylate in step D and diethylamine in step E. MS (ESI): predicted mass calcd. for $C_{23}H_{22}ClN_5O_2$, 435.9

Example 157

1-(7-Chloro-4-(pyrrolidin-1-yl)-6-(o-tolyl)quinazolin-2-yl)-1H-pyrazole-4-carboxylic acid

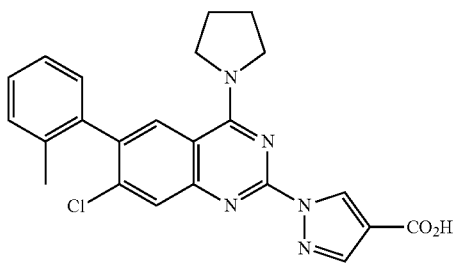

The above compound may be made analogous to Example 1 using ethyl 1-(7-chloro-4-oxo-6-(o-tolyl)-3,4-dihydroquinazolin-2-yl)-1H-pyrazole-4-carboxylate in step D and pyrrolidine in step E. MS (ESI): predicted mass calcd. for $C_{23}H_{20}ClN_5O_2$, 433.9

Example 158

1-(4-(Ethyl(methyl)amino)-7-chloro-6-(o-tolyl)quinazolin-2-yl)-1H-pyrazole-4-carboxylic acid

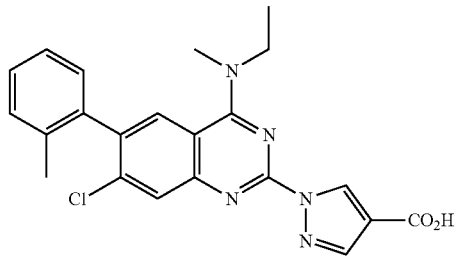 [SMILES: CCN(C)c1nc(-n2cc(C(=O)O)cn2)nc2cc(Cl)c(-c3ccccc3C)cc12]

The above compound may be made analogous to Example 1 using ethyl 1-(7-chloro-4-oxo-6-(o-tolyl)-3,4-dihydroquinazolin-2-yl)-1H-pyrazole-4-carboxylate in step D and N-methylethanamine in step E. MS (ESI): predicted mass calcd. for $C_{22}H_{20}ClN_5O_2$, 421.9

Example 159

1-(4-(Cyclopropylamino)-7-chloro-6-(o-tolyl)quinazolin-2-yl)-1H-pyrazole-4-carboxylic acid

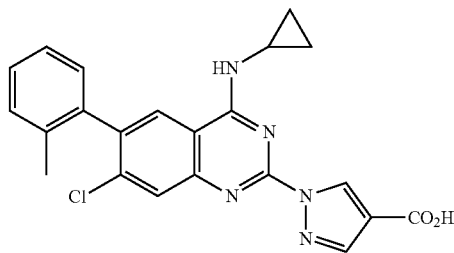 [SMILES: Cc1ccccc1-c1cc2c(NC3CC3)nc(-n3cc(C(=O)O)cn3)nc2cc1Cl]

The above compound may be made analogous to Example 1 using ethyl 1-(7-chloro-4-oxo-6-(o-tolyl)-3,4-dihydroquinazolin-2-yl)-1H-pyrazole-4-carboxylate in step D and cyclopropyl amine in step E. MS (ESI): predicted mass calcd. for $C_{22}H_{18}ClN_5O_2$, 419.9

Example 160

1-(7-chloro-6-isopropyl-4-morpholinoquinazolin-2-yl)-1H-pyrazole-4-carboxylic acid

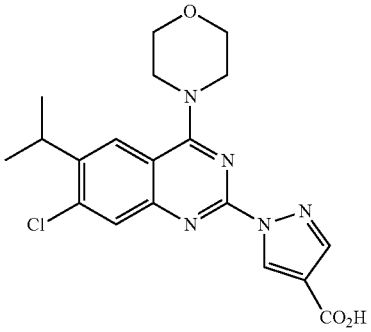 [SMILES: CC(C)c1cc2c(N3CCOCC3)nc(-n3cc(C(=O)O)cn3)nc2cc1Cl]

The titled compound was prepared in a manner analogous to EXAMPLE 1 steps B through F using 3-chloro-4-isopropylaniline in step B and morpholine in step E. MS (ESI): mass calcd. for $C_{19}H_{20}ClN_5O_3$, 401.9; m/z found, 402.1 [M+H]+. 1H NMR (400 MHz, DMSO-$d_6$): 12.77 (s, 1H), 9.02 (s, 1H), 8.11 (s, 1H), 7.88 (s, 2H), 3.97 (s, 4H), 3.81 (s, 4H), 3.33 (s, 1H), 1.31 (d, J=6.8 Hz, 6H).

Example 161

1-(7-chloro-4-(dimethylamino)-6-isopropylquinazolin-2-yl)-1H-pyrazole-4-carboxylic acid

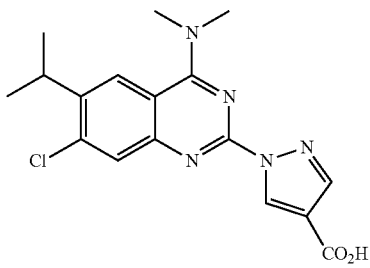 [SMILES: CC(C)c1cc2c(N(C)C)nc(-n3cc(C(=O)O)cn3)nc2cc1Cl]

The titled compound was prepared in a manner analogous to EXAMPLE 1 steps B through F using 3-chloro-4-isopropylaniline in step B and dimethylamine in step E. MS (ESI): mass calcd. for $C_{17}H_{18}ClN_5O_2$, 359.8; m/z found, 360.0 [M+H]+. 1H NMR (400 MHz, DMSO-$d_6$): 9.01 (s, 1H), 8.12 (s, 1H), 8.11 (s, 1H), 7.82 (s, 1H), 3.49 (s, 6H), 3.39 (dt, J=14.1, 7.2 Hz, 1H), 1.32 (d, J=6.8 Hz, 6H).

Example 162

1-(7-chloro-4-diethylamino-6-isopropylquinazolin-2-yl)-1H-pyrazole-4-carboxylic acid

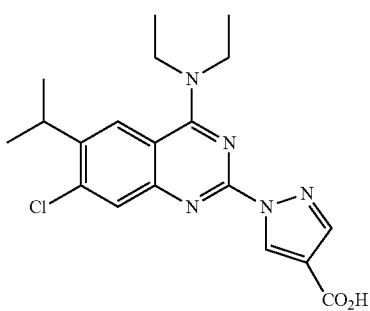 [SMILES: CCN(CC)c1nc(-n2cc(C(=O)O)cn2)nc2cc(Cl)c(C(C)C)cc12]

The titled compound was prepared in a manner analogous to EXAMPLE 1 steps B through F using 3-chloro-4-isopropylaniline in step B and diethylamine in step E. MS (ESI): mass calcd. for $C_{19}H_{22}ClN_5O_2$, 387.9; m/z found, 388.1 [M+H]+. 1H NMR (400 MHz, DMSO-$d_6$): 8.94 (s, 1H), 8.13 (s, 1H), 7.91 (s, 1H), 7.83 (s, 1H), 3.84 (q, J=6.7 Hz, 4H), 3.49-3.31 (m, 1H), 1.43 (t, J=6.7 Hz, 6H), 1.31 (d, J=6.7 Hz, 6H).

Example 163

1-(7-chloro-4-(pyrrolidin-1-yl)-6-isopropylquinazolin-2-yl)-1H-pyrazole-4-carboxylic acid

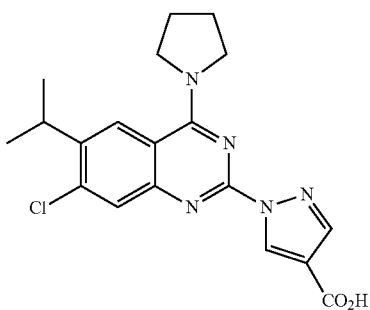 [SMILES: CC(C)c1cc2c(N3CCCC3)nc(-n3cc(C(=O)O)cn3)nc2cc1Cl]

The titled compound was prepared in a manner analogous to EXAMPLE 1 steps B through F using 3-chloro-4-isopropylaniline in step B and pyrrolidine in step E. MS (ESI): mass calcd. for $C_{19}H_{20}ClN_5O_2$, 385.9; m/z found, 386.1 [M+H]+. 1H NMR (400 MHz, DMSO-$d_6$): 8.98 (s, 1H), 8.19 (s, 1H), 8.08 (s, 1H), 7.78 (s, 1H), 4.01 (s, 4H), 3.45-3.33 (m, 1H), 2.03 (s, 4H), 1.32 (d, J=6.8 Hz, 6H).

Example 164

1-(7-chloro-4-(ethyl(methyl)amino)-6-isopropylquinazolin-2-yl)-1H-pyrazole-4-carboxylic acid

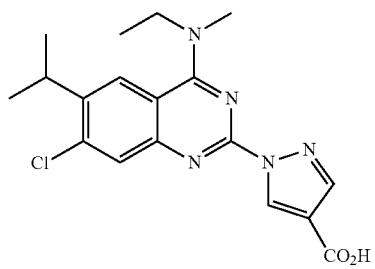 [SMILES: CCN(C)c1nc(-n2cc(C(=O)O)cn2)nc2cc(Cl)c(C(C)C)cc12]

The titled compound was prepared in a manner analogous to EXAMPLE 1 steps B through F using 3-chloro-4-isopropylaniline in step B and N-ethyl-N-methylamine in step E. MS (ESI): mass calcd. for $C_{18}H_{20}ClN_5O_2$, 373.9; m/z found, 374.1 [M+]+. 1H NMR (400 MHz, DMSO-$d_6$): 8.99 (s, 1H), 8.14 (s, 1H), 8.05 (s, 1H), 7.84 (s, 1H), 3.88 (q, J=7.1 Hz, 2H), 3.48 (s, 3H), 3.40 (dt, J=13.3, 6.8 Hz, 1H), 1.41 (t, J=6.9 Hz, 3H), 1.32 (d, J=6.8 Hz, 6H).

Example 165

1-(7-chloro-4-(cyclopropylamino)-6-isopropylquinazolin-2-yl)-1H-pyrazole-4-carboxylic acid

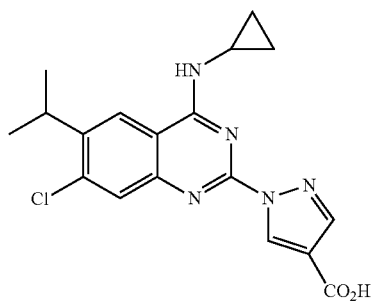 [SMILES: CC(C)c1cc2c(NC3CC3)nc(-n3cc(C(=O)O)cn3)nc2cc1Cl]

The titled compound was prepared in a manner analogous to EXAMPLE 1 steps B through F using 3-chloro-4-isopropylaniline in step B and cyclopropylamine in step E. MS (ESI): mass calcd. for $C_{18}H_{18}ClN_5O_2$, 371.8; m/z found, 372.1 [M+H]+. 1H NMR (400 MHz, DMSO-$d_6$): 12.75 (s, 1H), 9.04 (s, 1H), 8.87 (s, 1H), 8.27 (s, 1H), 8.11 (s, 1H), 7.78 (s, 1H), 3.42-3.33 (m, 1H), 3.21 (s, 1H), 1.32 (d, J=6.6 Hz, 6H), 0.93-0.90 (m, 2H), 0.76 (br s, 2H).

Examples 166-171 are prophetic Examples which may be synthesized using the general schemes provided above.

Example 166

1-(7-Chloro-4-morpholino-6-(piperidin-1-yl)quinazolin-2-yl)-1H-pyrazole-4-carboxylic acid

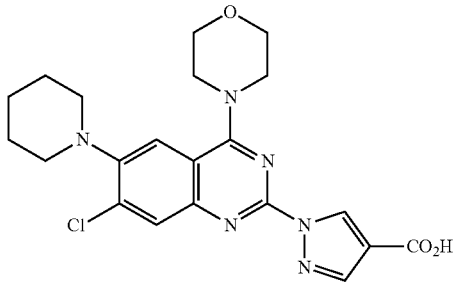 [SMILES: O=C(O)c1cnn(-c2nc(N3CCOCC3)c3cc(N4CCCCC4)c(Cl)cc3n2)c1]

The above compound may be made analogous to Example 1 using ethyl 1-(7-chloro-4-oxo-6-(piperidin-1-yl)-3,4-dihydroquinazolin-2-yl)-1H-pyrazole-4-carboxylate in step D and morpholine in step E. MS (ESI): predicted mass calcd. for $C_{21}H_{23}ClN_6O_3$, 442.9

Example 167

1-(4-(Dimethylamino)-7-chloro-6-(piperidin-1-yl)quinazolin-2-yl)-1H-pyrazole-4-carboxylic acid

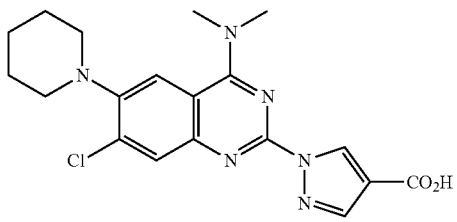 [SMILES: CN(C)c1nc(-n2cc(C(=O)O)cn2)nc2cc(Cl)c(N3CCCCC3)cc12]

The above compound may be made analogous to Example 1 using ethyl 1-(7-chloro-4-oxo-6-(piperidin-1-yl)-3,4-dihydroquinazolin-2-yl)-1H-pyrazole-4-carboxylate in step D and dimethylamine in step E. MS (ESI): predicted mass calcd. for $C_{19}H_{21}ClN_6O_2$, 400.9

Example 168

1-(4-(Diethylamino)-7-chloro-6-(piperidin-1-yl)quinazolin-2-yl)-1H-pyrazole-4-carboxylic acid

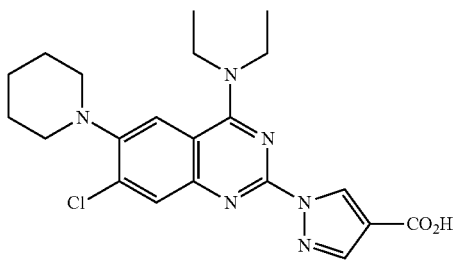 [SMILES: CCN(CC)c1nc(-n2cc(C(=O)O)cn2)nc2cc(Cl)c(N3CCCCC3)cc12]

The above compound may be made analogous to Example 1 using ethyl 1-(7-chloro-4-oxo-6-(piperidin-1-yl)-3,4-dihydroquinazolin-2-yl)-1H-pyrazole-4-carboxylate in step D and diethylamine in step E. MS (ESI): predicted mass calcd. for $C_{21}H_{25}ClN_6O_2$, 428.9

Example 169

1-(7-Chloro-6-(piperidin-1-yl)-4-(pyrrolidin-1-yl)quinazolin-2-yl)-1H-pyrazole-4-carboxylic acid

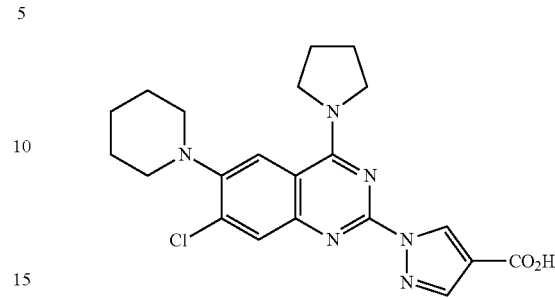

The above compound may be made analogous to Example 1 using ethyl 1-(7-chloro-4-oxo-6-(piperidin-1-yl)-3,4-dihydroquinazolin-2-yl)-1H-pyrazole-4-carboxylate in step D and pyrrolidine in step E. MS (ESI): predicted mass calcd. for $C_{21}H_{23}ClN_6O_2$, 410.2

Example 170

1-(4-(Ethyl(methyl)amino)-7-chloro-6-(piperidin-1-yl)quinazolin-2-yl)-1H-pyrazole-4-carboxylic acid

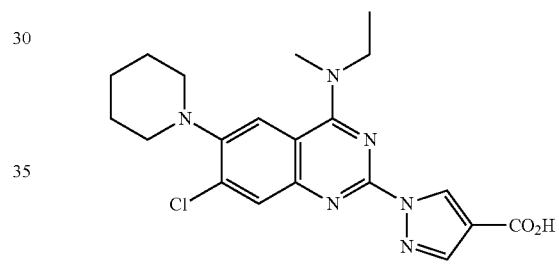

The above compound may be made analogous to Example 1 using ethyl 1-(7-chloro-4-oxo-6-(piperidin-1-yl)-3,4-dihydroquinazolin-2-yl)-1H-pyrazole-4-carboxylate in step D and N-methylethanamine in step E. MS (ESI): predicted mass calcd. for $C_{20}H_{23}ClN_6O_2$, 414.9

Example 171

1-(4-(Cyclopropylamino)-7-chloro-6-(piperidin-1-yl)quinazolin-2-yl)-1H-pyrazole-4-carboxylic acid

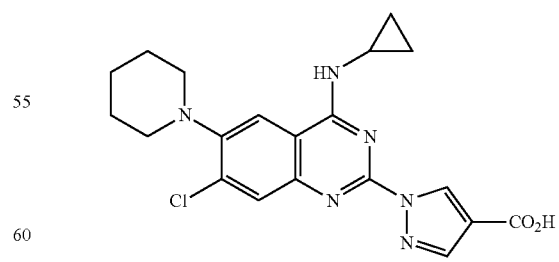

The above compound may be made analogous to Example 1 using ethyl 1-(7-chloro-4-oxo-6-(piperidin-1-yl)-3,4-dihydroquinazolin-2-yl)-1H-pyrazole-4-carboxylate in step D and cyclopropylamine in step E. MS (ESI): predicted mass calcd. for $C_{20}H_{21}ClN_6O_2$, 412.9

Example 172

1-(6-(cyclohexyloxy)-4-morpholinoquinazolin-2-yl)-1H-pyrazole-4-carboxylic acid

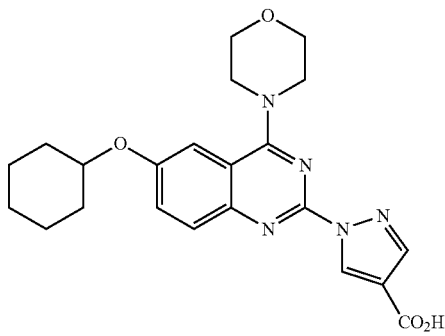 [SMILES: O=C(O)c1cnn(-c2nc(N3CCOCC3)c3cc(OC4CCCCC4)ccc3n2)c1]

The titled compound was prepared in a manner analogous to EXAMPLE 1 steps B through F using 4-cyclohexyloxyaniline in step B and morpholine in step E. MS (ESI): mass calcd. for $C_{22}H_{25}N_5O_4$, 423.5; m/z found, 424.2 [M+H]+. 1H NMR (400 MHz, DMSO-$d_6$): 12.75 (s, 1H), 9.01 (s, 1H), 8.10 (s, 1H), 7.81 (d, J=9.2 Hz, 1H), 7.56 (dd, J=9.1, 2.3 Hz, 1H), 7.30 (s, 1H), 4.52 (s, 1H), 3.84 (s, 8H), 1.97 (s, 2H), 1.75 (s, 2H), 1.62-1.22 (m, 6H).

Example 173

1-(6-(cyclohexyloxy)-4-(dimethylamino)quinazolin-2-yl)-1H-pyrazole-4-carboxylic acid

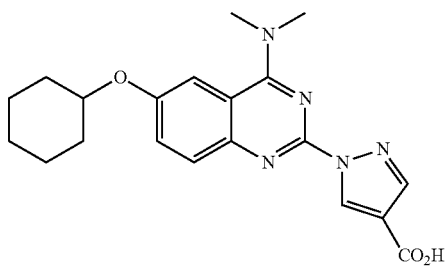

The titled compound was prepared in a manner analogous to EXAMPLE 1 steps B through F using 4-cyclohexyloxyaniline in step B and dimethylamine in step E. MS (ESI): mass calcd. for $C_{20}H_{23}N_5O_3$, 381.4; m/z found, 382.2 [M+H]+. 1H NMR (400 MHz, DMSO-$d_6$): 12.80 (s, 1H), 8.93 (s, 1H), 8.04 (s, 1H), 7.72 (d, J=9.0 Hz, 1H), 7.58-7.45 (m, 2H), 4.50 (s, 1H), 3.42 (s, 6H), 1.97 (s, 2H), 1.74 (s, 2H), 1.63-1.22 (m, 6H).

Example 174

1-(6-(cyclohexyloxy)-4-(diethylamino)quinazolin-2-yl)-1H-pyrazole-4-carboxylic acid

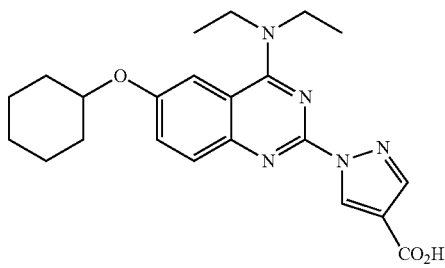 [SMILES: CCN(CC)c1nc(-n2cc(C(=O)O)cn2)nc2ccc(OC3CCCCC3)cc12]

The titled compound was prepared in a manner analogous to EXAMPLE 1 steps B through F using 4-cyclohexyloxyaniline in step B and diethylamine in step E. MS (ESI): mass calcd. for $C_{22}H_{27}N_5O_3$, 409.5; m/z found, 410.2 [M+H]+. 1H NMR (400 MHz, DMSO-$d_6$): 12.69 (s, 1H), 8.89 (s, 1H), 8.07 (s, 1H), 7.72 (d, J=9.1 Hz, 1H), 7.48 (d, J=9.1 Hz, 1H), 7.32 (s, 1H), 4.44 (s, 1H), 3.79 (q, J=6.6 Hz, 4H), 2.01 (s, 2H), 1.76 (s, 2H), 1.64-1.22 (m, 12H).

Example 175

1-(6-(cyclohexyloxy)-4-(pyrrolidin-1-yl)quinazolin-2-yl)-1H-pyrazole-4-carboxylic acid

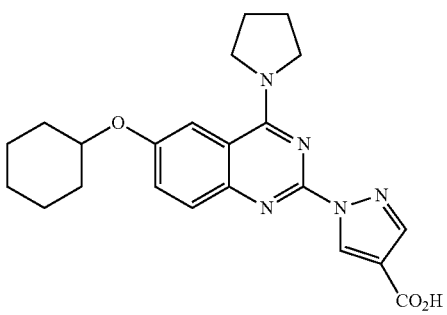 [SMILES: O=C(O)c1cnn(-c2nc(N3CCCC3)c3cc(OC4CCCCC4)ccc3n2)c1]

The titled compound was prepared in a manner analogous to EXAMPLE 1 steps B through F using 4-cyclohexyloxyaniline in step B and pyrrolidine in step E. MS (ESI): mass calcd. for $C_{22}H_{25}N_5O_3$, 407.5; m/z found, 408.2 [M+]+. 1H NMR (400 MHz, DMSO-$d_6$): 12.71 (s, 1H), 8.96 (s, 1H), 8.07 (s, 1H), 7.71-7.66 (m, 2H), 7.50 (dd, J=9.1, 2.4 Hz, 1H), 4.57-4.41 (m, 1H), 3.98 (s, 4H), 2.01 (s, 6H), 1.74 (s, 2H), 1.62-1.21 (m, 6H).

Example 176

1-(6-(cyclohexyloxy)-4-(cyclopropylamino)quinazolin-2-yl)-1H-pyrazole-4-carboxylic acid

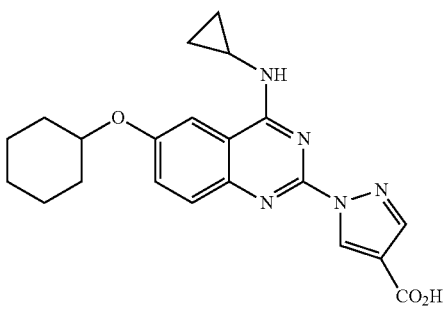 [SMILES: O=C(O)c1cnn(-c2nc(NC3CC3)c3cc(OC4CCCCC4)ccc3n2)c1]

The titled compound was prepared in a manner analogous to EXAMPLE 1 steps B through F using 4-cyclohexyloxyaniline in step B and cyclopropylamine in step E. MS (ESI): mass calcd. for $C_{21}H_{23}N_5O_3$, 393.5; m/z found, 394.2 [M+H]+. 1H NMR (400 MHz, DMSO-$d_6$): 9.07 (s, 1H), 8.85 (s, 1H), 8.17 (s, 1H), 7.86-7.70 (m, 2H), 7.51 (d, J=9.2 Hz, 1H), 4.54 (5, 1H), 3.29 (5, 1H), 1.95 (5, 2H), 1.76 (5, 2H), 1.63-1.20 (m, 6H), 0.95-0.89 (m, 2H), 0.78 (s, 2H).

Example 177

1-(6-(cyclohexyloxy)-4-(ethyl(methyl)amino)quinazolin-2-yl)-1H-pyrazole-4-carboxylic acid

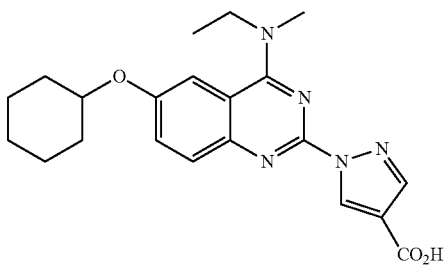 [SMILES: CCN(C)c1nc(-n2cc(C(=O)O)cn2)nc2ccc(OC3CCCCC3)cc12]

The titled compound was prepared in a manner analogous to EXAMPLE 1 steps B through F using 4-cyclohexyloxyaniline in step B and N-ethyl-N-methylamine in step E. MS (ESI): mass calcd. for $C_{21}H_{25}N_5O_3$, 395.5; m/z found, 396.2 [M+H]+. 1H NMR (400 MHz, DMSO-$d_6$): 12.75 (s, 1H), 8.91 (s, 1H), 8.04 (s, 1H), 7.72 (d, J=9.1 Hz, 1H), 7.49 (d, J=9.3 Hz, 1H), 7.45 (s, 1H), 4.48 (s, 1H), 3.80 (q, J=7.3 Hz, 2H), 3.38 (s, 3H), 1.99 (s, 2H), 1.75 (s, 2H), 1.62-1.25 (m, 9H).

Example 178

1-(6-benzyl-4-morpholinoquinazolin-2-yl)-1H-pyrazole-4-carboxylic acid

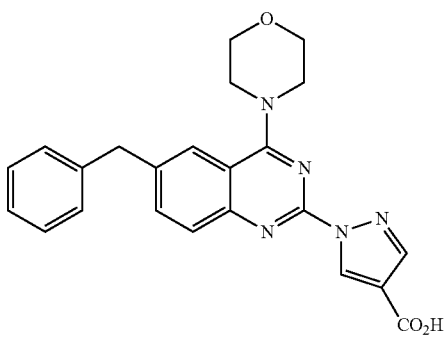 [SMILES: O=C(O)c1cnn(-c2nc(N3CCOCC3)c3cc(Cc4ccccc4)ccc3n2)c1]

The titled compound was prepared in a manner analogous to EXAMPLE 1 steps B through F using 4-benzylaniline in step B and morpholine in step E. MS (ESI): mass calcd. for $C_{23}H_{21}N_5O_3$, 415.2; m/z found, 416.2 [M+H]+. 1H NMR (400 MHz, DMSO-$d_6$): 12.75 (s, 1H), 9.00 (s, 1H), 8.09 (s, 1H), 7.80-7.68 (m, 3H), 7.36-7.17 (m, 5H), 4.15 (s, 2H), 3.85-3.83 (m, 4H), 3.78-3.77 (m, 4H).

Example 179

1-(6-benzyl-4-(dimethylamino)quinazolin-2-yl)-1H-pyrazole-4-carboxylic acid

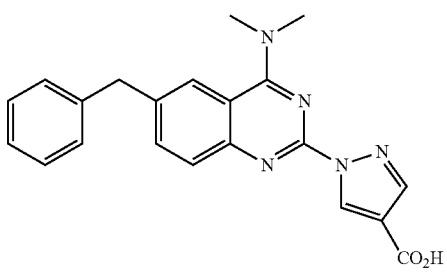 [SMILES: CN(C)c1nc(-n2cc(C(=O)O)cn2)nc2ccc(Cc3ccccc3)cc12]

The titled compound was prepared in a manner analogous to EXAMPLE 1 steps B through F using 4-benzylaniline in step B and dimethylamine in step E. MS (ESI): mass calcd. for $C_{21}H_{19}N_5O_2$, 373.4; m/z found, 374.2 [M+H]+. 1H NMR (400 MHz, DMSO-$d_6$): 12.71 (s, 1H), 8.97 (s, 1H), 8.07 (s, 1H), 8.04 (s, 1H), 7.70-7.63 (m, 2H), 7.31-7.28 (m, 4H), 7.24-7.18 (m, 1H), 4.13 (s, 2H), 3.41 (s, 6H).

Example 180

1-(6-benzyl-4-(diethylamino)quinazolin-2-yl)-1H-pyrazole-4-carboxylic acid

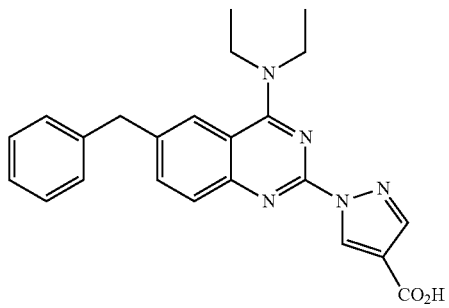 [SMILES: CCN(CC)c1nc(-n2cc(C(=O)O)cn2)nc2ccc(Cc3ccccc3)cc12]

The titled compound was prepared in a manner analogous to EXAMPLE 1 steps B through F using 4-benzylaniline in step B and diethylamine in step E. MS (ESI): mass calcd. for $C_{23}H_{23}N_5O_2$, 401.5; m/z found, 402.2 [M+H]+. 1H NMR (400 MHz, DMSO-$d_6$): 12.76 (s, 1H), 8.89 (s, 1H), 8.07 (s, 1H), 7.70 (s, 2H), 7.62 (s, 1H), 7.36-7.21 (m, 5H), 4.14 (s, 2H), 3.70 (q, J=6.8 Hz, 4H), 1.24 (t, J=6.9 Hz, 6H).

Example 181

1-(6-benzyl-4-(pyrrolidin-1-yl)quinazolin-2-yl)-1H-pyrazole-4-carboxylic acid

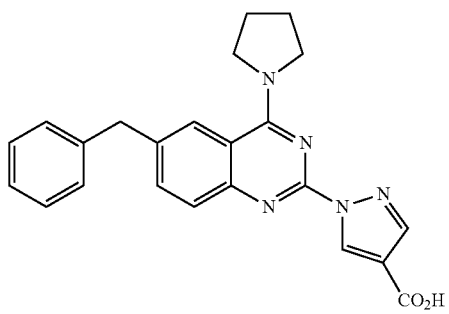 [SMILES: O=C(O)c1cnn(-c2nc(N3CCCC3)c3cc(Cc4ccccc4)ccc3n2)c1]

The titled compound was prepared in a manner analogous to EXAMPLE 1 steps B through F using 4-benzylaniline in step B and pyrrolidine in step E. MS (ESI): mass calcd. for $C_{23}H_{21}N_5O_2$, 399.5; m/z found, 400.3 [M+H]+. 1H NMR (400 MHz, DMSO-$d_6$): 8.88 (s, 1H), 8.14 (s, 1H), 7.99 (s, 1H), 7.64 (s, 2H), 7.31-2.29 (m, 4H), 7.23-7.16 (m, 1H), 4.12 (s, 2H), 3.93 (s, 4H), 2.00 (s, 4H).

Example 182

1-(6-benzyl-4-(cyclopropylamino)quinazolin-2-yl)-1H-pyrazole-4-carboxylic acid

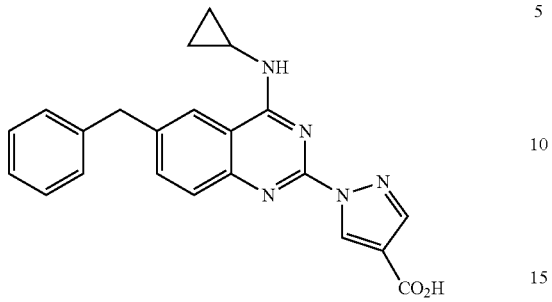

The titled compound was prepared in a manner analogous to EXAMPLE 1 steps B through F using 4-benzylaniline in step B and cyclopropyl amine in step E. MS (ESI): mass calcd. for $C_{22}H_{19}N_5O_2$, 385.4; m/z found, 386.1 [M+H]+. 1H NMR (400 MHz, DMSO-$d_6$): 8.96 (s, 1H), 8.76 (d, J=3.6 Hz, 1H), 8.31 (s, 1H), 8.01 (s, 1H), 7.66-7.60 (m, 2H), 7.32-7.23 (m, 4H), 7.22-7.13 (m, 1H), 4.05 (s, 2H), 3.24-3.18 (m, 1H), 0.92-0.82 (m, 2H), 0.81-0.71 (m, 2H).

Example 183

1-(6-benzyl-4-(ethyl(methyl)amino)quinazolin-2-yl)-1H-pyrazole-4-carboxylic acid

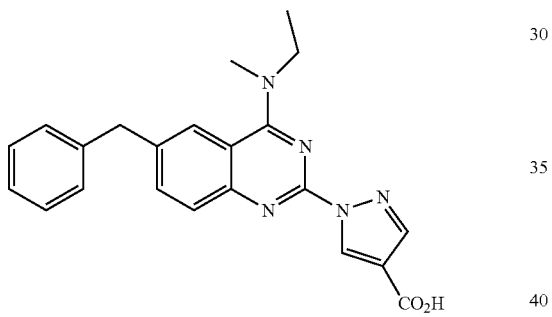

The titled compound was prepared in a manner analogous to EXAMPLE 1 steps B through F using 4-benzylaniline in step B and N-ethyl-N-methylamine in step E. MS (ESI): mass calcd. for $C_{22}H_{21}N_5O_2$, 387.4; m/z found, 388.1 [M+H]+. 1H NMR (400 MHz, DMSO-$d_6$): 8.94 (s, 1H), 8.07 (s, 1H), 7.88 (s, 1H), 7.68 (s, 2H), 7.34-7.28 (m, 4H), 7.21 (brs, 1H), 4.13 (s, 2H), 3.75 (q, J=6.8 Hz, 2H), 3.36 (s, 3H), 1.26 (t, J=6.9 Hz, 3H).

Example 184

1-(4-(morpholino)-6-isopropylquinazolin-2-yl)-1H-pyrazole-4-carboxylic acid

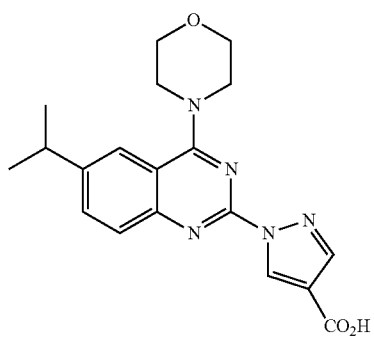 [SMILES: CC(C)c1ccc2nc(-n3cc(C(=O)O)cn3)nc(N3CCOCC3)c2c1]

The titled compound was prepared in a manner analogous to EXAMPLE 1 steps B through F using 4-isopropylaniline in step B and morpholine in step E. MS (ESI): mass calcd. for $C_{19}H_{21}N_5O_3$, 367.4; m/z found, 368.1 [M+H]+. 1H NMR (400 MHz, DMSO-$d_6$): 12.77 (s, 1H), 9.03 (s, 1H), 8.11 (s, 1H), 7.80 (s, 3H), 3.92 (s, 4H), 3.82 (s, 4H), 3.11 (dt, J=13.5, 6.7 Hz, 1H), 1.29 (d, J=6.8 Hz, 6H).

Example 185

1-(4-(dimethylamino)-6-isopropylquinazolin-2-yl)-1H-pyrazole-4-carboxylic acid

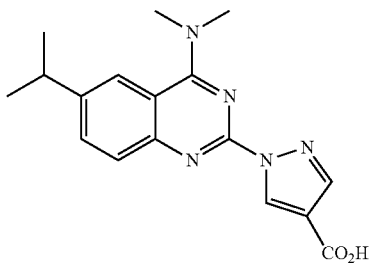 [SMILES: CC(C)c1ccc2nc(-n3cc(C(=O)O)cn3)nc(N(C)C)c2c1]

The titled compound was prepared in a manner analogous to EXAMPLE 1 steps B through F using 4-isopropylaniline in step B and dimethylamine in step E. MS (ESI): mass calcd. for $C_{17}H_{19}N_5O_2$, 325.4; m/z found, 326.2 [M+H]+. 1H NMR (400 MHz, DMSO-$d_6$): 12.66 (s, 1H), 9.00 (s, 1H), 8.08 (s, 1H), 8.02 (s, 1H), 7.82-7.69 (m, 2H), 3.45 (s, 6H), 3.10 (dt, J=13.6, 6.6 Hz, 1H), 1.29 (d, J=6.8 Hz, 6H).

Example 186

1-(4-(diethylamino)-6-isopropylquinazolin-2-yl)-1H-pyrazole-4-carboxylic acid

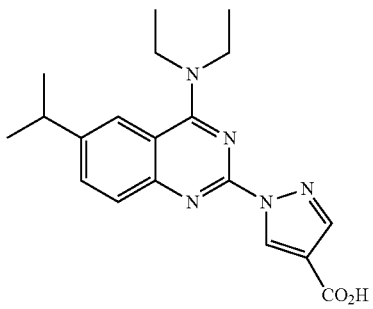

The titled compound was prepared in a manner analogous to EXAMPLE 1 steps B through F using 4-isopropylaniline in step B and diethylamine in step E. MS (ESI): mass calcd. for $C_{19}H_{123}N_5O_2$, 353.4; m/z found, 354.2 [M+H]+. 1H NMR (400 MHz, DMSO-$d_6$): 12.77 (s, 1H), 8.96 (s, 1H), 8.13 (s, 1H), 7.78 (t, J=13.6 Hz, 3H), 3.84 (q, J=6.7 Hz, 4H), 3.09 (dt, J=14.0, 7.0 Hz, 1H), 1.42 (t, J=6.9 Hz, 6H), 1.30 (d, J=6.9 Hz, 6H).

Example 187

1-(6-isopropyl-4-(pyrrolidin-1-yl)quinazolin-2-yl)-1H-pyrazole-4-carboxylic acid

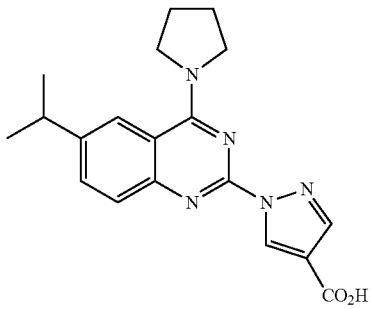 [SMILES: CC(C)c1ccc2nc(-n3cc(C(=O)O)cn3)nc(N3CCCC3)c2c1]

The titled compound was prepared in a manner analogous to EXAMPLE 1 steps B through F using 4-isopropylaniline in step B and pyrrolidine in step E. MS (ESI): mass calcd. for $C_{19}H_{21}N_5O_2$, 351.4; m/z found, 352.1 [M+H]. 1H NMR (400 MHz, DMSO-$d_6$): 8.96 (s, 1H), 8.08 (d, J=11.4 Hz, 2H), 7.78-7.63 (m, 2H), 3.98 (s, 4H), 3.13-3.05 (m, 1H), 2.02 (s, 4H), 1.29 (d, J=6.3 Hz, 6H).

Example 188

1-(4-(cyclopropylamino)-6-isopropylquinazolin-2-yl)-1H-pyrazole-4-carboxylic acid

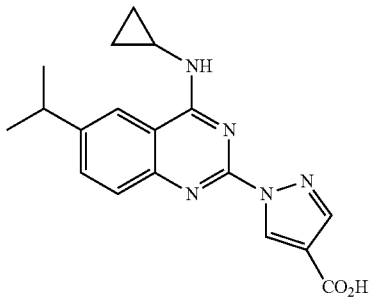 [SMILES: CC(C)c1ccc2nc(-n3cc(C(=O)O)cn3)nc(NC3CC3)c2c1]

The titled compound was prepared in a manner analogous to EXAMPLE 1 steps B through F using 4-isopropylaniline in step B and cyclopropylamine in step E. MS (ESI): mass calcd. for $C_{18}H_{19}N_5O_2$, 337.4; m/z found, 338.1 [M+H]+. 1H NMR (400 MHz, DMSO-$d_6$): 9.08 (s, 1H), 9.00 (s, 1H), 8.25 (s, 1H), 8.16 (s, 1H), 7.80-7.69 (m, 2H), 3.32 (s, 1H), 3.04 (dt, J=13.4, 6.7 Hz, 1H), 1.30 (d, J=6.9 Hz, 6H), 1.02-0.76 (m, 4H).

Example 189

1-(6-isopropyl-4-(ethyl(methyl)amino)quinazolin-2-yl)-1H-pyrazole-4-carboxylic acid

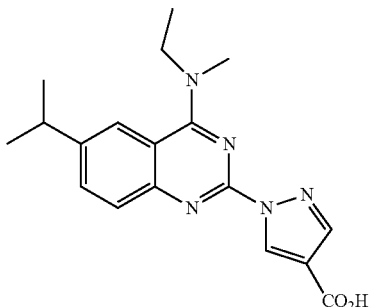

The titled compound was prepared in a manner analogous to EXAMPLE 1 steps B through F using 4-isopropylaniline in step B and N-ethyl-N-methylamine in step E. MS (ESI): mass calcd. for $C_{18}H_{21}N_6O_2$, 339.4; m/z found, 340.1 [M+H]+. 1H NMR (400 MHz, DMSO-$d_6$): 9.10 (s, 1H), 8.26 (s, 1H), 8.02 (s, 1H), 7.93-7.83 (m, 2H), 3.97 (q, J=6.9 Hz, 2H), 3.56 (s, 3H), 3.12 (dt, J=13.7, 6.9 Hz, 1H), 1.40 (t, J=7.0 Hz, 3H), 1.29 (d, J=6.9 Hz, 6H).

Examples 190-213 are prophetic Examples which may be synthesized using the general schemes provided above.

Example 190

1-(6-((2,6-Dimethylbenzyl)amino)-4-morpholinoquinazolin-2-yl)-1H-pyrazole-4-carboxylic acid

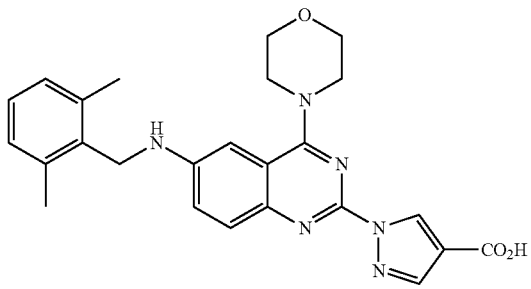 [SMILES: Cc1cccc(C)c1CNc1ccc2nc(-n3cc(C(=O)O)cn3)nc(N3CCOCC3)c2c1]

The above compound may be made analogous to Example 1 using ethyl 1-(6-((2,6-dimethylbenzyl)amino)-4-oxo-3,4-dihydroquinazolin-2-yl)-1H-pyrazole-4-carboxylate in step D and morpholine in step E. MS (ESI/CI): predicted mass $C_{25}H_{26}N_6O_3$, 458.2.

Example 191

1-(6-((2,6-Dimethylbenzyl)amino)-4-(dimethylamino)quinazolin-2-yl)-1H-pyrazole-4-carboxylic acid

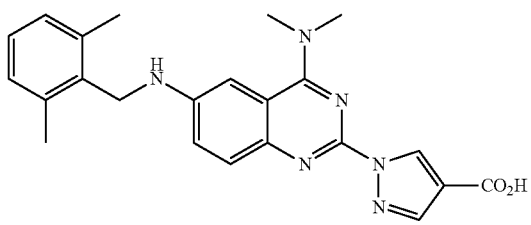 [SMILES: Cc1cccc(C)c1CNc1ccc2nc(-n3cc(C(=O)O)cn3)nc(N(C)C)c2c1]

The above compound may be made analogous to Example 1 using ethyl 1-(6-((2,6-dimethylbenzyl)amino)-4-oxo-3,4-dihydroquinazolin-2-yl)-1H-pyrazole-4-carboxylate in step D and dimethylamine in step E. MS (ESI/CI): predicted mass $C_{23}H_{24}N_6O_2$, 416.20.

Example 192

1-(6-((2,6-Dimethylbenzyl)amino)-4-(diethylamino)quinazolin-2-yl)-1H-pyrazole-4-carboxylic acid

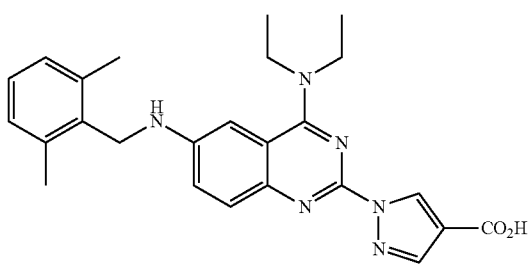 [SMILES: CCN(CC)c1nc(-n2cc(C(=O)O)cn2)nc2ccc(NCc3c(C)cccc3C)cc12]

The above compound may be made analogous to Example 1 using ethyl 1-(6-((2,6-dimethylbenzyl)amino)-4-oxo-3,4-dihydroquinazolin-2-yl)-1H-pyrazole-4-carboxylate in step D and diethylamine in step E. MS (ESI/CI): predicted mass $C_{25}H_{28}N_6O_2$, 444.2.

Example 193

1-(6-((2,6-Dimethylbenzyl)amino)-4-(pyrrolidin-1-yl)quinazolin-2-yl)-1H-pyrazole-4-carboxylic acid

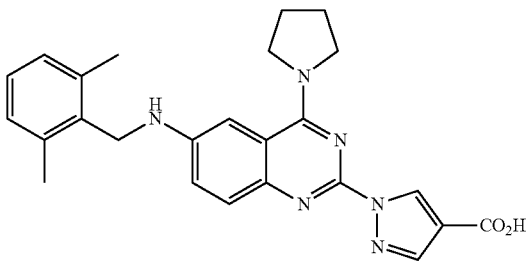 [SMILES: Cc1cccc(C)c1CNc1ccc2nc(-n3cc(C(=O)O)cn3)nc(N3CCCC3)c2c1]

The above compound may be made analogous to Example 1 using ethyl 1-(6-((2,6-dimethylbenzyl)amino)-4-oxo-3,4-dihydroquinazolin-2-yl)-1H-pyrazole-4-carboxylate in step D and pyrrolidine in step E. MS (ESI/CI): predicted mass $C_{25}H_{26}N_6O_2$, 442.2.

Example 194

1-(6-((2,6-Dimethylbenzyl)amino)-4-(cyclopropylamino)quinazolin-2-yl)-1H-pyrazole-4-carboxylic acid

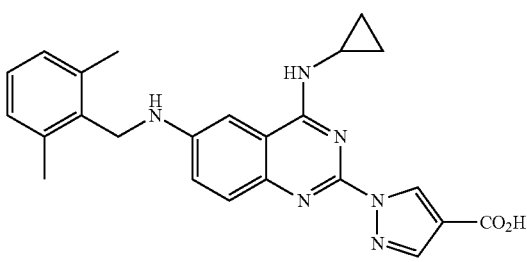 [SMILES: Cc1cccc(C)c1CNc1ccc2nc(-n3cc(C(=O)O)cn3)nc(NC3CC3)c2c1]

The above compound may be made analogous to Example 1 using ethyl 1-(6-((2,6-dimethylbenzyl)amino)-4-oxo-3,4-dihydroquinazolin-2-yl)-1H-pyrazole-4-carboxylate in step D and cyclopropylamine in step E. MS (ESI/CI): predicted mass $C_{24}H_{24}N_6O_2$, 428.2.

Example 195

1-(6-((2,6-Dimethylbenzyl)amino)-4-(ethyl(methyl)amino)quinazolin-2-yl)-1H-pyrazole-4-carboxylic acid

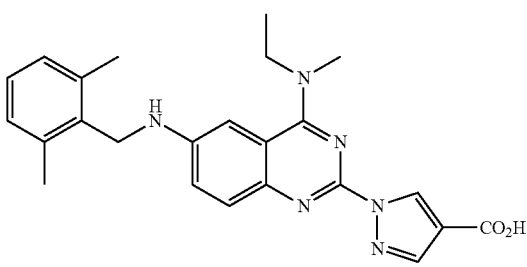 [SMILES: CCN(C)c1nc(-n2cc(C(=O)O)cn2)nc2ccc(NCc3c(C)cccc3C)cc12]

The above compound may be made analogous to Example 1 using ethyl 1-(6-((2,6-dimethylbenzyl)amino)-4-oxo-3,4-dihydroquinazolin-2-yl)-1H-pyrazole-4-carboxylate in step D and N-ethyl-N-methylamine in step E. MS (ESI/CI): predicted mass $C_{24}H_{26}N_6O_2$, 430.2.

Example 196

1-(4-Morpholino-6-(o-tolyl)quinazolin-2-yl)-1H-pyrazole-4-carboxylic acid

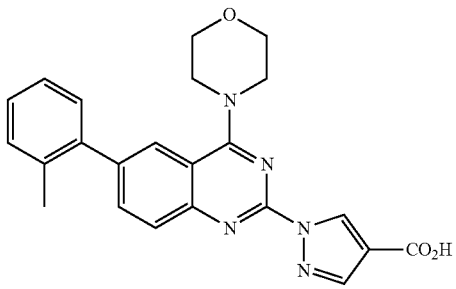 [SMILES: Cc1ccccc1-c1ccc2nc(-n3cc(C(=O)O)cn3)nc(N3CCOCC3)c2c1]

The above compound may be made analogous to Example 1 using ethyl 1-(6-(o-tolyl)-4-oxo-3,4-dihydroquinazolin-2-yl)-1H-pyrazole-4-carboxylate in step D and morpholine in step E. MS (ESI/CI): predicted mass $C_{23}H_{21}N_5O_3$, 415.2.

Example 197

1-(4-(Dimethylamino)-6-(o-tolyl)quinazolin-2-yl)-1H-pyrazole-4-carboxylic acid

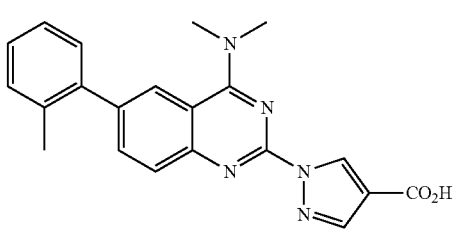 [SMILES: Cc1ccccc1-c1ccc2nc(-n3cc(C(=O)O)cn3)nc(N(C)C)c2c1]

The above compound may be made analogous to Example 1 using ethyl 1-(6-(o-tolyl)-4-oxo-3,4-dihydroquinazolin-2-yl)-1H-pyrazole-4-carboxylate in step D and dimethylamine in step E. MS (ESI/CI): predicted mass $C_{21}H_{19}N_5O_2$, 373.2.

Example 198

1-(4-(Diethylamino)-6-(o-tolyl)quinazolin-2-yl)-1H-pyrazole-4-carboxylic acid

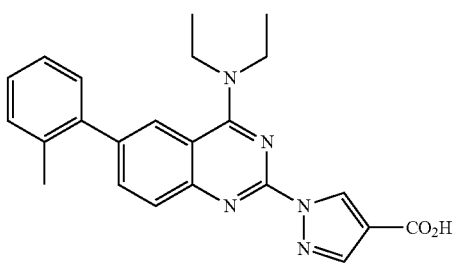 [SMILES: CCN(CC)c1nc(-n2cc(C(=O)O)cn2)nc2ccc(-c3ccccc3C)cc12]

The above compound may be made analogous to Example 1 using ethyl 1-(6-(o-tolyl)-4-oxo-3,4-dihydroquinazolin-2-yl)-1H-pyrazole-4-carboxylate in step D and diethylamine in step E. MS (ESI/CI): predicted mass $C_{23}H_{23}N_5O_2$, 401.2.

Example 199

1-(4-(Pyrrolidin-1-yl)-6-(o-tolyl)quinazolin-2-yl)-1H-pyrazole-4-carboxylic acid

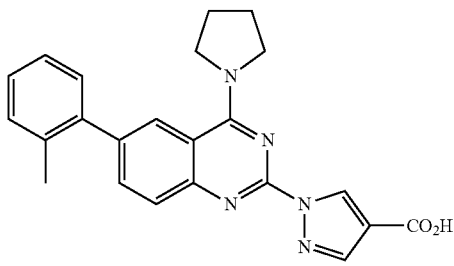 [SMILES: Cc1ccccc1-c1ccc2nc(-n3cc(C(=O)O)cn3)nc(N3CCCC3)c2c1]

The above compound may be made analogous to Example 1 using ethyl 1-(6-(o-tolyl)-4-oxo-3,4-dihydroquinazolin-2-yl)-1H-pyrazole-4-carboxylate in step D and pyrrolidine in step E. MS (ESI/CI): predicted mass $C_{23}H_{21}N_5O_2$, 399.2.

Example 200

1-(4-(Cyclopropylamino)-6-(o-tolyl)quinazolin-2-yl)-1H-pyrazole-4-carboxylic acid

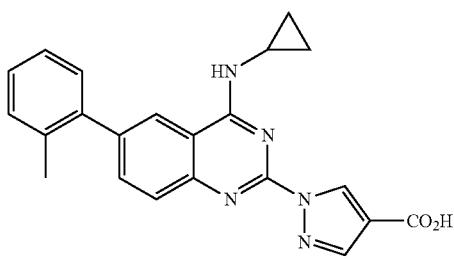 [SMILES: Cc1ccccc1-c1ccc2nc(-n3cc(C(=O)O)cn3)nc(NC3CC3)c2c1]

The above compound may be made analogous to Example 1 using ethyl 1-(6-(o-tolyl)-4-oxo-3,4-dihydroquinazolin-2-yl)-1H-pyrazole-4-carboxylate in step D and cyclopropylamine in step E. MS (ESI/CI): predicted mass $C_{22}H_{19}N_5O_2$, 385.2.

Example 201

1-(4-(Ethyl(methyl)amino)-6-(o-tolyl)quinazolin-2-yl)-1H-pyrazole-4-carboxylic acid

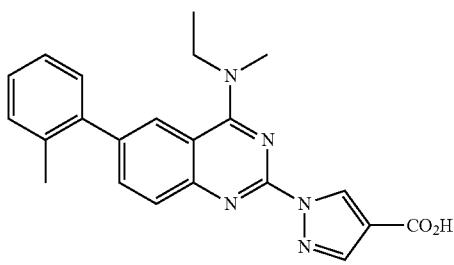 [SMILES: CCN(C)c1nc(-n2cc(C(=O)O)cn2)nc2ccc(-c3ccccc3C)cc12]

The above compound may be made analogous to Example 1 using ethyl 1-(6-(o-tolyl)-4-oxo-3,4-dihydroquinazolin-2-yl)-1H-pyrazole-4-carboxylate in step D and N-ethyl-N-methylamine in step E. MS (ESI/CI): predicted mass $C_{22}H_{21}N_5O_2$, 387.2.

Example 202

1-(4-Morpholino-6-(piperidin-1-yl)quinazolin-2-yl)-1H-pyrazole-4-carboxylic acid

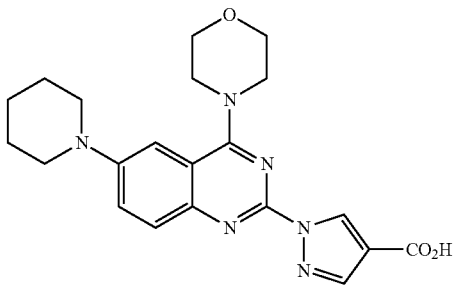 [SMILES: O=C(O)c1cnn(-c2nc(N3CCOCC3)c3cc(N4CCCCC4)ccc3n2)c1]

The above compound may be made analogous to Example 1 using ethyl 1-(6-(piperidin-1-yl)-4-oxo-3,4-dihydroquinazolin-2-yl)-1H-pyrazole-4-carboxylate in step D and morpholine in step E. MS (ESI/CI): predicted mass $C_{21}H_{24}N_6O_3$, 408.2.

Example 203

1-(4-(Dimethylamino)-6-(piperidin-1-yl)quinazolin-2-yl)-1H-pyrazole-4-carboxylic acid

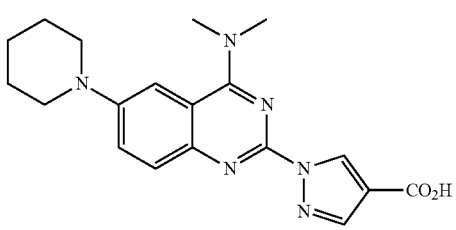 [SMILES: CN(C)c1nc(-n2cc(C(=O)O)cn2)nc2ccc(N3CCCCC3)cc12]

The above compound may be made analogous to Example 1 using ethyl 1-(6-(piperidin-1-yl)-4-oxo-3,4-dihydroquinazolin-2-yl)-1H-pyrazole-4-carboxylate in step D and dimethylamine in step E. MS (ESI/CI): predicted mass $C_{19}H_{22}N_6O_2$, 366.2.

Example 204

1-(4-(Diethylamino)-6-(piperidin-1-yl)quinazolin-2-yl)-1H-pyrazole-4-carboxylic acid

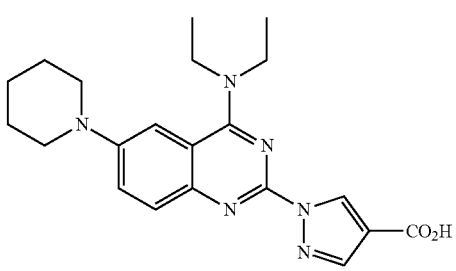 [SMILES: CCN(CC)c1nc(-n2cc(C(=O)O)cn2)nc2ccc(N3CCCCC3)cc12]

The above compound may be made analogous to Example 1 using ethyl 1-(6-(piperidin-1-yl)-4-oxo-3,4-dihydroquinazolin-2-yl)-1H-pyrazole-4-carboxylate in step D and diethylamine in step E. MS (ESI/CI): predicted mass $O_{21}H_{26}N_6O_2$, 394.2.

Example 205

1-(6-(Piperidin-1-yl)-4-(pyrrolidin-1-yl)quinazolin-2-yl)-1H-pyrazole-4-carboxylic acid

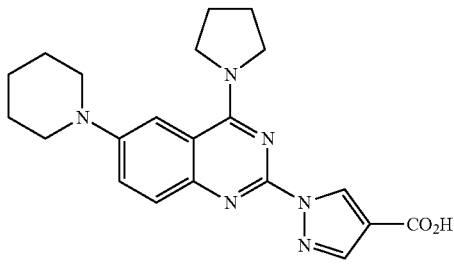 [SMILES: O=C(O)c1cnn(-c2nc(N3CCCC3)c3cc(N4CCCCC4)ccc3n2)c1]

The above compound may be made analogous to Example 1 using ethyl 1-(6-(piperidin-1-yl)-4-oxo-3,4-dihydroquinazolin-2-yl)-1H-pyrazole-4-carboxylate in step D and pyrrolidine in step E. MS (ESI/CI): predicted mass $O_{21}H_{24}N_6O_2$, 392.2.

Example 206

1-(4-(Cyclopropylamino)-6-(piperidin-1-yl)quinazolin-2-yl)-1H-pyrazole-4-carboxylic acid

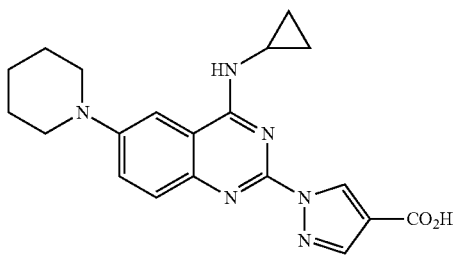 [SMILES: O=C(O)c1cnn(-c2nc(NC3CC3)c3cc(N4CCCCC4)ccc3n2)c1]

The above compound may be made analogous to Example 1 using ethyl 1-(6-(piperidin-1-yl)-4-oxo-3,4-dihydroquinazolin-2-yl)-1H-pyrazole-4-carboxylate in step D and cyclopropylamine in step E. MS (ESI/CI): predicted mass $C_{20}H_{22}N_6O_2$, 378.2.

Example 207

1-(4-(Ethyl(methyl)amino)-6-(piperidin-1-yl)quinazolin-2-yl)-1H-pyrazole-4-carboxylic acid

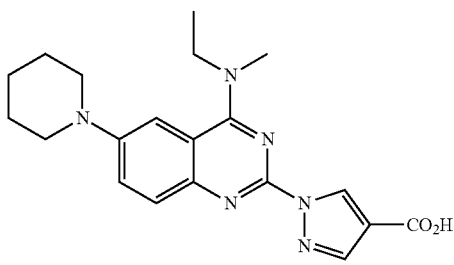 [SMILES: CCN(C)c1nc(-n2cc(C(=O)O)cn2)nc2ccc(N3CCCCC3)cc12]

The above compound may be made analogous to Example 1 using ethyl 1-(6-(piperidin-1-yl)-4-oxo-3,4-dihydroquinazolin-2-yl)-1H-pyrazole-4-carboxylate in step D and N-ethyl-N-methylamine in step E. MS (ESI/CI): predicted mass $C_{20}H_{24}N_6O_2$, 380.2.

Example 208

1-(6-(2,6-Dimethylphenoxy)-7-methyl-4-morpholinoquinazolin-2-yl)-1H-pyrazole-4-carboxylic acid

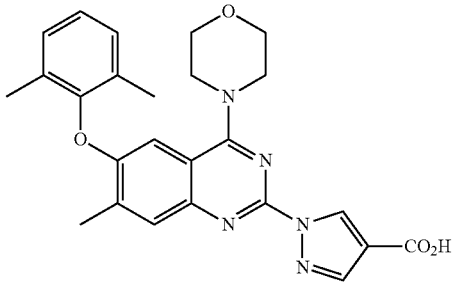 [SMILES: Cc1cc2nc(-n3cc(C(=O)O)cn3)nc(N3CCOCC3)c2cc1Oc1c(C)cccc1C]

The above compound may be made analogous to Example 1 using ethyl 1-(6-(2,6-dimethylphenoxy)-7-methyl-4-oxo-3,4-dihydroquinazolin-2-yl)-1H-pyrazole-4-carboxylate in step D and morpholine in step E. MS (ESI/CI): predicted mass $C_{25}H_{25}N_5O_4$, 459.2.

Example 209

1-(6-(2,6-Dimethylphenoxy)-7-methyl-4-dimethylaminoquinazolin-2-yl)-1H-pyrazole-4-carboxylic acid

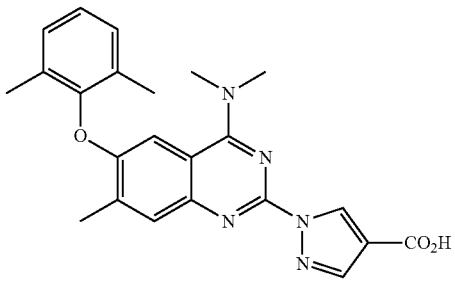 [SMILES: Cc1cc2nc(-n3cc(C(=O)O)cn3)nc(N(C)C)c2cc1Oc1c(C)cccc1C]

The above compound may be made analogous to Example 1 using ethyl 1-(6-(2,6-dimethylphenoxy)-7-methyl-4-oxo-3,4-dihydroquinazolin-2-yl)-1H-pyrazole-4-carboxylate in step D and dimethylamine in step E. MS (ESI/CI): predicted mass $C_{23}H_{23}N_5O_3$, 417.2.

Example 210

1-(6-(2,6-Dimethylphenoxy)-7-methyl-4-diethylaminoquinazolin-2-yl)-1H-pyrazole-4-carboxylic acid

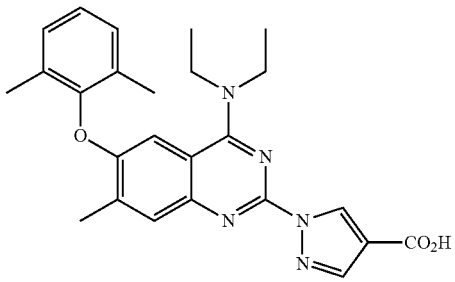 [SMILES: CCN(CC)c1nc(-n2cc(C(=O)O)cn2)nc2cc(C)c(Oc3c(C)cccc3C)cc12]

The above compound may be made analogous to Example 1 using ethyl 1-(6-(2,6-dimethylphenoxy)-7-methyl-4-oxo-3,4-dihydroquinazolin-2-yl)-1H-pyrazole-4-carboxylate in step D and diethylamine in step E. MS (ESI/CI): predicted mass $C_{25}H_{27}N_5O_3$, 445.2.

Example 211

1-(6-(2,6-Dimethylphenoxy)-7-methyl-4-(pyrrolidin-1-yl)quinazolin-2-yl)-1H-pyrazole-4-carboxylic acid

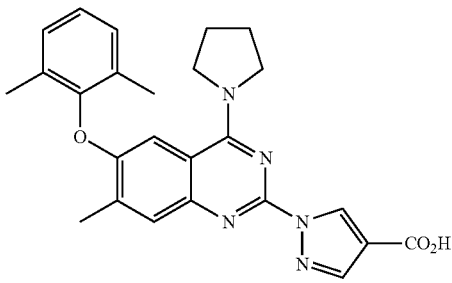 [SMILES: Cc1cc2nc(-n3cc(C(=O)O)cn3)nc(N3CCCC3)c2cc1Oc1c(C)cccc1C]

The above compound may be made analogous to Example 1 using ethyl 1-(6-(2,6-dimethylphenoxy)-7-methyl-4-oxo-3,4-dihydroquinazolin-2-yl)-1H-pyrazole-4-carboxylate in step D and pyrrolidine in step E. MS (ESI/CI): predicted mass $C_{25}H_{25}N_5O_3$, 443.2.

Example 212

1-(6-(2,6-Dimethylphenoxy)-7-methyl-4-cyclopropylaminoquinazolin-2-yl)-1H-pyrazole-4-carboxylic acid

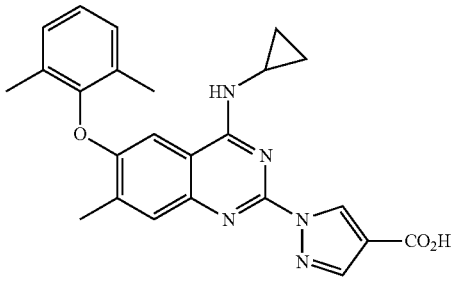 [SMILES: Cc1cc2nc(-n3cc(C(=O)O)cn3)nc(NC3CC3)c2cc1Oc1c(C)cccc1C]

The above compound may be made analogous to Example 1 using ethyl 1-(6-(2,6-dimethylphenoxy)-7-methyl-4-oxo-3,4-dihydroquinazolin-2-yl)-1H-pyrazole-4-carboxylate in step D and cyclopropylamine in step E. MS (ESI/CI): predicted mass $C_{24}H_{23}N_5O_3$, 429.2.

Example 213

1-(6-(2,6-Dimethylphenoxy)-4-(ethyl(methyl)amino)-7-methylquinazolin-2-yl)-1H-pyrazole-4-carboxylic acid

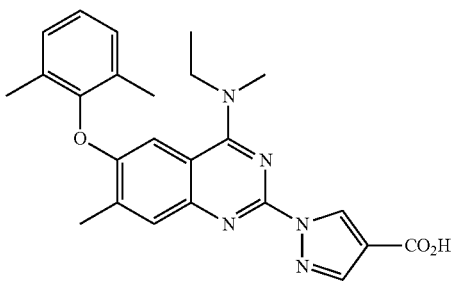 [SMILES: CCN(C)c1nc(-n2cc(C(=O)O)cn2)nc2cc(C)c(Oc3c(C)cccc3C)cc12]

The above compound may be made analogous to Example 1 using ethyl 1-(6-(2,6-dimethylphenoxy)-7-methyl-4-oxo-3,4-dihydroquinazolin-2-yl)-1H-pyrazole-4-carboxylate in step D and N-ethyl-N-methylamine in step E. MS (ESI/CI): predicted mass $C_{25}H_{24}N_5O_3$, 431.2.

Biological Protocols:

Expression and Purification of $PHD2_{181-417}$

The human PHD2 expression construct containing amino acids 181-417 of GenBank Accession ID NM_022051 was cloned into a pBAD vector (Invitrogen), incorporating both an N-terminal histidine tag and a Smt3-tag, both of which are cleaved by Ulp1. Protein production was achieved by expression in BL21 cells grown in Terrific Broth containing 100 µg/ml ampicillin. Cell cultures were inoculated at 37° C. and grown to an $OD_{600}$ of 0.8. Cultures were induced with 0.1% arabinose and grown overnight at 20° C. with continuous shaking at 225 rpm. Cells were then harvested by centrifugation and stored at −80° C. Cell pellets were suspended in Buffer A (50 mM Tris-HCl pH 7.2, 100 mM NaCl, 100 mM L-arginine, 1 mM TCEP, 0.05% (w/v) NP-40, 50 mM imidazole) followed by the addition of lysozyme and benzonase. Cells were lysed by sonication and the lysate was cleared by centrifugation (15,000 rpm, 90 min, 4° C.). The protein was purified by nickel affinity chromatography using a HisTrap Crude FF column (GE Healthcare). Samples were eluted in Buffer A with a 50-200 mM imidazole gradient. Cleavage of the Smt tag with Ulp1 protease was achieved via overnight incubation with dialyzing against Buffer A. The $PHD2_{181-417}$ sample was then passed over a second HisTrap Crude FF column (GE Healthcare) to remove uncleaved protein. The flow-through was then dialyzed into 50 mM MES pH 6.0, 1 mM TCEP, 5 mM NaCl for ion exchange chromatography on a HiTrap SP Cation Exchange column (GE Healthcare). The $PHD2_{181-417}$ protein was eluted with a 0-0.2 M NaCl gradient. Fractions were pooled for further purification by size exclusion chromatography over a Superdex 75 Size Exclusion Column (GE Healthcare). Final protein was concentrated to 4 mg/ml and dialyzed in 10 mM PIPES pH 7.0, 100 mM NaCl, 0.5 mM TCEP. The protein was determined to have a purity of >95% by gel electrophoresis.

Enzyme Activity Assay

The PHD enzymatic assay was performed in 0.5 ml of reaction mixture containing the following: purified $PHD2_{181-417}$ polypeptide (3 µg), synthetic HIF-1α peptide comprising residues [KNPFSTGDTDLDLEMLAPYIPMD-DDFQLRSFDQLS](10 µM, California Peptide Research Inc., Napa, Calif.), and [5-$^{14}$C]-2-oxoglutaric acid (50 mCi/mmol, Moravek Chemicals, Brea, Calif.) in reaction buffer (40 mM Tris-HCl, pH 7.5, 0.4 mg/ml catalase, 0.5 mM DTT, 1 mM ascorbate) for 10 minutes. Compounds were pre-incubated for 30 min before starting the reaction (all test compounds were dissolved at 10 mM in 100% DMSO (w/v) and were tested with final compound concentrations at 100 µM in 1% DMSO (w/v)). The reaction was stopped by addition of 50 µl of 70 mM $H_3PO_4$ and 50 µl of 500 mM $NaH_2PO_4$, pH 3.2. Detection of [$^{14}$C]-succinic acid was achieved by separating from [5-$^{14}$C]-2-oxoglutaric acid by incubating the reaction mixture with 100 µl of 0.16 M DNP prepared in 30% perchloric acid. Next, 50 µl of unlabeled 20 mM 2-oxoglutaric acid/20 mM succinic acid, serving as carrier for the radioactivity, was added to the mixture, and was allowed to proceed for 30 minutes at room temperature. The reaction was then incubated with 50 µl of 1 M 2-oxoglutaric acid for 30 additional minutes at room temperature to precipitate the excess DNP.

The reaction was then centrifuged at 2800×g for 10 minutes at room temperature to separate [$^{14}$C]-succinic acid in the supernatant from the precipitated [$^{14}$C]-dinitrophenylhydrazone. Fractions of the supernatant (400 µl) were counted using a beta counter (Beckman Coulter, Fullerton, Calif.). Inhibition of PHD2$_{181-417}$ activity was measured as a decrease in [$^{14}$C]-succinic acid production. The IC$_{50}$ values were estimated by fitting the data to a three-parameter logistic function using GraphPad Prism, version 4.02 (Graph Pad Software, San Diego, Calif.).

Cellular Assay

Hep-3B cells (ATCC, Manassas, Va.) were plated in 96-well plates at 20,000 cells per well in 100 µl of DMEM containing 10% fetal bovine serum, 1% non-essential amino acids, 50 IU/mL of penicillin and 50 µg/mL of streptomycin (all cell culture reagents from Invitrogen, Carlsbad, Calif.). Twenty-four hours after plating, compounds were added and incubated for an additional 24 hours. All compounds were tested with final compound concentrations at 100 µM. Fifty microliters of the supernatant was then transferred to a human Hypoxia assay kit (Meso-Scale Discovery, Gaithersburg, Md.). Erythropoietin in the supernatant was detected according to the manufacturer's instructions as follows. EPO detection plates were blocked with 3% BSA in PBS overnight and 50 µl of the supernatant was incubated at room temperature in an orbital shaker for 2 h. Twenty-five microliters of 0.5 µg/ml anti-EPO detection antibody was added for 2 hours at room temperature in an orbital shaker. After 3 washes in PBS, 150 µl of 1× read buffer is added and the plate is then read on the MSD SECTOR instrument. Data was analyzed by determining the percent of EPO secretion in the presence of 100 µM compound relative to an assay control compound, 7-[(4-Chloro-phenyl)-(5-methyl-isoxazol-3-ylamino)-methyl]-quinolin-8-ol.

Cellular Assay for HIF1-α

Hela cells (ATCC, Manassas, Va.) were plated in 96-well plates at 20,000 cells per well in 100 µl of DMEM containing 10% fetal bovine serum, 1% non-essential amino acids, 50 IU/mL of penicillin and 50 µg/mL of streptomycin (all cell culture reagents from Invitrogen, Carlsbad, Calif.). 24 hours after plating, changed media to 100 ul of DMEM without 10% fetal bovine serum, 1.1 µl of the stock solution for each compound was added and incubated for 6 hours. All compounds were tested with a final compound concentration of 100 µM. The supernatant was removed and the cells were lysed in 55 µl of MSD lysis buffer containing protease inhibitors. 50 µl of the cell lysate was then transferred to a blocked MSD human HIF-1α detection plate (Meso-Scale Discovery, Gaithersburg, Md., as per manufacturers protocol), and incubated at room temperature on an orbital shaker for 2 hour. After 3 washes in PBS, 25 µl of 20 nM anti-HIF1α detection antibody was added and incubated for 1 hour at room temperature on an orbital shaker. After 3 washes in PBS, 150 µl of 1× read buffer was added and the plate was then read on a MSD SECTOR instrument. Data was analyzed by determining the percent of HIF stimulation in the presence of 100 µM compound relative to an assay control compound, 7-[(4-Chloro-phenyl)-(5-methyl-isoxazol-3-ylamino)-methyl]-quinolin-8-ol.

Results for the compounds tested in these assays are presented in Table 1 as an average of results obtained (NT=not tested).

TABLE 1

| Ex | Chemical Name | Enzyme pIC$_{50}$ | Cellular % EPO Stimulation | % HIF Stimulation |
|---|---|---|---|---|
| 1 | 1-[4-Amino-6-(2,6-dimethyl-phenoxy)-7-fluoro-quinazolin-2-yl]-1H-pyrazole-4-carboxylic acid; | 7.2 | 51 | NT |
| 2 | 1-[6-(2,6-Dimethyl-phenoxy)-7-fluoro-4-methylamino-quinazolin-2-yl]-1H-pyrazole-4-carboxylic acid; | 7.2 | 10 | NT |
| 3 | 1-[4-Dimethylamino-6-(2,6-dimethyl-phenoxy)-7-fluoro-quinazolin-2-yl]-1H-pyrazole-4-carboxylic acid; | 7.2 | 68 | NT |
| 4 | 1-[6-(2,6-Dimethyl-phenoxy)-7-fluoro-4-piperidin-1-yl-quinazolin-2-yl]-1H-pyrazole-4-carboxylic acid; | 6.9 | 17 | NT |
| 5 | 1-[6-(2,6-Dimethyl-phenoxy)-7-fluoro-4-pyrrolidin-1-yl-quinazolin-2-yl]-1H-pyrazole-4-carboxylic acid; | 7.4 | 25 | NT |
| 6 | 1-[6-(2,6-Dimethyl-phenoxy)-7-fluoro-4-phenylamino-quinazolin-2-yl]-1H-pyrazole-4-carboxylic acid; | 7.4 | 22 | NT |
| 7 | 1-[4-(2-Chloro-phenylamino)-6-(2,6-dimethyl-phenoxy)-7-fluoro-quinazolin-2-yl]-1H-pyrazole-4-carboxylic acid; | 7.2 | 13 | NT |
| 8 | 1-[6-(2,6-Dimethyl-phenoxy)-7-fluoro-4-propylamino-quinazolin-2-yl]-1H-pyrazole-4-carboxylic acid; | 7.2 | 59 | NT |
| 9 | (rac)-1-[6-(2,6-Dimethyl-phenoxy)-7-fluoro-4-(2-methoxy-1-methyl-ethylamino)-quinazolin-2-yl]-1H-pyrazole-4-carboxylic acid; | 7.1 | 86 | NT |
| 10 | 1-[4-(2-Diethylamino-ethylamino)-6-(2,6-dimethyl-phenoxy)-7-fluoro-quinazolin-2-yl]-1H-pyrazole-4-carboxylic acid; | 5.9 | 13 | NT |
| 11 | 1-[6-(2,6-Dimethyl-phenoxy)-4-dibutylamino-7-fluoro-quinazolin-2-yl]-1H-pyrazole-4-carboxylic acid; | 7.1 | 9 | NT |

TABLE 1-continued

| Ex | Chemical Name | Enzyme pIC$_{50}$ | Cellular % EPO Stimulation | % HIF Stimulation |
|---|---|---|---|---|
| 12 | 1-[6-(2,6-Dimethyl-phenoxy)-4-dipropylamino-7-fluoro-quinazolin-2-yl]-1H-pyrazole-4-carboxylic acid; | 7.4 | 9 | NT |
| 13 | 1-(4-((Cyclohexylmethyl)amino)-6-(2,6-dimethylphenoxy)-7-fluoroquinazolin-2-yl)-1H-pyrazole-4-carboxylic acid; | 6.9 | 10 | NT |
| 14 | 1-((4-Cyclopropylamino)-6-(2,6-dimethylphenoxy)-7-fluoroquinazolin-2-yl)-1H-pyrazole-4-carboxylic acid; | 7.1 | 86 | NT |
| 15 | 1-((4-Cyclopropanemethylamino)-6-(2,6-dimethylphenoxy)-7-fluoroquinazolin-2-yl)-1H-pyrazole-4-carboxylic acid; | 7.2 | 64 | NT |
| 16 | 1-(6-(2,6-Dimethylphenoxy)-7-fluoro-4-((tetrahydro-2H-pyran-4-yl)amino)quinazolin-2-yl)-1H-pyrazole-4-carboxylic acid; | 7.1 | 71 | NT |
| 17 | 1-(6-(2,6-Dimethylphenoxy)-7-fluoro-4-(4-methyl-1,4-diazepan-1-yl)quinazolin-2-yl)-1H-pyrazole-4-carboxylic acid; | 6.7 | NT | 47 |
| 18 | 1-(6-(2,6-Dimethylphenoxy)-7-fluoro-4-thiomorpholinoquinazolin-2-yl)-1H-pyrazole-4-carboxylic acid; | 7.0 | NT | 15 |
| 19 | 1-(6-(2,6-dimethylphenoxy)-7-fluoro-4-(4-hydroxypiperidin-1-yl)quinazolin-2-yl)-1H-pyrazole-4-carboxylic acid; | 6.9 | NT | 140 |
| 20 | 1-(6-(2,6-Dimethylphenoxy)-7-fluoro-4-morpholinoquinazolin-2-yl)-1H-pyrazole-4-carboxylic acid; | 7.0 | 54 | NT |
| 21 | 1-(4-(4-Acetamidopiperidin-1-yl)-6-(2,6-dimethylphenoxy)-7-fluoroquinazolin-2-yl)-1H-pyrazole-4-carboxylic acid; | 6.9 | NT | 62 |
| 22 | 1-(6-Cyclohexyl-4-methylamino-quinazolin-2-yl)-1H-pyrazole-4-carboxylic acid; | 7.1 | 48 | NT |
| 23 | 1-[6-Cyclohexyl-4-(2,6-dimethyl-benzylamino)-quinazolin-2-yl]-1H-pyrazole-4-carboxylic acid; | 5.9 | 7 | NT |
| 24 | 1-(4-Amino-6-cyclohexylquinazolin-2-yl)-1H-pyrazole-4-carboxylic acid; | 7.5 | 36 | NT |
| 25 | 1-(6-Cyclohexyl-4-(pyrrolidin-1-yl)quinazolin-2-yl)-1H-pyrazole-4-carboxylic acid; | 6.4 | 39 | NT |
| 26 | 1-(6-Cyclohexyl-4-(piperidin-1-yl)quinazolin-2-yl)-1H-pyrazole-4-carboxylic acid; | 7.1 | 20 | NT |
| 27 | 1-(6-Cyclohexyl-4-(diethylamino)quinazolin-2-yl)-1H-pyrazole-4-carboxylic acid; | 7.3 | 45 | NT |
| 28 | 1-(6-Cyclohexyl-4-(phenylamino)quinazolin-2-yl)-1H-pyrazole-4-carboxylic acid; | 7.3 | 31 | NT |
| 29 | 1-(4-((2-Chlorophenyl)amino)-6-cyclohexylquinazolin-2-yl)-1H-pyrazole-4-carboxylic acid; | 7.1 | NT | 7.8 |
| 30 | 1-(4-(4-Cyanopiperidin-1-yl)-6-cyclohexylquinazolin-2-yl)-1H-pyrazole-4-carboxylic acid; | 6.9 | NT | 77 |
| 31 | 1-(6-Cyclohexyl-4-(4-fluoropiperidin-1-yl)quinazolin-2-yl)-1H-pyrazole-4-carboxylic acid; | 7.1 | NT | 34 |
| 32 | 1-(6-Cyclohexyl-4-(cyclopropylamino)quinazolin-2-yl)-1H-pyrazole-4-carboxylic acid; | 6.7 | 49 | NT |
| 33 | 1-(6-Cyclohexyl-4-morpholinoquinazolin-2-yl)-1H-pyrazole-4-carboxylic acid; | 6.8 | 36 | NT |
| 34 | 1-(6-Cyclohexyl-4-thiomorpholinoquinazolin-2-yl)-1H-pyrazole-4-carboxylic acid; | 6.9 | 20 | NT |
| 35 | 1-(4-Cyanamido-6-cyclohexylquinazolin-2-yl)-1H-pyrazole-4-carboxylic acid; | 7.2 | 67 | NT |
| 36 | 1-(4-(tert-Butylamino)-6-cyclohexylquinazolin-2-yl)-1H-pyrazole-4-carboxylic acid; | 6.8 | NT | 23 |
| 37 | 1-(4-(Azepan-1-yl)-6-cyclohexylquinazolin-2-yl)-1H-pyrazole-4-carboxylic acid; | 7.1 | 17 | NT |

TABLE 1-continued

| Ex | Chemical Name | Enzyme pIC$_{50}$ | Cellular % EPO Stimulation | % HIF Stimulation |
|---|---|---|---|---|
| 38 | 1-(6-Cyclohexyl-4-(dimethylamino)quinazolin-2-yl)-1H-pyrazole-4-carboxylic acid; | 7.2 | 61 | NT |
| 39 | 1-(6-Cyclohexyl-4-((cyclohexylmethyl)amino)quinazolin-2-yl)-1H-pyrazole-4-carboxylic acid; | 6.9 | NT | 6.1 |
| 40 | 1-(6-Cyclohexyl-4-(methylsulfonamido)quinazolin-2-yl)-1H-pyrazole-4-carboxylic acid; | 6.6 | NT | 6.7 |
| 41 | 1-(4-(Dimethylamino)-6-phenylquinazolin-2-yl)-1H-pyrazole-4-carboxylic acid; | 7.2 | 43 | NT |
| 42 | 1-(4-(Ethyl(methyl)amino)-6-phenylquinazolin-2-yl)-1H-pyrazole-4-carboxylic acid; | 7.3 | 56 | NT |
| 43 | 1-(6-Phenyl-4-(pyrrolidin-1-yl)quinazolin-2-yl)-1H-pyrazole-4-carboxylic acid; | 7.3 | NT | 57 |
| 44 | 1-(6-Phenyl-4-(phenylamino)quinazolin-2-yl)-1H-pyrazole-4-carboxylic acid | 7.1 | NT | 22 |
| 45 | 1-(6-Phenyl-4-(piperidin-1-yl)quinazolin-2-yl)-1H-pyrazole-4-carboxylic acid; | 7.2 | 8 | NT |
| 46 | 1-(4-(Diethylamino)-6-phenylquinazolin-2-yl)-1H-pyrazole-4-carboxylic acid; | 7.4 | 26 | NT |
| 47 | 1-(4-((2-Chlorophenyl)amino)-6-phenylquinazolin-2-yl)-1H-pyrazole-4-carboxylic acid; | 6.6 | NT | 10 |
| 48 | 1-(4-(Azepan-1-yl)-6-phenylquinazolin-2-yl)-1H-pyrazole-4-carboxylic acid; | 7.2 | NT | 23 |
| 49 | 1-(4-((Cyclohexylmethyl)amino)-6-phenylquinazolin-2-yl)-1H-pyrazole-4-carboxylic acid; | 6.9 | NT | 3.8 |
| 50 | 1-(4-Cyanamido-6-phenylquinazolin-2-yl)-1H-pyrazole-4-carboxylic acid; | 7.1 | NT | 9.6 |
| 51 | 1-(4-(Cyclopropylamino)-6-phenylquinazolin-2-yl)-1H-pyrazole-4-carboxylic acid; | 6.5 | NT | 40 |
| 52 | 1-(4-(tert-Butylamino)-6-phenylquinazolin-2-yl)-1H-pyrazole-4-carboxylic acid; | 6.5 | NT | 37 |
| 53 | 1-(4-Amino-6-phenylquinazolin-2-yl)-1H-pyrazole-4-carboxylic acid; | 7.0 | NT | 16 |
| 54 | 1-(6-Phenyl-4-thiomorpholinoquinazolin-2-yl)-1H-pyrazole-4-carboxylic acid; | 6.8 | 25 | NT |
| 55 | 1-(4-(4-Acetamidopiperidin-1-yl)-6-phenylquinazolin-2-yl)-1H-pyrazole-4-carboxylic acid; | 6.7 | NT | 28 |
| 56 | 1-(6-Phenyl-4-((tetrahydro-2H-pyran-4-yl)amino)quinazolin-2-yl)-1H-pyrazole-4-carboxylic acid; | 6.2 | NT | 25 |
| 57 | 1-(4-(4-Methyl-1,4-diazepan-1-yl)-6-phenylquinazolin-2-yl)-1H-pyrazole-4-carboxylic acid; | 6.4 | NT | 30 |
| 58 | 1-(4-Morpholino-6-phenylquinazolin-2-yl)-1H-pyrazole-4-carboxylic acid; | 6.5 | NT | 49 |
| 59 | 1-(4-(4-Cyanopiperidin-1-yl)-6-phenylquinazolin-2-yl)-1H-pyrazole-4-carboxylic acid; | 6.4 | NT | 45 |
| 60 | 1-(6-(4-Chlorophenoxy)-4-(diethylamino)quinazolin-2-yl)-1H-pyrazole-4-carboxylic acid; | 7.3 | 22 | NT |
| 61 | 1-(6-(4-Chlorophenoxy)-4-(pyrrolidin-1-yl)quinazolin-2-yl)-1H-pyrazole-4-carboxylic acid; | 7.3 | 96 | NT |
| 62 | 1-(6-(4-Chlorophenoxy)-4-(cyclopropylamino)quinazolin-2-yl)-1H-pyrazole-4-carboxylic acid; | 7.0 | 32 | NT |
| 63 | 1-(6-(4-Chlorophenoxy)-4-(piperidin-1-yl)quinazolin-2-yl)-1H-pyrazole-4-carboxylic acid; | 7.6 | 39 | NT |
| 64 | 1-(6-(4-Chlorophenoxy)-4-((cyclohexylmethyl)amino)quinazolin-2-yl)-1H-pyrazole-4-carboxylic acid; | 7.5 | NT | 1.5 |
| 65 | 1-(6-(4-chlorophenoxy)-4-(4-cyanopiperidin-1-yl)quinazolin-2-yl)-1H-pyrazole-4-carboxylic acid; | 7.4 | 77 | NT |
| 66 | 1-(4-(Azepan-1-yl)-6-(4-chlorophenoxy)quinazolin-2-yl)-1H-pyrazole-4-carboxylic acid; | 7.5 | NT | 14 |

TABLE 1-continued

| Ex | Chemical Name | Enzyme pIC$_{50}$ | Cellular % EPO Stimulation | % HIF Stimulation |
|---|---|---|---|---|
| 67 | 1-(6-(4-Chlorophenoxy)-4-thiomorpholinoquinazolin-2-yl)-1H-pyrazole-4-carboxylic acid; | 7.3 | NT | 31 |
| 68 | 1-(6-(4-Chlorophenoxy)-4-((tetrahydro-2H-pyran-4-yl)amino)quinazolin-2-yl)-1H-pyrazole-4-carboxylic acid; | 6.9 | 40 | NT |
| 69 | 1-(6-(4-Chlorophenoxy)-4-(phenylamino)quinazolin-2-yl)-1H-pyrazole-4-carboxylic acid; | 7.7 | 23 | NT |
| 70 | 1-(4-(4-Acetamidopiperidin-1-yl)-6-(4-chlorophenoxy)quinazolin-2-yl)-1H-pyrazole-4-carboxylic acid; | 7.1 | 16 | NT |
| 71 | 1-(6-(4-Chlorophenoxy)-4-(4-methyl-1,4-diazepan-1-yl)quinazolin-2-yl)-1H-pyrazole-4-carboxylic acid; | 6.7 | 17 | NT |
| 72 | 1-(4-(tert-Butylamino)-6-phenoxyquinazolin-2-yl)-1H-pyrazole-4-carboxylic acid; | 6.7 | NT | 32 |
| 73 | 1-(6-Phenoxy-4-(pyrrolidin-1-yl)quinazolin-2-yl)-1H-pyrazole-4-carboxylic acid; | 7.2 | 36 | NT |
| 74 | 1-(4-(Diethylamino)-6-phenoxyquinazolin-2-yl)-1H-pyrazole-4-carboxylic acid; | 7.3 | NT | 81 |
| 75 | 1-(4-(Cyclopropylamino)-6-phenoxyquinazolin-2-yl)-1H-pyrazole-4-carboxylic acid; | 6.8 | 20 | NT |
| 76 | 1-(6-Phenoxy-4-((tetrahydro-2H-pyran-4-yl)amino)quinazolin-2-yl)-1H-pyrazole-4-carboxylic acid; | 6.5 | NT | 19 |
| 77 | 1-(4-(Dimethylamino)-7-phenoxyquinazolin-2-yl)-1H-pyrazole-4-carboxylic acid; | 7.4 | 75 | NT |
| 78 | 1-(7-Phenoxy-4-(pyrrolidin-1-yl)quinazolin-2-yl)-1H-pyrazole-4-carboxylic acid; | 7.3 | 38 | 64 |
| 79 | 1-(7-Phenoxy-4-(piperidin-1-yl)quinazolin-2-yl)-1H-pyrazole-4-carboxylic acid; | 7.0 | 38 | NT |
| 80 | 1-(4-(Dimethylamino)-7-phenylquinazolin-2-yl)-1H-pyrazole-4-carboxylic acid; | 6.0 | NT | 7.8 |
| 81 | 1-(7-Phenyl-4-(pyrrolidin-1-yl)quinazolin-2-yl)-1H-pyrazole-4-carboxylic acid; | 5.5 | NT | 10 |
| 82 | 1-(7-Phenyl-4-(piperidin-1-yl)quinazolin-2-yl)-1H-pyrazole-4-carboxylic acid; | 6.1 | NT | 4.6 |
| 83 | 1-(4-(Diethylamino)-7-phenoxyquinazolin-2-yl)-1H-pyrazole-4-carboxylic acid; | 7.7 | 25 | NT |
| 84 | 1-(4-((Cyclohexylmethyl)amino)-7-phenoxyquinazolin-2-yl)-1H-pyrazole-4-carboxylic acid; | 6.8 | NT | 4.6 |
| 85 | 1-(4-(4-Isopropylpiperidin-1-yl)-7-phenoxyquinazolin-2-yl)-1H-pyrazole-4-carboxylic acid; | 6.8 | NT | 1.7 |
| 86 | 1-(4-(Cyclopropylamino)-7-phenoxyquinazolin-2-yl)-1H-pyrazole-4-carboxylic acid; | 6.3 | NT | 13 |
| 87 | 1-(4-(Azepan-1-yl)-7-phenoxyquinazolin-2-yl)-1H-pyrazole-4-carboxylic acid; | 7.2 | NT | 20 |
| 88 | 1-(4-(Diethylamino)-6-(piperidin-1-yl)quinazolin-2-yl)-1H-pyrazole-4-carboxylic acid; | 7.0 | 94 | 122 |
| 89 | 1-(4-Morpholino-7-phenoxyquinazolin-2-yl)-1H-pyrazole-4-carboxylic acid; | 6.2 | NT | 17 |
| 90 | 1-(7-Phenoxy-4-thiomorpholinoquinazolin-2-yl)-1H-pyrazole-4-carboxylic acid; | 6.3 | NT | 7.7 |
| 91 | 1-(4-(4-Fluoropiperidin-1-yl)-7-phenoxyquinazolin-2-yl)-1H-pyrazole-4-carboxylic acid; | 6.3 | NT | 18 |
| 92 | 1-(4-(Dibutylamino)-7-phenoxyquinazolin-2-yl)-1H-pyrazole-4-carboxylic acid; | 7.1 | NT | 4.1 |
| 93 | 1-(4-(Dipropylamino)-7-phenoxyquinazolin-2-yl)-1H-pyrazole-4-carboxylic acid; | 7.2 | NT | 43 |
| 94 | 1-(4-(Ethyl(methyl)amino)-7-phenoxyquinazolin-2-yl)-1H-pyrazole-4-carboxylic acid; | 7.2 | NT | 83 |

TABLE 1-continued

| Ex | Chemical Name | Enzyme pIC$_{50}$ | Cellular % EPO Stimulation | % HIF Stimulation |
|---|---|---|---|---|
| 95 | 1-(4-((2-Methoxyethyl)(methyl)amino)-7-phenoxyquinazolin-2-yl)-1H-pyrazole-4-carboxylic acid; | 6.8 | NT | 46 |
| 96 | 1-(7-Bromo-4-(diethylamino)quinazolin-2-yl)-1H-pyrazole-4-carboxylic acid; | 6.9 | NT | 72 |
| 97 | 1-(4-(Cyclohexylamino)-7-phenoxyquinazolin-2-yl)-1H-pyrazole-4-carboxylic acid; | 7.0 | NT | 55 |
| 98 | 1-(4-((Cyclopropylmethyl)amino)-7-phenoxyquinazolin-2-yl)-1H-pyrazole-4-carboxylic acid; | 6.7 | NT | 46 |
| 99 | 1-(4-(tert-Butylamino)-7-phenoxyquinazolin-2-yl)-1H-pyrazole-4-carboxylic acid. | 6.3 | NT | 31 |
| 100 | 1-(7-Fluoro-6-(cyclohexyloxy)-4-morpholinoquinazolin-2-yl)-1H-pyrazole-4-carboxylic acid. | 6.6 | 18 | NT |
| 101 | 1-(7-fluoro-6-(cyclohexyloxy)-4-(dimethylamino)quinazolin-2-yl)-1H-pyrazole-4-carboxylic acid | 7.1 | 85 | NT |
| 102 | 1-(7-fluoro-6-(cyclohexyloxy)-4-(pyrrolidin-1-yl)quinazolin-2-yl)-1H-pyrazole-4-carboxylic acid. | 7.5 | 37 | NT |
| 103 | 1-(7-fluoro-6-(cyclohexyloxy)-4-(pyrrolidin-1-yl)quinazolin-2-yl)-1H-pyrazole-4-carboxylic acid. | 7.3 | 31 | NT |
| 104 | 1-(7-fluoro-6-(cyclohexyloxy)-4-(ethyl(methyl)amino)quinazolin-2-yl)-1H-pyrazole-4-carboxylic acid. | 7.1 | 49 | NT |
| 105 | 1-(7-fluoro-6-(cyclohexyloxy)-4-(cyclopropylamino)quinazolin-2-yl)-1H-pyrazole-4-carboxylic acid. | 7.2 | 29 | NT |
| 136 | 1-(7-chloro-6-(cyclohexyloxy)-4-morpholinoquinazolin-2-yl)-1H-pyrazole-4-carboxylic acid. | 6.7 | 33 | NT |
| 137 | 1-(7-chloro-6-(cyclohexyloxy)-4-(dimethylamino)quinazolin-2-yl)-1H-pyrazole-4-carboxylic acid. | 7.4 | 32 | NT |
| 138 | 1-(7-chloro-6-(cyclohexyloxy)-4-(diethylamino)quinazolin-2-yl)-1H-pyrazole-4-carboxylic acid. | 7.5 | NT | NT |
| 139 | 1-(7-chloro-6-(cyclohexyloxy)-4-(pyrrolidin-1-yl)quinazolin-2-yl)-1H-pyrazole-4-carboxylic acid | 7.1 | NT | NT |
| 140 | 1-(7-chloro-6-(cyclohexyloxy)-4-(ethyl(methyl)amino)quinazolin-2-yl)-1H-pyrazole-4-carboxylic acid. | 7.2 | 29 | NT |
| 141 | 1-(7-chloro-6-(cyclohexyloxy)-4-(cyclopropylamino)quinazolin-2-yl)-1H-pyrazole-4-carboxylic acid. | 7.0 | NT | NT |
| 160 | 1-(7-chloro-6-isopropyl-4-morpholinoquinazolin-2-yl)-1H-pyrazole-4-carboxylic acid | 6.8 | 28 | NT |
| 161 | 1-(7-chloro-4-(dimethylamino)-6-isopropylquinazolin-2-yl)-1H-pyrazole-4-carboxylic acid. | 7.4 | 32 | NT |
| 162 | 1-(7-chloro-4-diethylamino-6-isopropylquinazolin-2-yl)-1H-pyrazole-4-carboxylic acid. | 7.2 | 40 | NT |
| 163 | 1-(7-chloro-4-(pyrrolidin-1-yl)-6-isopropylquinazolin-2-yl)-1H-pyrazole-4-carboxylic acid. | 7.3 | 26 | NT |
| 164 | 1-(7-chloro-4-(ethyl(methyl)amino)-6-isopropylquinazolin-2-yl)-1H-pyrazole-4-carboxylic acid. | 7.4 | 57 | NT |
| 165 | 1-(7-chloro-4-(cyclopropylamino)-6-isopropylquinazolin-2-yl)-1H-pyrazole-4-carboxylic acid. | 7.0 | 24 | NT |
| 172 | 1-(6-(cyclohexyloxy)-4-morpholinoquinazolin-2-yl)-1H-pyrazole-4-carboxylic acid | 6.4 | 18 | NT |
| 173 | 1-(6-(cyclohexyloxy)-4-(dimethylamino)quinazolin-2-yl)-1H-pyrazole-4-carboxylic acid. | 7.4 | 62 | NT |

TABLE 1-continued

| Ex | Chemical Name | Enzyme pIC$_{50}$ | Cellular % EPO Stimulation | % HIF Stimulation |
|---|---|---|---|---|
| 174 | 1-(6-(cyclohexyloxy)-4-(diethylamino)quinazolin-2-yl)-1H-pyrazole-4-carboxylic acid. | 7.2 | 35 | NT |
| 175 | 1-(6-(cyclohexyloxy)-4-(pyrrolidin-1-yl)quinazolin-2-yl)-1H-pyrazole-4-carboxylic acid | 7.2 | 46 | NT |
| 176 | 1-(6-(cyclohexyloxy)-4-(cyclopropylamino)quinazolin-2-yl)-1H-pyrazole-4-carboxylic acid. | 6.8 | 35 | NT |
| 177 | 1-(6-(cyclohexyloxy)-4-(ethyl(methyl)amino)quinazolin-2-yl)-1H-pyrazole-4-carboxylic acid. | 7.3 | 56 | NT |
| 178 | 1-(6-benzyl-4-morpholinoquinazolin-2-yl)-1H-pyrazole-4-carboxylic acid | 6.5 | NT | NT |
| 179 | 1-(6-benzyl-4-(dimethylamino)quinazolin-2-yl)-1H-pyrazole-4-carboxylic acid. | 7.1 | NT | NT |
| 180 | 1-(6-benzyl-4-(diethylamino)quinazolin-2-yl)-1H-pyrazole-4-carboxylic acid. | 7.1 | NT | NT |
| 181 | 1-(6-benzyl-4-(pyrrolidin-1-yl)quinazolin-2-yl)-1H-pyrazole-4-carboxylic acid. | 7.1 | NT | NT |
| 182 | 1-(6-benzyl-4-(cyclopropylamino)quinazolin-2-yl)-1H-pyrazole-4-carboxylic acid. | 7.1 | NT | NT |
| 183 | 1-(6-benzyl-4-(ethyl(methyl)amino)quinazolin-2-yl)-1H-pyrazole-4-carboxylic acid. | 7.2 | NT | NT |
| 184 | 1-(4-(morpholino)-6-isopropylquinazolin-2-yl)-1H-pyrazole-4-carboxylic acid. | 5.7 | 24 | NT |
| 185 | 1-(4-(dimethylamino)-6-isopropylquinazolin-2-yl)-1H-pyrazole-4-carboxylic acid. | 7.0 | 62 | NT |
| 186 | 1-(4-(diethylamino)-6-isopropylquinazolin-2-yl)-1H-pyrazole-4-carboxylic acid | 7.0 | 43 | NT |
| 187 | 1-(6-isopropyl-4-(pyrrolidin-1-yl)quinazolin-2-yl)-1H-pyrazole-4-carboxylic acid. | 6.8 | 28 | NT |
| 188 | 1-(4-(cyclopropylamino)-6-isopropylquinazolin-2-yl)-1H-pyrazole-4-carboxylic acid | 6.0 | 35 | NT |
| 189 | 1-(6-isopropyl-4-(ethyl(methyl)amino)quinazolin-2-yl)-1H-pyrazole-4-carboxylic acid. | 6.8 | 36 | NT |

What is claimed is:

1. A compound of the formula (I):

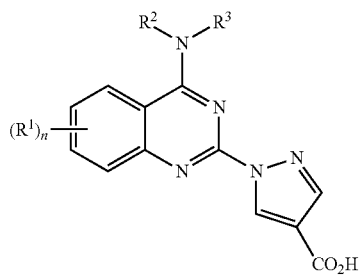

Formula (I)

wherein:

n is 0-3

$R^1$ is a member independently selected from the group consisting of halo, —O—$R^c$, —$C_{1-4}$alkyl, cyclohexyl, phenyl optionally substituted with —$C_{1-4}$alkyl, benzyl optionally substituted with —$C_{1-4}$alkyl, and —$NR^aR^b$;

$R^a$ is H and $R^b$ is benzyl optionally substituted with —$C_{1-4}$alkyl, or $R^a$ and $R^b$ are taken together with the nitrogen to which they are attached to form a piperidine ring;

$R^c$ is cyclohexyl, phenyl optionally substituted with one or more $R^d$ members;

$R^d$ is a member independently selected from the group consisting of —H, halo, and —$C_{1-4}$alkyl;

$R^2$ is a member independently selected from the group consisting of —H, and —$C_{1-4}$alkyl, $R^3$ is a member independently selected from the group consisting of —H, —$C_{1-4}$alkyl optionally substituted with —$OCH_3$ or —$N(C_{1-4}alkyl)_2$, cyano, —$SO_2CH_3$, tetrahydropyran, —$(CH_2)_mC_{3-8}$cycloalkyl, —$(CH_2)_m$phenyl optionally substituted with one or more halo, or —$C_{1-4}$alkyl;

m is 0-1;

$R^2$ and $R^3$ can be taken together with the nitrogen to which they are attached to form a 4 to 7 membered heterocycloalkyl ring optionally containing O, N, S optionally substituted with —OH, cyano, halo, —N—C(O)$C_{1-4}$alkyl, and —$C_{1-4}$alkyl;

and enantiomers, diastereomers, racemates, and pharmaceutically acceptable salts thereof.

2. A compound as defined in claim 1, where $R^1$ is a member independently selected from the group consisting of bromo, chloro, fluoro, methyl, isopropyl, cyclohexyl, cyclohexyloxy, phenyl, 2-methylphenyl, benzyl, phenoxy, 4-chlorophenoxy, 2,6-dimethyl-phenoxy, piperidinyl, and (2,6-dimethylbenzyl)amino.

3. A compound of claim 1 where n is 1.
4. A compound of claim 1 where n is 2.
5. A compound of claim 1 where n is 3.
6. A compound as defined in claim 1, where $R^a$ is H and $R^b$ is 2,6-dimethylbenzyl.
7. A compound as defined in claim 1, where $R^c$ is a member selected from the group consisting of phenyl, cyclohexyl, 4-chlorophenyl, and 2,6-dimethyl-phenyl.
8. A compound as defined in claim 1, where $R^d$ is a member selected from the group consisting of —H, chloro, and —CH$_3$.
9. A compound as defined in claim 1, where $R^2$ is —H and $R^3$ is a member selected from the group consisting of H, cyano, methyl, ethyl, propyl, tertbutyl, cyclopropyl, cyclopropylmethyl, tetrahydropyranyl, cyclohexylmethyl, phenyl, 2-chlorophenyl, 2,6-dimethylbenzyl, and —SO$_2$CH$_3$.
10. A compound as defined in claim 1, where $R^2$ is selected from the group consisting of methyl, ethyl, propyl, and butyl.
11. A compound as defined in claim 1, where $R^3$ is selected from the group consisting of methyl, ethyl, propyl, butyl, tertbutyl, 2-methoxyethyl, 2-methoxy-1-methyl-ethyl and diethylamino-ethyl.
12. A compound as defined in claim 1, where $R^2$ and $R^3$ are taken together with the nitrogen to which they are attached to form pyrrolidine, piperidine, 4-methyl-1,4-diazepane, thiomorpholine, 4-hydroxypiperidine, morpholine, 4-acetamidopiperidine, 4-cyanopiperidine, 4-fluoropiperidine, azepane, or 4-isopropylpiperidine.
13. A compound as defined in claim 1, where n is 2, $R^1$ is a member independently selected from the group consisting of halo, cyclohexyl, and 2,6-dimethyl-phenoxy, and $R^2$ and $R^3$ are $C_{1-4}$alkyl, or $R^2$ and $R^3$ are taken together with the nitrogen to which they are attached to form morpholine.
14. A pharmaceutical composition comprising a pharmaceutically acceptable excipient
and an effective amount of compound having PHD inhibitor activity of formula (I):

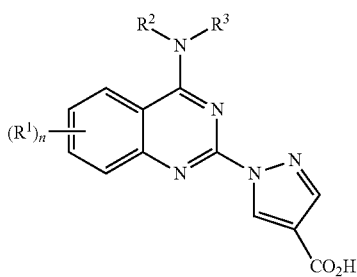

Formula (I)

wherein:
n is 0-3
$R^1$ is a member independently selected from the group consisting of halo, —O—$R^c$, —$C_{1-4}$alkyl, cyclohexyl, phenyl optionally substituted with —$C_{1-4}$alkyl, benzyl optionally substituted with —$C_{1-4}$alkyl, and —NR$^a$R$^b$;
$R^a$ is H and $R^b$ is benzyl optionally substituted with —$C_{1-4}$alkyl, or $R^a$ and $R^b$ are taken together with the nitrogen to which they are attached to form a piperidine ring;
$R^c$ is cyclohexyl, phenyl optionally substituted with one or more $R^d$ members;
$R^d$ is a member independently selected from the group consisting of —H, halo, and —$C_{1-4}$alkyl;
$R^2$ is a member independently selected from the group consisting of —H, and —$C_{1-4}$alkyl,
$R^3$ is a member independently selected from the group consisting of —H, —$C_{1-4}$alkyl optionally substituted with —OCH$_3$ or —N($C_{1-4}$alkyl)$_2$, cyano, —SO$_2$CH$_3$, tetrahydropyran, —(CH$_2$)$_m$C$_{3-8}$cycloalkyl, —(CH$_2$)$_m$ phenyl optionally substituted with one or more halo, or —$C_{1-4}$alkyl;
m is 0-1;
$R^2$ and $R^3$ can be taken together with the nitrogen to which they are attached to form a 4 to 7 membered heterocycloalkyl ring optionally containing O, N, S optionally substituted with —OH, cyano, halo, —N—C(O)C$_{1-4}$alkyl, and —$C_{1-4}$alkyl;
and enantiomers, diastereomers, racemates, and pharmaceutically acceptable salts thereof.
15. A pharmaceutical composition comprising an effective amount of at least on chemical entity of claim 1.
16. A method for the treatment of anemia, hypoxia, ischemia, peripheral vascular disease, myocardial infarction, stroke, diabetes, obesity, inflammatory bowel disease,
ulcerative colitis, Crohn's disease, wounds, infection, burns and bone fracture comprising the step of administering to a patient in need thereof a therapeutically effective amount of compound having PHD inhibitor activity of formula (I):

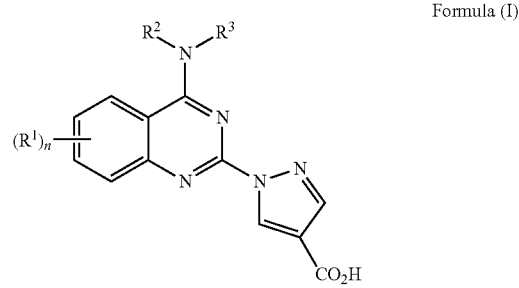

Formula (I)

wherein:
n is 0-3
$R^1$ is a member independently selected from the group consisting of halo, —O—$R^c$, —$C_{1-4}$alkyl, cyclohexyl, phenyl optionally substituted with —$C_{1-4}$alkyl, benzyl optionally substituted with —$C_{1-4}$alkyl, and —NR$^a$R$^b$;
$R^a$ is H and $R^b$ is benzyl optionally substituted with —$C_{1-4}$alkyl, or $R^a$ and $R^b$ are taken together with the nitrogen to which they are attached to form a piperidine ring;
$R^c$ is cyclohexyl, phenyl optionally substituted with one or more $R^d$ members;
$R^d$ is a member independently selected from the group consisting of —H, halo, and —$C_{1-4}$alkyl;
$R^2$ is a member independently selected from the group consisting of —H, and —$C_{1-4}$alkyl,
$R^3$ is a member independently selected from the group consisting of —H, —$C_{1-4}$alkyl optionally substituted with —OCH$_3$ or —N($C_{1-4}$alkyl)$_2$, cyano, —SO$_2$CH$_3$, tetrahydropyran, —(CH$_2$)$_m$C$_{3-8}$cycloalkyl, —(CH$_2$)$_m$ phenyl optionally substituted with one or more halo, or —$C_{1-4}$alkyl;
m is 0-1;
$R^2$ and $R^3$ can be taken together with the nitrogen to which they are attached to form a 4 to 7 membered heterocycloalkyl ring optionally containing O, N, S optionally substituted with —OH, cyano, halo, —N—C(O)C$_{1-4}$alkyl, and —C$_{1-4}$alkyl;

and enantiomers, diastereomers, racemates, and pharmaceutically acceptable salts thereof.

17. A method for treating a hypoxic disorder comprising the step of administering to a patient in need thereof a therapeutically effective amount of compound having PHD inhibitor activity of formula (I):

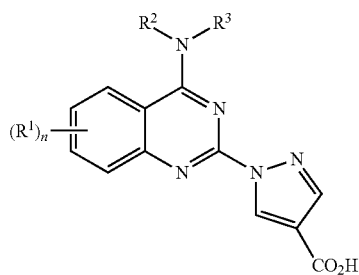

Formula (I)

wherein:

n is 0-3

$R^1$ is a member independently selected from the group consisting of halo, —O—$R^c$, —C$_{1-4}$alkyl, cyclohexyl, phenyl optionally substituted with —C$_{1-4}$alkyl, benzyl optionally substituted with —C$_{1-4}$alkyl, and —NR$^a$R$^b$;

$R^a$ is H and $R^b$ is benzyl optionally substituted with —C$_{1-4}$alkyl, or $R^a$ and $R^b$ are taken together with the nitrogen to which they are attached to form a piperidine ring;

$R^c$ is cyclohexyl, phenyl optionally substituted with one or more $R^d$ members;

$R^d$ is a member independently selected from the group consisting of —H, halo, and —C$_{1-4}$alkyl;

$R^2$ is a member independently selected from the group consisting of —H, and —C$_{1-4}$alkyl, $R^3$ is a member independently selected from the group consisting of —H, —C$_{1-4}$alkyl optionally substituted with —OCH$_3$ or —N(C$_{1-4}$alkyl)$_2$, cyano, —SO$_2$CH$_3$, tetrahydropyran, —(CH$_2$)$_m$C$_{3-8}$cycloalkyl, —(CH$_2$)$_m$phenyl optionally substituted with one or more halo, or —C$_{1-4}$alkyl;

m is 0-1;

$R^2$ and $R^3$ can be taken together with the nitrogen to which they are attached to form a 4 to 7 membered heterocycloalkyl ring optionally containing O, N, S optionally substituted with —OH, cyano, halo, —N—C(O)C$_{1-4}$alkyl, and —C$_{1-4}$alkyl;

and enantiomers, diastereomers, racemates, and pharmaceutically acceptable salts thereof.

18. The method of claim 17, wherein said hypoxic disorder is selected from the group consisting of anemia, ischemia, stroke, myocardial infarction, and coronary artery disease.

19. A method for treating diabetes comprising administering a therapeutically effective amount of a compound of claim 1 to a patient in need thereof.

20. A method for wound treatment comprising administering a therapeutically effective amount of a compound of claim 1 to a patient in need thereof.

21. A method for treating a metabolic disorder comprising administering a therapeutically effective amount of a compound of claim 1 to a patient in need thereof.

22. The method of claim 21 wherein said metabolic disorder is obesity or diabetes.

\* \* \* \* \*